United States Patent
Hawkins et al.

(10) Patent No.: US 7,833,993 B2
(45) Date of Patent: *Nov. 16, 2010

(54) IMMUNOMODULATORY COMPOUNDS AND METHODS OF USE THEREOF

(75) Inventors: Lynn D. Hawkins, Concord, MA (US); Sally T. Ishizaka, Weston, MA (US)

(73) Assignee: Eisai R&D Management Co., Ltd., Tokyo (JP)

( * ) Notice: Subject to any disclaimer, the term of this patent is extended or adjusted under 35 U.S.C. 154(b) by 413 days.

This patent is subject to a terminal disclaimer.

(21) Appl. No.: 11/077,344

(22) Filed: Mar. 9, 2005

(65) Prior Publication Data

US 2005/0164988 A1 Jul. 28, 2005

Related U.S. Application Data

(63) Continuation of application No. 10/157,791, filed on May 28, 2002, now abandoned, which is a continuation-in-part of application No. 09/918,849, filed on Jul. 31, 2001, now Pat. No. 6,551,600, which is a continuation-in-part of application No. 09/496,152, filed on Feb. 1, 2000, now Pat. No. 6,290,973.

(60) Provisional application No. 60/118,131, filed on Feb. 1, 1999.

(51) Int. Cl.
- *A61K 31/6615* (2006.01)
- *C07F 9/10* (2006.01)
- *C07F 9/113* (2006.01)

(52) U.S. Cl. .................. 514/103; 514/104; 562/12; 562/14; 562/20

(58) Field of Classification Search ................. None
See application file for complete search history.

(56) References Cited

U.S. PATENT DOCUMENTS

| | | |
|---|---|---|
| 5,484,911 A | 1/1996 | Hong et al. |
| 5,635,188 A | 6/1997 | Bystryn |
| 5,681,824 A * | 10/1997 | Christ et al. .................. 514/53 |
| 5,895,653 A | 4/1999 | Eibl et al. |
| 5,904,925 A | 5/1999 | Exner |
| 5,961,970 A | 10/1999 | Lowell et al. |
| 5,985,284 A | 11/1999 | Lowell |
| 6,136,797 A | 10/2000 | Zilch et al. |
| 6,146,632 A | 11/2000 | Momin et al. |
| 6,146,659 A * | 11/2000 | Rahman ..................... 424/450 |
| 6,165,502 A | 12/2000 | Oleske et al. |
| 6,172,049 B1 | 1/2001 | Dwyer et al. |
| 6,180,111 B1 | 1/2001 | Stein et al. |
| 6,284,267 B1 * | 9/2001 | Aneja ........................ 424/450 |
| 6,290,973 B1 * | 9/2001 | Hawkins et al. .......... 424/278.1 |
| 6,306,404 B1 | 10/2001 | LaPosta et al. |
| 6,355,257 B1 | 3/2002 | Johnson et al. |
| 6,437,165 B1 | 8/2002 | Mandala et al. |
| 6,461,637 B1 * | 10/2002 | Rahman ..................... 424/450 |
| 6,521,776 B2 | 2/2003 | Hawkins et al. |
| 6,551,600 B2 * | 4/2003 | Hawkins et al. .......... 424/278.1 |
| 6,630,161 B1 | 10/2003 | Leesman ..................... 424/455 |
| 6,835,721 B2 * | 12/2004 | Hawkins et al. ............ 514/120 |
| 7,416,726 B2 | 8/2008 | Ravetch |
| 7,560,584 B2 * | 7/2009 | Hawkins et al. ............ 558/166 |
| 7,683,200 B2 * | 3/2010 | Fang et al. .................. 558/166 |
| 2002/0049314 A1 * | 4/2002 | Hawkins et al. .............. 536/53 |
| 2002/0176861 A1 * | 11/2002 | Hawkins et al. .......... 424/184.1 |
| 2003/0153532 A1 * | 8/2003 | Hawkins et al. .............. 514/78 |
| 2004/0006242 A1 | 1/2004 | Hawkins et al. |
| 2005/0123566 A1 | 6/2005 | Hawkins et al. |
| 2005/0164988 A1 | 7/2005 | Hawkins et al. |
| 2007/0020232 A1 * | 1/2007 | Rossignol et al. .......... 424/85.1 |
| 2007/0027111 A1 * | 2/2007 | Hawkins et al. .............. 514/78 |
| 2007/0292418 A1 | 12/2007 | Fields et al. |

FOREIGN PATENT DOCUMENTS

| | | |
|---|---|---|
| EP | 0 390 216 A2 | 3/1990 |
| JP | 02-261866 | 10/1990 |
| WO | WO 93/04672 A1 | 3/1993 |
| WO | WO 95/11700 A1 | 5/1995 |
| WO | WO 98/57659 | 12/1998 |
| WO | WO 98/57659 A1 | 12/1998 |
| WO | WO 00/44758 | 8/2000 |
| WO | WO 00/44758 A1 | 8/2000 |
| WO | WO 00/73263 A1 | 12/2000 |

(Continued)

OTHER PUBLICATIONS

Gokhale et al., "An improved method of encapsulation of doxorubicin in liposomes: pharmacological, toxicological, and therapeutic evaluation" British Journal of cancer (1996) vol. 74, pp. 43-48.*

U.S. Appl. No. 11/605,557, filed Nov. 2006, Fields et al.*

Cheung C. W., et al. "American Chemical Society—226$^{th}$ National Meeting: New drugs highlights: Sep. 7-11, 2003, New York, NY, USA" IDRUGS, (2003) 6/10. pp. 939-942.

Eustache, et al., "New Acyclic Analogues of Lipid A: Synthesis of 4-Phosphonoxybutyl and 3-Phosphonoxypropyl Glycosides of 2-amino-2-deoxy-D-glucose", Carbohydrate Research, vol. 251, pp. 251-267 (1994).

(Continued)

*Primary Examiner*—Eric S Olson
(74) *Attorney, Agent, or Firm*—Myers Bigel Sibley & Sajovec P.A.

(57) ABSTRACT

The present invention is directed to methods of treating diseases and disorders related to immune responses by administering one or more immunomodulatory compounds. In particular, the invention is directed to methods of stimulating and reducing immune responses, treating autoimmune conditions, treating allergic reactions and asthma, and preventing ischemic damage and asthma by administering one or more immunomodulatory compounds.

12 Claims, 6 Drawing Sheets

FOREIGN PATENT DOCUMENTS

| WO | WO 01/46127 | 6/2001 |
|---|---|---|
| WO | WO 01/46127 A1 | 6/2001 |
| WO | WO 01/90129 | 11/2001 |
| WO | WO 01/90129 A2 | 11/2001 |
| WO | WO 02/09752 | 2/2002 |
| WO | WO 02/09752 A2 | 2/2002 |
| WO | WO03/003985 A2 | 1/2003 |
| WO | WO 03/011223 | 2/2003 |
| WO | WO 03/011223 A2 | 2/2003 |

OTHER PUBLICATIONS

Jiang Z., et al. "Synthetic vaccines: The role of adjuvants in immune targeting." Current Medical Chesmistry, (2003) 10/15. pp. 1423-1439.

Hawkins, et al., "A Novel Class of Endotoxin Receptor Agonists with Simplified Structure, Toll-Like Receptor 4-Dependent Immunostimulatory Action, and Adjuvant Activity", Journal of Pharmacology and Experimental Therapeutics, vol. 300; No. 2, pp. 655-661 (2002).

Homma, et al., "Structural Requirements of Lipid A Responsible for the Functions: A Study with Chemically Synthesized Lipid A and Its Analogues", J. Biochem, vol. 98, pp. 395-406 (1985).

Lien, et al., "A Novel Synthetic Acyclic Lipid A-like Agonist Activates Cells via the Lipopolysaccharide/Toll-like Receptor 4 Signaling Pathway", The Journal of Biological Chemistry, vol. 276, No. 3, pp. 1873-1880 (2001).

Matsuura, et al., "Activity of Monosaccharide Lipid A Analogues in Human Monocytic Cells as Agonists or Antagonists of Bacterial Lipopolysaccharide", Infection and Immunity, vol. 67, No. 12, pp. 6286-6292 (1999).

Przetak, et al., "Novel Synthetic LPS Receptor Agonists Boost Systemic and Mucosal Antibody Responses in Mice", Vaccine 21, pp. 961-970 (2003).

Przetak et al., Vaccine, (2003), 21 (9-10), 961-970.

Seydel, et al., "The Generalized Endotoxic Principle", Eur. J. Immunol., vol. 33, pp. 1586-1592 (2003).

The Merck Manual of Diagnosis and Therapy ($17^{th}$ Ed) (1999), p. 1420-1421.

Gokhale et al., "An improved method of encapsulation of doxorubicin in liposomes: pharmacological, toxicological, and therapeutic evaluation," Br. J. Cancer 74:43-48 (1996).

Hawkins et al., "Inhibition of endotoxins response by synthetic TLR4 antagonists," Curr. Topics Med. Chem. 4:1147-71 (2004).

Merriam-Webster's Collegiate Dictionary, 10th edition, published 1998 by Merriam-Webster, Inc., p. 924.

Rossignol and Lynn, "TLR4 antagonists for endotoxemia and beyond," Curr. Opin. Invest. Drugs 6:295-502 (2005).

The Merck Manual of Diagnosis and Therapy, 17th Edition, 1999, published by Merck Research Laboratories, pp. 397-398, 948-949, 1916, and 1979-1981.

The Oxford Textbook of Oncology, 1995, published by Oxford University Press, pp. 447-453.

U.S. Appl. No. 10/157,791, filed May 28, 2002; Office Action Mailed: Sep. 9, 2004.

U.S. Appl. No. 10/157,791, filed: May 28, 2002; Office Action Mailed: Jun. 16, 2005.

U.S. Appl. No. 11/411,564, filed: Apr. 26, 2006; Office Action Mailed: Oct. 2, 2008.

U.S. Appl. No. 11/024,328, filed: Dec. 28, 2004; Office Action Mailed: Sep. 17, 2007.

U.S. Appl. No. 11/024,328, filed: Dec. 28, 2004; Office Action Mailed: Mar. 6, 2008.

U.S. Appl. No. 11/411,332, filed: Apr. 26, 2006; Office Action Mailed: Oct. 25, 2007.

U.S. Appl. No. 11/411,332, filed: Apr. 26, 2006; Office Action Mailed: Jul. 14, 2008.

U.S. Appl. No. 11/605,557, filed: Nov. 28, 2006; Office Action Mailed: Jun. 26, 2008.

Baldridge et al., "Taking a Toll on human disease: Toll-like receptor 4 agonists as vaccine adjuvants and monotherapeutic agents," Exp. Opin. Biol. Ther. 4:1129-1138 (2004).

Baselga et al., "Recombinant Humanized Anti-HER2 Antibody (Herceptin™) Enhances the Antitumor Activity of Paclitaxel and Doxorubicin against HER2/neu Overexpressing Human Breast Cancer Xenografts," Cancer Res. 58:2825-2831 (1998).

Belimezi et al., "Growth inhibiton of breast cancer cell lines overexpressing Her2/neu by a novel internalized fully human Fab antibody fragment," Cancer Immunol. Immunother. 55:1091-1099 (2006).

Clynes et al., "Inhibitory Fc receptors modulate in vivo cytoxicity against tumor targets," Nature Med. 6:443-446 (2000).

Coelho et al., "Isolation and characterisation of a human anti-idiotypic scFv used as a surrogate tumour antigen to elicit an anti-HER-2/neu humoral response in mice," British J. Cancer 90:2032-2041 (2004).

Cooper et al., "CPG 7909, an Immunostimulatory TLR9 Agonist Oligodeoxynucleotide, as Adjuvant to Engerix-B® HBV Vaccine in Healthy Adults: A Double-Blind Phase I/II Study," J. Clin. Immunol. 24:693-701 (2004).

Cragg et al., "Antibody specificity controls in vivo effector mechanisms of anti-CD20 reagents," Blood 103:2738-2743 (2004).

Dalpke et al., "CpG DNA in the Prevention and Treatment of Infections," Biodrugs 16:419-431 (2002).

Eisai Research Inst. Product Datasheet for E6020 or ER-804057 (pp. 1-5; Mar. 1999)..

Hawkins et al., "A Novel Class of Endotoxin Receptor Agonists with Simplified Structure, Toll-Like Receptor 4-Dependent Immunostimulatory Action, and Adjuvant Activity," J. Pharmacol. Exp. Ther. 300:655-661 (2002).

Jiang and Koganty, "Synthetic Vaccines: The Role of Adjuvants in Immune Targeting," Curr. Med. Chem. 10:1423-1439 (2003).

Overholser et al., "Epidermal Growth Factor Receptor Blockade by Antibody IMC-C225 Inhibits Growth of a Human Pancreatic Carcinoma Xenograft in Nude Mice," Cancer 89:74-82 (2000).

Ross et al., "The HER-2/neu Gene and Protein in Breast Cancer 2003: Biomarker and Target of Therapy," Oncologist 8:307-325 (2003).

Schuster et al., "Cancer Immunotherapy," Biotechnol. J. 1:138-147 (2006).

Skinner et al., "Imiquimod" Dermatol. Clin. 21:291-300 (2003).

Zhang et al., "FCGR2A and FCGR3A Polymorphisms Associated With Clinical Outcome of Epidermal Growth Factor Receptor-Expressing Metatastic Colorectal Cancer Patients Treated With Single-Agent Cetuximab," J. Clin. Oncol. 25:3712-3718 (2007).

U.S. Appl. No. 11/411,332, filed: Apr. 26, 2006; Office Action Mailed: Mar. 10, 2009.

U.S. Appl. No. 11/605,557, filed: Nov. 28, 2006; Office Action Mailed: Feb. 26, 2009.

U.S. Appl. No. 11/411,564, filed Apr. 26, 2006; Office Action Mailed: May 12, 2009.

U.S. Appl. No. 11/411,564, filed Apr. 26, 2006; Office Action Mailed: Oct. 7, 2009.

U.S. Appl. No. 11/605,557, filed Nov. 28, 2006; Office Action Mailed: Sep. 4, 2009.

U.S. Appl. No. 11/411,332, filed Apr. 26, 2006; Office Action Mailed: Sep. 24, 2009.

Berzoksky and Berkower. "Chapter 8: Immunogenicity and Antigen Structure" Fundamental Immunology, William E. Paul, ed., Raven Press NY, p. 242 (1993).

Bhattacharya et al. "Synthesis and Vesicle Formation from Novel Pseudoglyceryl Dimeric Lipids. Evidence of Formation of Widely Different Membrane Organizations with Exceptional Thermotropic Properties" Chemical Communications 23:2287-2288 (1997).

Cespedes et al. "Mouse Models in Oncogenesis and Cancer Therapy" Clin. Transl. Oncol. 8(5):318-329 (2006).

Chatterjee et al. "Idiotypic Antibody Immunotherapy of Cancer" Cancer Immunology Immunotherapy 38:75-82 (1994).

Cheung and Paterson. "American Chemical Society—$226^{th}$ National Meeting: New Drug Highlights" IDRUGS 6(10):939-942 (2003).

Defoort et al. "Macromolecular Assemblage in the Design of a Synthetic AIDS Vaccine" PNAS 89:3879-3883 (1992).

Dennis. "Off by a Whisker" *Cancer News Feature* 442:739-741 (2006).
Dermer. "Another Anniversary for the War on Cancer" *Biotechnology* 12:320 (1994).
Dullenkopf et al. "Synthesis of a Structurally Defined Antigen-Immunostimulant Combination for Use in Cancer Vaccines" *Chem. Euro. J.* 5(8):2432-2438 (1999).
Duralski et al. "Synthesis of Isotopically Labelled Cardiolipins" *Tetrahedron Letters, NL*, Elsevier Science Publishers, Amsterdam 39:1607-1610 (1998).
Eustache et al. "New Acyclic Analogues of Lipid A: Synthesis of 4-Phosphonoxybutyl and 3-Phosphonoxypropyl Glycosides of 2-Amino-2-Deoxy-D-Glucose" *Carbohydrate Research* 251:251-267 (1994).
Gregoriadis et al. "Liposomes as Immunological Adjuvants and Vaccine Carriers" *Journal of Controlled Release* 41(1/02):49-56 (1996).
Gura. "Systems for Identifying New Drugs are Often Faulty" *Science* 278:1041-1042 (1997).
Hawkins et al. "A Novel Class of Endotoxin Receptor Agonists with Simplified Structure, Toll-Like Receptor 4-Dependent Immunostimulatory Action, and Adjuvant Activity" *Journal of Pharmacology and Experimental Therapeutics* 300(2):655-661 (2002).
Hoffmann et al. "Induction of Tumor Cytotoxicity in Murine Bone Marrow-Derived Macrophages by Two Synthetic Lipopeptide Analogues" *Biol. Chem.* 370:575-582 (1989).
Homma et al. "Structural Requirements of Lipid A Responsible for the Functions: A Study with Chemically Synthesized Lipid A and its Analogues" *J. Biochem.* 98:395-406 (1985).
Inoue and Nojima. "Immunochemical Studies of Phospholipids. I. Reactivity of Various Synthetic Cardiolipin Derivatives with Wassermann Antibody" *Chem. Phys. Lipids* 1(4):360-367 (1967).
Inoue and Nojima. "Immunochemical Studies of Phospholipids. II. Syntheses of Cardiolipin and its Analogues" *Chemical and Pharmaceutical Bulletin* 16(1):76-81 (1968).
Inoue and Nojima. "Immunochemical Studies of Phospholipids IV: The Reactivities of Antisera Against Natural Cardiolipin and Synthetic Cardiolipin Analogues-Containing Antigens" *Chem. Phys. Lipids (CPLIA4)* 3(1):70-77 (1969).
Jain. "Barriers to Drug Delivery in Solid Tumors" *Scientific American* pp. 58-65 (1994).
Jain et al. "Effect of the Structure of Phospholipid on the Kinetics of Intravesicle Scooting of Phospholipase $A_2$" *Biochimica et Biophysica Acta* 860(3):462-474 (1986).
Jiang and Koganty. "Synthetic Vaccines: The Role of Adjuvants in Immune Targeting" *Current Medicinal Chemistry* 10:1423-1439 (2003).
Kamitakahara et al. "A Lysoganglioside/poly-L-glutamic Acid Conjugate as a Picomolar Inhibitor of Influenza Hemagglutinin" *Angew. Chem. Int. Ed.* 37(11):1524-1528 (1998).
Lien et al. "A Novel Synthetic Acyclic Lipid A-Like Agonist Activates Cells Via the Lipopolysaccharide/Toll-Like Receptor 4 Signaling Pathway" *J. Biol. Chem.* 276(3):1873-1880 (2001).
Matsuura et al. "Activity of Monosaccharide Lipid A Analogues in Human Monocytic Cells as Agonists or Antagonists of Bacterial Lipopolysaccharide" *Infection and Immunity* 67(12):6286-6292 (1999).
Mitchell. "Immunotherapy as Part of Combinations for the Treatment of Cancer" *International Immunopharmacology* 3:1051-1059 (2003).
Przetak et al. "Novel Synthetic LPS Receptor Agonists Boost Systemic and Mucosal Antibody Responses in Mice" *Vaccine* 21:961-970 (2003).
Reichel et al. "Synthetic Carbohydrate-Based Vaccine: Synthesis of an L-Glycero-D-Manno-Heptose Antigen-T-Epitope-Lipopeptide Conjugate" *Chem. Commun.* pp. 2087-2088 (1997).
Schuster et al. "Cancer Immunotherapy" *Biotechnol. J.* 1:138-147 (2006).
Seaver. "Monoclonal Antibodies in Industry: More Difficult Than Originally Thought" *Genetic Engineering News* 14(14):10 and 21 (1994).
Seydel et al. "The Generalized Endotoxic Principle" *Eur. J. Immunol.* 33:1586-1592 (2003).
The Merck Manual of Diagnosis and Therapy ($17^{th}$ Ed.) pp. 1420-1421 (1999).
Toyokuni et al. "Synthetic Vaccines: Synthesis of a Dimeric Tn Antigen-Lipopeptide Conjugate that Elicits Immune Responses Against Tn-Expressing Glycoproteins" *J. Am. Chem. Soc.* 116:395-396 (1994).
Vogel. "Immunologic Adjuvants for Modern Vaccine Formulations" *Annals of the New York Academy of Sciences* 754:153-160 (1995).
Voskoglou-Nomikos et al. "Clinical Predictive Value of the in Vitro Cell Line, Human Xenograft, and Mouse Allograft Preclinical Cancer Models" *Clinical Cancer Research* 9:4227-4239 (2003).
Weissig et al. "Functionalized Liposomes with Immunological Adjuvant Effects" *Wiss Z. Martin Luther Univ. Halle-Wittenberg, Math. Naturwiss. Reihe* 39(6):101-109 (1990) (German Language Only).
Wiesmuller et al. "Novel Low-Molecular-Weight Synthetic Vaccine Against Foot-and-Mouth Disease Containing a Potent B-Cell and Macrophage Activator" *Vaccine* 7:29-33 (1989).
Wiesmuller et al. "Solid Phase Peptide Synthesis of Lipopeptide Vaccines Eliciting Epitope-Specific B-, T-Helper and T-Killer Cell Response" *Int. J. Peptide Protein Res.* 40:255-260 (1992).
Wikipedia, online encyclopedia. "Toll-Like Receptor" Definition from Wikipedia.org, (http://en.wikipedia.org/wiki/Toll_Like_Receptor) Accessed Jul. 12, 2006 (5 pages).
Roitt et al. "Adjuvants" *Immunology* 8.9 Gower Medical Publishing, London (1985).
Beckman et al., "Antibody Constructs in Cancer Therapy: Protein Engineering Strategies to Improve Exposure in Solid Tumors," *Cancer* 109:170-179 (2007).
Berenbaum, "Synergy, additivism and antagonism in immunosuppression," *Clin. Exp. Immunol.* 28:1-18 (1977).
Berenbaum, "What is Synergy?," *Pharmacol. Rev.* 41:93-141 (1989).
Braga et al., "Making crystals from crystals: a green route to crystal engineering and polymorphism," *Chem. Commun.* pp. 3635-3645 (2005).
Fujimori et al., "A Modeling Analysis of Monoclonal Antibody Percolation Through Tumors: A Binding-Site Barrier," *J. Nuc. Med.* 31:1191-1198 (1990).
Jain et al., "Polymorphism in Pharmacy," *Indian Drugs* 23:315-329 (1986).
Lederman et al., "A Single Amino Acid Substitution in a Common African Allele of the CD4 Molecule Ablates Binding of the Monoclonal Antibody, OKT4," *Mol. Immunol.* 28:1171-1181 (1991).
Li et al., "β-Endorphin omission analogs: Dissociation of immunoreactivity from other biological activities," *Proc. Natl. Acad. Sci. USA* 77:3211-3214 (1980).
Pharmaceutical Dosage Forms: Tablets, vol. 2, Published 1990 by Marcel Dekker, Inc., ed. by Lieberman, Lachman, and Schwartz, pp. 462-472 (1990).
Rudnik et al., "Affinity and Avidity in Antibody-Based Tumor Targeting," *Can. Biotherp. Radiopharm.* 24:155-162 (2009).
Tallarida, "Drug Synergism and Dose-Effect Data Analysis," Ed. Chapman & Hall, pp. 1-8, 10-13 and 57-71 (2000).
Talmadge et al., "Murine Models to Evaluate Novel and Conventional Therapeutic Strategies for Cancer," *Am. J. Pathol.* 170:793-804 (2007).
Thurber et al., "Antibody tumor penetration: Transport opposed by systemic and antigen-mediated clearance," *Adv. Drug Deliv. Rev.* 60:1421-1434 (2008).
Vippagunta et al., "Crystalline Solids," *Adv. Drug Deliv. Rev.* 48:3-26 (2001).
U.S. Appl. No. 11/411,332, filed Apr. 26, 2006; Office Action Mailed: Jan. 22, 2010.
U.S. Appl. No. 11/605,557, filed Nov. 28, 2006; Office Action Mailed: Jan. 22, 2010.
U.S. Appl. No. 11/411,564, filed Apr. 26, 2006; Office Action Mailed: Mar. 18, 2010.

* cited by examiner

IMMUNOMODULATORY COMPOUNDS AND METHODS OF USE THEREOF

BACKGROUND OF THE INVENTION

The immune system provides vital defenses against invading pathogens, such as bacteria, viruses, parasites, helminthes, and other foreign invaders, as well as providing protection against the proliferation of neoplastic cells. The elimination of pathogens and neoplastic cells requires stimulation of the immune system. However, in certain cases immune responses and immune stimulation can also cause or contribute to diseases and pathologies such as autoimmune disease, inflammation, allergy, anaphylaxis, and septic shock.

The generation of effective treatments for these diseases and pathologies has proved elusive. For example, broad spectrum immunosuppressants such as cyclosporine A and steroids can be used to treat autoimmune diseases, allergies, and other pathologies, but these treatments can present severe side effects. Similarly, current treatments for inflammatory conditions such as chronic adrenocortical disorder and hyperfunction, allergies, rheumatoid arthritis, lupus, inflammatory bowel disease, pneumonia, bronchial asthma, hematological disorders, dermatitis and eczema can present undesired side effects of these agents including hypertension, atherosclerosis, diabetes, hyperglycemia, bone thinning and electrolyte imbalance.

Improved treatments for diseases and pathologies associated with the immune system and immune responses requires the ability to modulate and redirect certain immune responses so as to suppress harmful responses without compromising an individual's ability to eliminate infections.

SUMMARY OF THE INVENTION

In one aspect, the present invention provides a method for inducing or stimulating an immune response by administering an effective amount of a compound of the formula I, II, or III.

In another aspect, the invention provides a method for upregulating an immune response by administering an effective amount of a compound of the formula I, II, or III.

In another aspect, the invention provides a method for reducing an immune response in a subject, the method comprising administering to the subject a compound of the formula I, II, or III.

In another aspect, the invention provides a method for desensitizing a subject against the occurrence of an allergic reaction in response to contact with a particular allergen or antigen, comprising administering to the subject an effective amount of a compound of the formula I, II, or III.

In another aspect, the invention provides a method for treating a subject having an autoimmune disease, comprising administering to the subject an effective amount of a compound of the formula I, II, or III.

In another aspect, the invention provides a method for treating a subject having an inflammatory condition, comprising administering to the subject an effective amount of a compund of the formula I, II, or III.

In another aspect, the invention provides a method for preventing or reducing ischemic damage in a subject requiring surgery, comprising administering to the subject an effective amount of a compound of the formula I, II, or III.

In another aspect, the invention provides a method for preventing, ameliorating, or delaying the onset of asthma in a subject, comprising administering to the subject an effective amount of a compound of the formula I, II, or III.

In another aspect, the invention provides an immunostimulatory remedy containing as the active ingredient a compound of the formula I, II, or III.

DETAILED DESCRIPTION OF THE PREFERRED EMBODIMENTS

Figure 1:
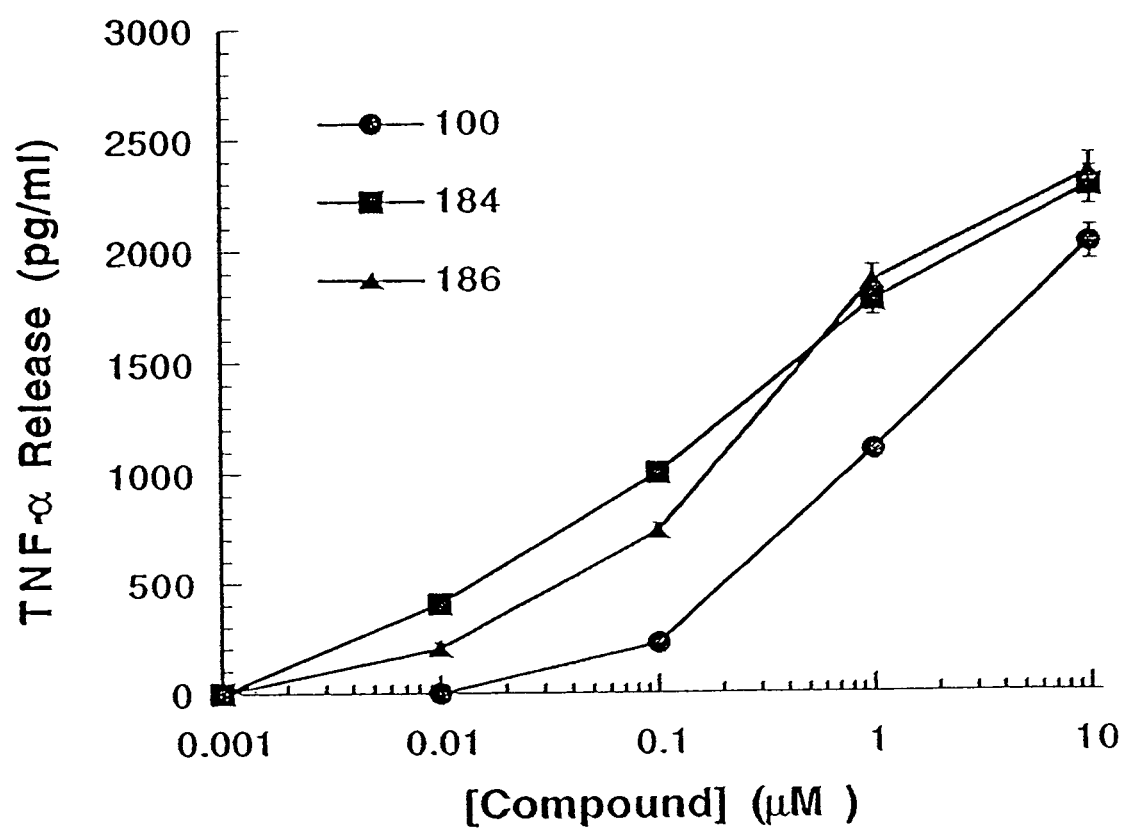
FIG. 1 is a graph that shows the results of an in vitro assay for induction of TNF-alpha cytokine release by compounds 100, 184 or 186 of the invention.

The present invention is directed in part to methods of using immunomodulatory compounds of the formula I, II, or III:

I:

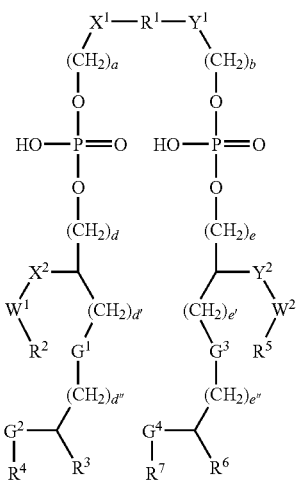

-continued

II:

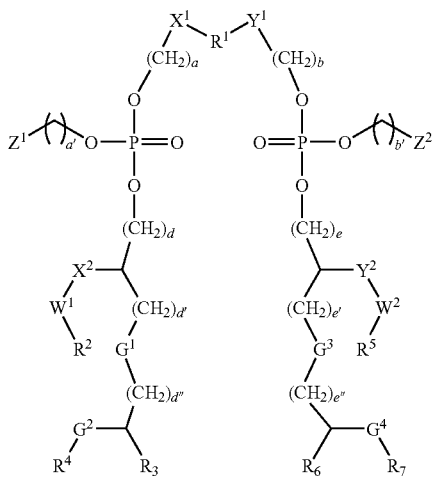

III:

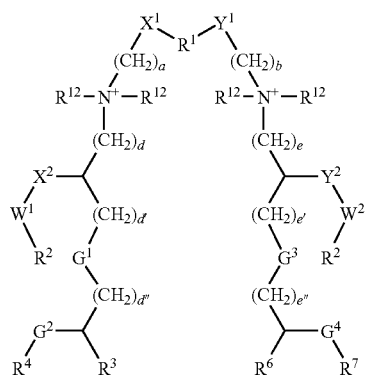

Wherein for each of formula I, II, or III:
$R^1$ is selected from the group consisting of
(a) C(O);
(b) C(O)-$C_{1-14}$ alkyl-C(O), wherein said $C_{1-14}$ alkyl is optionally substituted with hydroxy, $C_{1-5}$ alkoxy, $C_{1-5}$ alkylenedioxy, $C_{1-5}$ alkylamino, or $C_{1-5}$-alkyl-aryl, wherein said aryl moiety of said $C_{1-15}$-alkyl-aryl is optionally substituted with $C_{1-5}$ alkoxy, $C_{1-5}$ alkyl amino, $C_{1-5}$ alkoxy-amino, $C_{1-5}$ alkylamino-$C_{1-5}$ alkoxy, —O-$C_{1-5}$ alkylamino-$C_{1-5}$ alkoxy, —O-$C_{1-5}$ alkylamino-C(O)-$C_{1-5}$ alkyl C(O)OH, —O-$C_{1-5}$ alkylamino-C(O)-$C_{1-5}$ alkyl-C(O)-$C_{1-5}$ alkyl;
(c) $C_2$ to $C_{15}$ straight or branched chain alkyl optionally substituted with hydroxy or alkoxy; and
(d) —C(O)-$C_{6-12}$ arylene-C(O)— wherein said arylene is optionally substituted with hydroxy, halogen, nitro or amino;
a and b are independently 0, 1, 2, 3 or 4;
d, d', d, e, e' and e" are independently an integer from 1 to 4;
$X^1$, $X^2$, $Y^1$ and $Y^2$ are independently selected from the group consisting of null, oxygen, NH and N(C(O)$C_{1-4}$ alkyl), and N($C_{1-4}$ alkyl)$_2$;
$W^1$ and $W^2$ are independently selected from the group consisting of carbonyl, methylene, sulfone and sulfoxide;

$R^2$ and $R^5$ are independently selected from the group consisting of:
(a) $C_2$ to $C_{20}$ straight chain or branched chain alkyl which is optionally substituted with oxo, hydroxy or alkoxy,
(b) $C_2$ to $C_{20}$ straight chain or branched chain alkenyl or dialkenyl which is optionally substituted with oxo, hydroxy or alkoxy;
(c) $C_2$ to $C_{20}$ straight chain or branched chain alkoxy which is optionally substituted with oxo, hydroxy or alkoxy;
(d) —NH-$C_2$ to $C_{20}$ straight chain or branched chain alkyl, wherein said alkyl group is optionally substituted with oxo, hydroxy or alkoxy; and (e) 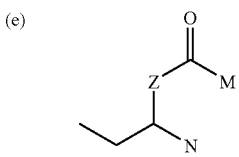

wherein Z is selected from the group consisting of O and NH, and M and N are independently selected from the group consisting of $C_2$ to $C_{20}$ straight chain or branched chain alkyl, alkenyl, alkoxy, acyloxy, alkylamino, and acylamino; $R^3$ and $R^6$ are independently selected from the group consisting of $C_2$ to $C_{20}$ straight chain or branched chain alkyl or alkenyl optionally substituted with oxo or fluoro;
$R^4$ and $R^7$ are independently selected from the group consisting of C(O)$C_2$ to $C_{20}$ straight chain or branched chain alkyl or alkenyl; $C_2$ to $C_{20}$ straight chain or branched chain alkyl; $C_2$ to $C_{20}$ straight chain or branched chain alkoxy; $C_2$ to $C_{20}$ straight chain or branched chain alkenyl; wherein said alkyl, alkenyl or alkoxy groups can be independently and optionally substituted with hydroxy, fluoro or $C_1$ to $C_5$ alkoxy;
$G^1$, $G^2$, $G^3$ and $G^4$ are independently selected from the group consisting of oxygen, methylene, amino, thiol, —NHC(O)—, and —N(C(O)$C_{1-4}$ alkyl)-;
or $G^2R^4$ or $G^4R^7$ may together be a hydrogen atom or hydroxyl;
or a pharmaceutically acceptable salt thereof;
and wherein for Formula II:
a' and b' are independently 2, 3, 4, 5, 6, 7, or 8, preferably 2;
$Z^1$ is selected from the group consisting of —OP(O)(OH)$_2$, —P(O)(OH)$_2$, —OP(O)(OR$^8$)(OH) where $R^8$ is a C1-C4 alkyl chain, —OS(O)$_2$OH, —S(O)$_2$OH—, —CO$_2$H, —OB(OH)$_2$, —OH, —CH$_3$, —NH$_2$, NR$^9_3$ where $R^9$ is a C1-C4 alkyl chain;
$Z^2$ is —OP(O)(OH)$_2$, —P(O)(OH)$_2$', —OP(O)(OR$^{10}$)(OH) where $R^{10}$ is a $C_1$-$C_4$ alkyl chain, —OS(O)$_2$OH, —S(O)$_2$OH, CO$_2$H, —OB(OH)$_2$, —OH, CH$_3$, —NH$_2$, —NR$^{11}$, where $R^{11}$ is a $C_1$-$C_4$ alkyl chain;
and wherein for Formula 3:
$R^{12}$ is selected from H and a C1-C4 alkyl chain;
or a pharmaceutical salt thereof,
with the proviso that the compounds of formula I, II, or III are not

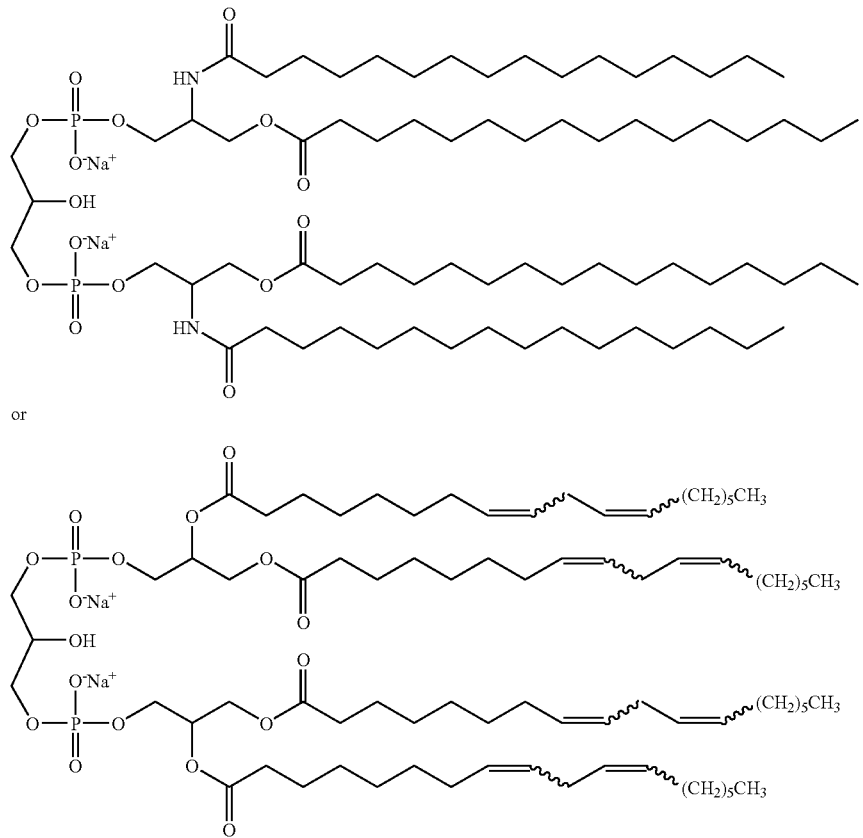

or

In preferred compounds of the invention, one or more of the following is present: each of a and b is 2; each of $X^1$ and $Y^1$ is NH; $R^1$ is C(O) or C(O)-$C_{1-14}$alkyl-C(O); each of d' and e' is 1; each of d" and e" is 1; X is O or NH, more preferably NH; and W is C(O); or each of d' and e' are 2.

In further preferred embodiments, R' is a C(O)$C_{1-14}$ alkyl-C(O), wherein said $C_{1-14}$ alkyl is substituted, for example with a $C_{1-5}$ alkoxy group;

In a most preferred embodiment, the invention is directed to compounds ER 803022, ER 803058, ER 803732, ER 804053, ER 804057, ER 804058, ER 804059, ER 80442, ER 804680 and ER 804764, and compositions containing these compounds.

Definitions

Carbonyl, as used herein, is a (C=O) moiety.

Dicarbonyl, as used herein, is a moiety with the structure (C=O)-alkyl-(C=O) or (C=O)-aryl-(C=O), which is bonded to a molecule through the carbon atoms of both of the terminal carbonyl moieties.

Oxo, as used herein, is a =O group.

Alkyl ester, as used herein, is a moiety with the structure O—(C=O)-alkyl, which is bonded to a molecule through the non-double bonded oxygen of the ester group.

Alkenyl ester, as used herein, is a moiety with the structure O—(C=O)-carbon chain, where the carbon chain contains a carbon-to-carbon double bond, which is bonded to a molecule through the non-double bonded oxygen of the ester group.

The term "alkylene" means a bivalent straight chain or branched alkyl hydrocarbon group.

The term "alkenylene" means a bivalent straight chain or branched hydrocarbon group having a single carbon to carbon double bond.

The term "dialkenylene" means a bivalent unsaturated straight chain or branched chain hydrocarbon group having two carbon to carbon double bonds.

The term "arylene" refers to a bivalent aromatic group.

The abbreviation "Boc" as used herein means t-butyloxycarbonyl.

As used herein with reference to compounds and compositions of the invention, the term "type 1" refers to those compounds of the invention corresponding to formula I above where the values of a and b are the same; the values of d and e are the same; the values of d' and e' are the same; the values of d" and e" are the same; $X^1$ and $Y^1$ are the same; $X^2$ and $Y^2$ are the same; $W^1$ and $W^2$ are the same; $R^2$ and $R^5$ are the same; $G^1$ and $G^3$ are the same; $R^3$ and $R^6$ are the same; $G^2$ and $G^4$ are the same; and $R^4$ and $R^7$ are the same. "Type 2", as used herein, refers to compounds or compositions corresponding to formula I where any one or more of the following applies: the values of a and b are different, the values of d and e are the same, the values of d' and e' are different; the values of d" and e" are the same; $X^1$ and $Y^1$ are different; $X^2$ and $Y^2$ are different; $W^1$ and $W^2$ are different; $R^2$ and $R^5$ are different; $G^1$ and $G^3$ are different; $R^3$ and $R^6$ are different; $G^2$ and $G^4$ are different; or $R^4$ and $R^7$ are different.

All patents, patent applications, and publications referred to herein are incorporated by reference in their entirety. In case of a conflict in terminology, the present specification is controlling.

Methods of Modulating Immune Responses

The present invention is directed to methods of modulating immune responses by administering immunomodulatory compounds that elicit cytokines and activate immune cells. In particular, the present invention is directed to methods of using immunomodulatory compounds to stimulate immune responses directed against pathogens or neoplastic cells, or to suppress immune responses associated with inflammation, allergy, and anaphylaxis.

As used herein "immunomodulatory compounds" describes compounds which, when administered to a subject, stimulate the production of cytokines and elicit particular responses by immune cells. The stimulation of cytokines is known to enhance the activity of some immune cells and to suppress the activity of other immune cells.

The immunomodulatory compounds used in the methods of the invention are ligands for the TLR4 receptor. TLR4 is a member of the Toll-like receptor (TLR) family of receptors. In humans, the TLR family comprises ten known receptors, designated TLR1-10. TLR receptors are associated with innate immune recognition of pathogens, and known TLR ligands are associated with pathogens or tissue damage. For example, other known TLR4 ligands include bacterial endotoxin (also known as lipopolysaccharide, or LPS), parasite lipoproteins, human heat shock protein 70, and human necrotic cell debris. Ligands to other known TLRs are also associated with pathogens and tissue damage, and include peptidoglycan, which is recognized by TLR2, flagellin, which is recognized by TLR5, and unmethylated bacterial CpG DNA sequences, which are recognized by TLR9.

Recognition of ligand by TLR4 results in the secretion of cytokines and activation of various pathways and behaviors in immune cells. TLR4 ligands typically elicit a set of cytokines that includes IL-1$\beta$, IL-6, IL-10, IL-12, and TNF$\alpha$. Many of the cytokines elicited by TLR4 ligands have known immunomodulatory or immunoprotective effects. At least two of these cytokines, IL-10 and IL-12, play a role in regulating inflammatory responses. For example, IL-10 has anti-inflammatory properties, and is associated with T cell populations that down-regulate inflammatory reactions. IL-10 may also be involved in down-regulating responses mediated by the Th1 subset of T helper cells, which are associated with many forms of inflammatory disease such as rheumatoid arthritis and Crohn's disease. Thus, TLR4 ligands can be useful for modulating responses mediated by Th1 cells. As another example, IL-12 is associated with Th1 related functions involved in suppressing certain aspects of allergic disease, including B cell synthesis of IgE, which are mediated through the Th2 subset of T helper cells. Thus, TLR4 agonists and related compounds may be useful for down-regulating Th2 responses and resolving conditions dependent on IL-4 or other Th2 associated cytokines.

As described in more detail in the Examples provided below, the immunomodulatory compounds used in the methods of the invention can elicit production of cytokines, including IL-1$\alpha$, IL-1$\beta$, IL-6, IL-10, IL12, interferon-$\alpha$, interferon-$\gamma$, and GM-CSF.

Thus, in one aspect, the invention provides a method of inducing or stimulating an immune response in an animal by administering a compound of the formula I, II, or III. As used herein, inducing or stimulating an immune response means stimulating the production of cytokines, stimulating the proliferation of immune cells, stimulating the activation of immune cells, or stimulating the lytic activity of immune cells. Examples of immune responses stimulated by the methods of the invention are the secretion of cytokines, the activation of NK cells, the proliferation of B cells, T cells, macrophages, monocytes, and other immune cells, and other immune responses. These responses may in turn enhance or down-regulate other immune functions.

The methods of the invention can be used to stimulate immune responses to treat a variety of infections, including, but not limited to, gram-positive and gram-negative bacterial infections, viral infections, fungal infections, and parasitic infections. The methods of the invention can also be used to treat neoplastic conditions, including, but not limited to biliary tract cancers, brain cancer, breast cancer, cervical cancer, choriocarcinoma, colon cancer, endometrial cancer, esophageal cancer, gastric cancer, intraepithelial neoplasms, lymphomas, liver cancer, lung cancer, melanoma, neuroblastomas, oral cancer, ovarian cancer, pancreatic cancer, prostate cancer, rectal cancer, sarcomas, skin cancer, testicular cancer, thyroid cancer, renal cancer, and other carcinomas and sarcomas.

In another aspect, the invention provides a method for upregulating an immune response in a subject by administering an immunomodulatory compound of the formula I, II, or III. As used herein, upregulating an immune response means to increase an existing immune response or a component of an existing immune response. Methods for upregulating immune responses can be used to treat any of the infections or neoplastic disorders described above herein. Methods for upregulating immune responses can also be used to treat autoimmune, inflammatory, or allergic disorders by altering the balance of Th1 and Th2 responses. For example, administration of the immunomodulatory compounds of the invention can be used to alter the balance of Th1 and Th2 responses, thereby reducing a subject's immune response to animal danders, pollen, dust mites, hymenoptera venoms, and other antigens or allergens. Administration of the immunomodulatory compounds of the invention can also be used to treat conditions such as asthma, atopic dermatitis, allergic rhinitis, eczema, urticaria, and food allergies.

In another aspect, the invention provides a method for reducing an immune response in a subject by administering an immunomodulatory compound of the formula I, II, or III. As used herein, reducing an immune response in a subject means to cause a decrease in the production of cytokines, the proliferation of lymphocytes, monocytes, macrophages, dendritic cells, or natural killer cells, to cause a decrease in the lytic activity of natural killer cells, or to cause a decrease in the lytic activity of cytotoxic T cells.

In another aspect, the invention provides a method of desensitizing a subject against the occurrence of an allergic reaction in response to contact with a particular antigen or allergen, comprising administering an immunostimulatory compound of formula I, II, or III as the active ingredient. As used herein, desensitizing a subject means to reduce the immune response of the subject to exposure to particular allergens or antigens. For example, the subject may display decreased production of IgE, decreased production of IgE producing B cells, decreased production of histamine, or decreased release of cytokines in response to exposure to an allergen or antigen.

In another aspect, the invention provides a method of preventing, ameliorating, or delaying the onset of asthma in a subject by administering a compound of formula I, II, or III to the subject.

Recent studies have indicated that exposure to microbial agents during childhood can confer a protective benefits, such as providing protection against development of asthma and other allergic conditions. It has been suggested that providing safe and effective antigens that mimic the protective effects of microbial pathogens without the associated risks could confer similar protection against development of allergy and asthma (Liu, A. H. (2002) *J. Allergy Clin Immunol.* 109: 379-92).

In the methods of the invention, at least one of the immunostimulatory compounds according to the formula I, II, or III is administered to a subject at risk of developing allergies or asthma. Preferably, the subject is a juvenile subject.

The TLR ligand endotoxin is associated with a phenomenon known as endotoxin tolerance. Endotoxin (also known as lipopolysaccharide, or LPS) is a glycolipid found in the cell membranes of Gram-negative bacteria. Endotoxin is one of the most potent known stimulators of immune responses, and exposure to endotoxin induces cytokine production by monocytes and macrophages. Endotoxin tolerance refers to the observation that an initial low or sublethal dose of endotoxin results in a decreased immune response to a later, high dose of endotoxin, and can protect against lethal subsequent doses of endotoxin. The decreased immune response is manifested in the down-regulation of macrophage responsiveness, and decreased levels of cytokine release compared to individuals who were not pretreated, or tolerized, with low doses of endotoxin.

Similarly, administration of the immunomodulatory compounds described herein can suppress subsequent responses to TLR4 ligands such as endotoxin. Moreover, administration of the immunomodulatory compounds described herein can also down regulate responses mediated by subsequent exposure to other TLR ligands, including TLR2 ligands, such as lipoprotein, and TLR9 ligands, such as unmethylated CpG nucleic acids, as described in more detail in Example 7.

Administration of the immunomodulatory compounds of the invention can be used to suppress the ability of TLR ligands such as bacterial DNA, viral RNA, endogenous human heat shock proteins, parasitic or bacterial lipids, glycolipids or lipoproteins to stimulate immune responses.

TLR ligands such as endotoxin are shown to elicit or exacerbate a number of immune-based diseases. For example, intestinally derived endotoxin is released during graft-versus-host disease after bone marrow grafting, and increases the severity of post-graft symptoms. Endotoxin is the active principle in eliciting lung responses to environmental or occupational irritants such as grain dust, cotton dust, or poultry processing dusts. Environmental endotoxin is found to enhance bronchial responses in pre-existing asthma. A TLR9 ligand is found to enhance proliferation of B cells associated with secretion of autoantibodies in systemic lupus erythematosus. Tolerization of TLRs may prevent TLR ligands from exacerbating or causing diseases or syndromes such as systemic lupus erythematosus, asthma, atherosclerosis, graft-versus-host disease, grain dust fever, inflammatory bowel disease, rheumatoid arthritis, mucositis, and others.

In another aspect, the invention provides a method of preventing or reducing ischemic damage in a subject requiring surgery by administering a compound of formula I, II, or III prior to performing surgery on the subject.

Ischemia and reperfusion result in tissue injury in a number of organs, including heart, brain, kidney, and gastrointestinal tract. Ischemia/reperfusion injury is associated with a number of surgical procedures, including transplantation of organs such as kidney, liver and heart, procedures that require periods of hyperperfusion, and revascularization procedures.

The administration of the TLR4 ligand endotoxin has been shown to induce cross-tolerance to insults other than endotoxemia. Pretreatment of subjects with endotoxin has been shown to provide protection against ischemia-reperfusion injury in the myocardium, liver, and kidney (Meldrum, et al. (1996) *Arch. Surg.* 131: 1203-1208, Colletti, et al. (1994) *J. Surg. Res.* 57: 337-343, and Heemann et al. (2000) *Am. J. Path.* 156: 287-293).

In the methods of the invention, at least one of the immunostimulatory compounds according to the formula I, II, or III, is administered to a subject prior to surgery. The compound or compounds can be administered from several hours up to three days prior to surgery.

In another aspect, the invention provides a method of treating autoimmune condition by administering an immunostimulatory compound of formula I, II, or III.

Innate immunity has been implicated in the development and progression of autoimmune conditions including type I diabetes mellitus, systemic lupus erythamatosus, and others. The modulation of autoimmune responses is mediated by toll-like receptor-ligand interactions, and recent evidence indicates that TLR ligands can be used to modulate autoimmune responses. A TLR-9 mediated mechanism enhances proliferation of B cells associated with secretion of autoantibodies in systemic lupus erythematosus. B cells activated by endotoxin have been shown to prevent the onset of autoimmune diabetes in nonobese diabetic mice (Tian, J., et al. (2001) *J. Immunol.* 167: 1081-9). Thus, modulation of immune responses by TLR ligands can provide treatments for autoimmune conditions.

In the methods of the invention, at least one immunomodulatory compound defined by the general formula I, II, or III is administered to a subject suffering from an autoimmune disorder or other disorder having an autoimmune component. Administration of an immunomodulatory compound can modulate the release of cytokines and suppress T-cell subsets involved in autoimmune disease. Many autoimmune disorders are associated with Th1 cytokine patterns. Redirection of T help to Th2 may treat these diseases. Alternatively, tolerization of TLRs using these immunostimulatory compounds may suppress aspects of the disease that are mediated by TLR stimulation.

Diseases and conditions that can be treated by the methods of the invention include, but are not limited to, systemic lupus erythematosis, sceleroderma, Sjögren's syndrome, multiple sclerosis and other demyelinating diseases, rheumatoid arthritis, juvenile arthritis, myocarditis, Graves' disease, uveitis, Reiter's syndrome, gout, osteoarthritis, polymyositis, primary biliary cirrhosis, Crohn's disease, ulcerative colitis, aplastic anemia, Addison's disease, insulin-dependent diabetes mellitus, and other diseases.

In another aspect, the invention provides a method of treating an inflammatory condition by administering an immunomodulatory compound of formula I, II, or III.

As discussed herein, the immunomodulatory compounds used in the methods of the invention elicit the production of cytokines such as IL-1α, IL-1β, IL-6, IL-10, IL12, interferon-α, interferon-γ, and GM-CSF. The cytokines IL-1α, IL-1β, and IL-10 are associated with the suppression of inflammatory responses, and agents that stimulate the production of these cytokines can be used to treat inflammatory conditions.

Inflammatory conditions that can be treated according to the methods of the invention include, but are not limited to, inflammatory bowel disease, multiple sclerosis, autoimmune diabetes, atopic dermatitis, urticaria, contact sensitivity, cutaneous allergic conditions, psoriasis, chronic adrenocortical disorder and hyperfunction, rheumatoid arthritis, lupus, pneumonia, bronchial asthma, hematological disorders, dermatitis and eczema.

The invention also provides immunostimulatory remedies comprising as the active ingredient a compound of the formula I, II, or III.

The host animals to which the immunomodulatory compounds of the present invention are usefully administered include human as well as non-human mammals, birds, fish, reptiles, etc.

The specific formulation of therapeutically effective compositions of the present invention may thus be carried out in any suitable manner which will render the immunomodulatory compound or compounds bioavailable, safe and effective in the subject to whom the formulation is administered.

The modes of administration may comprise the use of any suitable means and/or methods for delivering the immunomodulatory compound to one or more corporeal loci of the host animal where the adjuvant and associated antigens are immumostimulatively effective. Delivery modes may include, without limitation, parenteral administration methods, such as subcutaneous (SC) injection, transmucosal, intranasal (IN), ophthalmic, transdermal, intramuscular (IM), intradermal (ID), intraperitoneal (IP), intravaginal, pulmonary, and rectal administration, as well as non-parenteral, e.g., oral, administration.

The dose rate and suitable dosage forms for the immunomodulatory compounds of the present invention may be readily determined by those of ordinary skill in the art without undue experimentation, by use of conventional antibody titer determination techniques and conventional bioefficacy/biocompatibility protocols, and depending on the desired therapeutic effect, and the desired time span of bioactivity.

The immunomodulatory compounds of the present invention may be usefully administered to the host animal with any other suitable pharmacologically or physiologically active agents, e.g., antigenic and/or other biologically active substances.

Formulations of the invention can include additional components such as saline, oil, squalene, oil-water dispersions, liposomes, and the like.

General Synthetic Methods

1. Synthesis of Diamide Compounds

In general, a 2-amino-1,3-dihydroxypropane or (±) serinol is transformed into the 2-azido compound by reaction with trifluoromethanesulfonyl azide followed by protection as the peracetate for easy manipulation. The resulting compound is deacetylated, followed by reaction with an appropriately activated primary alcohol of a diol moiety. The primary alcohol moiety of the product of this reaction is then protected, e.g., by using TBDPSCL, followed by reaction with phosgene and then allyl alcohol, to yield a fully protected diol. The protected diol is then treated to cleave the protecting group from the primary alcohol. The unprotected alcohol is reacted with a properly functionalized phosphorylating reagent with formula (11) as indicated in the Examples, to form a phosphate ester compound. The azido moiety of the product is reduced, and then reacted with an activated acyl acid to form an amide. The protected terminal amine on the functionalized phosphate is deprotected, and subsequently reacted with a phosgene or a dicarboxylic acid in the presence of a dehydrating agent, such as EDC. The phosphate groups of the resulting compound are then deprotected, yielding a racemic amide.

2. Synthesis of Chiral Diamide Compounds of Type 1

In general, a chiral amino acid ester with the desired structure is protected with a benzimidate ester. The protected compound is reacted with a reducing agent, e.g., DIBAL or the like, to reduce the acid moiety of the amino acid to an alcohol. The resulting alcohol compound is reacted with an appropriately activated primary alcohol of a diol moiety, followed by cleavage of the benzimidate protecting group, yielding an amino-diol. The diol is then reacted with an appropriate acid chloride to yield a diol-amide.

The diol-amide is then reacted with a properly functionalized phosphorylating reagent at the free primary hydroxyl group. The resulting compound is esterified at the secondary alcohol group with an appropriate acyl moiety. The N-BOC group is then cleaved from the amino group introduced by phosphorylating reagent (11), yielding a phosphate ester compound with a free primary amine. This product is then reacted with phosgene or a dicarboxylic acid in the presence of a dehydrating agent, to yield a diamide product. The protected phosphate groups of the diamide product are then deprotected, typically with palladium(0) and phenylsilane.

3. Synthesis of Chiral Diamide Compounds of Type 2

Chiral diamide compounds of Type 2 are synthesized essentially as described for chiral diamide compounds of Type 1, up to the point just after cleavage of the protecting group from the primary amine group of the phosphate ester compound. At this point, a dicarboxylic acid which has one of the acid moieties protected is reacted with the primary amine group, to yield a monoamide. The protecting group on the other carboxylic acid is then cleaved, providing a free carboxylic acid which can then be reacted with a primary amine from an alternative, appropriately substituted phosphate system, in the presence of a dehydrating agent to yield a diamide of type 2, which can then be treated to deprotect the phosphate group or groups to yield a desired compound of the invention.

In the special case of chiral urea compounds of type 2 of the invention, the primary amino group of the N-BOC amino group of the phosphate ester is deprotected and then reacted with trichloromethyl chloroformate or the like, in order to form an isocyanate compound. The isocyanate is then reacted with a primary amine from an alternative, appropriately substituted phosphate system to yield a urea product of type 2. This product can then be treated to deprotect the phosphate group or groups.

4. Glycerol Diamide Analogs

These compounds of the invention have an ester moiety attached to the carbon which is beta to the phosphate group, instead of an amide moiety.

In general, these compounds are prepared by the etherification of a protected chiral glycerol with an activated primary alcohol of a diol moiety, followed by esterification of the secondary alcohol moiety and subsequent deprotection of the glycerol moiety, to yield a new diol. The primary hydroxyl group of the diol is then protected, and the secondary hydroxyl group is condensed with an acyl moiety to yield a diester. The primary hydroxyl is deprotected, followed by esterification with a phosphorylating agent, of which compound (11), below is exemplary. Following deprotection of the amine group introduced by the phosphorylating agent, the product is reacted with phosgene or a dicarboxylic acid using a dehydrating agent such as EDC. Subsequent deprotection of the phosphate groups yield compounds of the invention.

In the synthesis described generally above, the substituent at $R^1$ of the compounds of the invention can easily be varied by utilizing different dicarboxylic acid compounds. Such acids can be coupled to the amine group of the phosphate ester intermediate of the reaction scheme outlined above, either using a dehydrating agent such as EDC, or by activating the dicarboxylic acid by synthesizing, e.g., the corresponding diacid chloride.

The substituents represented by variables $R^2$ and $R^5$ in formula I above can easily be varied by utilizing an appropriate activated acid or acid chloride in the amidation or esterification reaction of the heteroatom represented by X or Y in formula I.

The substituents represented by variables $R^3$ and $R^6$ of formula I can be varied by using an intermediate containing the desired number of carbon atoms which also contains an activated carbon functionality, e.g., a halogen or sulfonate (OSO$_2$CH$_3$, OSO$_2$CF$_3$, OSO$_2$CH$_2$C$_6$H$_4$-p-CH$_3$) which can be reacted with the azido diol, amino alcohol, or glycerol starting materials.

The substituents represented by variables R$^4$ and R$^7$ in formula I above can be varied by using an appropriate activated acid or acid chloride in the esterification of the secondary hydroxyl group used in the reaction schemes outlined above.

The values of a and b in compounds of formula I can be varied by using the appropriate compound (11) below. The values of variables d and e in compounds of formula I can be modified by using the appropriate 2-aminodiol or 2-hydroxydiol starting materials.

SYNTHETIC EXAMPLES

All reaction products in the synthetic methods described below gave satisfactory NMR spectra and thin layer chromatography profiles on silica gel. All chromatography was performed on silica gel and the elution monitored by thin layer chromatography. All completed reactions were determined by thin layer chromatographic analysis. All reactions were run under nitrogen at room temperature unless otherwise specified. All reaction solvents were anhydrous unless otherwise noted. The typical work-up for the chemical reactions described below includes aqueous washings, drying over anhydrous sodium sulfate and removal of solvent under reduced pressure.

Example 1

Succinate-1

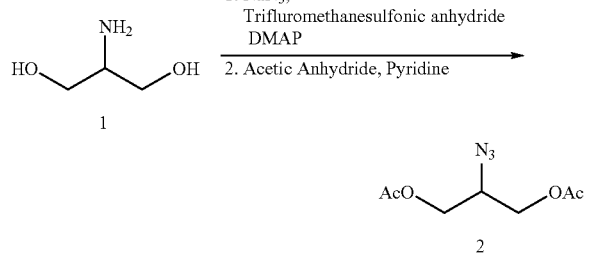

To a solution of sodium azide (107.67 g) in 250 mL of water was added 300 mL of methylene chloride. The mixture was cooled to 0° C. and trifluoromethanesulfonic anhydride (57 mL) was added dropwise at a 0.32 mL/minute rate. The mixture was stirred for an additional 6 hours at 0° C. and stored at −20° C. for 72 hours. The mixture was warmed to 10° C. followed by extraction with methylene chloride in a Teflon® separatory funnel. The combined organic layers were dried (magnesium sulfate). The above suspension was slowly filtered into a stirred solution of (±)-2-amino-1,3-dihydroxypropane (1) (9.89 g) in methanol (200 mL) and 4-N,N-dimethylaminopyridine (DMAP, 54 g) at 10° C. The resultant reaction mixture was stirred for 17 hours at room temperature.

The solvent was removed under reduced pressure and the residue dissolved in pyridine (200 mL) and cooled to 0° C. Acetic anhydride (50 mL) was added dropwise and the mixture stirred for 20 hours at room temperature. Additional acetic anhydride (20 mL) was added and after 4 hours, the mixture was poured onto ice and worked up in the usual manner. Chromatography gave 16 g of diacetate (2) as an oil.

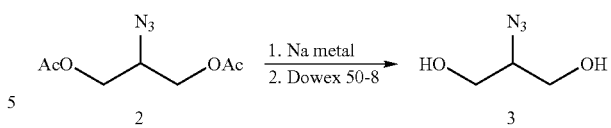

The diacetate (2) (16 g) was dissolved in methanol (150 mL) and sodium metal (2.0 g) was slowly added. The mixture was stirred for 90 minutes and Dowex® 50-8 resin was added until the pH was less than or equal to 7. The mixture was filtered followed by concentration of the filtrate and chromatography to give 6.73 g of the diol (3).

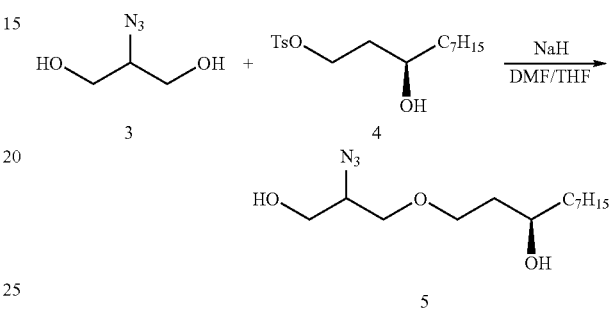

To a suspension of sodium hydride (1.24 g of a 60% oil dispersion washed three times with hexanes and dried under nitrogen) in dimethylformamide (DMF, 200 mL) was added dropwise the azido-diol (3) (6.73 g) in THF (100 mL), followed by the dropwise addition of 3-R-hydroxy-1-O-tosyl-1-decanol (4) (tosylate, 9.44 g) in THF (100 mL). The mixture was stirred for 16 hours, diluted with methanol (200 mL), stirred with Amberlite® 25H$^+$ for 25 minutes and concentrated to dryness. Chromatography gave 4.37 g of (5).

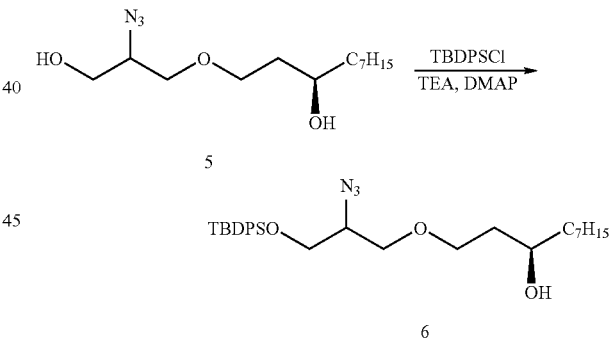

To a solution of the diol (5) (5.32 g) in methylene chloride (30 mL) was added triethylamine (TEA, 6 mL) and DMAP (trace), followed by t-butyldiphenylsilyl chloride (TBDPSCl, 5 mL) and the mixture was stirred overnight. The mixture was worked up as usual. Chromatography gave 3.6 g of secondary alcohol (6) as an oil.

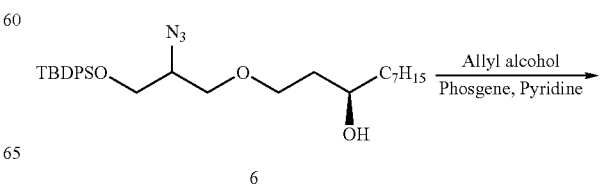

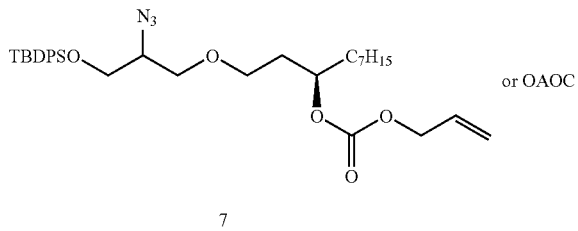

To a solution of the secondary alcohol (6) (2.95 g) in toluene (30 mL) was added pyridine (1.8 mL) followed by a slow addition of phosgene (4.5 mL of a 1.93 M solution in toluene) at 0° C. After stirring at 0° C. for 20 minutes, allyl alcohol (3.1 mL) was added dropwise. After an additional stirring for 60 minutes at room temperature, the reaction was worked up in the usual way. Chromatography gave 3.24 g of protected alcohol (7) as an oil.

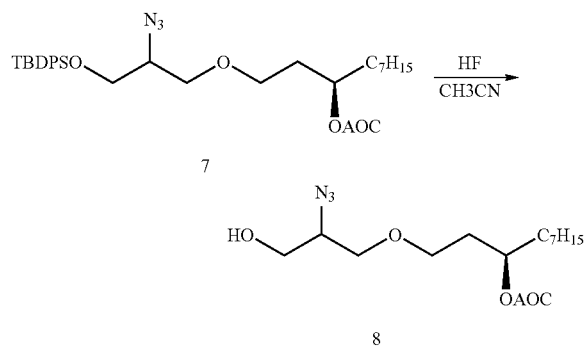

To a solution of protected alcohol (7) (1.29 g) in methylene chloride (3 mL) was added hydrofluoric acid (HF, 4 mL) in acetonitrile (12 mL). The mixture was stirred overnight and worked up in the usual way. Chromatography gave 150 mg of the alcohol (8) as an oil.

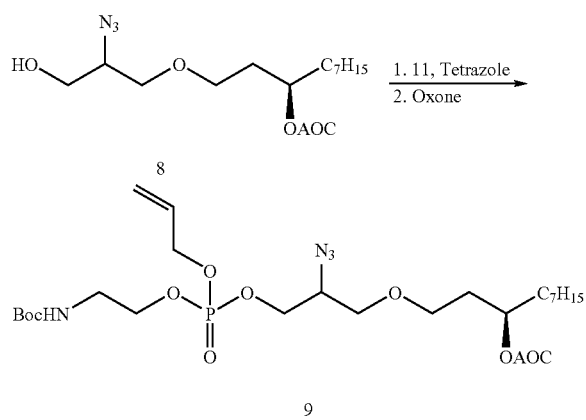

To a solution of alcohol (8) (150 mg) in methylene chloride (0.6 mL) was added tetrazole (74 mg) and the phosphorylating reagent (11) (175 mg). After 30 minutes, oxone (323 mg) in a cooled THF (0.5 mL)-water (0.5 mL) solution was added to the cooled reaction mixture. After 3 hours, the reaction was worked up in the usual way. Chromatography gave 242 mg of (9) as an oil.

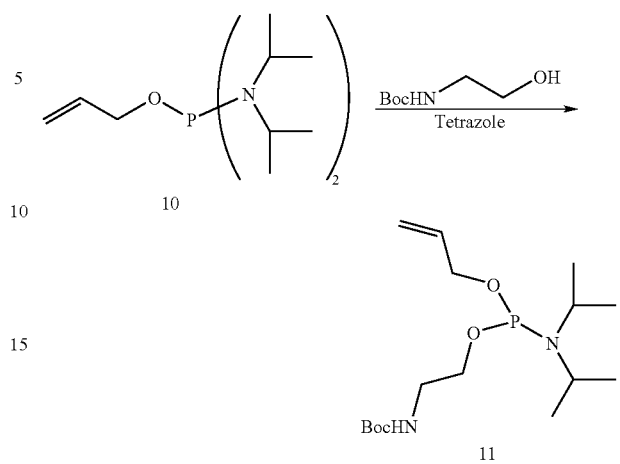

To make phosphorylating reagent 11, to a solution of distilled diisopropylamine (9.0 mL) in methylene chloride was added tetrazole (4.51 g) at room temperature followed by stirring for 1.5 hours. Allyl phosphorodiamidite (10) (20.5 mL) was added dropwise at a 6.5 mL/hour rate followed by stirring for an additional 3 hours. N-Boc-2-aminoethanol (10.36 g) in methylene chloride (50 mL) was added to the above reaction mixture dropwise at a 8.4 mL/hour rate followed by stirring for an additional 18 hours. The white suspension was filtered through Celite 545 with two 20 mL washings with methylene chloride. The filtrate was concentrated followed by the suspension and filtering of the residue with hexanes (200 mL). The resulting hexanes filtrate was concentrated to dry and azeotroped with 2,10-mL portions of toluene to provide the crude product (11) (21.54 g) as an oil.

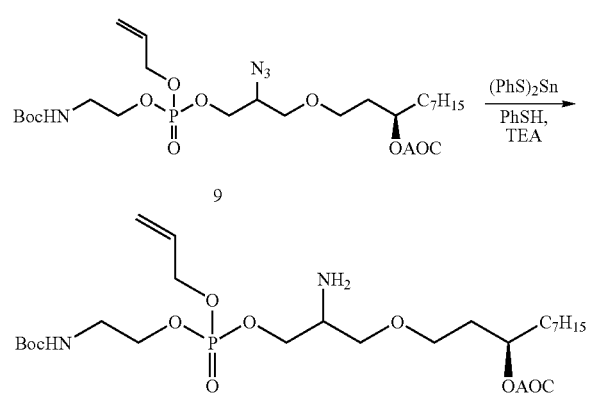

To a suspension of dithiophenol tin (1.3 g) in methylene chloride (7.8 mL) was added thiophenol (400 μL) followed by TEA (543 mL). The reaction mixture was stirred at room temperature for 15 minutes followed by stopping the stirring and allowing the residue to settle to the bottom of the flask. 1.0 mL of the above solution was added to a solution of the azide (9) (242 mg) in methylene chloride (0.5 mL) and allowed to stir for 30 minutes. Quenching with 0.1 N NaOH followed by the usual work-up afforded 193.1 mg of the amine (12) as an oil.

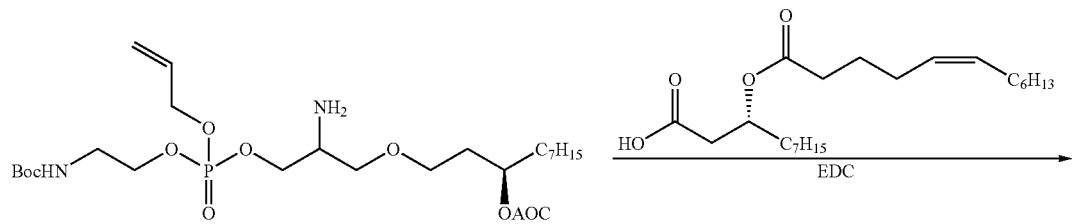

12

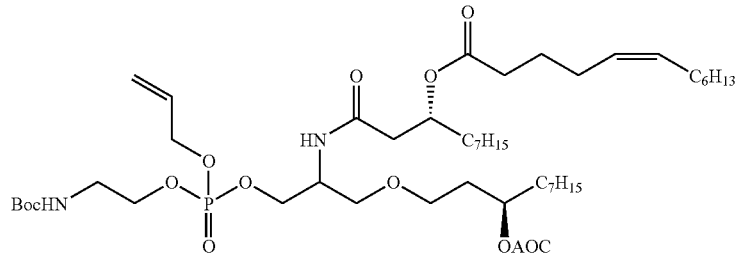

13

To a dried solution of the amine (12) (193 mg) and acyl acid (which can be made according to Christ et al., U.S. Pat. No. 5,530,113) (132 mg) in methylene chloride was added 1-(3-dimethylaminopropyl)-3-ethylcarbodiimide hydrochloride (EDC, 93 mg). After stirring at room temperature for 90 minutes the reaction was quenched and processed in the usual way to provide 232 mg of protected phosphate (13) as an oil.

To a solution of the protected phosphate (13) (232 mg) in methylene chloride (1 mL) was added triethylsilane (TES, 120 μL) and trifluoroacetic acid (TFA, 1.2 mL) followed by stirring for 30 minutes. The TFA was removed under reduced pressure followed by azeotroping with 3, 5-mL portions of toluene. 20 mL of methylene chloride was added and the mixture was worked up in the usual manner to give 174 mg of free amine (14) as an oil.

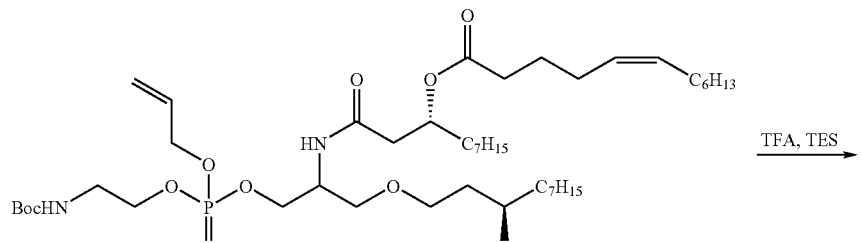

13

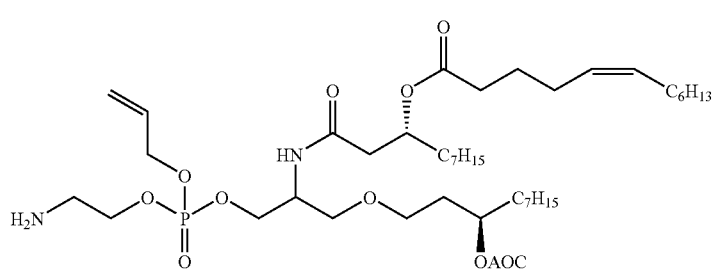

14

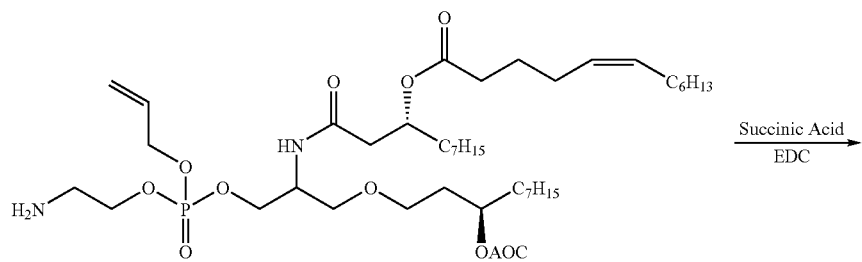
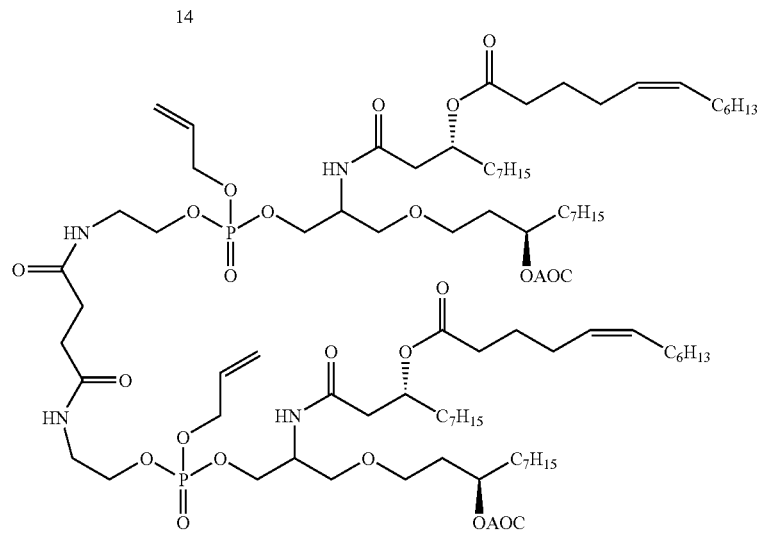
To a dried solution of the free amine (14) (174 mg) in methylene chloride (0.5 mL) was added succinic acid (12.1 mg) and EDC (59 mg). After 1 hour, the reaction was worked up in the usual manner. Chromatography gave 143.1 mg of blocked diphosphate (15) as an oil.
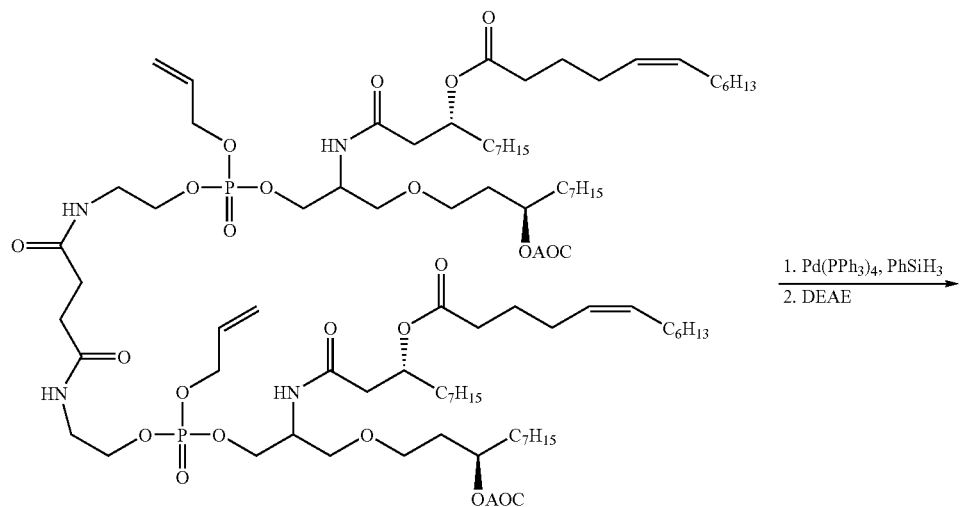

-continued

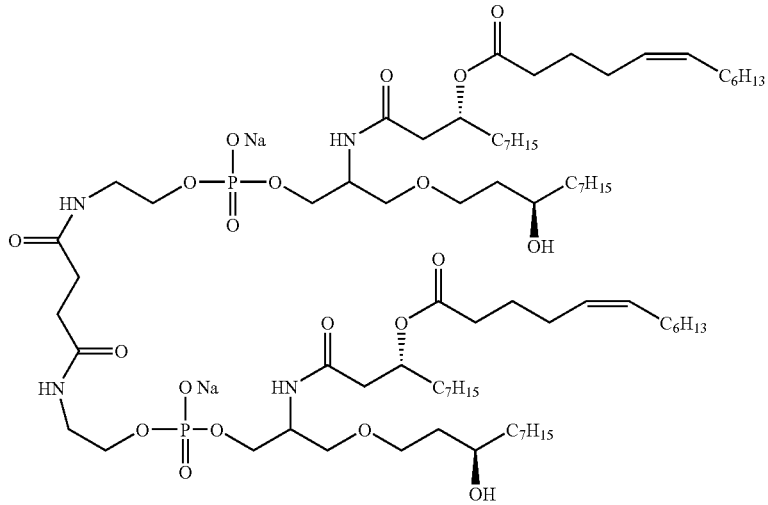

16

To a solution of blocked diphosphate (15) (177.9 mg) in degassed chloroform (1.7 mL) in a dry box was first added phenylsilane (PhSiH$_3$, 50 μL) and then tetrakis-triphenylphosphine palladium (0) (Pd(PPH$_3$)$_4$, 70 mg). After 1 hour, the reaction was removed from the box and chloroform: methanol: water, 2:3:1, was added and the mixture stirred for 1 hour. It was poured onto a diethylamino-ethylcellulose (DEAE) chromatography column. Elution of the column with a linear gradient of 0.0 M to 0.1 M ammonium acetate in chloroform:methanol: water, 2:3:1, extraction of the desired fractions with an equal volume of chloroform, concentration to dryness and the addition of 0.1 N NaOH (175 μL) followed by lyopholization gave 136.2 mg of (16) as a white solid.

Example 2

Chiral Malonate-Type 1

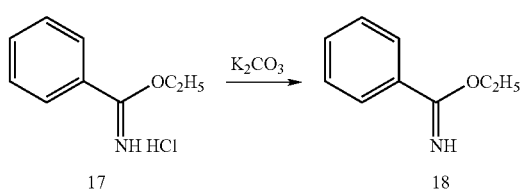

To a cooled solution of potassium carbonate (165 g) in water (575 mL) was added methylene chloride (200 mL) followed by ethyl benzimidate hydrochloride (17) (100 g) after which time the mixture was stirred for 8 minutes. The layers were separated and the aqueous layer extracted with methylene chloride. The organic layers were combined, dried and the solvent removed under reduced pressure to give 83 g of (18).

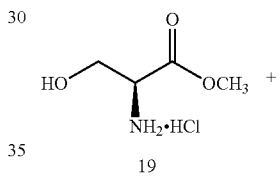

19

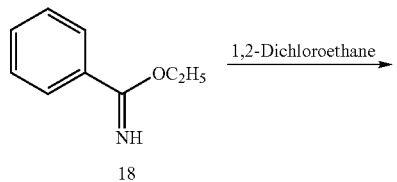

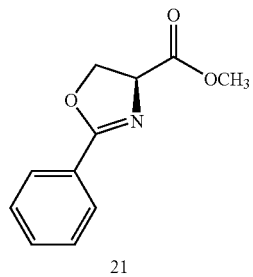

21

To a solution of L-serine methyl ester hydrochloride (19) (41.6 g) in 1,2-dichloroethane (450 mL) was added ethyl benzimidate (18) (36 g). The mixture was heated to reflux for 20 hours, cooled, filtered through diatomaceous earth, and concentrated to dryness to give 56 g of ethyl ester (21) as a white solid.

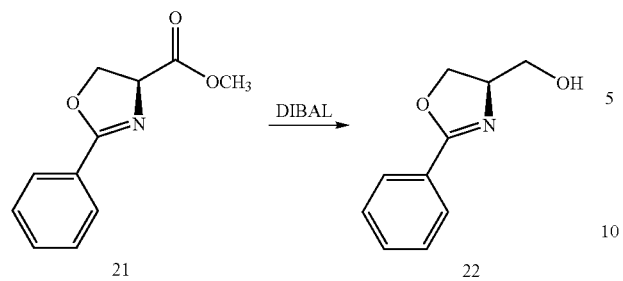

To an ice cold solution of ethyl ester (21) (56 g) in THF (500 mL) was added dropwise diisobutylaluminum hydride (DIBAL, 545 mL of a 1 M solution in hexane). The mixture was allowed to warm to room temperature overnight and then carefully poured onto an aqueous solution of Rochelle's salt (500 g in 1.0 L water). The mixture stirred for 1 hour and worked up in the usual manner. Chromatography gave 25.5 g of alcohol (22) as a white solid.

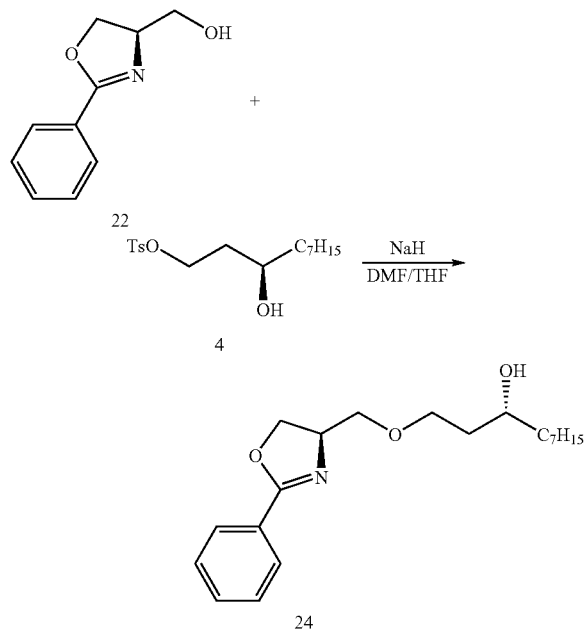

To a suspension of washed sodium hydride (5.3 g of a 60% oil dispersion) in DMF (200 mL) was added the alcohol (22) (24 g) in 250 mL of THF After 30 minutes, the tosylate (4) was added in 250 mL of THF over 2.5 hours and stirred overnight. The mixture was cooled in ice, methanol was added, the solvent removed under reduced pressure and chromatographed to give 4.32 g of alcohol (24) as an oil.

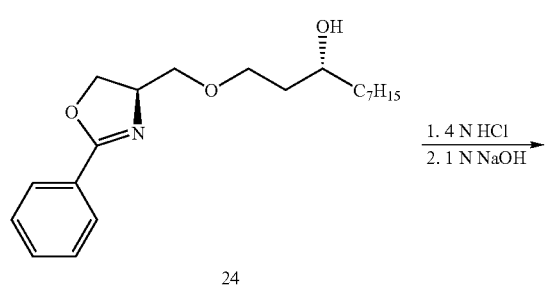

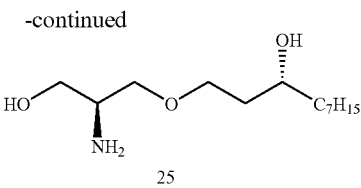

The alcohol (24) (4.3 g) was dissolved in 4 N aqueous hydrochloric acid and heated to reflux for 20 hours. The mixture was cooled, filtered, extracted with ether, made basic with sodium hydroxide and extracted twice with chloroform. The combined chloroform layers were dried and the solvent removed to give 2.88 g of diol (25) as an oil.

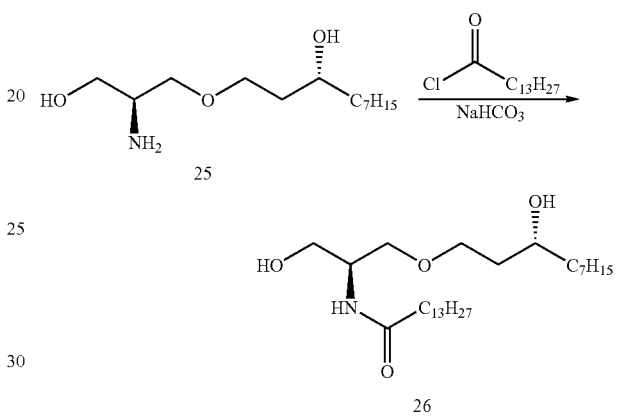

The diol (25) (2.88 g) was dissolved in saturated aqueous sodium bicarbonate (45 mL) and THF (25 mL) and allowed to stir for five minutes. Myristoyl chloride (3.4 mL) was added dropwise over a 25-minute period after which time the reaction mixture was allowed to stir for an additional hour. The reaction was worked up in the usual manner and chromatographed to give 3.07 g of alcohol (26) as an oil.

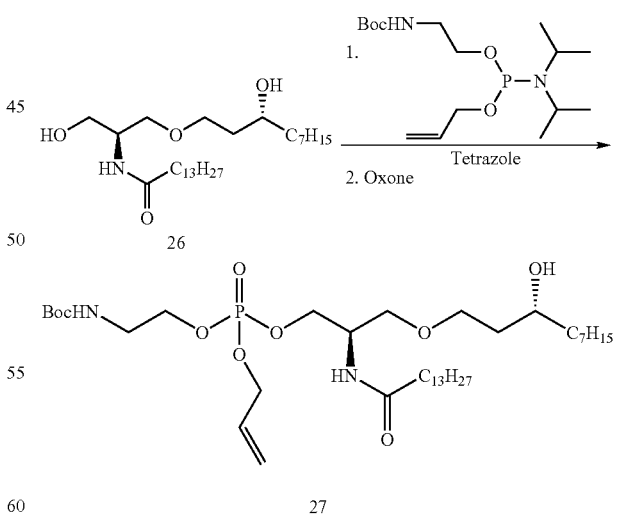

To a solution of the alcohol (26) (1.78 g) in methylene chloride (140 mL) was added tetrazole (683 mg), followed by the phosphorylating reagent (11) (1.6 mL). After 30 minutes, the mixture was cooled in ice, and THF (105 mL) was added followed by an oxone solution (3 g in 90 mL of water). After 5 minutes, the ice bath was removed and the mixture stirred for 30 minutes. The reaction was worked up in the usual manner and chromatographed to give 2.99 g of alcohol (27) as an oil.

pressure. The residue was dissolved in methylene chloride and worked up in the usual manner to give 154 mg of amine (29) as an oil.

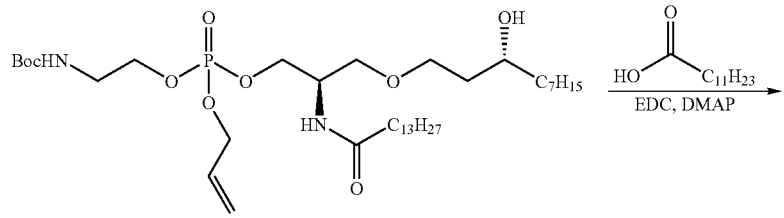

27

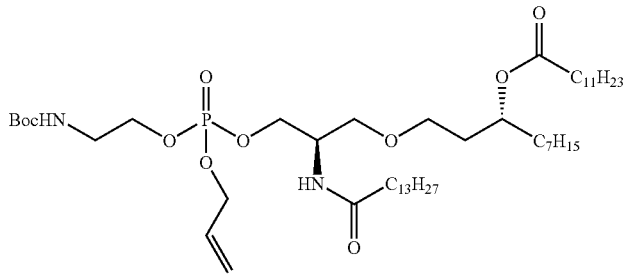

28

To a solution of the alcohol (27) (3.9 g) in methylene chloride (126 mL) was added EDC (10.8 g), DMAP (66 mg) and dodecyl acid (1.62 g) and stirred overnight. Additional acid (1.6 g), EDC (1 g) and DMAP (0.5 g) was added. After 3 hours, the reaction was worked up in the usual manner and chromatographed to give 2.07 g of N-BOC-protected amine (28).

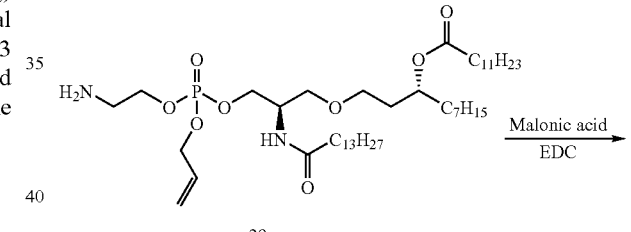

29

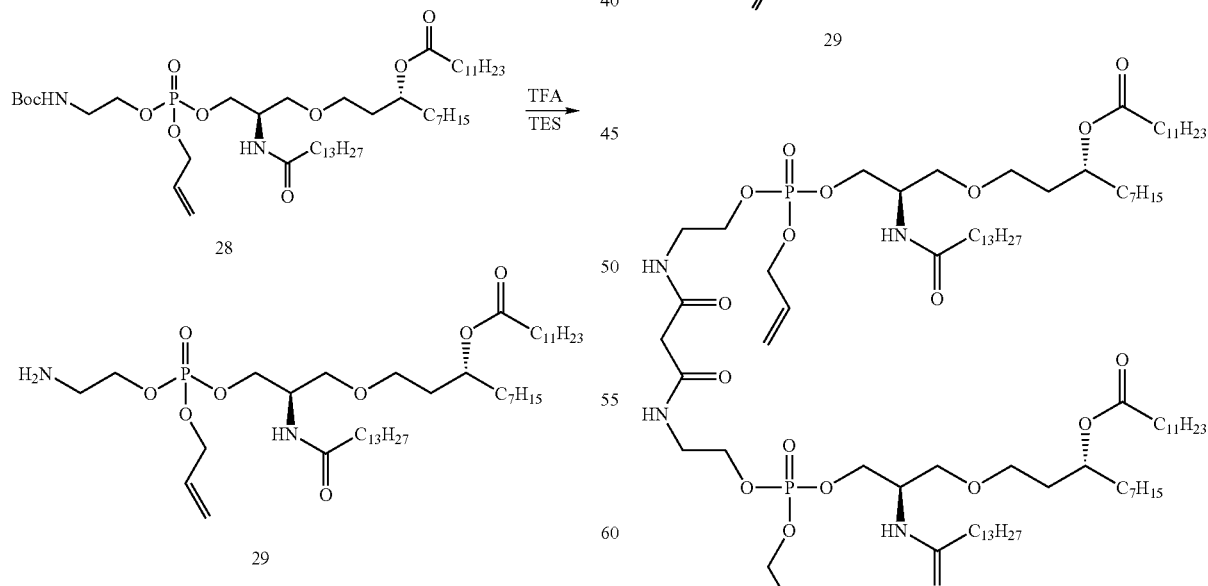

30

To a solution of the N-BOC-protected amine (28)(187.3 mg) in methylene chloride (1.5 mL) was added TES (240 µL) and TFA (300 µL) and the mixture stirred for 45 minutes. Toluene was added and the solvent removed under reduced To an ice cold solution of the amine (29) (75.6 mg) and malonic acid (4.8 mg) in methylene chloride (0.5 mL) was added EDC (27 mg), followed by removal of the cooling bath. After 1 hour, a trace of DMAP was added. After 2.5 hours, the mixture was directly chromatographed to give 54.1 mg of dimer product (30).

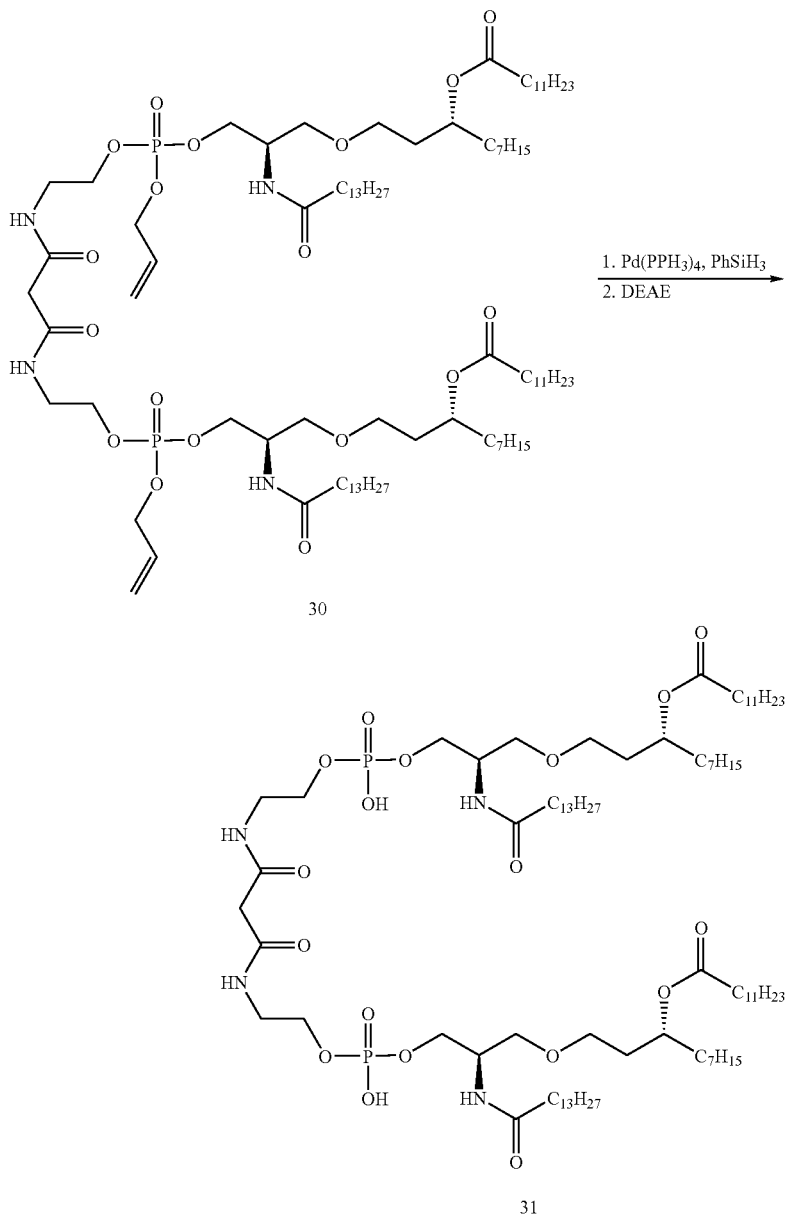

To a solution of the dimer (30) (54 mg) in degassed chloroform (2 mL) was added PhSiH$_3$ (14 μL) and Pd(PPh$_3$)$_4$ (18 mg) followed by removal of the cooling bath. After 1 hour, the reaction was quenched with chloroform:methanol:water (2:3:1) and poured onto a DEAE cellulose chromatography column and chromatographed to give a semi-solid. The solid was dissolved in sterile water and 0.1 N aqueous sodium hydroxide (306 μL) was added and the mixture lyophilized to yield white solid (31) (25 mg).

Example 3

Chiral Malonate-Type 2

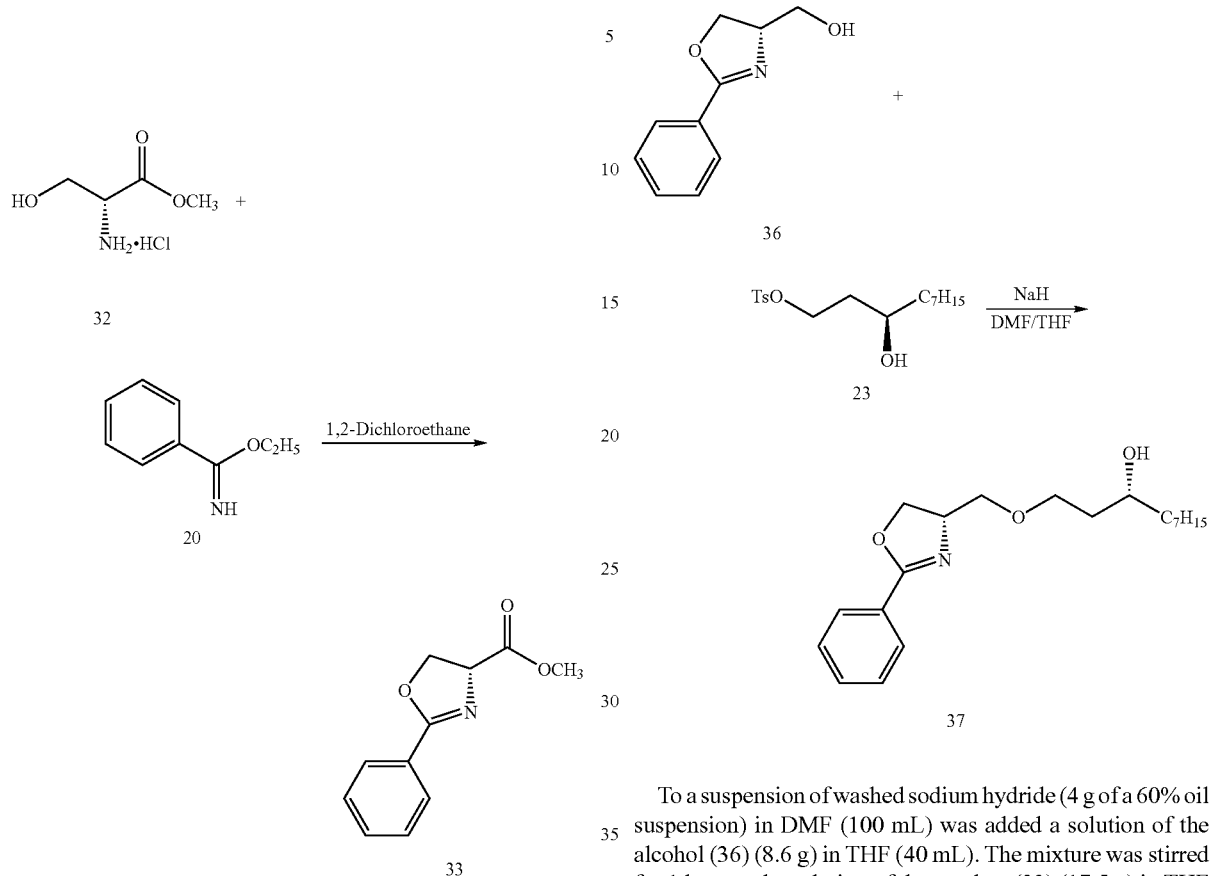

To a solution of D-serine methyl ester hydrochloride (32) (25 g) in dichloroethane (270 mL) was added ethyl benzimidate (20) (24 g). After 20 hours at reflux, the mixture was cooled to room temperature, filtered through diatomaceous earth and the solvent removed under reduced pressure to give 34 g of methyl ester (33) as a white solid.

To a suspension of washed sodium hydride (4 g of a 60% oil suspension) in DMF (100 mL) was added a solution of the alcohol (36) (8.6 g) in THF (40 mL). The mixture was stirred for 1 hour and a solution of the tosylate (23) (17.5 g) in THF (40 mL) was added. The mixture was stirred overnight and then additional tosylate (23) was added (5 g) and stirred for another 4 hours. Methanol was added to the cooled reaction mixture, the solvent was removed under reduced pressure, and the residue was chromatographed to give 1.03 g of alcohol (37) as a solid.

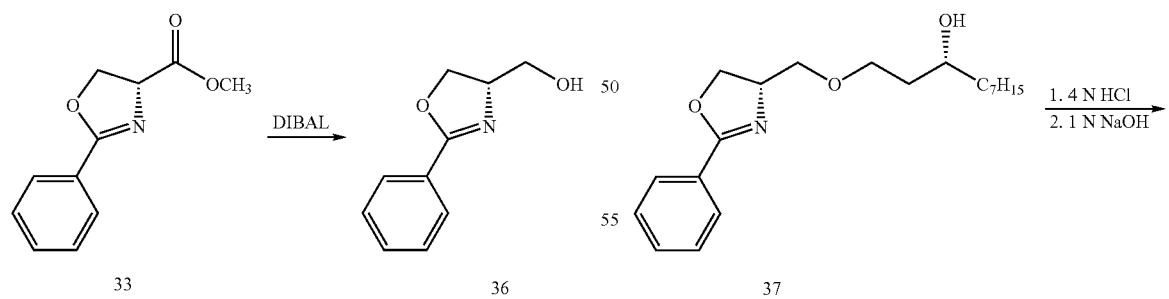

To a ice cold solution of the methyl ester (33) (34 g) in THF (300 mL) was added dropwise a solution of DIBAL in hexane (1.0 M, 322 mL). The mixture was allowed to warm to room temperature overnight and then carefully poured into an aqueous solution of Rochelle's salt. The mixture was then stirred for 1 hour and worked up. Chromatography gave 18.6 g of alcohol (36) as a white solid.

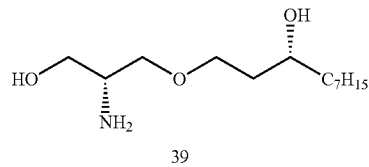

The alcohol (37) (1.03) was dissolved in 4 N aqueous hydrochloric acid (25 mL) and the mixture was heated to 100° C. for 20 hours. Additional hydrochloric acid (5 mL) was added and the reflux continued for 6 hours. The mixture was cooled, washed with ether, made basic with 1 N aqueous sodium hydroxide, and extracted (3×) with chloroform. The combined chloroform layers were dried and the solvent removed under reduced pressure to give 553 mg of amino-diol (39).

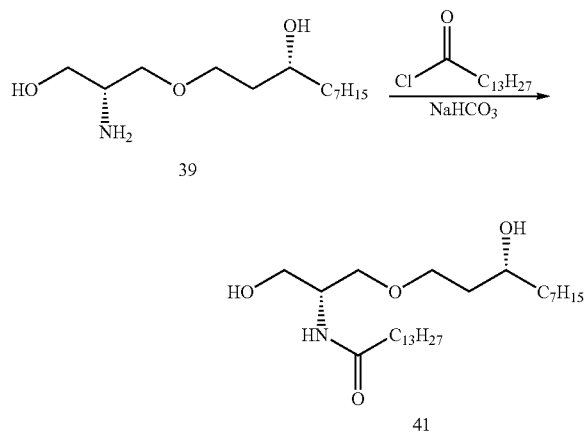

To a solution of amino-diol (39) (553 mg) in THF (3 mL) was added saturated aqueous sodium bicarbonate (6 mL) followed by myristoyl chloride (628 μL). After 50 minutes, the reaction was worked up in the usual way. Chromatography gave 389 mg of amide-diol (41) as an oil.

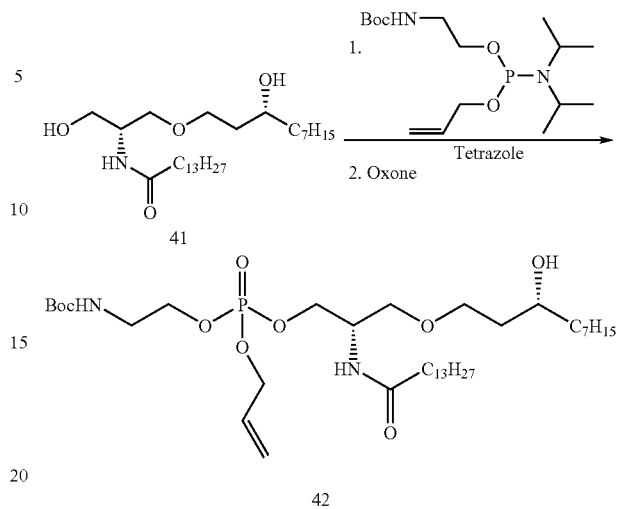

To a solution of the amide-diol (41) (531 mg) in methylene chloride (40 mL) was added tetrazole (203 mg) and the mixture was stirred for 5 minutes. Then phosphorylating reagent (11) (482 mg) was added. After 20 minutes, additional phosphorylating reagent (11) (100 mg) was added and after an additional 20 minutes, 100 mg more was added. After an additional 20 minutes, 50 mg more was added. After 20 minutes, the mixture was poured into a cold solution of THF (30 mL)/oxone (1.07 g)/water (30 mL). The mixture was stirred at 0° C. for 5 minutes, and then 20 minutes at room temperature after which time the reaction was worked up in the usual manner. Chromatography gave 852 mg of phosphate alcohol (42) as an oil.

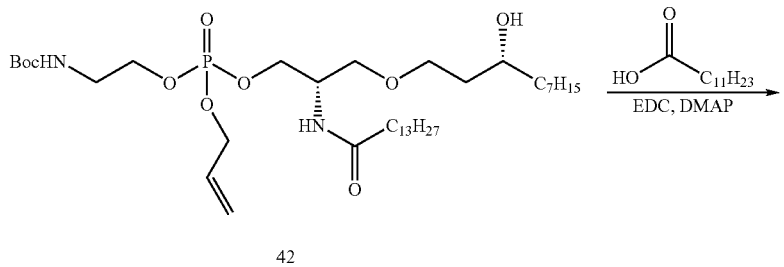

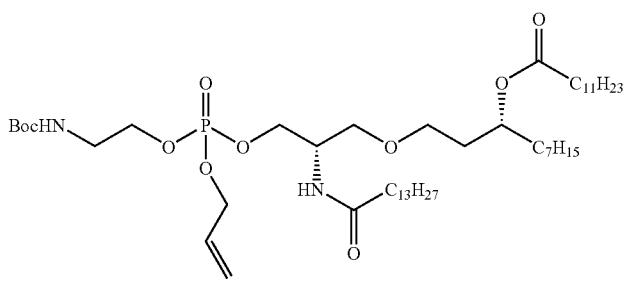

To a solution of the phosphate alcohol (42) (3.9 g) in methylene chloride (126 mL) was added EDC (10.8 g), DMAP (66 mg) and dodecyl acid (1.62 g). The reaction mixture was stirred overnight. Additional acid (1.6 g), EDC (1 g) and DMAP (0.5 g) was added. After 3 hours, the reaction was worked up in the usual manner and chromatographed to give 2.07 g of protected amine (43).

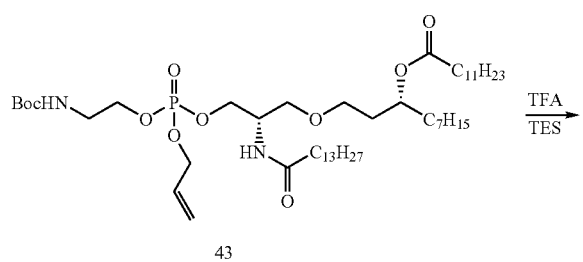

43

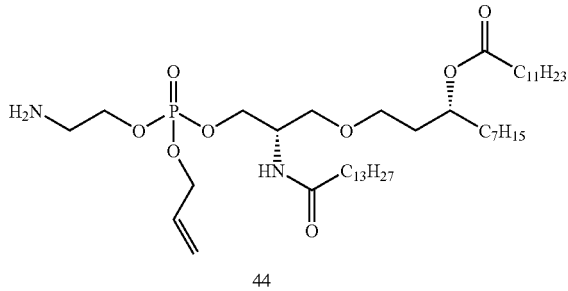

44

To a solution of the protected amine (43) (194 mg) in methylene chloride (1.5 mL) was added TES (240 μL), and TFA (300 μL). The mixture was stirred for 20 minutes and additional TES (50 μL) and TFA (50 μL) was added. After 1 hour, toluene was added and the solvent removed under reduced pressure and then the mixture was worked up in the usual manner. The crude free amine product (44) was used immediately in the next reaction.

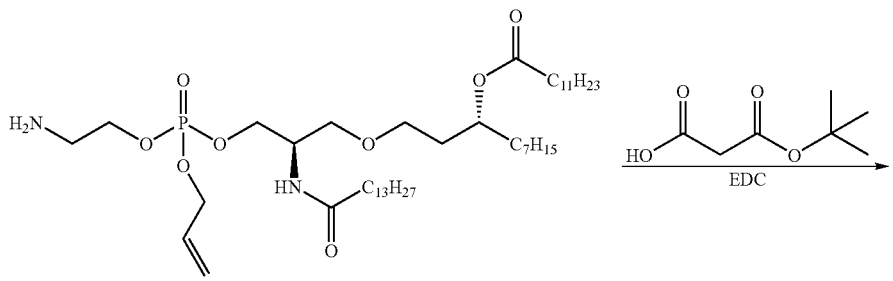

29

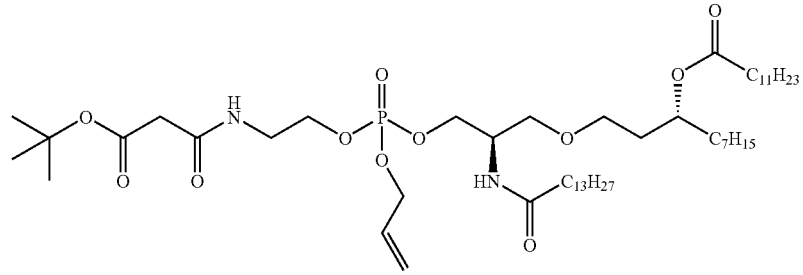

45

To an ice cold solution of the free amine (29) (43.5 mg) in methylene chloride (250 μL) was added mono-t-butyl malonate (8.3 μL), EDC (12.4 mg) and a trace of DMAP. The ice bath was removed and after 2 hours, the reaction was worked up in the usual manner. Chromatography gave 44 mg of amide (45).

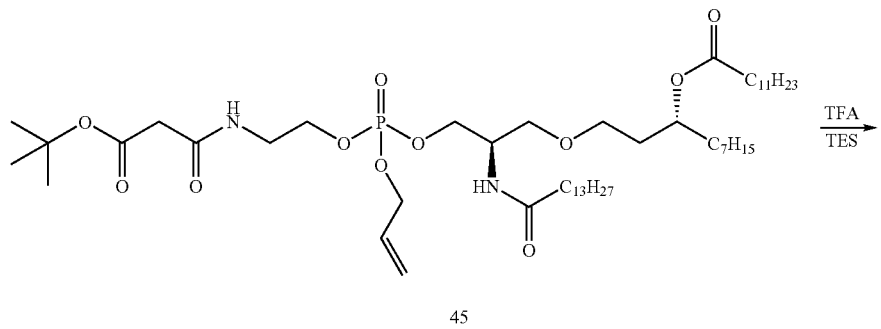
45
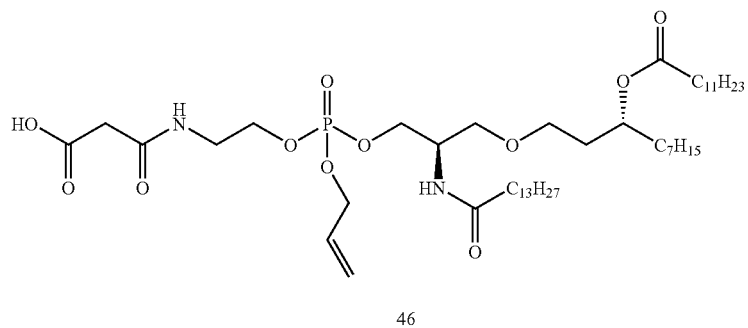
46
To a solution of the amide (45) (44 mg) in methylene chloride (0.5 mL) was added TES (90 μL) and TFA (100 mL). After 2 hours, toluene was added and the solvent removed under reduced pressure. The mixture was worked up in the usual manner to give 44.2 mg of free acid (46).
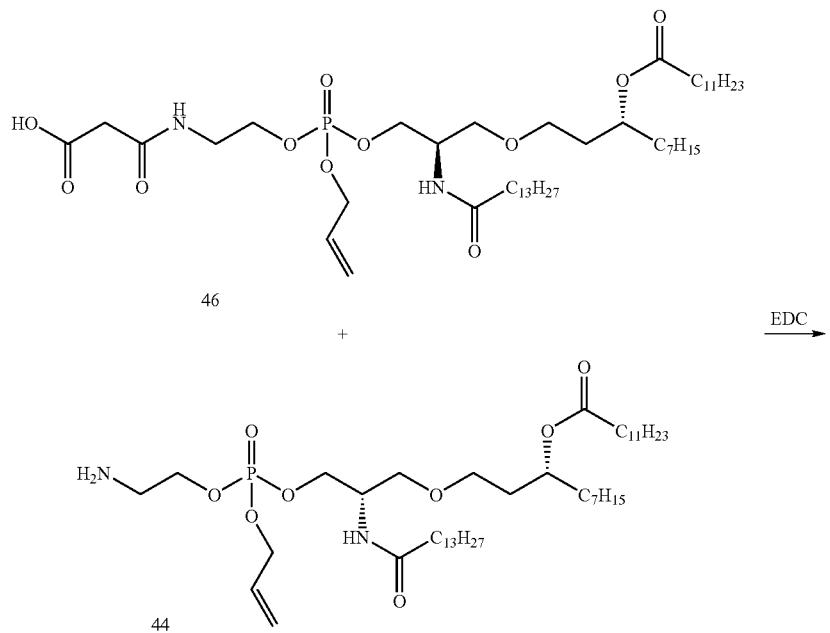

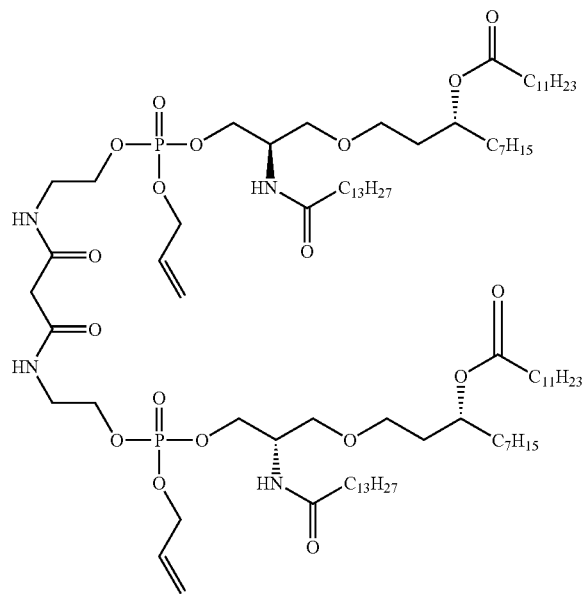
47
To an ice cold solution of the free acid (46) (41 mg) and the free amine (44) (26.3 mg) in methylene chloride (500 µL) was added EDC (13 mg) and the mixture was stirred for 30 minutes. Additional EDC (5 mg) and DMAP (2 mg) was added and after 1 hour, the reaction was worked up in the usual manner. Chromatography gave 32.7 mg of coupled compound 47 as an oil.
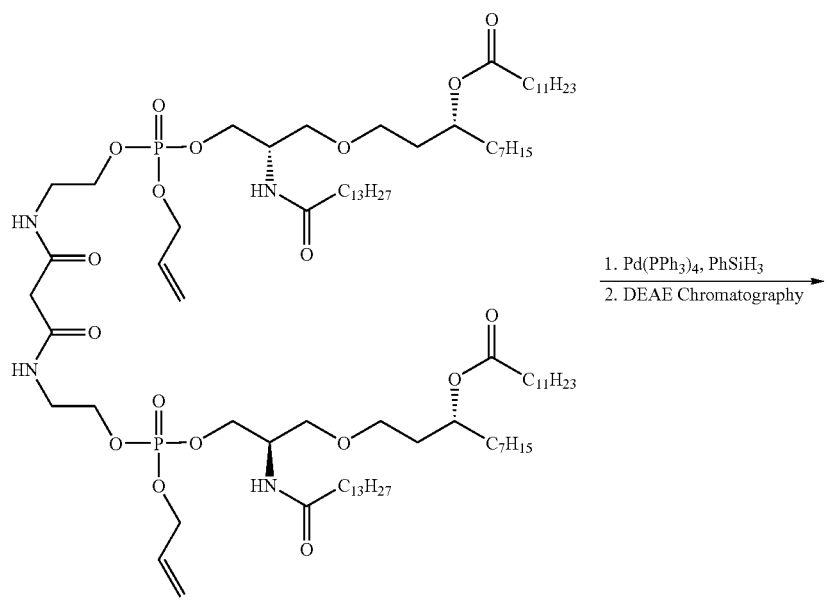
47
1. Pd(PPh$_3$)$_4$, PhSiH$_3$
2. DEAE Chromatography

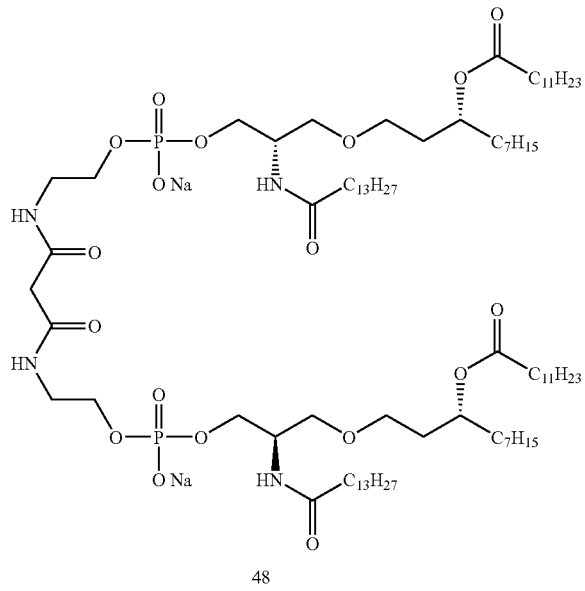

48

To a solution of the coupled compound (47) (32.7 mg) in degassed chloroform (1.5 mL) in a dry box was added PhSiH$_3$ (8.5 µL) and Pd(PPH$_3$)$_4$ (11 mg). The mixture was removed from the box and cooled in ice. After 5 minutes, the ice bath was removed and after 1 hour, chloroform:methanol:water (2:3:1) was added and the mixture stirred for 15 minutes and stored in the freezer overnight. The mixture was then poured onto a DEAE chromatography column. Chromatography gave 13.9 mg of a compound (48) as a white powder after 0.1 N NaOH treatment followed by lyophilization.

Example 4

Chiral Urea-Type 1

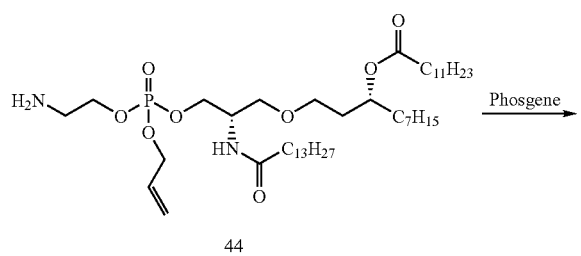

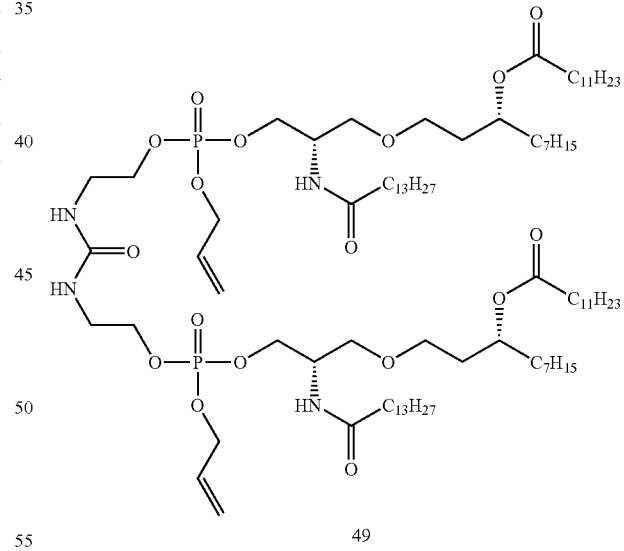

49

To a solution of amine (44) (46.1 mg) in toluene was added saturated sodium bicarbonate (0.5 mL) followed by phosgene (15 µL of a 1.93 M solution in toluene). After 30 minutes, additional phosgene (10 µL) was added. After 2 hours, additional phosgene (5 µL) was added. The reaction was quenched with aqueous sodium bicarbonate and worked up in the usual manner to give 29.6 mg of urea (49) with protected phosphates.

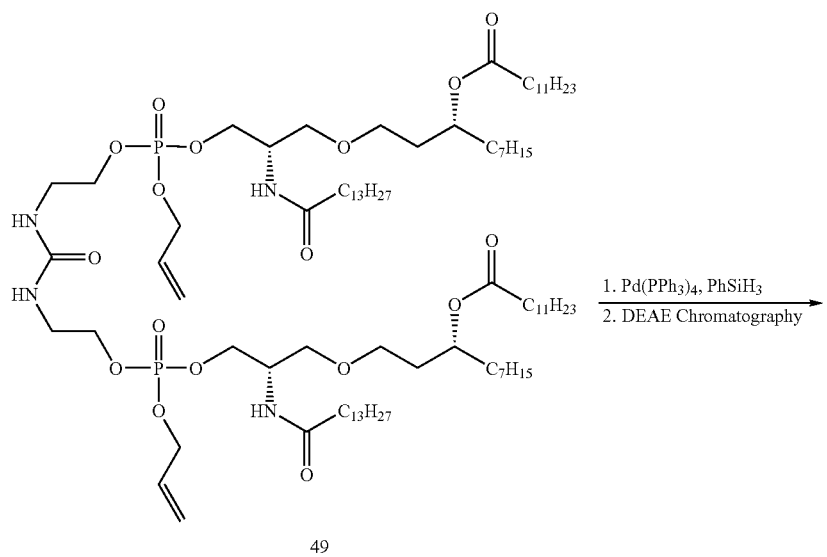

49

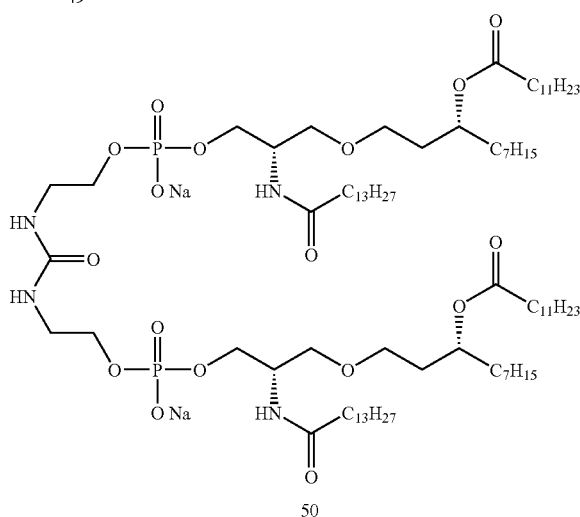

50

To a solution of the urea with protected phosphates (49) (29.6 mg) in degassed chloroform (1.5 mL) in a dry box was added PhSiH$_3$ (8 μL). The reaction vessel was removed from the dry box and placed on ice. Pd(PPh$_3$)$_4$ (10 mg) was added and after 5 minutes the ice bath removed. After 1 hour, the reaction was quenched by addition of chloroform:methanol:water. The mixture was stirred for 15 minutes and stored overnight in the freezer. It was chromatographed on DEAE to give 24.1 mg of (50) as a white powder after 0.1 N NaOH treatment followed by lyophilization.

Example 5

Chiral Urea-Type 2

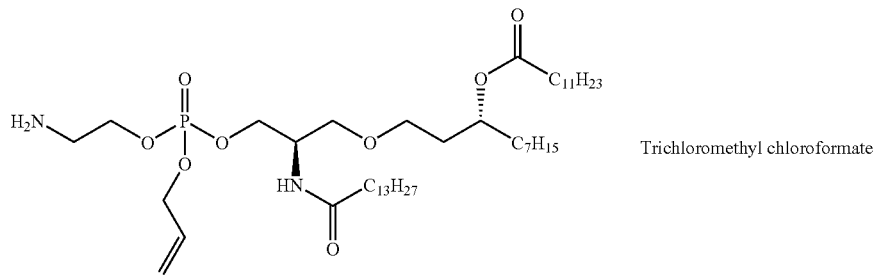

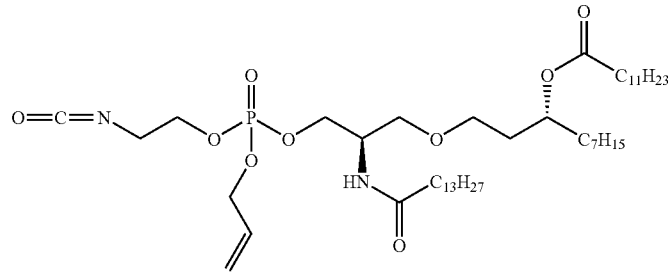

51

To an ice-cold solution of trichloromethyl chloroformate (2.6 μL) in methylene chloride (200 μL) was added a solution of free amine (29) (35 mg) and 1,8-bis-(dimethylamino)-naphthalene in methylene chloride (200 μL). After 5 minutes, the ice bath was removed. After 15 minutes, additional methylene chloride was added and the mixture worked up in the usual manner. Chromatography gave 9.4 mg of isocyanate (51) as an oil.

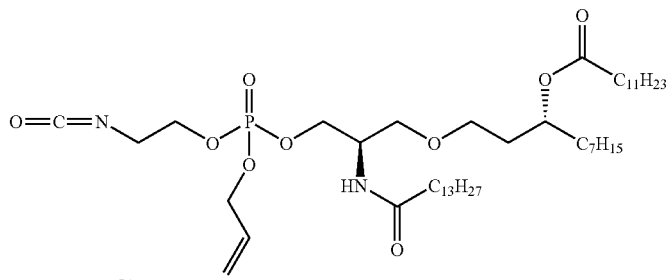

51

+

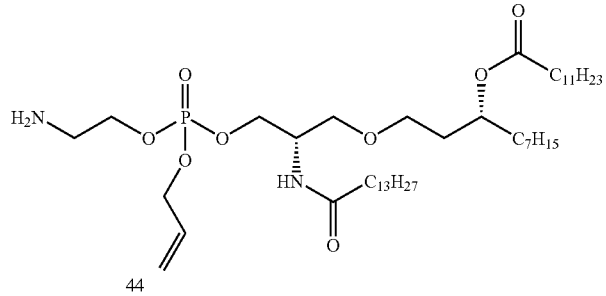

44

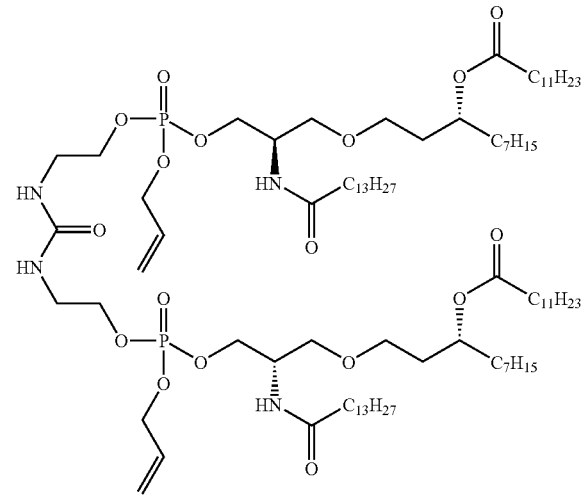

61

To a solution of the isocyanate (51) (9.4 mg) in methylene chloride (0.2 mL) was added a solution of the amine (44) (10.3 mg) in methylene chloride. After 15 minutes, the reaction was worked up in the usual manner. Chromatography gave 5.5 mg of coupled compound (61) as an oil.

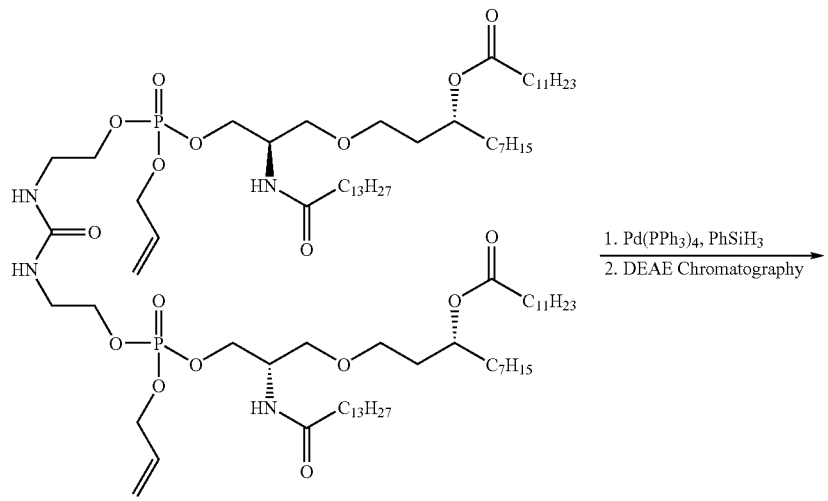

61

1. Pd(PPh$_3$)$_4$, PhSiH$_3$
2. DEAE Chromatography

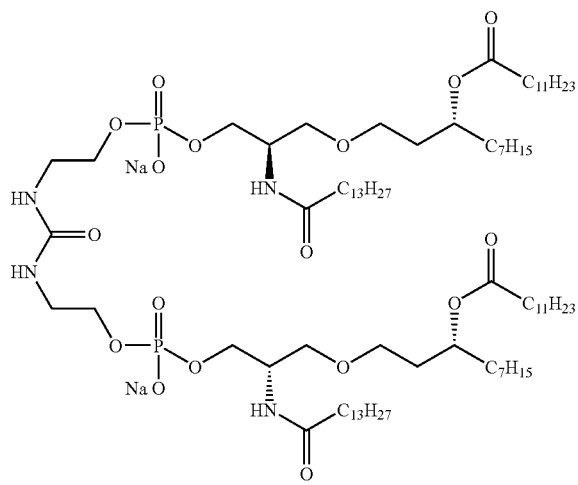

62

To a solution of the coupled compound (61) (25.2 mg) in degassed chloroform (0.5 mL) in a dry box was added PhSiH$_3$ (6.6 μL) and Pd(PPH$_3$)$_4$ (8.8 mg). The mixture was removed from the box and cooled in ice. After 5 minutes, the ice bath was removed and after 1 hour, chloroform:methanol:water (2:3:1) was added and the mixture stirred for 15 minutes and stored in the freezer overnight. The mixture was then poured onto a DEAE chromatography column. Chromatography gave 7.5 mg of (62) as a white powder after 0.1 N NaOH treatment followed by lyophilization.

Example 6

Chiral Glycerol Analogue of Type 1

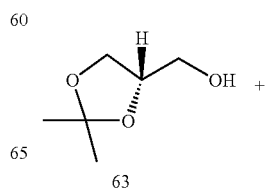

63

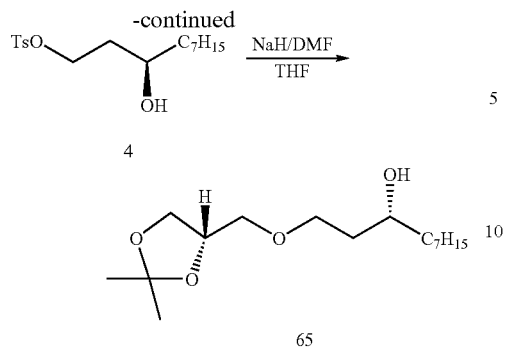

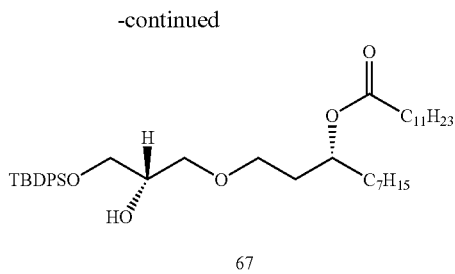

67

A solution of the diol (66) (0.22 g), DMAP (6.3 mg), TEA (100 μL) and TBDPSCl (164 mL) was stirred for 24 hours at room temperature. Methanol (2 mL) and a trace of aqueous hydrochloric acid was added followed by extraction with methylene chloride. The mixture was worked up in the usual way. The residue was chromatographed to give 0.3 g of alcohol (67) as an oil.

To a stirred suspension of sodium hydride (145.5 mg of 60% oil dispersion washed with hexanes) in DMF (12 mL) was added (S)-(+)-alcohol (63) (0.41 mL) in 8 mL of THF dropwise over a 1 hour period. The mixture was stirred for an additional 30 minutes followed by a dropwise addition of the tosylate (4) (0.789 g) in 10 mL of THF over a 10-minute period. The resulting reaction mixture was stirred overnight. The usual work up gave 0.56 mg of the desired adduct (65).

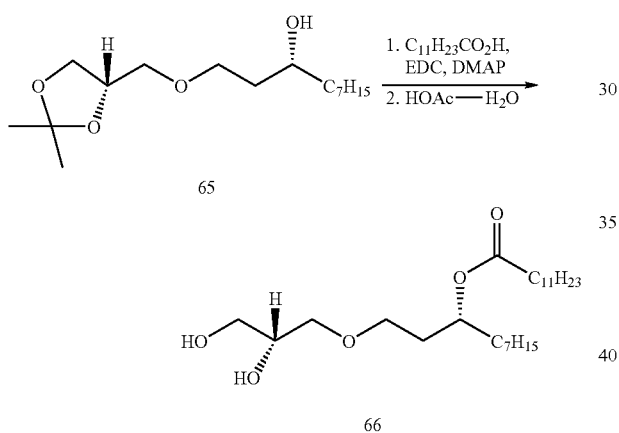

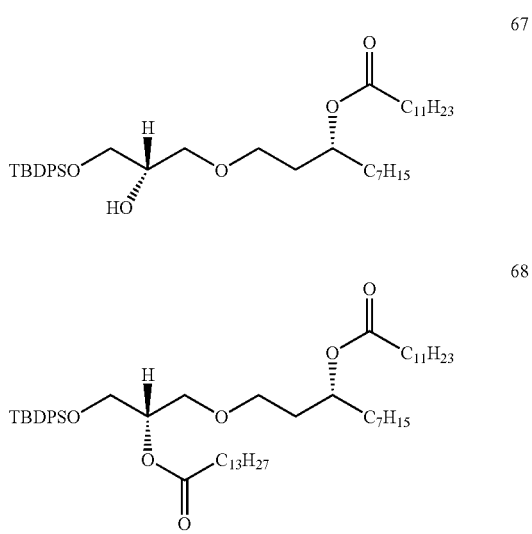

A solution of lauric acid (1.40 g), EDC (1.35 g), DMAP (0.04 g) and the alcohol adduct (65) (0.564 g) in 4 mL of methylene chloride was stirred for 15 hours at room temperature. Brine and saturated aqueous sodium bicarbonate (1:1) were added and the mixture extracted with methylene chloride. The mixture was worked up in the usual manner and chromatographed. The desired fraction was dissolved in 20 mL of 4:1 acetic acid:water and stirred for 15 hours. The solvent was removed under reduced pressure and the residue chromatographed to give 0.77 g of semi-solid diol (66).

A solution of the alcohol (67) (0.3 g), DMAP (5.5 mg), EDC (258 mg), myristic acid (308 mg) in methylene chloride (4 mL) was stirred for 18 hours at room temperature followed by the addition of brine and saturated sodium bicarbonate. The mixture was worked up in the usual way and chromatographed to give 0.4 g of silyl protected ether product (68).

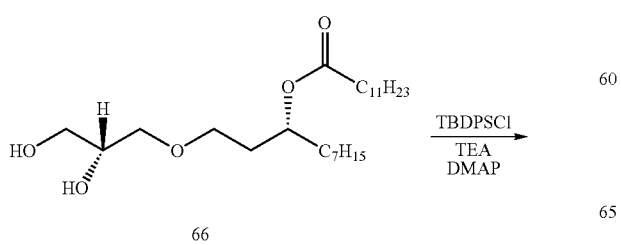

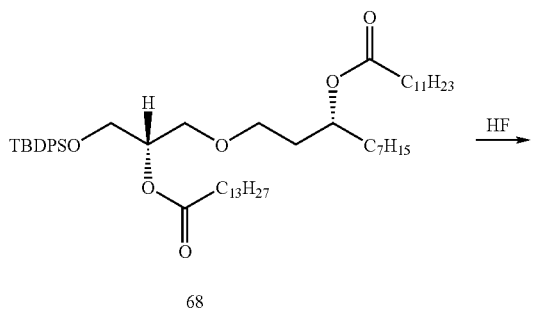

-continued

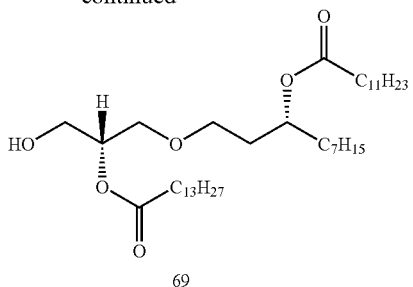

To a solution of the silyl protected ether (68) (195 mg) in acetonitrile (2.7 mL) was added 48% hydrofluoric acid (0.756 ml). After 30 hours, saturated sodium bicarbonate was added and the mixture worked up in the usual way. Chromatography gave 94.7 mg of free alcohol (69).

To a solution of the free alcohol (69) (57 mg) in methylene chloride (0.5 mL) was added tetrazole (15.6 mg) and phosphorylating reagent (11) (40 mg) at room temperature. After four hours, the mixture was cooled to 0° C. followed by the addition of oxone (82 mg) in THF (0.5 mL): water (0.6 mL). The mixture was warmed to room temperature and stirred for 80 minutes. The final reaction mixture was worked up in the usual manner. Chromatography gave 72 mg of protected phosphate (70).

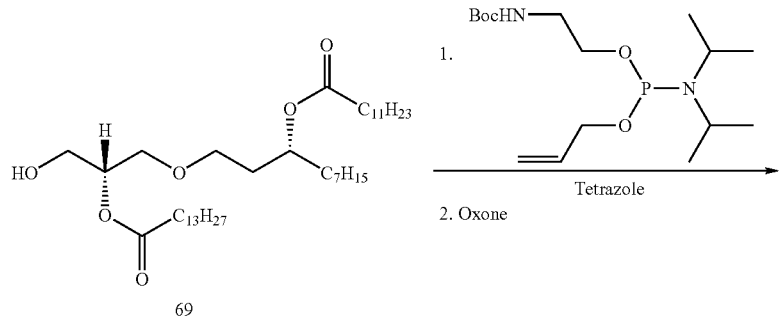

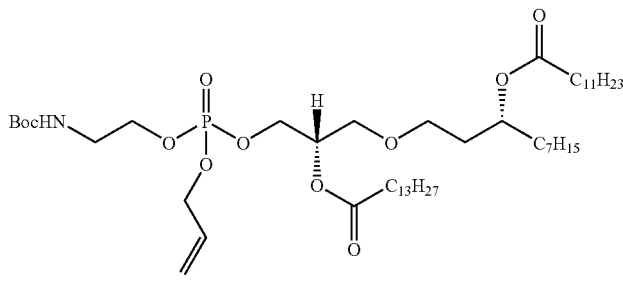

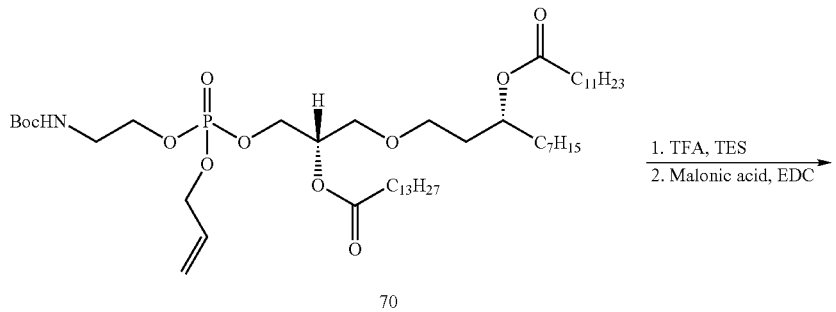

-continued

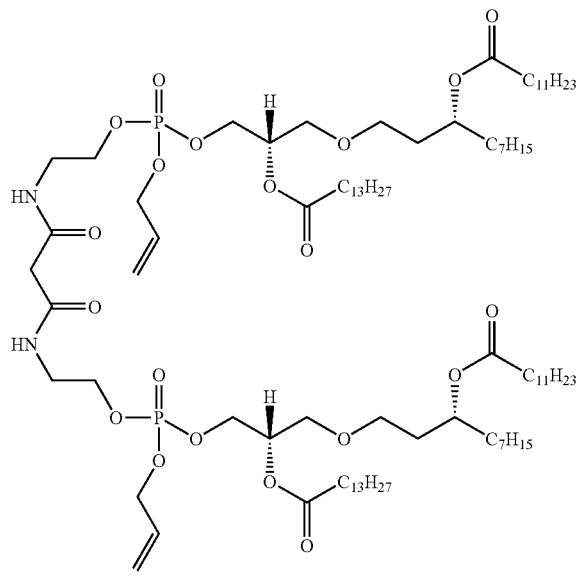
71

To a solution of the protected phosphate (70) (72 mg) in methylene chloride (1 mL) was added TES (120 μL) and trifluoroacetic acid (0.6 mL) followed by stirring for 1 hour. The TFA was removed under reduced pressure followed by azeotroping with 10 mL of toluene. 20 mL of methylene chloride was added and the mixture was worked up in the usual manner to give 0.52 g of an oil.

The crude amine was dissolved in methylene chloride (0.7 mL) followed by the addition of malonic acid (4.5 mg) and EDC (25.6 mg). The mixture was stirred overnight and worked up in the usual way to give 32.5 mg of the dimer product (71).

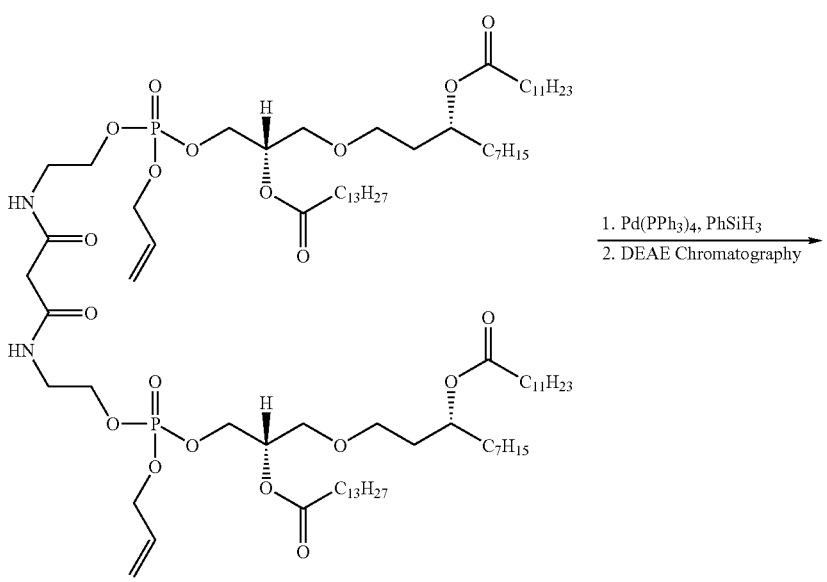
71

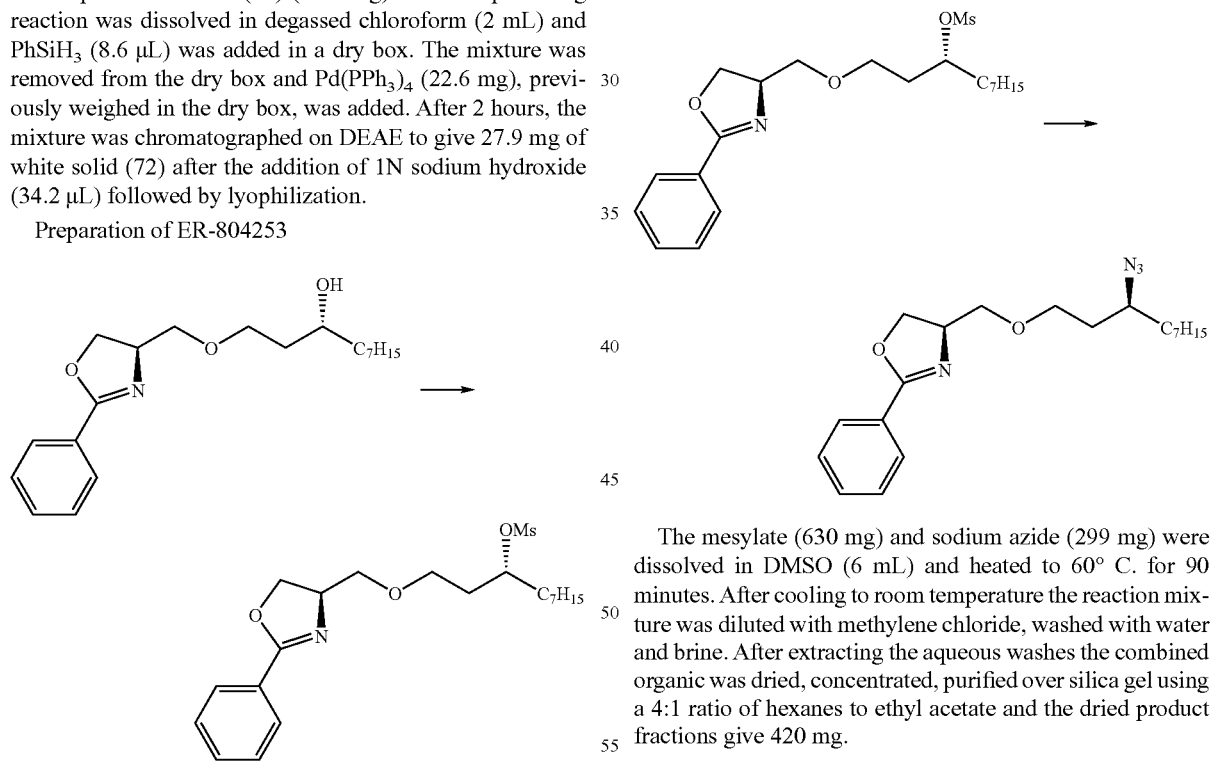

72

The protected dimer (71) (32.5 mg) from the preceding reaction was dissolved in degassed chloroform (2 mL) and PhSiH$_3$ (8.6 µL) was added in a dry box. The mixture was removed from the dry box and Pd(PPh$_3$)$_4$ (22.6 mg), previously weighed in the dry box, was added. After 2 hours, the mixture was chromatographed on DEAE to give 27.9 mg of white solid (72) after the addition of 1N sodium hydroxide (34.2 µL) followed by lyophilization.

Preparation of ER-804253

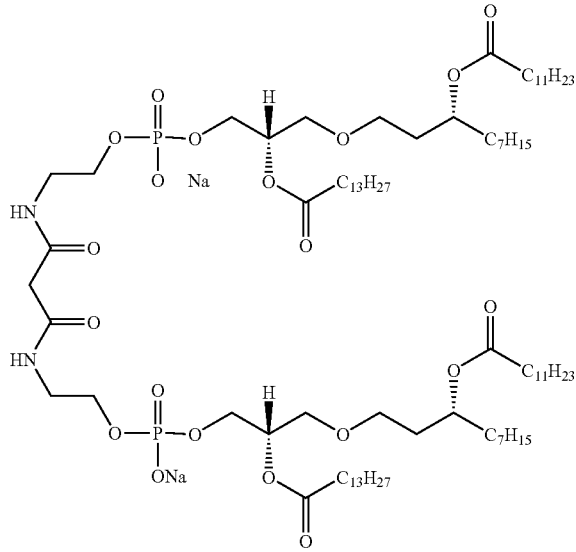

The alcohol (558 mg) was dissolved in methylene chloride (5 mL) cooled to 0° C. and triethylamine (0.466 mL) was added under a nitrogen atmosphere. After stirring for 5 minutes methanesulfonyl chloride (0.142 mL) was added dropwise. The mixture was stirred for an additional 5 minutes at 0° C. and then warmed to room temperature. After stirring for an additional hour, the mixture was worked up with sat. sodium bicarbonate, extracted with ethyl acetate and the extract washed with water, dilute aqueous hydrochloric acid, water, brine, dried and the solvent removed to give 630 mg.

The mesylate (630 mg) and sodium azide (299 mg) were dissolved in DMSO (6 mL) and heated to 60° C. for 90 minutes. After cooling to room temperature the reaction mixture was diluted with methylene chloride, washed with water and brine. After extracting the aqueous washes the combined organic was dried, concentrated, purified over silica gel using a 4:1 ratio of hexanes to ethyl acetate and the dried product fractions give 420 mg.

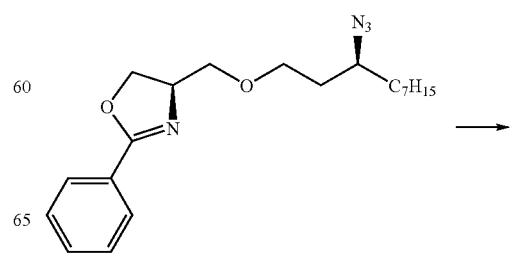

-continued

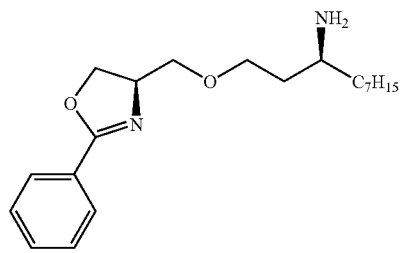

The azide (295 mg) was dissolved in ethanol (5 mL) and Lindlar catalyst (200 mg) was added. After stirring under an atmosphere of hydrogen gas at atmospheric pressure, the filtered solution was dried to give 274 mg.

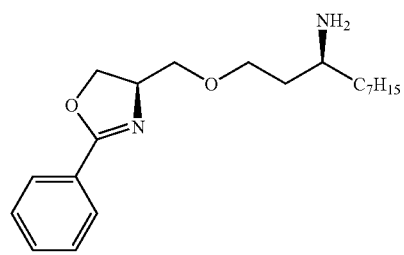

The amine (930 mg) was dissolved in THF (10 mL) and sat. sodium bicarbonate (22 mL). After stirring for 5 minutes, lauroyl chloride (0.712 mL) was added dropwise over 20 minutes. The final mixture was extracted with chloroform, dried to give 1.45 g.

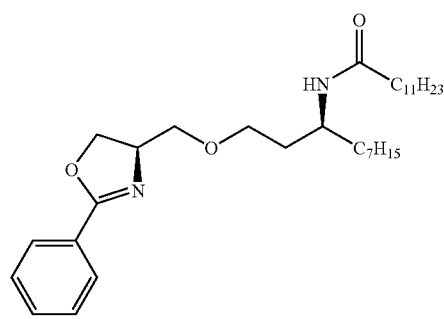

-continued

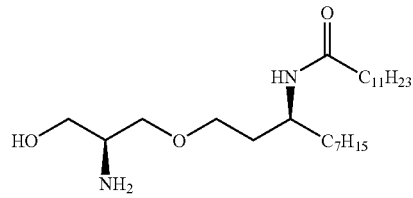

The amide (1.11 g) was dissolved in methanol (14 mL) and 4 N hydrochloric acid (8 mL) added. The mixture was stirred for 1 our at 50° C. and then concentrated. Methanol (16 mL) and 40% sodium hydroxide (8 mL) was added and the mixture refluxed for 1 hour. It was cooled, extracted with methylene chloride and the extract washed with water, dried and the solvent removed to give 930 mg.

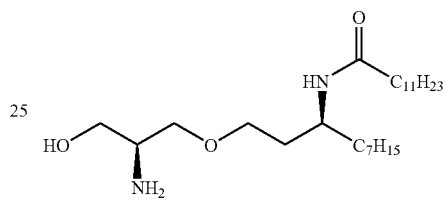

The amino alcohol was dissolved in THF (6 mL) and saturated sodium bicarbonate added (13 mL). After 5 minutes the mixture was cooled to 0° C. and myristoyl chloride (300 μL) added. After 30 minutes, the mixture was worked up in the usual way to give 430 mg.

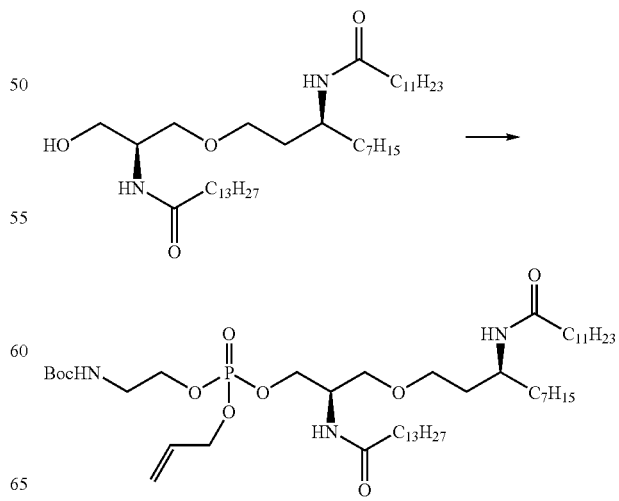

The alcohol (101.7 mg) was dissolved in ice cold methylene chloride and phosphorylating reagent 11 (90 µL) was added and the mixture stirred for 30 minutes. Ice cold oxone (166.3 mg) was added and the mixture stirred for 30 minutes. The reaction was quenched with thiosulfate. The mixture was worked up the usual way and chromatographed to give 174 mg (not purified)

The protected amine from the above reaction was dissolved in ice cold methylene chloride (1 mL), trifluoroacetic acid (1 mL) was added and the mixture stirred for 1 hour. The TFA was removed and the mixture purified to give 106.7 mg.

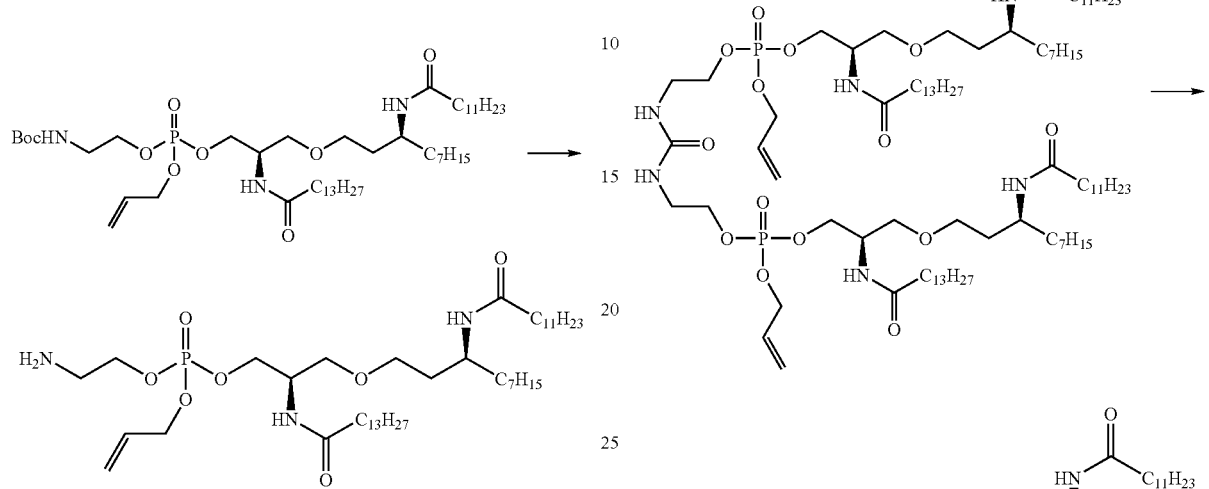

The amine was dissolved in methylene chloride (3 mL) and saturated. sodium bicarbonate solution (3 mL) was added. The mixture was cooled in ice and phosgene in toluene (0.55 equiv.) was added dropwise. The mixture was stirred for 20 minutes and worked up to give 112.3 mg.

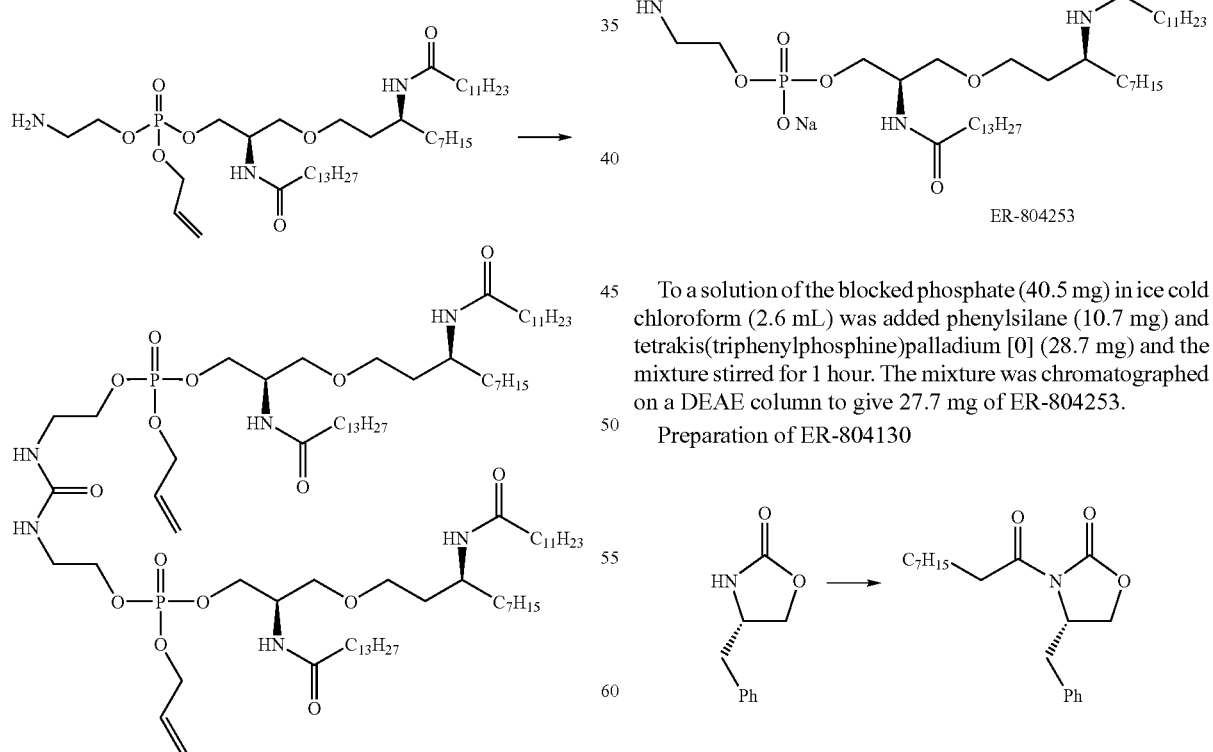

To a solution of the blocked phosphate (40.5 mg) in ice cold chloroform (2.6 mL) was added phenylsilane (10.7 mg) and tetrakis(triphenylphosphine)palladium [0] (28.7 mg) and the mixture stirred for 1 hour. The mixture was chromatographed on a DEAE column to give 27.7 mg of ER-804253.

Preparation of ER-804130

To a solution of the amide (3 g) in THF (65 mL) at −78° C. was added an equivalent of butyllithium, followed by a solution of nonanoyl chloride in THF (6 mL). Aqueous ammonium chloride was added and the mixture worked up in the usual manner to give 5.35 g.

To a solution of the alcohol (5 g) in ice cold methylene chloride (100 mL) was added triethylamine (4.1 mL) and mesyl chloride (2.1 mL). The mixture was stirred for 4 hours and worked up in the usual manner to give 6.99 g.

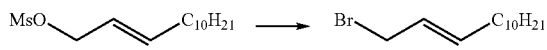

The a solution of the mesylate (6.99 g) in ice cold DMF (100 mL) was added potassium bromide. The mixture was allowed to warm to room temperature and stirred for five hours. It was worked up in the usual manner to give 4.63 g of clear oil.

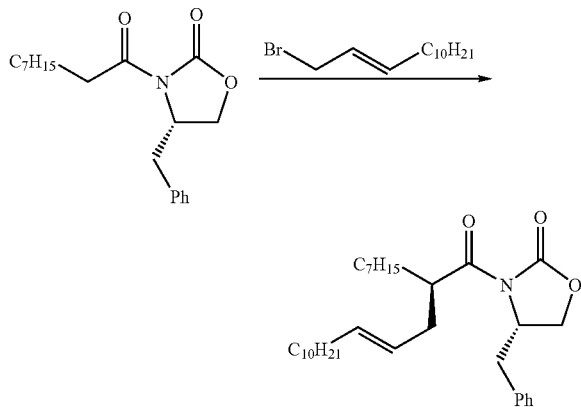

A solution of the amide (2.8 g) in THF (15 mL) was added to a −78° C. solution of sodium bis-trimethylsilylamide in THF (15 mL). After 1 hour, the bromide was added and the mixture allowed to warm to room temperature and worked up in the usual manner to give 1.02 g.

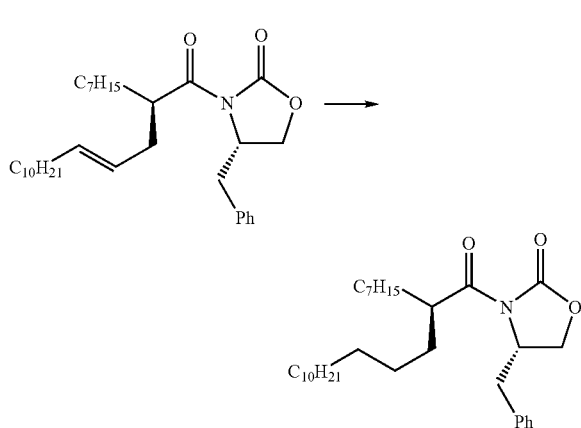

To a solution of the olefin (1.02 g) in EtOAc was added palladium on carbon (126 mg) and the mixture placed under hydrogen. After 4 hours, the mixture was worked up in the usual manner to give 1.0 g.

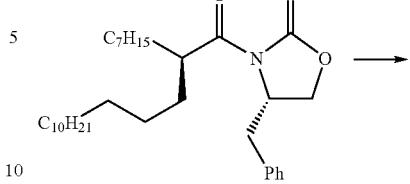

To a solution of the amide (1.0 g) in ice cold THF (20 mL) was added water, hydrogen peroxide and lithium hydroxide. The next day, the mixture was worked up in the usual manner to give 590 mg of acid.

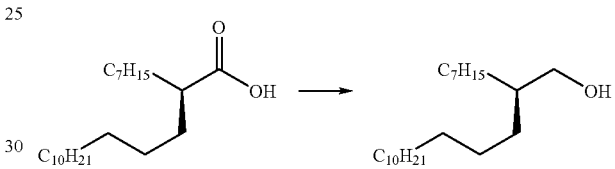

To a solution of the acid in ice cold THF (10 mL) was added diborane:THF complex and the mixture allowed to warm slowly. After seven hours, dilute hydrochloric acid was added carefully and the mixture worked up in the usual manner. The crude material was dissolved in ice cold ether and LAH solution (2 mL, of 1M) added. After 5 minutes, the mixture was worked up in the usual manner to give 556 mg of the alcohol.

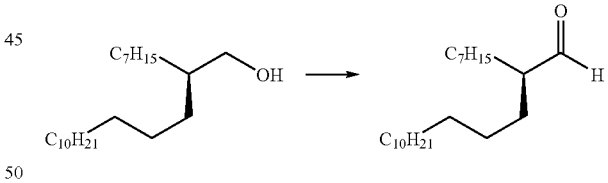

To a −78° C. solution of oxalyl chloride (2.2 mL) in methylene chloride (10 mL) was added DMSO (1.1 mL) and after 2 minutes the alcohol (556 mg) was added in methylene chloride (5 mL). After 20 minutes, triethylamine (1 mL) was added and the mixture warmed to 0° C. The mixture was diluted with ether and worked up in the usual manner to give 567 mg.

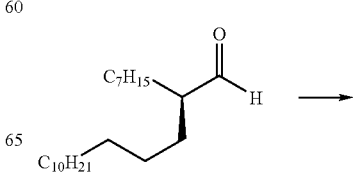

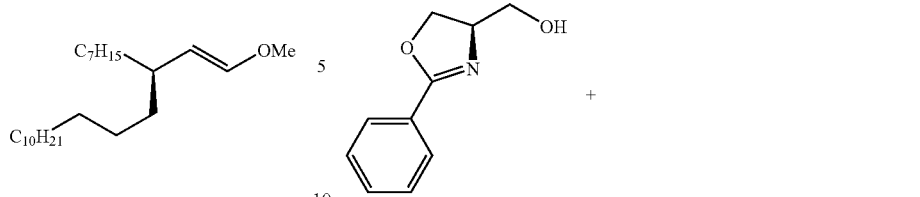

The Wittig reagent (679 mg) was suspended in THF (10 mL) and KHMDS solution (4 mL of 0.5 M) added. After 20 minutes, the mixture was cooled to −78° C. and the aldehyde (567 mg) in THF (5 mL) was added. After 15 minutes, the mixture was worked up in the usual manner to give 342 mg.

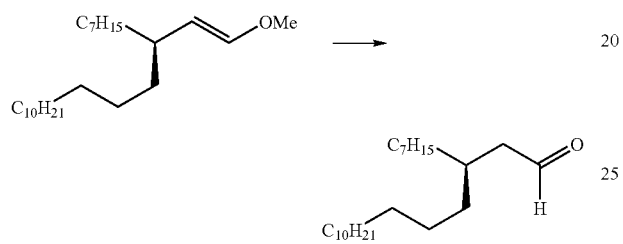

To a solution of the enol ether (342 mg) in acetonitrile (3.5 mL) and water (0.15 mL) was added hydroiodic acid. After 4 hours, the mixture was worked up in the usual manner to give 325 mg.

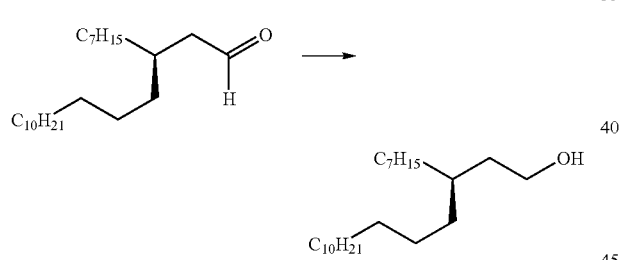

To a solution of the aldehyde (325 mg) in methanol (10 mL) was added sodium borohydride (38 mg). After 3 hours, the reaction was worked up in the usual manner to give 303 mg of the alcohol.

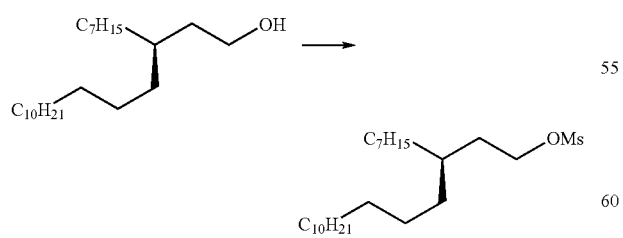

To an ice cold solution of the alcohol (303 mg) in methylene chloride (10 mL) was added triethylamine (150 μL) and mesyl chloride (76 μL). After 4 hours, the reaction was worked up in the usual manner to give 352 mg.

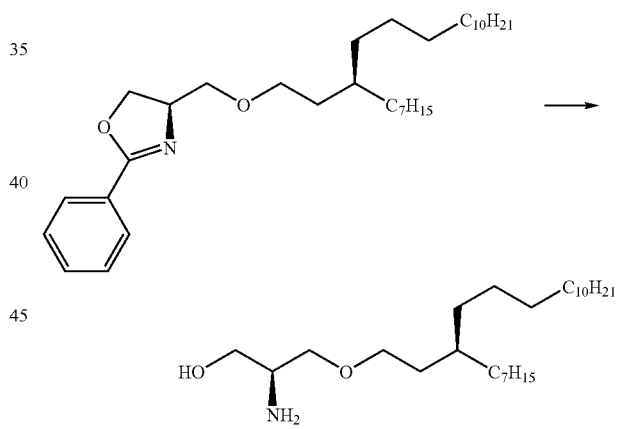

To a solution of the oxazoline (1 mL) in ice cold THF (5 mL) was added potassium t-butoxide solution (2.2 mL of 1M). After 30 minutes, the mesylate was added in THF (5 mL) and the mixture stirred for 8 hours. The usual work-up gave 318.5 mg.

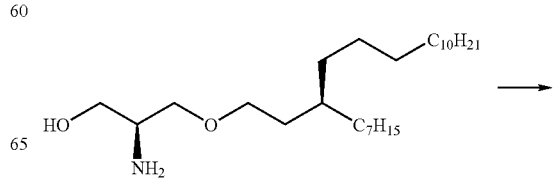

A solution of the oxazoline in methanol (8 mL) and hydrochloric acid (4 mL of 4M) was warmed to 50° C. for 90 minutes. Additional methanol was added and the solvent removed. The residue was dissolved in methanol (8 mL) and sodium hydroxide solution (4 mL) and briefly warmed to 50° C. The mixture was cooled and extracted with chloroform. The usual work-up gave 114 mg.

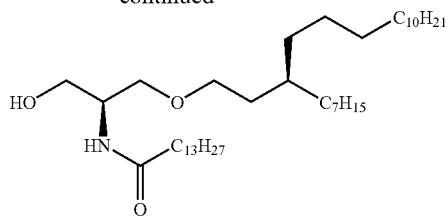

To a solution of the amine (114 mg) in THF (2 mL) and saturated aqueous sodium bicarbonate (2 mL) was added the acid chloride. After 30 minutes additional acid chloride was added. After 30 minutes, the reaction was worked up in the usual manner to give 146 mg.

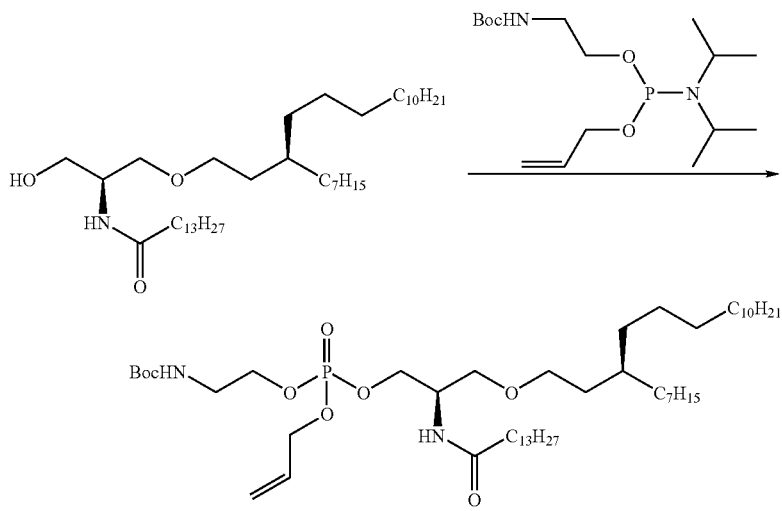

To a solution of tetrazole (48 mg), the phosphorylating reagent (122 mg) in ice cold methylene chloride (2 mL) was added the alcohol (146 mg). Oxone (230 mg) in water (1 mL) and THF (2 mL) was added. After 90 minutes, thiosulfate was used to quench the reaction. Standard work up gave 140 mg.

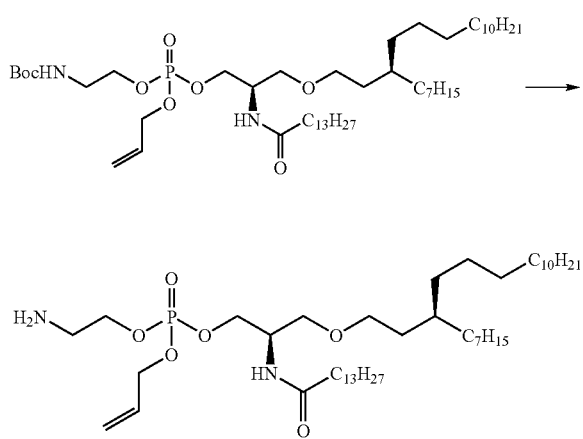

To a solution of the substrate in ice cold methylene chloride was added triethylsilane (370 µL) and trifluoroacetic acid (110 µL). After 5 minutes, the volatiles were removed to give 148 mg.

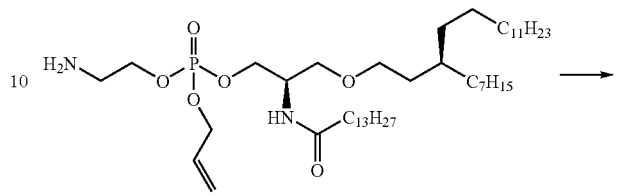

-continued

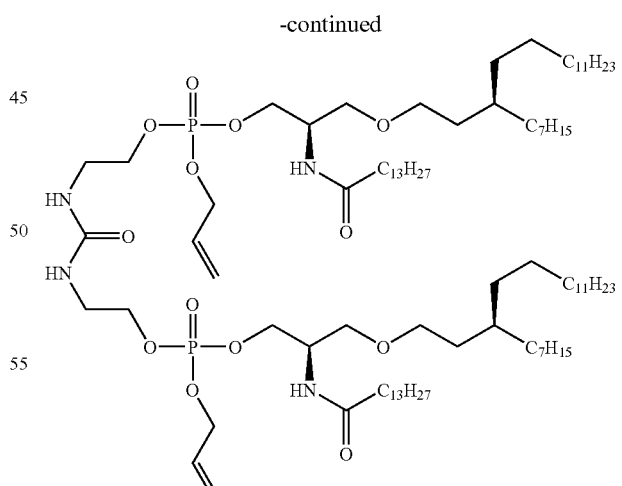

To a solution of the amine (66.9 mg) in ice cold methylene chloride (0.8 mL) was added saturated aqueous sodium bicarbonate (0.8 mL) and phosgene solution (20 µL of 1.93 M). After one hour, additional phosgene (10 µL) was added. After 30 minutes, the usual work-up gave 47.7 mg.

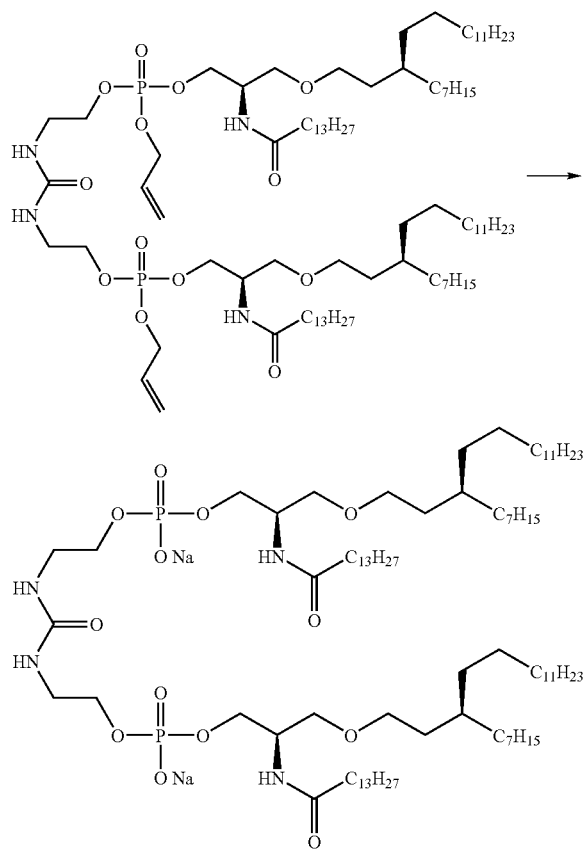

To a solution of phenylsilane (15 μL), tetrakis(triphenylphosphine) palladium [0] (24.8 mg) in ice cold chloroform under an inert atmosphere was added the substrate. After 5 minutes, the mixture was applied to a DEAE column and chromatographed to give 31 mg of ER-804130.

Preparation of ER-804558

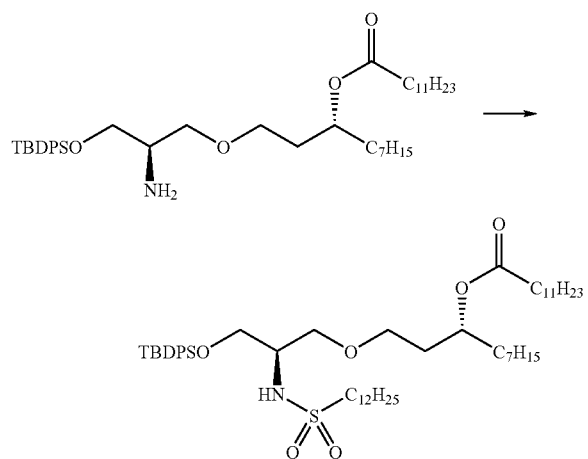

To a solution of the amine (325 mg) in methylene chloride was added triethylamine (321 mL) and 1-dodecanesulfonyl chloride. After 3 hours, the usual work up gave 384 mg.

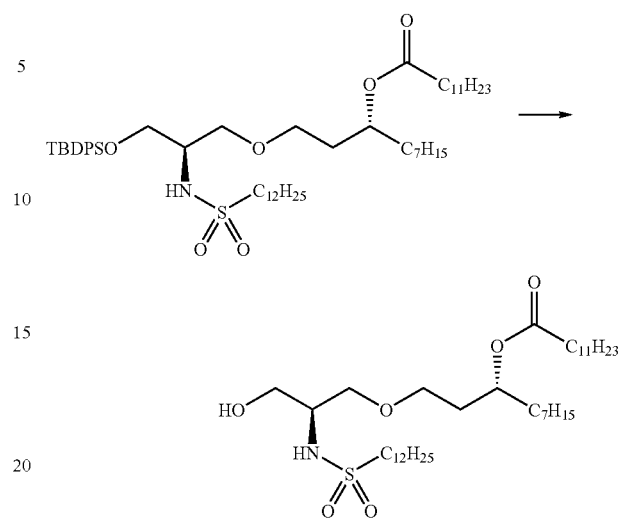

To a solution of the protected alcohol (384 mg) in THF (4 mL) was added tetrabutylammonium fluoride (123 mg) and acetic acid (29 μL). After 2 hours, the usual work up gave 180 mg.

The remainder of the synthesis was completed as outlined above for other compounds of the present invention, i.e. phosphorylating, deblocking, coupling with phosgene, and deprotecting with phenylsilane and palladium.

Preparation of ER-804442

The diol amine was mono-protected as its t-butyl-diphenylsilylether outlined above.

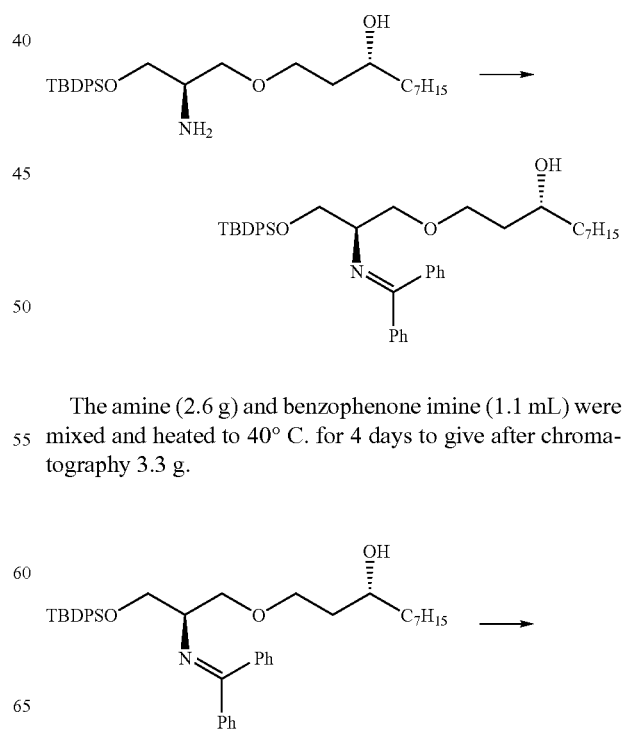

The amine (2.6 g) and benzophenone imine (1.1 mL) were mixed and heated to 40° C. for 4 days to give after chromatography 3.3 g.

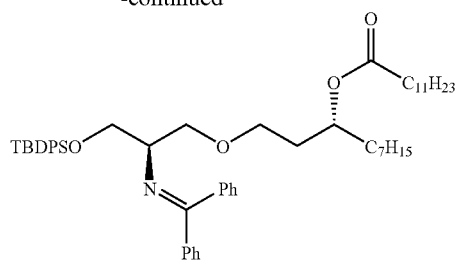

To a solution of the imine (3.3 g) was in ice cold methylene chloride was added lauric acid (1.5 g), EDC (1.7 g) and DMAP (155 mg). The next day, the reaction was worked up in the usual manner to give 3.15 g.

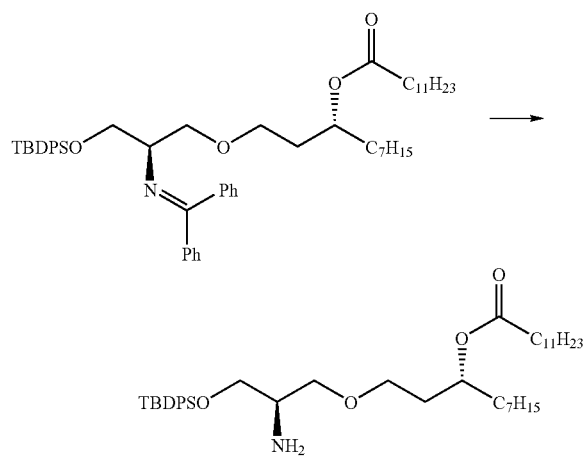

To a solution of the imine (3.14 g) in ether was added 1 N aqueous hydrochloric acid. The next day, the reaction was worked up in the usual manner to give 2.81 g.

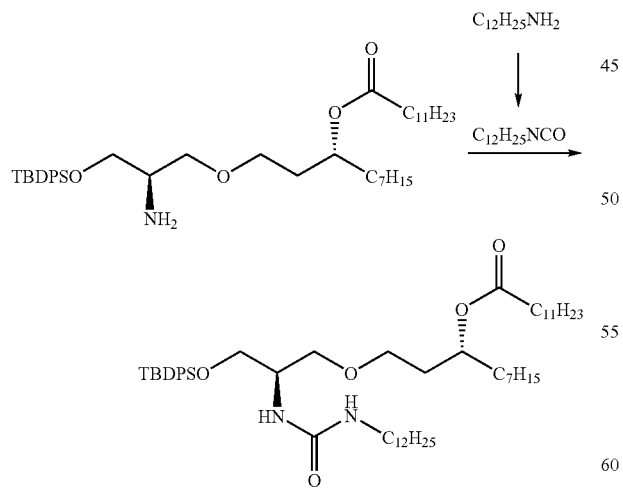

To a solution of trichloromethylchloroformate (12 μL) in ice cold methylene chloride (250 μL) was added dodecylamine (18 μL) and diisopropylethylamine (27 μL). After 30 minutes, the solvent was removed. The residue was dissolved in ice cold methylene chloride, to which was added the amine (55.6 mg) and additional diisopropylethylamine (13 μL). After 2 hours, the usual work up gave, after chromatography, 60.9 mg.

This product was de-protected with fluoride, phosphorylated, de-protected with TFA, dimerized with phosgene, and un-blocked with phenylsilane and palladium as outlined above to give ER-804442.

Preparation of ER-804221

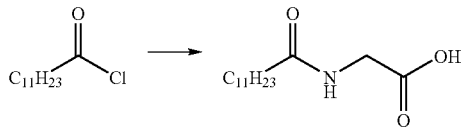

To an ice cold solution of glycine (8.26 g) in aqueous sodium hydroxide (4.4 g in 60 mL) was added lauroyl chloride (21.8 g). After 1 hour, acid was added and the mixture worked up in the usual way. Recrystallization from ethyl acetate gave 9.7 g.

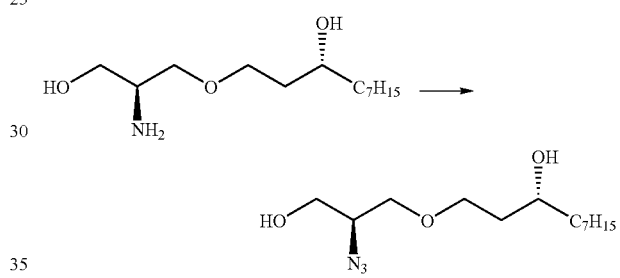

To an ice cold solution of the amine (1.4 g) in methanol was added triflic azide (20 mg). The next day, additional azide was added. After 2 hours, the reaction was worked up in the usual manner to give after chromatography 1.14 g.

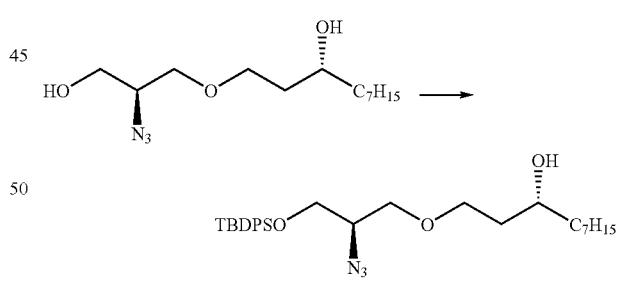

To a solution of the alcohol (1.14 g) in methylene chloride was added t-butyl-diphenylsilyl chloride (1.09 mL), triethylamine (1.8 mL) and DMAP (50 mg). After 3 hours, the usual work up gave 1.4 g.

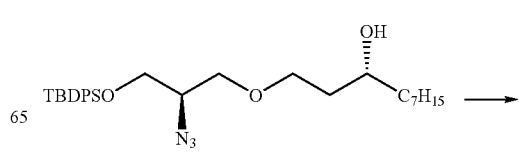

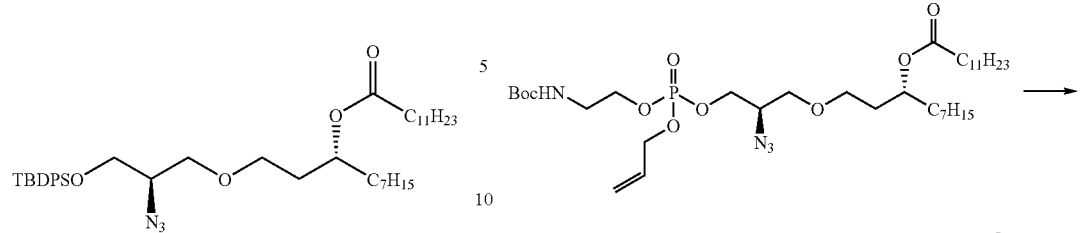

To a solution of the alcohol (1.4 g) in ice cold methylene chloride was added lauric acid (826 mg), EDC (1.05 g) and DMAP (33 mg). The next day, the usual work up gave after chromatography 778 mg.

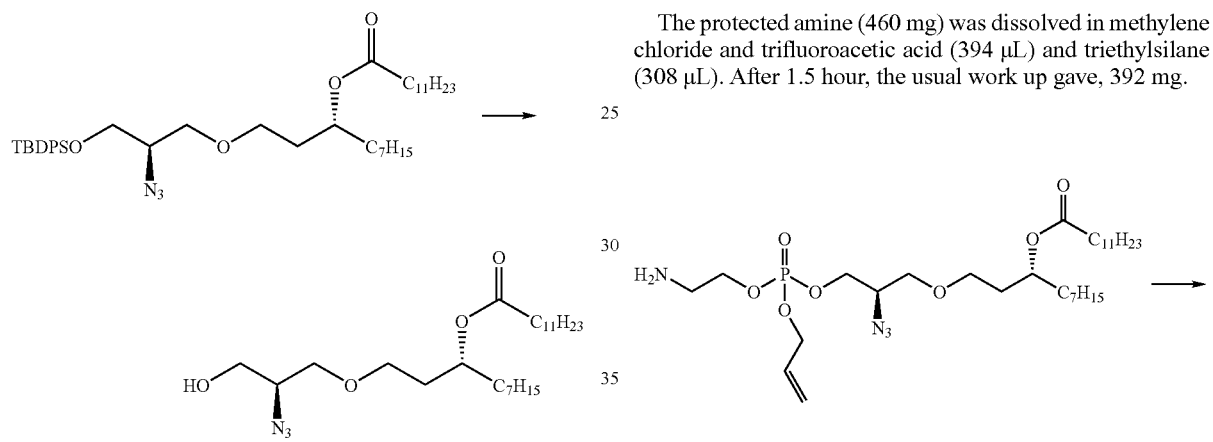

To a solution of the azide (778 mg) in THF was added acetic acid (77 μL) and TBAF (323 mg). The next day, the usual work up gave, after chromatography, 428 mg.

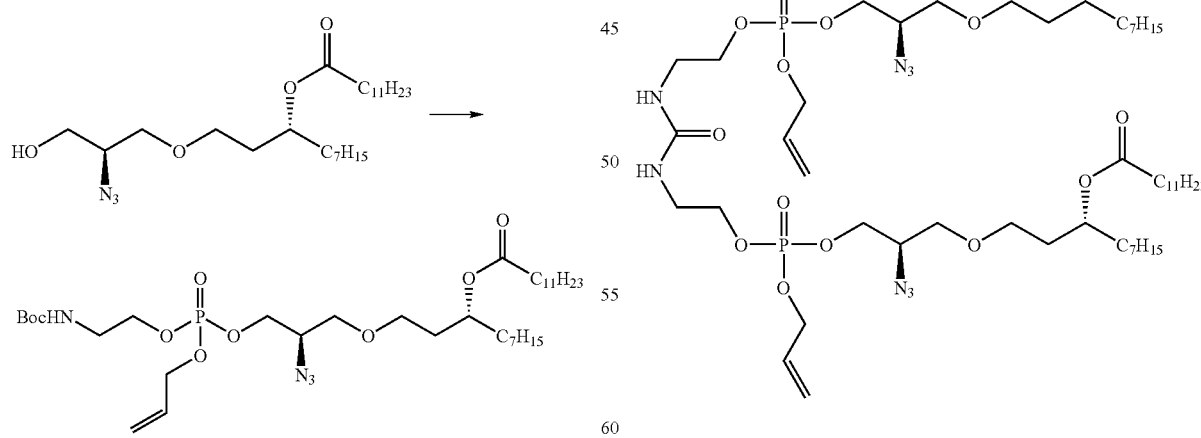

To a solution of the azide (460 mg) in methylene chloride was added tetrazole (165 mg), the phosphorylating reagent (390 mg), and after 30 minutes, oxone in water (722 mg in 3 mL). The reaction was quenched with thiosulfate. Usual work up, after chromatography, gave 392 mg.

The protected amine (460 mg) was dissolved in methylene chloride and trifluoroacetic acid (394 μL) and triethylsilane (308 μL). After 1.5 hour, the usual work up gave, 392 mg.

To an ice cold solution of the amine in methylene chloride (5.5 mL) was added saturated sodium bicarbonate (5.5 mL), and phosgene (164 μL of a 1.93 M solution in toluene). After 15 minutes, the usual work up, after chromatography gave 342 mg.

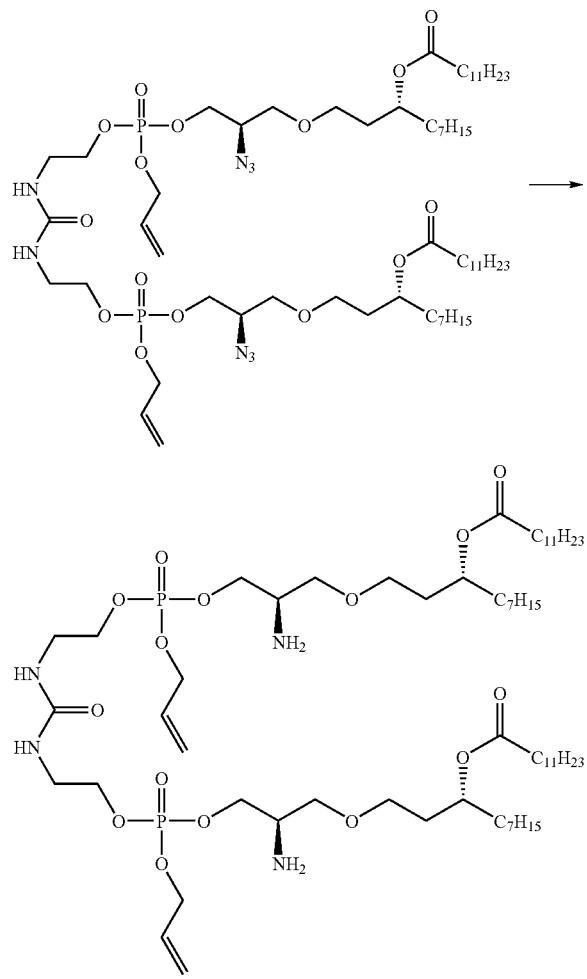

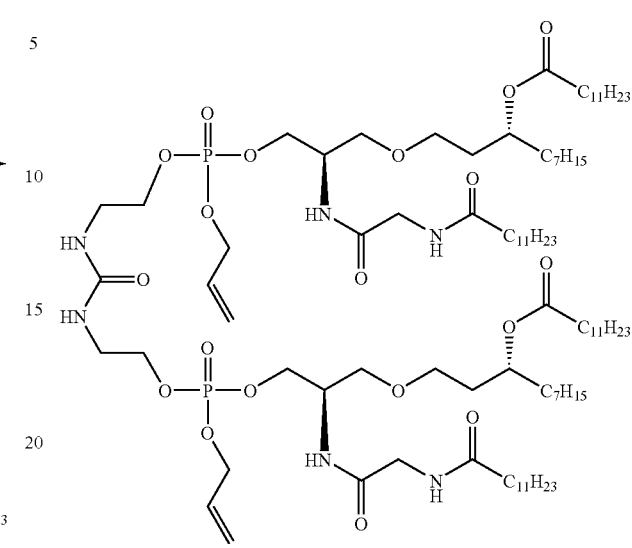

To a ice cold solution of the azide (187 mg) in methylene chloride was added the tin reagent (1.5 mL) which was prepared as outlined in U.S. Pat. No. 5,756,718 incorporated herein by reference. After 30 minutes, the mixture was chromatographed to give 187 mg.

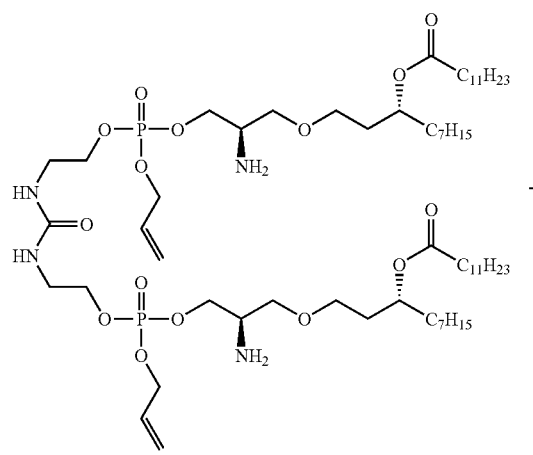

To a ice cold solution of the urea (55 mg) in methylene chloride was added the acid (59 mg) (prepared as above) and EDC (44 mg). The next day, additional EDC (5 mg) and acid (5 mg) was added. After 2 hours, the normal work up provided 45.7 mg.

Normal removal of the protecting groups with phenylsilane and palladium gave ER-804221.

ER-804222 was prepared in a similar manner except that the condensation product between lauryl chloride and glycine, 15-methylmyristic acid was used.

Preparation of ER-804281

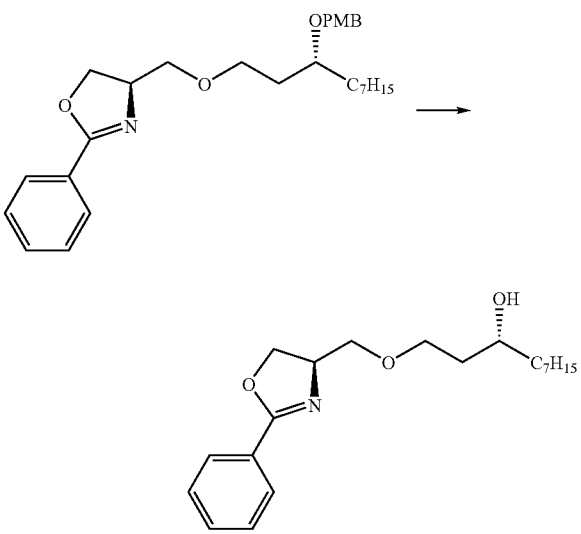

To a ice cold solution of the protected alcohol (8.3 g) in acetonitrile: water was added CAN (41.4 g). After 1 hour, the usual work up gave 5.7 g.

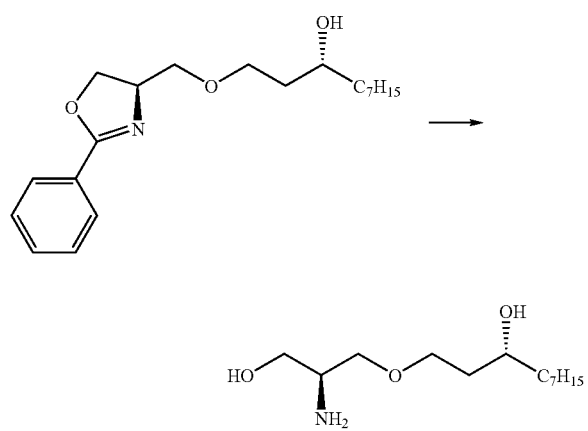

A solution of the alcohol (5.63 g) in 4 N HCl solution was heated to reflux for 1 hour, cooled, neutralized with sodium hydroxide and worked up in the usual manner to give 2.1 g.

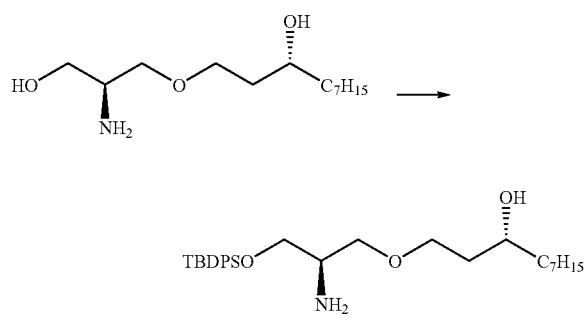

To an ice cold solution of the alcohol (2.2 g) in rmiethylene chloride was added imidazole (0.7 g), t-butyl-diphenylsilyl chloride in 15 mL of methylene chloride. The next day, the usual work up gave 1.54 g.

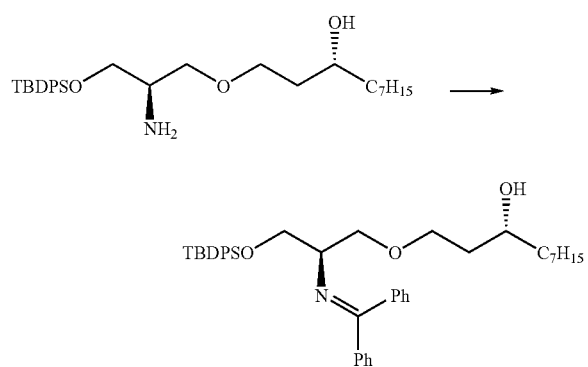

To a solution of the alcohol (1.93 g) in methylene chloride (40 mL) was added benzophenone imine (0.8 mL). After 1 day, the mixture was heated to reflux overnight. The usual work up gave 1.67 g.

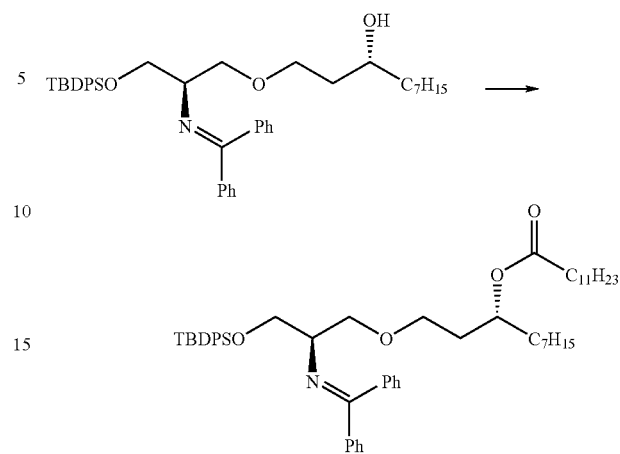

To an ice cold solution of the alcohol (1.67 g) in methylene chloride was added DMAP (159 mg), EDC (0.99 g) and lauric acid (1.04 g). After one day, the usual work up gave 74% yield.

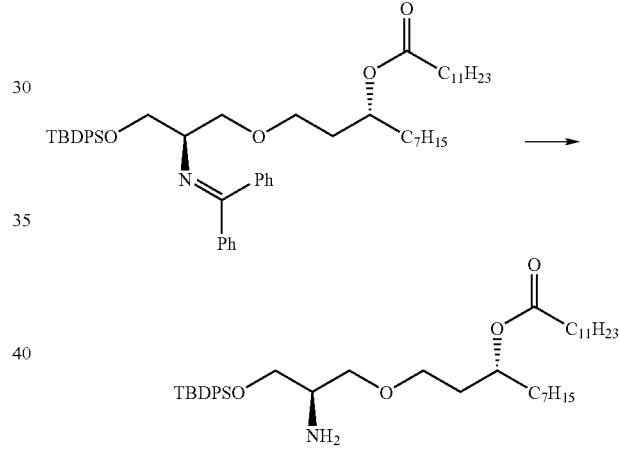

To an ice cold solution of the imine (2.9 g) in ether (50 mL) was added 1 N HCl (50 mL). The next day, the usual work up gave 2.09 g.

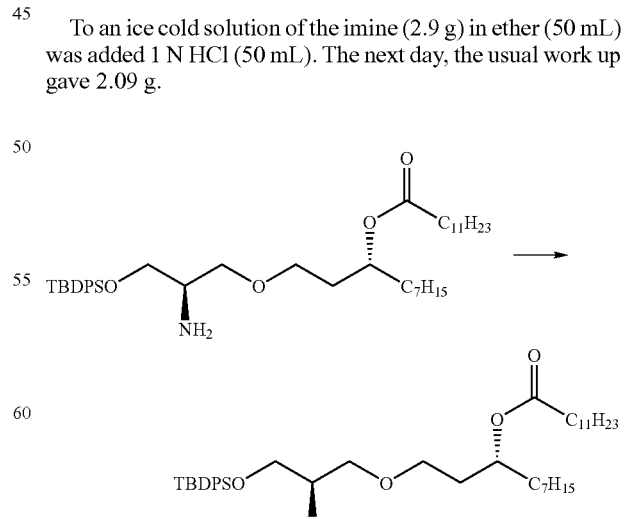

To a solution of the amine (1.24 g) in dichloroethane was added sodium cyanoborohydride (178 mg) and tetradecanal (411 mg). The next day, the usual work up gave 1.5 g.

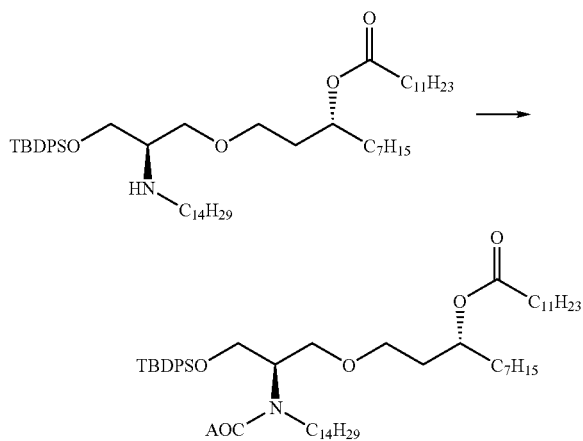

To a ice cold solution of the amine (221 mg) in dioxane was added allyl chloroformate (40 mg) and 308 μL of 1 N NaOH solution. After 2 hours, the usual work up gave 200 mg.

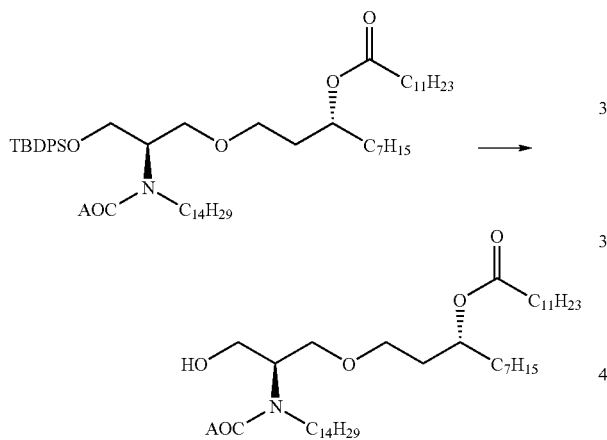

To an ice cold solution of the protected alcohol (365 mg) in THF was added TBAF (1924 μL) and acetic acid (122 μL). The next day, the usual work up gave 271 mg.

This material was phosphorylated, deblocked with TFA, dimerized with phosgene and the allyl protecting groups removed with phenylsilane and palladium as described above to give ER-804281.

Preparation of ER-804339
ER-804281→ER-804339

To a ice cold solution of ER-804281 (7 mg) in methylene chloride was added triethylamine (5 μL), DMAP (0.6 mg) and acetyl chloride (1.8 μL). After 4 days, the usual work-up gave 1.1 mg.

Preparation of ER-804674
ER-804281→ER-804674

To a solution of ER-804281 (12.7 mg) in THF (1.0 mL) was added methyl iodide (9.2 mg) and sodium bicarbonate (6.8 mg). The mixture was stirred for 5 days and sodium bicarbonate (14 mg) and additional methyl iodide (8 mL) was added. After an additional 3 days, additional bicarbonate (28 mg) and MeI (16 μL). After an additional 6 days, the mixture was worked up to give 9.1 mg of product.

Preparation of ER-804596

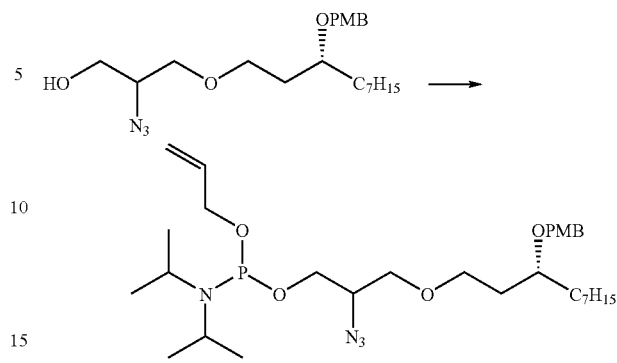

To a solution of the alcohol (393 mg) in methylene chloride (2 mL) was added diisopropylamine (210 μL), tetrazole (105 mg) and phosphorylating reagent (as described above) (488 mg). After 2⅕ hours, the usual work up gave the desired product.

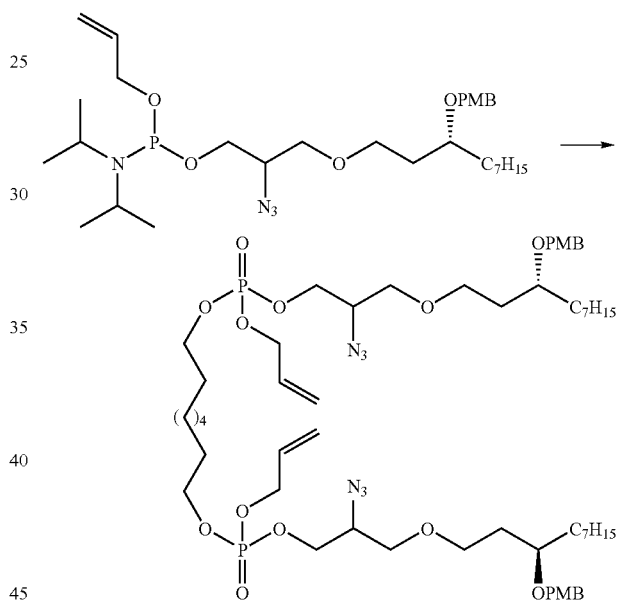

To a solution of the diol (73 mg) in acetonitrile was added tetrazole (175 mg), the azide (1 equivalent). After 3 hours, the mixture was cooled and ozone (1229 mg) added. The next day, usual work up gave the desired product.

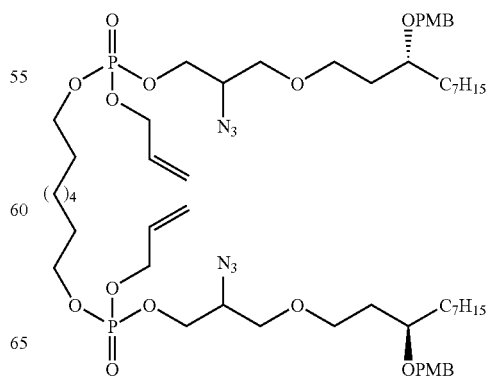

-continued

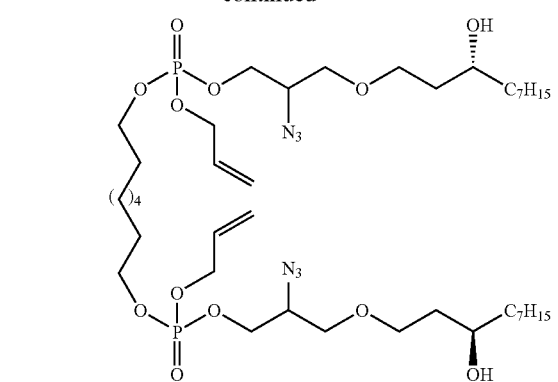

To an ice cold solution of the protected alcohol (92.9 mg) in acetonitrile:water (6 mL:1.5 mL) was added CAN (358 mg). After 1 hour, the usual work up provided 68.5 mg.

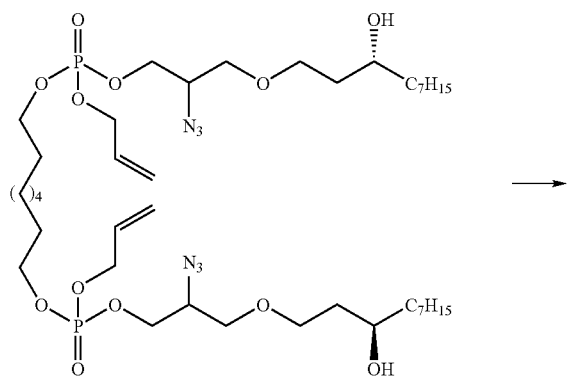

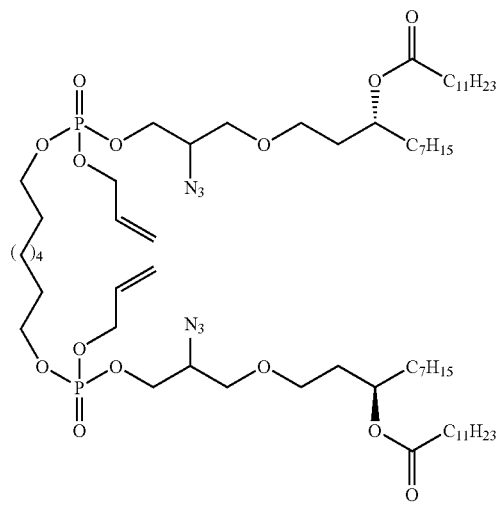

To an ice cold solution of the diol (68.5 mg) in methylene chloride was added lauric acid (76.5 mg), DMAP (4.7 mg) and EDC (73 mg). The next day, the usual work up gave 76.5 mg.

The azides were reduced using the tin reagent described above. The diamine was acylated with dodecanoyl chloride, and the protecting groups removed with phenylsilane and palladium as described above to give ER-804596.

Preparation of ER-804732

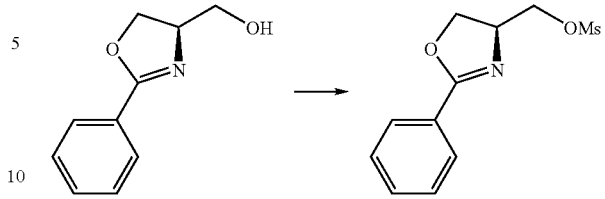

The alcohol (7.04 g) was dissolved in methylene chloride (300 mL) with triethylamine (11.13 mL) and then cooled to 0° C. under a nitrogen atmosphere. Methanesulfonyl chloride (3.69 mL) was added dropwise after which time the reaction was stirred at room temperature for 1 hour. The usual work up gave 5.551 g.

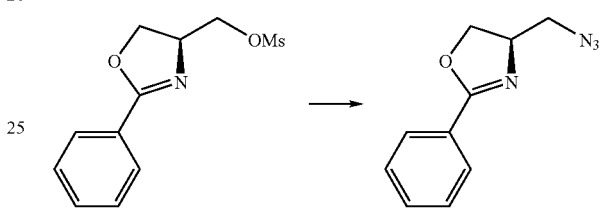

The mesylated (1.114 g) was dissolved in DMF (30 mL) followed by sodium azide (0.9337 g). The reaction mixture was warmed to 57° C. and stirred for 16 hours and then to 104° C. for and additional 3 hours. After cooling to room temperature the mixture was worked up in the usual manner and gave 0.466 g.

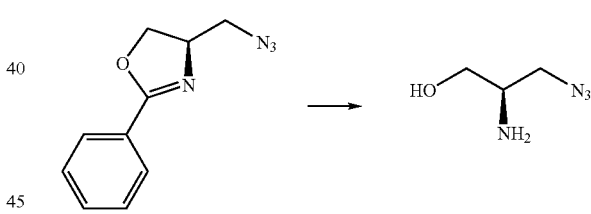

The protected aminoalcohol (0.466 g) was hydrolyzed using 4 N HCl (15 mL) at 107° C. for 3 hours. After cooling to room temperature, the reaction mixture was filtered and extracted with ethyl ether, dried, concentrated and used in the next reaction.

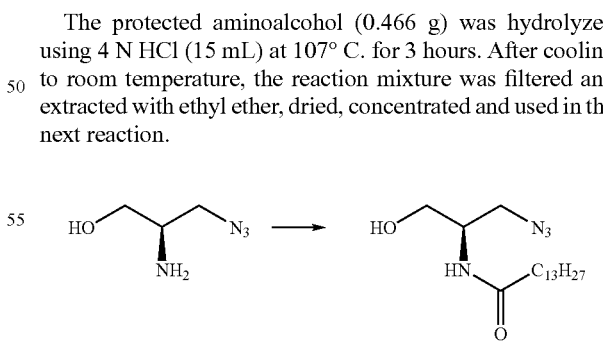

The crude aminoalcohol was dissolved in THF (5 mL) with saturated sodium bicarbonate (6 mL) and cooled to 0° C. Myristoyl chloride (0.79 mL) was added dropwise after which time the reaction was warmed to room temperature and stirred for 2 hours. The reaction mixture was worked up using the usual methods and gave 0.751 g.

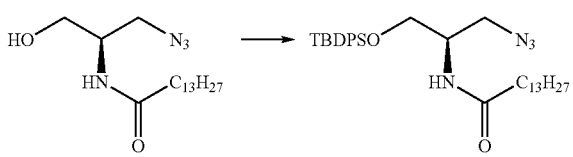

The alcohol (0.185 g) was dissolved in DMF (3.0 mL) with imidazole (0.077 g) and tert-butyldiphenylsilyl chloride (0.197 mL). The reaction mixture was stirred at room temperature for 16 hours after which time the usual work up gave 0.320 g.

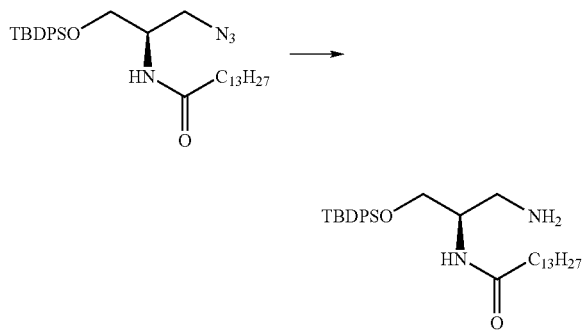

The azide (0.975 g) was dissolved in methanol (20 mL) with 10% palladium on carbon (0.180 g). The mixture was stirred under an atmosphere of hydrogen gas under atmospheric pressure for 2 hours after which time the gas was evacuated and the mixture filtered over Celite 545 and concentrated. Purification using the usual methods gave 0.873 g.

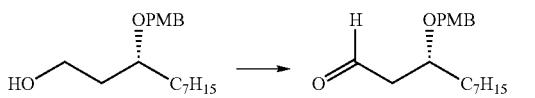

DMSO (1.5 mL) was added dropwise to oxalyl chloride (0.92 mL) in methylene chloride (30 mL) at 78° C. After stirring for 15 minutes the alcohol (1.727 g) in methylene chloride (30 mL) was added dropwise and stirred for an additional 30 minutes. Triethylamine (4.90 mL) was added dropwise, the reaction was warmed to 0° C. and quenched using saturated ammonium chloride. Purification of the crude product using silica gel chromatography with 20% ethyl acetate in hexanes gave 1.653 g.

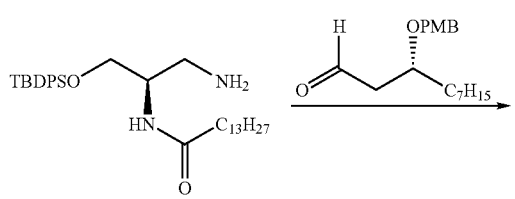

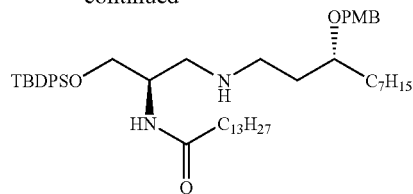

-continued

The primary amine (0.135 g) and aldehyde (0.077 g) were dissolved in 1,2-dichloroethane (5 mL) followed by the addition of sodium cyanoborohydride (0.032 g). The reaction was stirred for 20 hours after which time acetic acid (0.02 mL) was added and the reaction worked up in the usual manner to give 0.103 g.

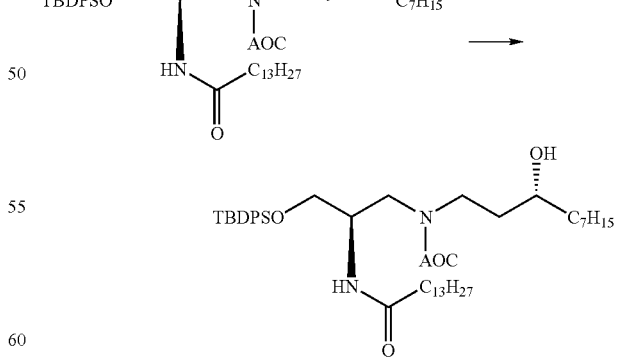

The secondary amine was dissolved in 1,4-dioxane (15 mL) and cooled to 0° C. followed by the slow addition of 1 M sodium hydroxide (3.0 mL). After stirring for 10 minutes allyl chloroformate (0.236 mL) was added dropwise after which time the reaction was warmed to room temperature and stirred for 16 hours. Work up in the usual manner gave 0.613 g.

The para-methoxybenzyl ether (0.613 g) was dissolved in a 4 to 1 ratio of acetonitrile to water (15 mL), cooled to 0° C. and then CAN (1.525 g) was added. The reaction mixture was stirred at 0° C. for 2 hours and then worked up in the usual manner to give 0.357 g.

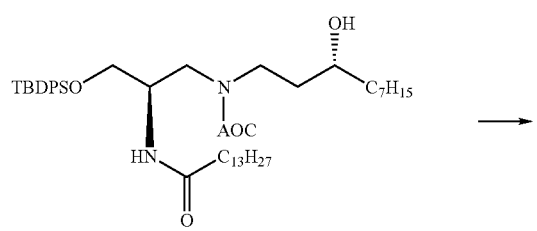

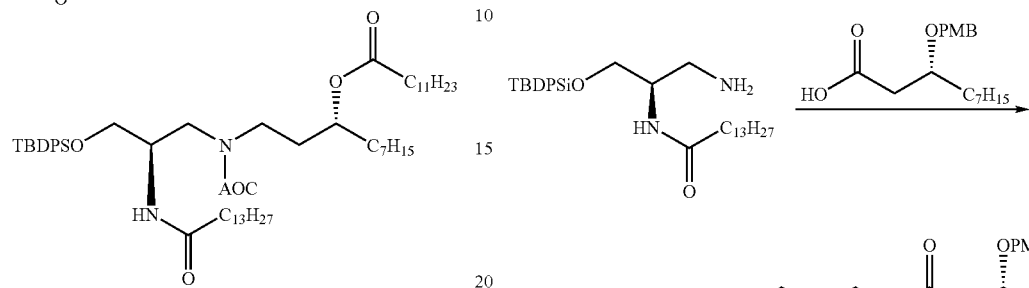

The alcohol (0.357 g) was dissolved in methylene chloride (5 mL) with lauric acid (0.184 g), EDC (0.175 g) and cooled to 0° C. 4-Dimethylaminopyridine (0.012 g) was added and the resulting mixture was stirred at room temperature for 2 hours. Work up in the usual manner gave

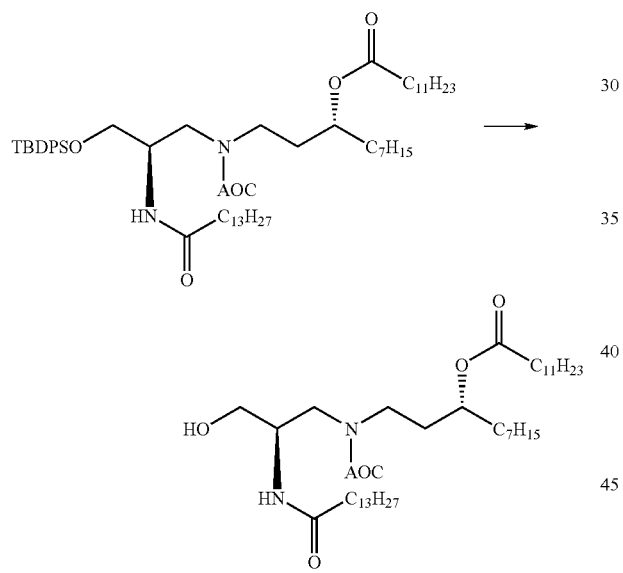

The silyl protected alcohol (0.211 g) was dissolved in THF (5 mL) with acetic acid (0.03 mL). Tetrabutylammonium fluoride (0.115 g) was added in one portion and the reaction mixture was stirred at room temperature for 16 hours. A normal work up gave 0.150 g.

This material was phosphorylated, deblocked with TFA, dimerized with phosgene and the allyl protecting groups removed with phenylsilane and palladium as descried above to give ER-804732.

Preparation of ER-804680

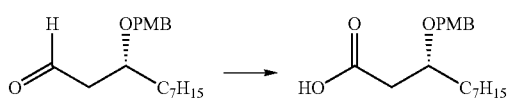

The aldehyde (1.54 g) was dissolved in THF (28 mL) and cooled to 0° C. after which time 2-methyl-2-butene (14 mL) and tert-butyl alcohol (28 mL) was added. A stirred suspension of sodium chlorite (3.70 g) and sodium trihydrogen phosphate (4.09 g) in water (42.7 mL) was added to the above mixture and stirred at 0° C. for 1.5 hours. The completed reaction was diluted with ethyl acetate (100 mL) and washed with 10% sodium bisulfite, brine, dried, concentrated and silica gel chromatographed to give 1.55 g.

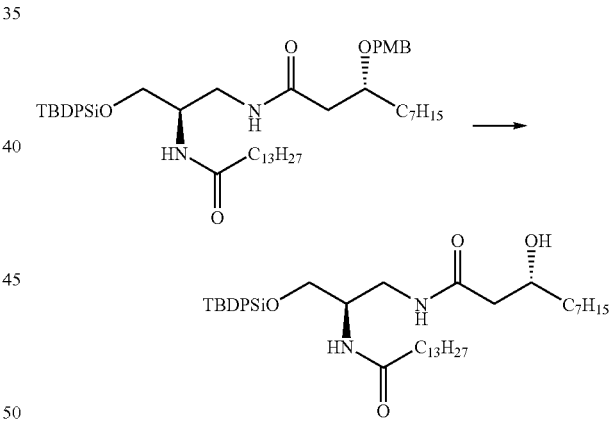

The amine (0.553 g) and acid (0.381 g) were mixed in methylene chloride (8 mL) and cooled to 0° C. after which time EDC (0.230 g) was added and the reaction mixture was stirred at room temperature for 72 hours. The usual work up gave 0.567 g.

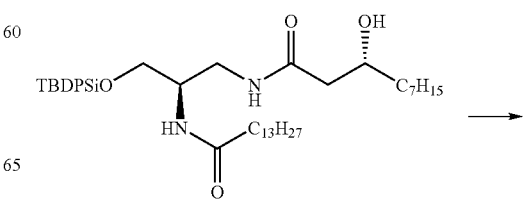

The methoxybenzyl ether (0.567 g) was dissolved in a 1 to 1 ratio of acetonitrile to water (16 mL) with methylene chloride (8 mL) and cooled to 0° C. CAN (1.53 g) was added and the reaction mixture was stirred for 1 hour after which time it was worked up in the usual manner to give the crude alcohol.

-continued

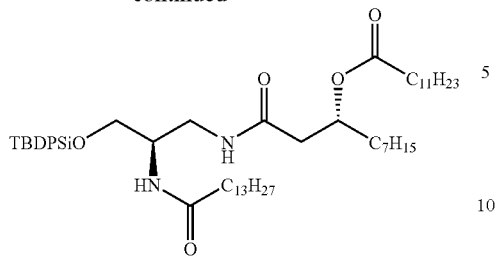

The crude alcohol from above was dissolved in methylene chloride (15 mL) with lauric acid (0.280 g) and 4 dimethylaminopyridine (0.017 g). The reaction mixture was cooled to 0° C. and EDC (0.267 g) was added in one portion after which time the reaction mixture was warmed to room temperature and stirred for 16 hours. Normal work up procedures provided 0.622 g.

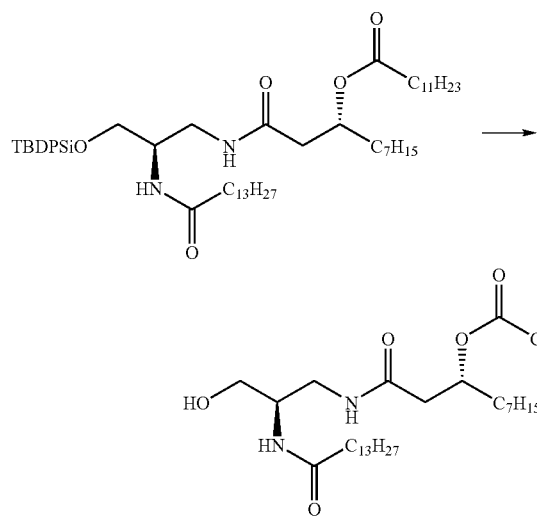

The silyl ether (0.563 g) was dissolved in THF (10 mL) with acetic acid (0.087 mL). Tert-butylammonium fluoride (0.330 g) was added and the reaction was stirred at room temperature for 16 hours. Work up in the usual manner gave 0.384 g.

This material was phosphorylated, deblocked with TFA, dimerized with phosgene and the allyl protecting groups removed with phenylsilane and palladium as described above to give ER-804780.

Preparation of ER-804679

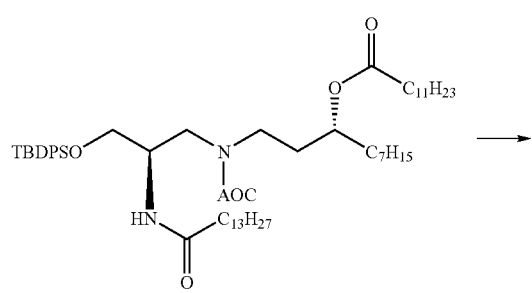

-continued

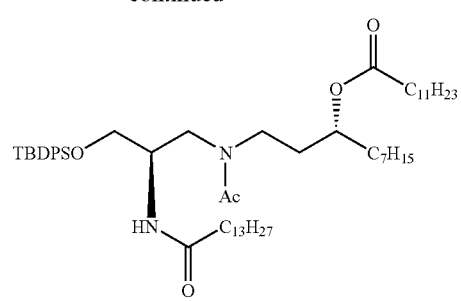

The protected secondary amine (0.071 g) was dissolved in degassed chloroform (3 mL) with phenylsilane (0.017 mL) and acetic anhydride (0.014 mL). The reaction mixture was cooled to 0° C. followed by the addition of tetrakistriphenylphosphine palladium (0) (0.002 g). The reaction mixture was warmed to room temperature and allowed to stir for 30 minutes. The completed reaction was diluted with methylene chloride, washed with water, dried, concentrated, and chromatographed to give 0.068 g.

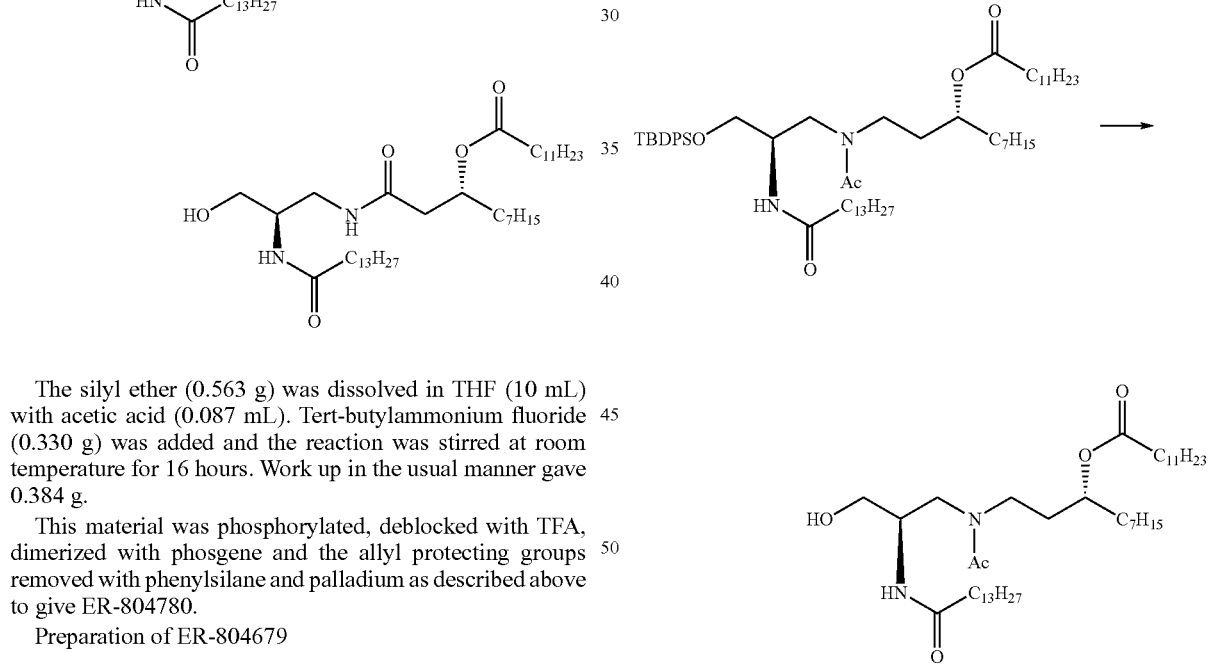

The silyl ether was deprotected in THF (5 mL) with acetic acid (0.025 mL) with the addition of tert-butylammonium fluoride (0.092 g). After stirring at room temperature for 16 hours the reaction was worked up in the usual manner to give 0.120 g.

This material was phosphorylated, deblocked with TFA, dimerized with phosgene and the allyl protecting groups removed with phenylsilane and palladium as described above to give ER-804679.

Preparation of ER-804764

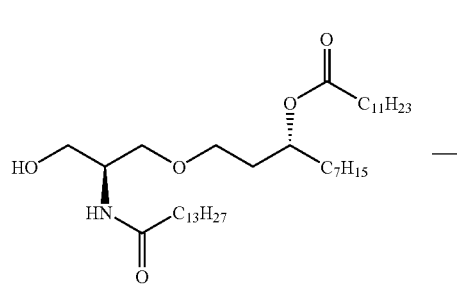

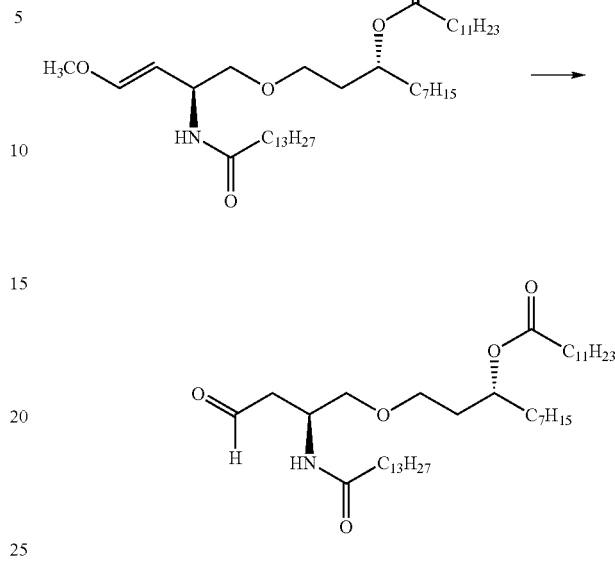

DMSO (0.33 mL) was added dropwise to oxalyl chloride (0.203 mL) in methylene chloride (10 mL) at 78° C. After stirring for 15 minutes the alcohol (0.993 g) in methylene chloride (3 mL) was added dropwise and stirred for an additional 30 minutes. Triethylamine (1.08 mL) was added dropwise, the reaction was warmed to 0° C. and quenched using saturated ammonium chloride. Purification of the crude product using silica gel chromatography with 20% ethyl acetate in hexanes gave 0.743 g.

The enol ether (0.193 g) was hydrolyzed with 57% hydrogen iodide (0.114 L) in acetonitrile (2 mL). After stirring at room temperature for 2 hours the reaction was quenched with saturated sodium bicarbonate, extracted with methylene chloride, and dried to give 0.211 g crude aldehyde.

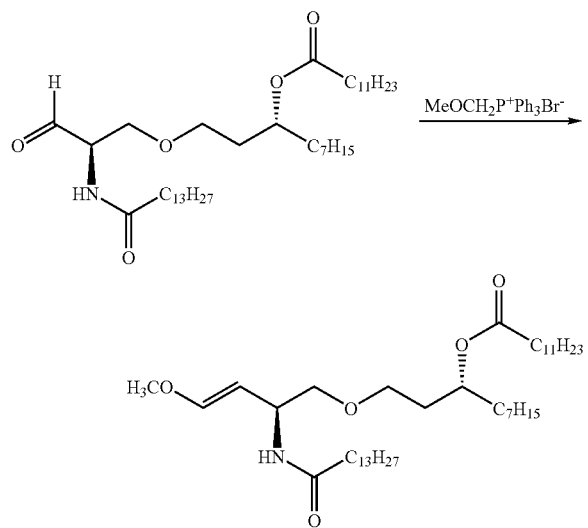

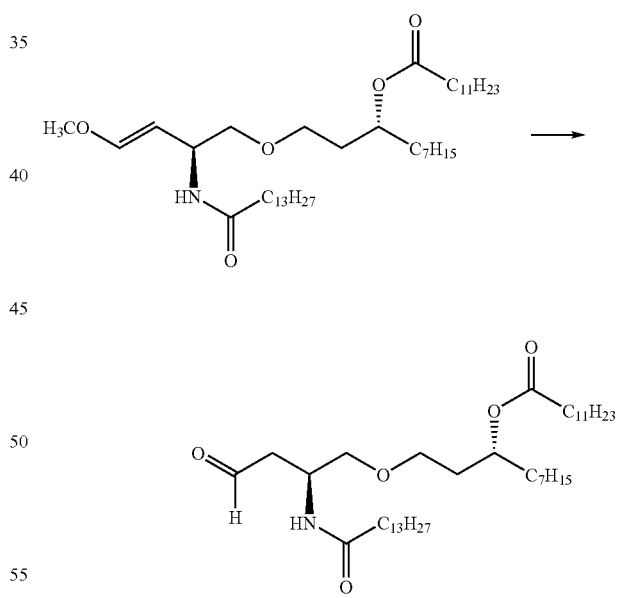

The 1.6 M n-butyl lithium in hexanes (1.5 mL) was added dropwise to the phosphonium salt (0.797 g) in THF (10 mL) at 0° C. After stirring for 30 minutes the aldehyde (0.734 g) in THF (15 mL) was added dropwise. After stirring at room temperature for one hour the reaction was worked up in the usual manner to give 0.193 g.

The crude aldehyde (0.211 g) was dissolved in methanol (3 mL) and sodium borohydride (0.033 g) was added at 0° C. After stirring for 30 minutes the reaction was diluted with water, extracted with methylene chloride, dried, concentrated and purified by silica gel chromatography to give 0.148 g.

This material was phosphorylated, deblocked with TFA, dimerized with phosgene and the allyl protecting groups removed with phenylsilane and palladium as described above to give ER-804764.

Preparation of ER-804772

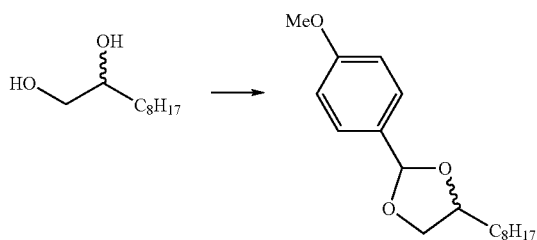

The commercially available diol (1.486 g) was mixed with the acetal (1.864 g) and para-toluenesulfonic acid (0.195 g) in DMF (10 mL). After stirring for 20 hours at room temperature under a nitrogen atmosphere, the reaction was quenched with sat. sodium bicarbonate, extracted with methylene chloride, dried and concentrated via high vacuum. Silica gel chromatography of the resultant crude product using 10% ethyl acetate in hexanes gave 2.084 g.

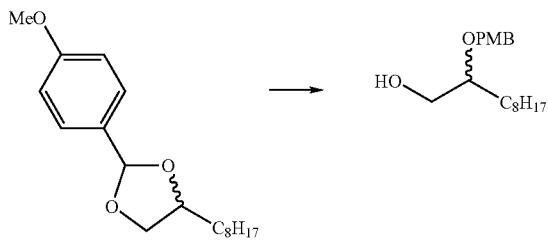

The acetal (2.084 g) was cooled to 78° C. under a nitrogen atmosphere in methylene chloride (30 mL) followed by the dropwise addition of 1.0 M DIBAL in hexanes (14.3 mL). After additional DIBAL (14 mL) was added, the reaction mixture was stirred for 1 hour, warmed to room temperature and quenched with sodium, potassium tartarate. The normal work up gave 2.1 g.

The alcohol (1.286 g) was mixed with triethylamine (0.883 g) in methylene chloride (15 µL) and cooled to 0° C. Methanesulfonyl chloride (0.575 g) was added dropwise followed by stirring for 20 minutes at 0° C. and room temperature for 2 hours. The normal work up gave 1.496 g.

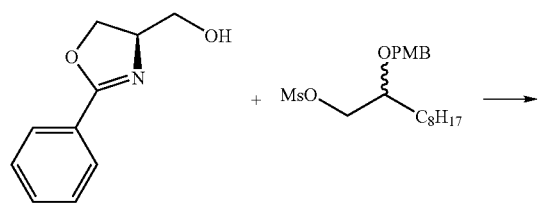

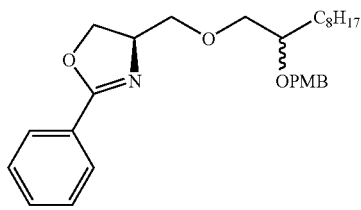

The alcohol (1.495 g) in DMF (10 mL) was added dropwise to a stirring suspension of washed 60% sodium hydride (0.257 g) in DMF (20 mL) at 0° C. After stirring for 3 hours the mesylate (0.925 g) in DMF (10 mL) was added dropwise. After stirring for an additional 3 days, the reaction was quenched and worked up in the usual manner gave 0.905 g.

As with examples provided above, the para-methoxybenzyl protecting group was hydrolyzed with CAN, the protected amino alcohol hydrolyzed using aqueous HCl then KOH, acylation of the amine with tetradecanoyl chloride, silylation of the primary alcohol with TBDPS, acylation of the secondary alcohol with dodecanoyl chloride, and hydrolysis of the silyl protecting group using TBAF to give the primary alcohol. This material was phosphorylated, deblocked with TFA, dimerized with phosgene and the allyl protecting groups removed with phenylsilane and palladium as described above to give ER-804772.

Preparation of ER-804947

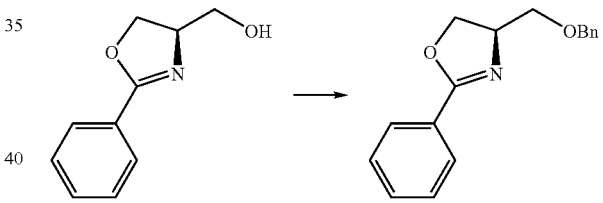

The alcohol (0.263 g) in THF (5 mL) was added dropwise to washed 60% sodium hydride (0.216 g) in DMF (2.0 mL) at room temperature under a nitrogen atmosphere. The reaction mixture was stirred for 30 minutes after which time benzyl bromide (0.272 mL) with a catalytic amount (0.05 g) of tetrabutylammonium iodide. The final reaction mixture was stirred for an additional hour after which time the mixture was quenched and worked up in the usual manner to give 0.365 g.

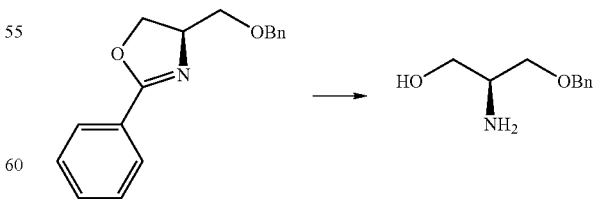

The protected aminoalcohol (0.189 g) was hydrolyzed using 4 N hydrochloric acid (2.5 mL) followed by 40% sodium hydroxide (2.5 mL) as described previously to provide 0.121 g.

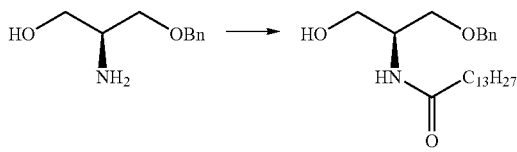

The aminoalcohol (0.121 g) was dissolved in methylene chloride (2 mL) with saturated sodium bicarbonate (2 mL). After cooling to 0° C., myristoyl chloride (0.199 mL) was added dropwise. After continued stirring for 2 hours the mixture was worked up in the usual manner and gave 0.181 g.

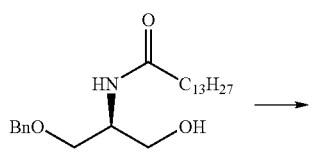

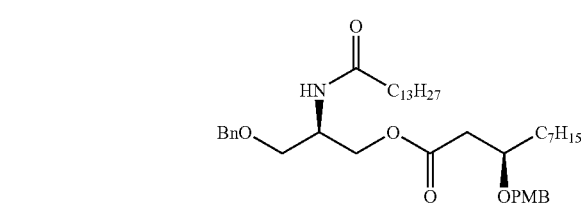

The alcohol (0.181 g) was dissolved in methylene chloride (5 mL) with the acid (0.180 g) and 1-[3-(dimethylamino)propyl]-3-ethylcarbodiimide (EDC 0.133 g). The mixture was cooled to 0° C. and 4-dimethylaminopyridine was added follow by stirring for 16 hours at room temperature. The usual work up gave 0.310 g.

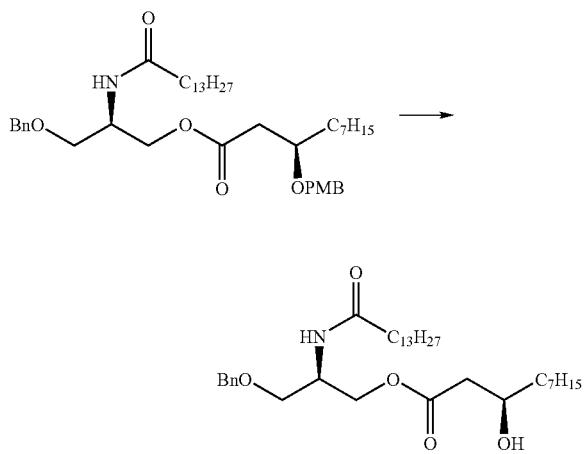

The para-methoxybenzyl ether (0.305 g) was dissolved in acetonitrile (8 mL) with water (2 mL) and cooled to 0° C. Cerium ammonium nitrate (1.110 g) was added and the reaction mixture was stirred for 2 hours after which time using the normal work up gave crude alcohol.

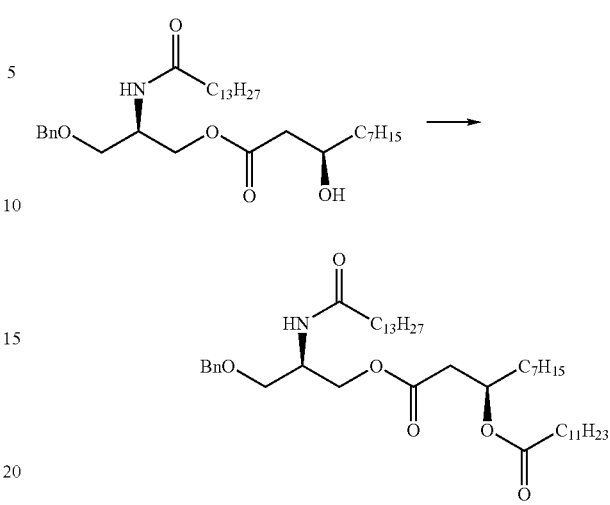

The crude alcohol was dissolved in methylene chloride (8 mL) with lauric acid (0.126 g) and 4-dimethylaminopyridine (0.011 g). After cooling to 0° C., EDC (0.119 g) was added and the mixture was stirred at room temperature for 16 hours. The usual work up gave 0.355 g.

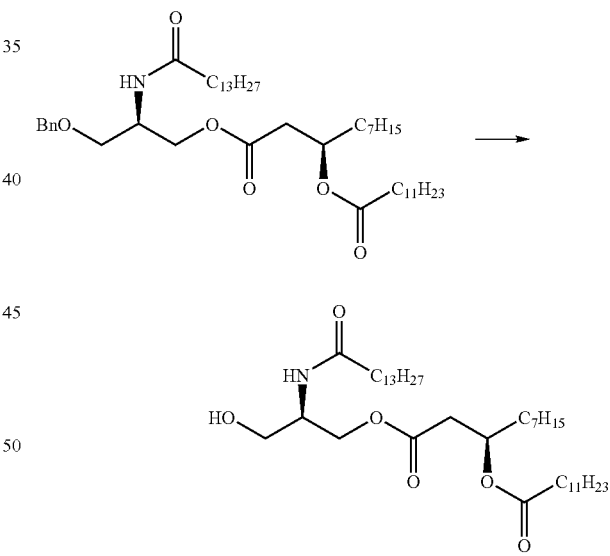

The benzyl ether (0.355 g) was dissolved in ethyl acetate (50 mL) with palladium hydroxide (0.048 g) and acetic acid (0.25 mL). The reaction mixture was placed under 50 psi of a hydrogen atmosphere and shaken for 10 hours. Work up in the usual manner gave 0.255 g.

This material was phosphorylated, deblocked with TFA, dimerized with phosgene and the allyl protecting groups removed with phenylsilane and palladium as described above to give ER-804947.

Reaction Scheme for Quarternary Amine Analogue

Persons familiar with the art can easily envision the preparation of quaternary amine compounds. As exemplified in the Scheme below, oxidation of an alcohol to an aldehyde, reductive animation with the appropriately functionalized amine, followed by protection of the ensuing secondary amine with a protecting group such as Fmoc provides the desired protected intermediate. Selective deprotection of the Boc-group on the primary amine followed by condensation with the appropriate linker such as phosgene provides the protected dimer. The final desired product can be produced by the deprotection of the secondary amine followed by dialkylation of the amine in the presence of an simple alkyl halide, such as methyl iodide. The product is purified by cation exchange chromatography using CM-Sephadex using dilute HCl as the eluting counter ion, followed by silica gel chromatography, and then anion exchange with SP-Sephadex containing the appropriate anionic counter ion using similar elution solvents as described in the previous experimentals.

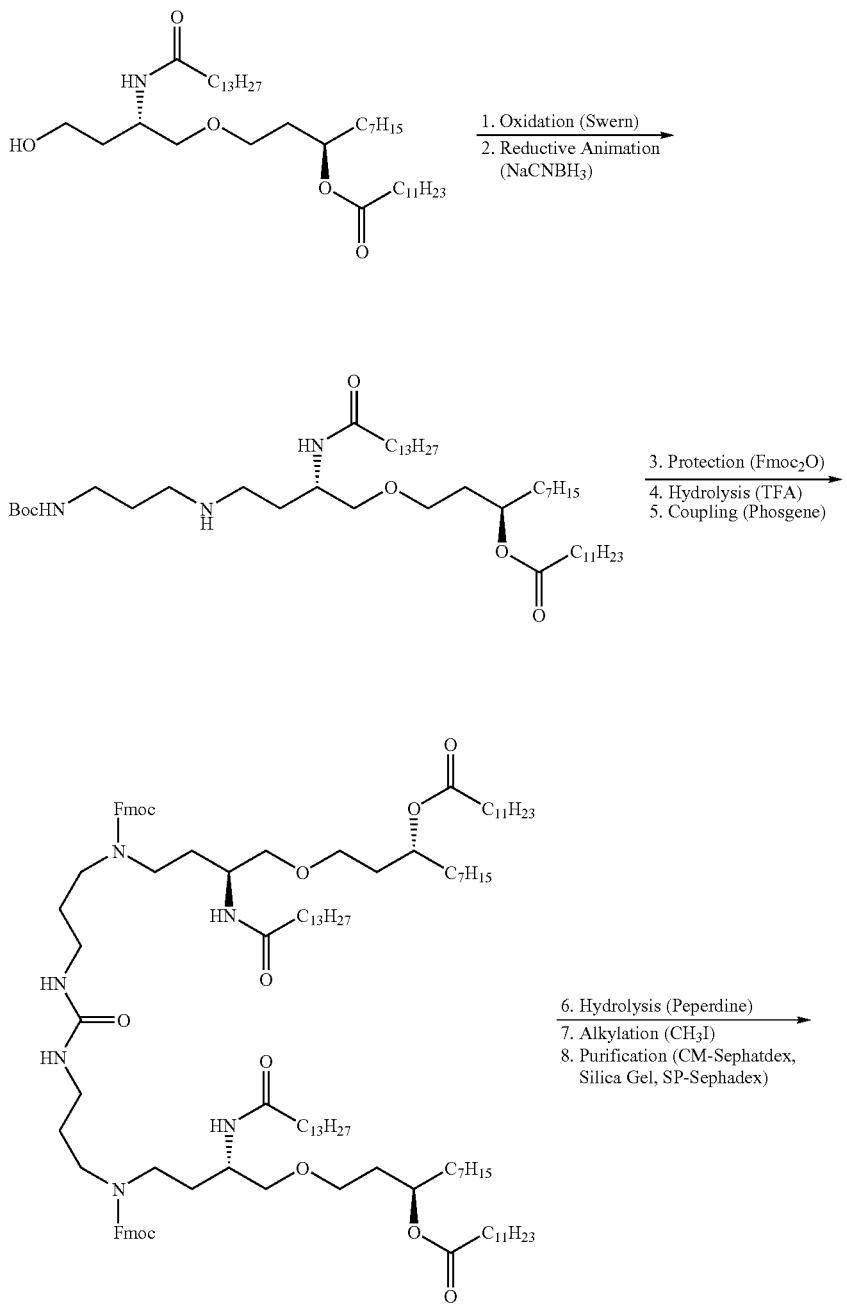

-continued

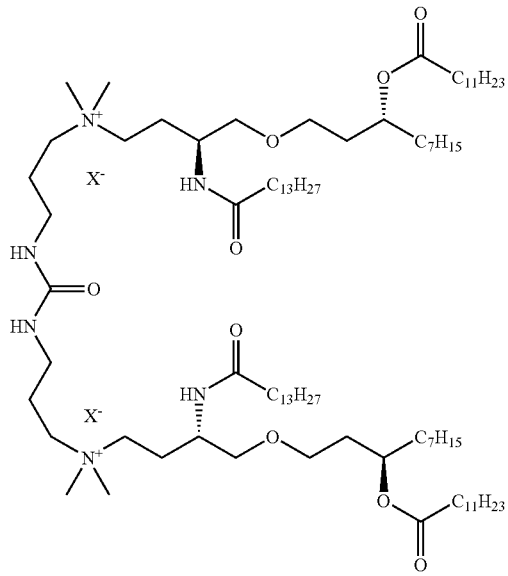

BIOLOGICAL EXAMPLES

Example 7

Induction of Cytokines (In Vitro)

E. Assays in Human Whole Blood

The most readily available human system to test compound activity on monocytes/macrophages is in whole blood. Various concentrations of compounds of the invention were added as 10× stocks in 50 µl of $Ca^{++}$, $Mg^{++}$-free Hank's balanced salt solution (HBSS) followed by 50 µl of HBSS into 400 µl of heparinized whole blood obtained from normal volunteers (18-51 years old; 110-230 lb.) into the wells of plastic assay plates, for a total volume of 500 µl/well (final concentration of whole blood was 80%). After a 3-hour incubation with gentle shaking at 37° C. in a 5% $CO_2$ atmosphere, the assay plates were centrifuged at 1000×g for 10 min. at 4° C. and plasma was drawn off and frozen at −80° C. Plasma samples were analyzed for TNF-alpha, IL-10, and IL-12 by ELISA (Genzyme Corp., Cambridge, Mass.). Each assay point was tested in triplicate.

As shown in FIG. 1, compounds such as 100, 184 and 186 stimulate blood-borne cells to release TNF-alpha. This stimulatory activity can be compared to that of 10 ng/ml endotoxin (or LPS) present in similar incubations in the same assay. As shown in Table 1, activity of compounds (tested at 10 µM) ranges from inactive (such as compound 110) to compounds demonstrating greater activity than the LPS standard.

Figure 2:
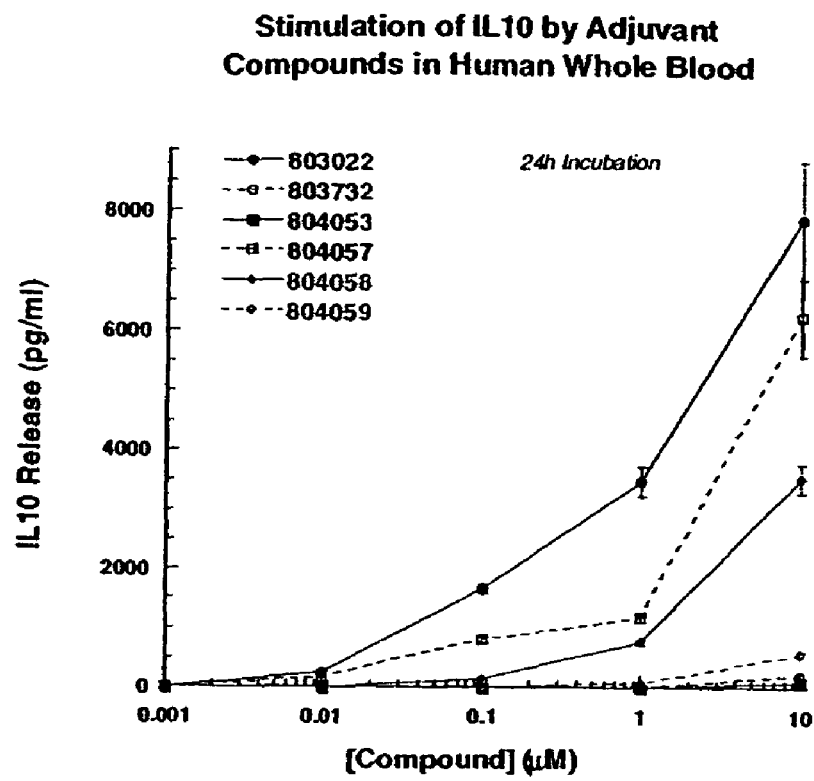
FIG. 2 is a graph that shows the results of an in vitro assay for induction of IL-10 and IL-12 release by compounds ER803022, ER803702, ER804053, ER804057, ER804058, and ER804059.
Figure 2:
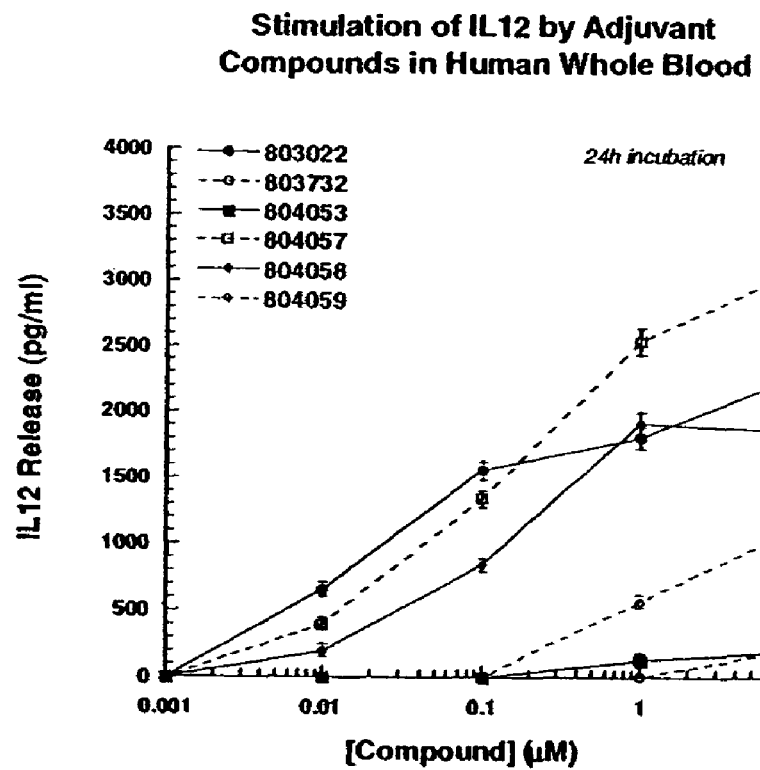

As shown in FIG. 2, compounds such as 803022, 804057, and 804058 stimulate blood-borne cells to release IL-10. Compounds 803022, 804057, 804058, and 804059 stimulate blood-borne cells to release IL-12.

As shown in Table 2, a variety of cytokines are secreted by nonadherent and adherent peripheral blood mononuclear cells (PBMC) when treated with compound 804057, including IL1-α, IL-1β, IL-6, IL-10, IL-12, Interferon-α, Interferon-γ, GM-CSF, and TNFα.

B. Cultured Human Cell Lines

Similar results can be obtained when compounds of the invention are tested in a cell-culture model. In this assay, compounds of the invention are tested for their ability to stimulate secretion of alkaline phosphatase from THP-1 cells that have been transfected with the gene for secreted alkaline phosphatase under the control of the TNF-alpha promoter, as described in detail in Goto et al., Molecular Pharmacology 49; 860-873 (1996). In this assay, however, the effects of removing serum[1]—a condition that may more-likely mimic a subcutaneous environment—can be evaluated. As shown in FIG. 2 and described in Table 1, results from these assays indicate that compounds of the invention stimulate induction of genes under the control of the TNF-alpha promoter when added to cells in the absence as well as the presence of serum.

[1] This is important to determine if serum components such as lipopolysaccharide binding protein are necessary for drug activity.

TABLE 1
| | | Whole Blood (% of LPS at 10 μM) | THP-1 cell Stimulation (% of compound 100 at 10 μM)[1] | |
|---|---|---|---|---|
| ER# | Compound | | +serum | −serum |
| | MPL Standard | 29[2] | | |
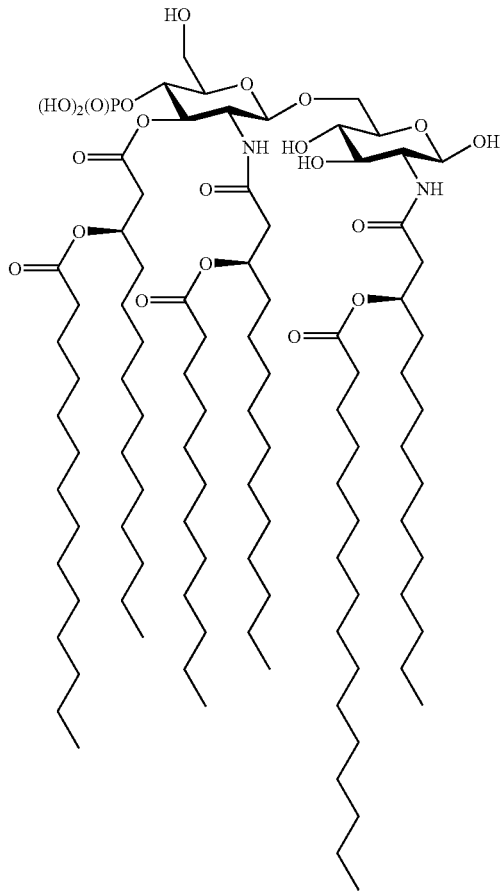

TABLE 1-continued

Stimulation of cytokine release by compounds in vitro

| ER# | Compound | Whole Blood (% of LPS at 10 μM) | THP-1 cell Stimulation (% of compound 100 at 10 μM)[1] +serum −serum |
|---|---|---|---|
| 112022 | (structure) | | $131 \pm 10.2$ (n = 6) |
| 111230 | (structure) | | 49 |

TABLE 1-continued
Stimulation of cytokine release by compounds in vitro
| ER# | Compound | Whole Blood (% of LPS at 10 μM) | THP-1 cell Stimulation (% of compound 100 at 10 μM)[1] +serum | −serum |
|---|---|---|---|---|
| 111231 | 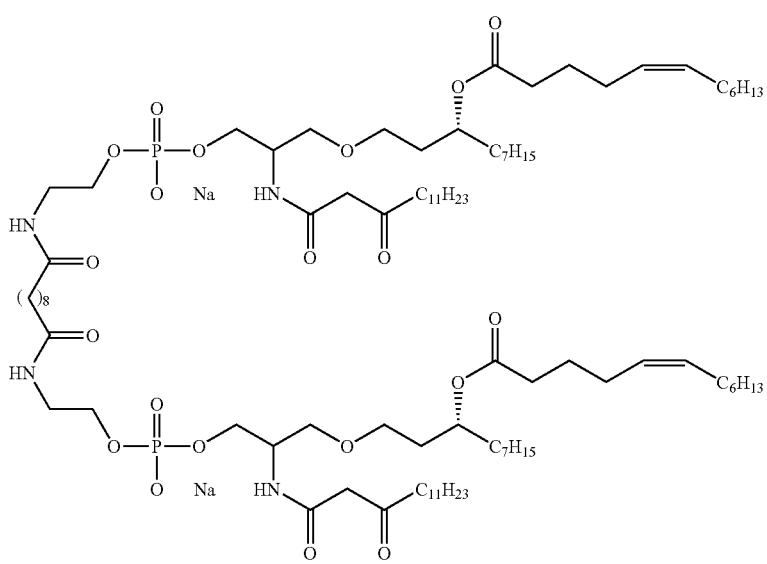 | | 17 | |
| 111232 | 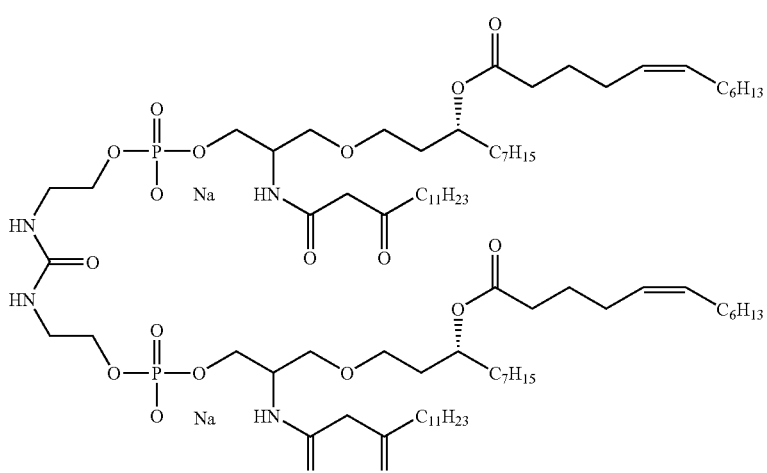 | 158 | 155 | 225 |

TABLE 1-continued

Stimulation of cytokine release by compounds in vitro

| ER# | Compound | Whole Blood (% of LPS at 10 μM) | THP-1 cell Stimulation (% of compound 100 at 10 μM)[1] +serum | −serum |
|---|---|---|---|---|
| 111233 | | | | 141 |
| 112043 | | | 0 | |
| 112044 | | | 0 | |

TABLE 1-continued
Stimulation of cytokine release by compounds in vitro
| ER# | Compound | Whole Blood (% of LPS at 10 μM) | THP-1 cell Stimulation (% of compound 100 at 10 μM)[1] +serum | −serum |
|---|---|---|---|---|
| 112047 | | | 0 | |
| 112048 | | | 0 | 24 |
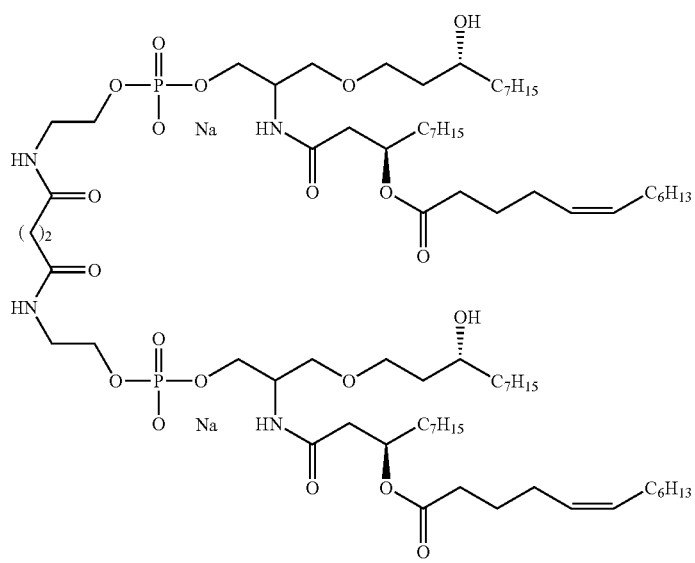

TABLE 1-continued

Stimulation of cytokine release by compounds in vitro

| ER# | Compound | Whole Blood (% of LPS at 10 μM) | THP-1 cell Stimulation (% of compound 100 at 10 μM)[(1)] +serum | −serum |
|---|---|---|---|---|
| 112049 | (structure) | | 0 | |
| 112063 | (structure) | | 0 | |

TABLE 1-continued

Stimulation of cytokine release by compounds in vitro

| ER# | Compound | Whole Blood (% of LPS at 10 μM) | THP-1 cell Stimulation (% of compound 100 at 10 μM)[1] | |
|---|---|---|---|---|
| | | | +serum | −serum |
| 112064 | | | 50 | |
| 112065 | | | 86 | |

TABLE 1-continued
Stimulation of cytokine release by compounds in vitro
| ER# | Compound | Whole Blood (% of LPS at 10 μM) | THP-1 cell Stimulation (% of compound 100 at 10 μM)[1] | |
|---|---|---|---|---|
| | | | +serum | −serum |
| 112066 | 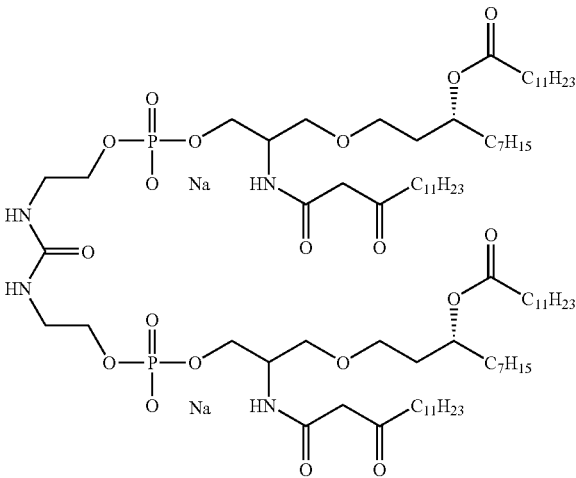 | 162 | 330 | |
| 112071 | 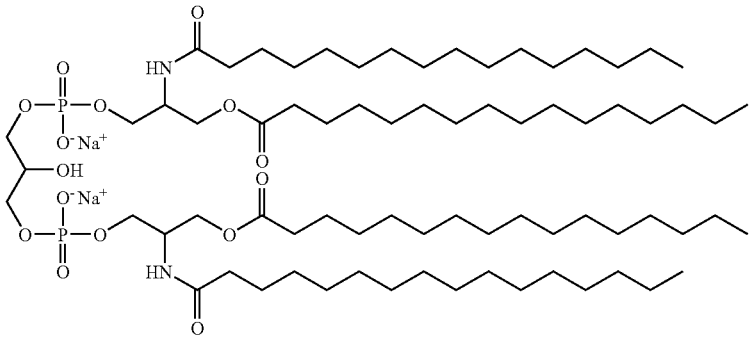 | | 0 | |
| 112072 | 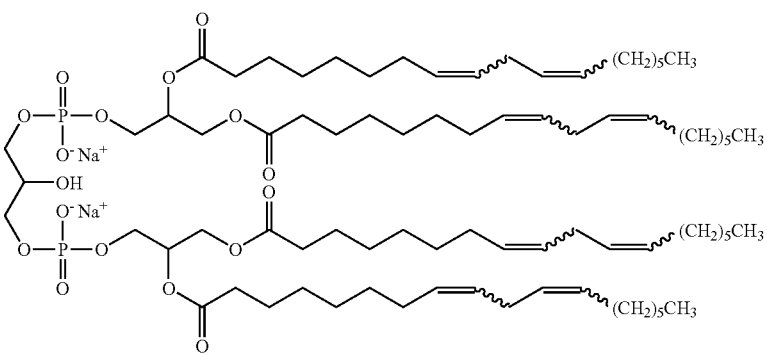 | | 0 | |

TABLE 1-continued

Stimulation of cytokine release by compounds in vitro

| ER# | Compound | Whole Blood (% of LPS at 10 μM) | THP-1 cell Stimulation (% of compound 100 at 10 μM)[1] +serum | −serum |
|---|---|---|---|---|
| 112091 | | 0 | | |
| 112092 | | 0 | | |

TABLE 1-continued

Stimulation of cytokine release by compounds in vitro

| ER# | Compound | Whole Blood (% of LPS at 10 μM) | THP-1 cell Stimulation (% of compound 100 at 10 μM)[1] +serum −serum |
|---|---|---|---|
| 112093 | | 0 | |
| 112098 | | 0 | |

TABLE 1-continued

Stimulation of cytokine release by compounds in vitro

| ER# | Compound | Whole Blood (% of LPS at 10 μM) | THP-1 cell Stimulation (% of compound 100 at 10 μM)[1] | |
|---|---|---|---|---|
| | | | +serum | −serum |
| 112049 | | | 0 | |
| 112100 | | | 0 | |

TABLE 1-continued
Stimulation of cytokine release by compounds in vitro
| ER# | Compound | Whole Blood (% of LPS at 10 μM) | THP-1 cell Stimulation (% of compound 100 at 10 μM)[1] +serum | -serum |
|---|---|---|---|---|
| 112859 | 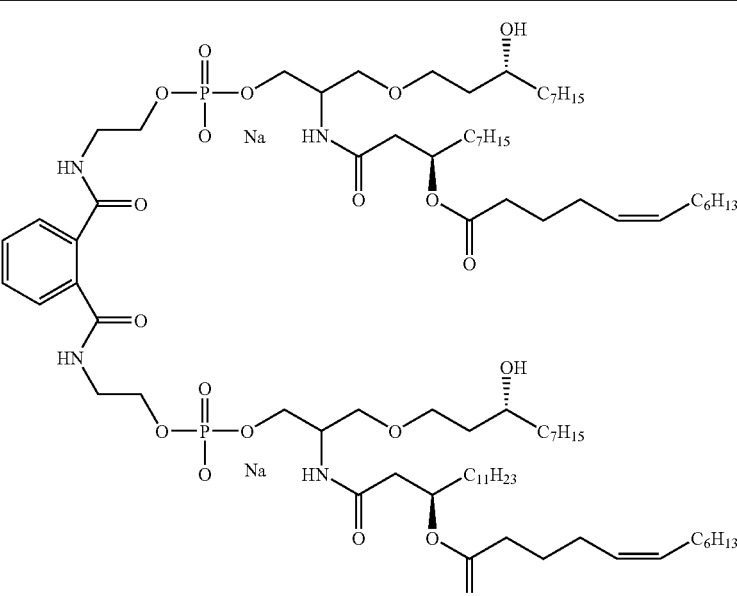 | | 0 | |
| 112860 | 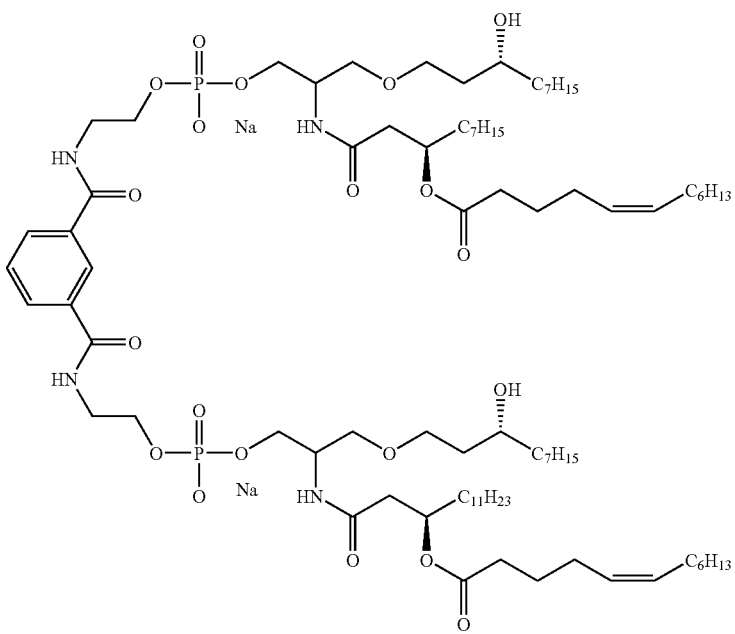 | | 0 | |

TABLE 1-continued

Stimulation of cytokine release by compounds in vitro

| ER# | Compound | Whole Blood (% of LPS at 10 μM) | THP-1 cell Stimulation (% of compound 100 at 10 μM)[1] | |
|---|---|---|---|---|
| | | | +serum | −serum |
| 112861 | | 0 | | |
| 113634 | | 0 | | |

TABLE 1-continued

Stimulation of cytokine release by compounds in vitro

| ER# | Compound | Whole Blood (% of LPS at 10 μM) | THP-1 cell Stimulation (% of compound 100 at 10 μM)[1] +serum | −serum |
|---|---|---|---|---|
| 113635 | | 0 | | |
| 113643 | | 0 | | |

TABLE 1-continued

Stimulation of cytokine release by compounds in vitro

| ER# | Compound | Whole Blood (% of LPS at 10 μM) | THP-1 cell Stimulation (% of compound 100 at 10 μM)[1] | |
|---|---|---|---|---|
| | | | +serum | −serum |
| 113644 | | 0 | | |
| 113651 | | 133 ± 4.4 (n = 4) | 215 | 254 |

TABLE 1-continued
Stimulation of cytokine release by compounds in vitro
| ER# | Compound | Whole Blood (% of LPS at 10 μM) | THP-1 cell Stimulation (% of compound 100 at 10 μM)[1] | |
|---|---|---|---|---|
| | | | +serum | −serum |
113665
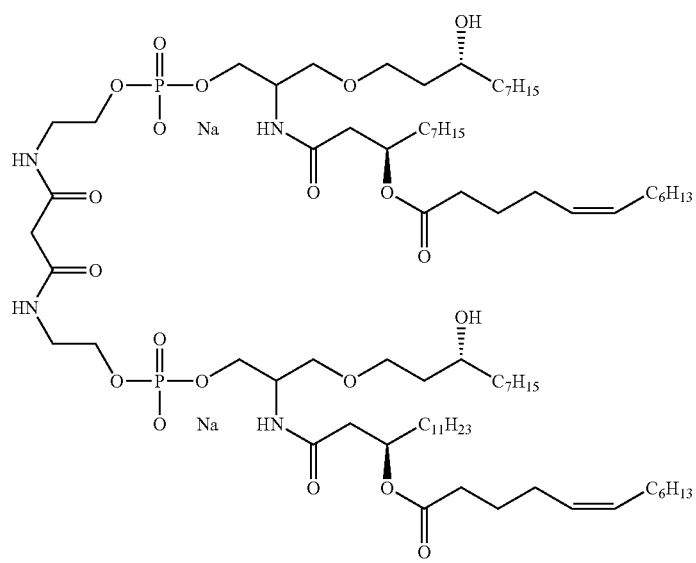
113666
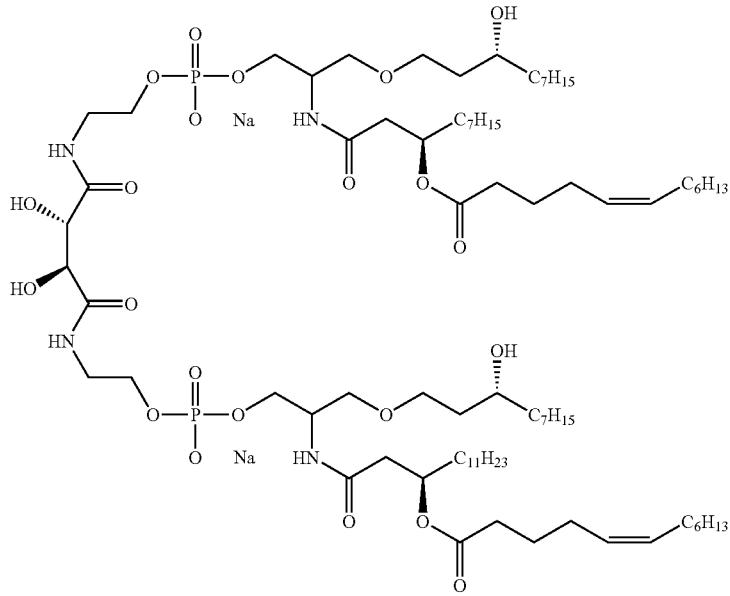

TABLE 1-continued
Stimulation of cytokine release by compounds in vitro
| ER# | Compound | Whole Blood (% of LPS at 10 μM) | THP-1 cell Stimulation (% of compound 100 at 10 μM)[1] | |
|---|---|---|---|---|
| | | | +serum | −serum |
| 118023 | 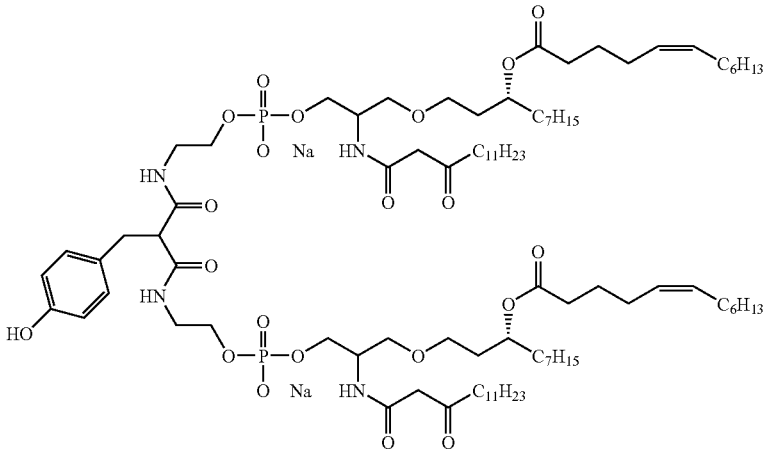 | | 63 | |
| 019772 | 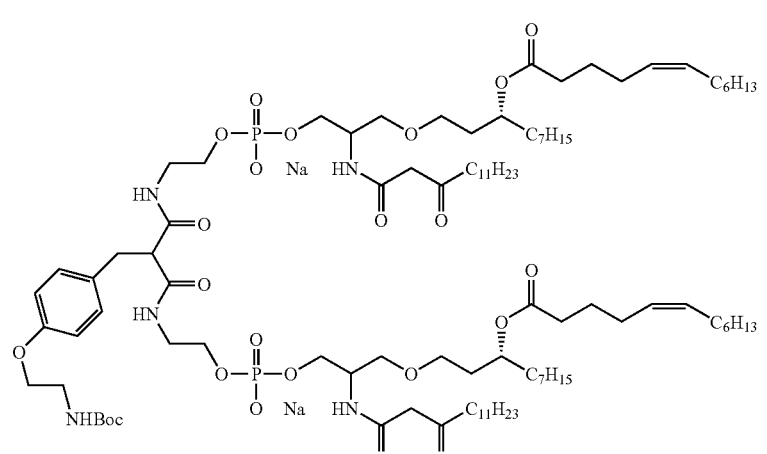 | | 69 | |

TABLE 1-continued

Stimulation of cytokine release by compounds in vitro

| ER# | Compound | Whole Blood (% of LPS at 10 μM) | THP-1 cell Stimulation (% of compound 100 at 10 μM)[1] | |
|---|---|---|---|---|
| | | | +serum | −serum |
| 118989 | (structure) | 159 | | |
| 118999 | (structure) | 105 | | |

TABLE 1-continued

Stimulation of cytokine release by compounds in vitro

| ER# | Compound | Whole Blood (% of LPS at 10 μM) | THP-1 cell Stimulation (% of compound 100 at 10 μM)[1] +serum −serum |
|---|---|---|---|
| 119000 | | 60 | |
| 119001 | | 113 | |

TABLE 1-continued
Stimulation of cytokine release by compounds in vitro
| ER# | Compound | Whole Blood (% of LPS at 10 μM) | THP-1 cell Stimulation (% of compound 100 at 10 μM)[1] +serum  −serum |
|---|---|---|---|
| 118949 | 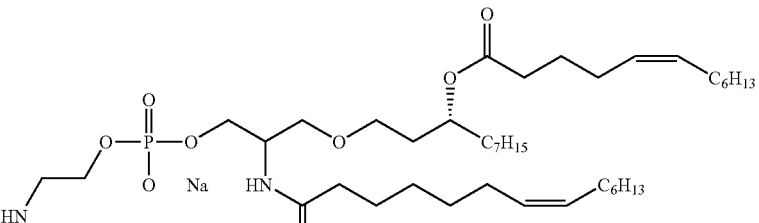 | 138 | |
| 119327 | 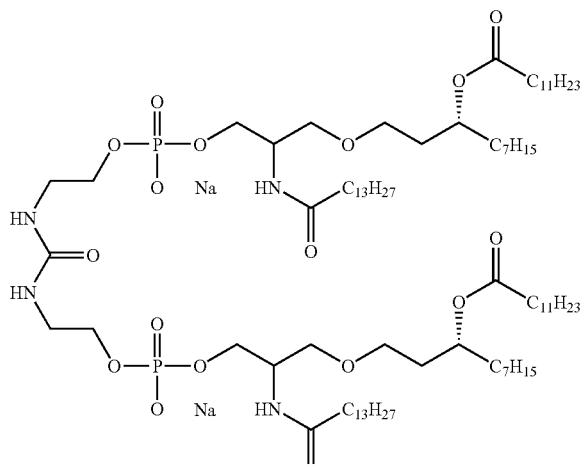 | 165 ± 33 (n = 3) | |

TABLE 1-continued
Stimulation of cytokine release by compounds in vitro
| ER# | Compound | Whole Blood (% of LPS at 10 μM) | THP-1 cell Stimulation (% of compound 100 at 10 μM)[1] +serum / −serum |
|---|---|---|---|
| 119328 | 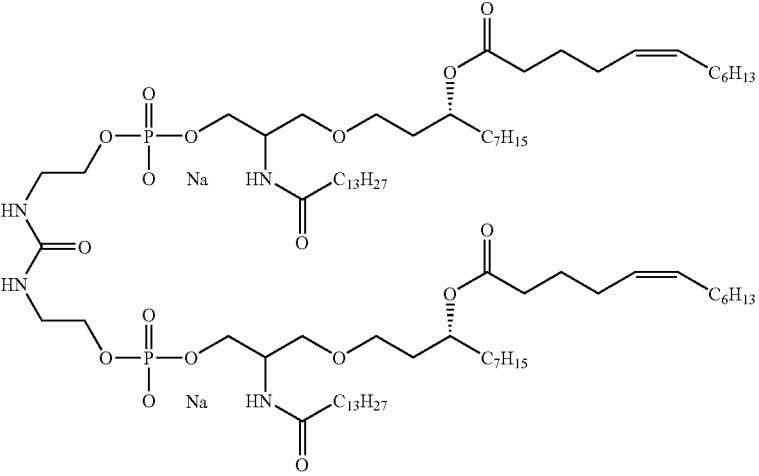 | 181 ± 42 (n = 3) | |
| 119329 | 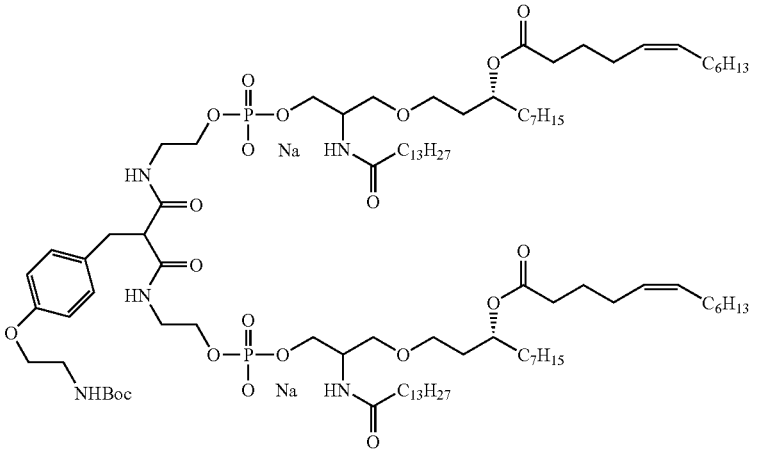 | 2 ± 2 (n = 2) | |
| 119521 | 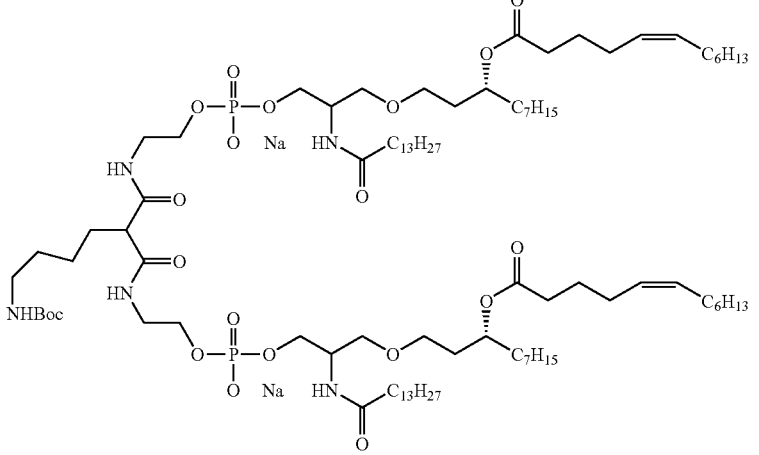 | | 103 |

TABLE 1-continued

Stimulation of cytokine release by compounds in vitro

| ER# | Compound | Whole Blood (% of LPS at 10 μM) | THP-1 cell Stimulation (% of compound 100 at 10 μM)[1] +serum | −serum |
|---|---|---|---|---|
| 119522 | | 129 | | |
| 119523 | | 176 | | |
| 803022 | | 164 | | |

TABLE 1-continued

Stimulation of cytokine release by compounds in vitro

| ER# | Compound | Whole Blood (% of LPS at 10 μM) | THP-1 cell Stimulation (% of compound 100 at 10 μM)[1] +serum / −serum |
|---|---|---|---|
| 803045 | *(structure)* | | 65 |
| 803056 | *(structure)* | | 151 ± 42 |

TABLE 1-continued

Stimulation of cytokine release by compounds in vitro

| ER# | Compound | Whole Blood (% of LPS at 10 μM) | THP-1 cell Stimulation (% of compound 100 at 10 μM)[1] +serum −serum |
|---|---|---|---|
| 803058 | | | 149 ± 37 (n = 2) |
| 803059 | | | 2 |

TABLE 1-continued

Stimulation of cytokine release by compounds in vitro

| ER# | Compound | Whole Blood (% of LPS at 10 µM) | THP-1 cell Stimulation (% of compound 100 at 10 µM)[1] +serum | −serum |
|---|---|---|---|---|
| 803592 | 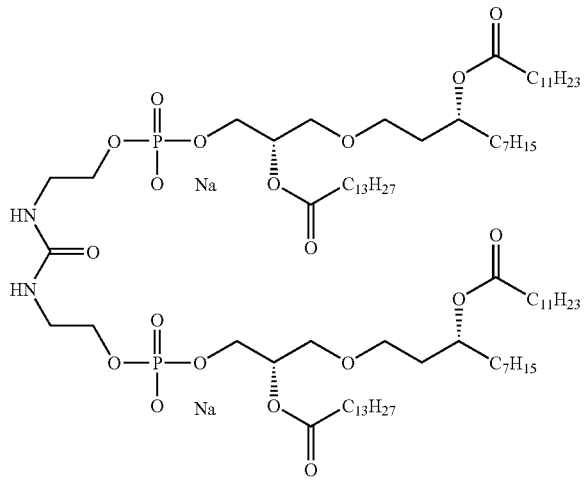 | | 15 | |

[1]Response in each assay was compared to 10 µM compound 100 internal standard which typically induced 2-3 fold increase in TNF-alpha PLAP expression over basal.
[2]Tested at @ 5.8 µM.

TABLE 2

Cytokines Resulting from Stimualtion of Human PBMC by ER804057

| Cytokine | Cell population | Length of Stimulation (hrs) | Cytokine Production (pg/mL) | |
|---|---|---|---|---|
| | | | Medium | ER804057 (50 nM) |
| IL-1α | Nonadherent PBMC | 24 hrs | 4 | 108 |
| | Adherent PBMC | 4 hrs | 0 | 8 |
| IL-1β | Nonadherent PBMC | 24 hrs | 4 | 431 |
| | Adherent PBMC | 4 hrs | 0 | 55 |
| IL-6 | Adherent PBMC | 4 hrs | <2 | 551 |
| IL-10 | Adherent PBMC | 24 hrs | 17 | 175 |
| IL-12p70 | Whole blood | 24 hrs | 0 | 1332 |
| Interferon-α | Adherent PBMC | 4 hrs | 61 | 345 |
| | Adherent PBMC | 48 hrs | 5 | 175 |
| Interferon-γ | Nonadherent PBMC | 24 hrs | 4 | 331 |
| GM-CSF | Nonadherent PBMC | 24 hrs | 14 | 353 |
| TNF-α | Adherent PBMC | 4 hrs | 7 | 3627 |

C. Murine Splenocytes

The ability of compounds to stimulate cytokine release from splenocytes can be assessed in a mouse model. Spleen cells harvested from C57BL/6 mice are cultured for 24 hours in RPMI 1640 cell culture medium containing 5% FBS, 1 mM sodium pyruvate, 2 mM L-glutamine, 100 U/ml penicillin/streptomycin and 50 µM beta-mercaptoethanol, various concentrations of test compound for 20-24 hours, after which the cell culture supernatant is tested for the presence of cytokines.

Figure 3:
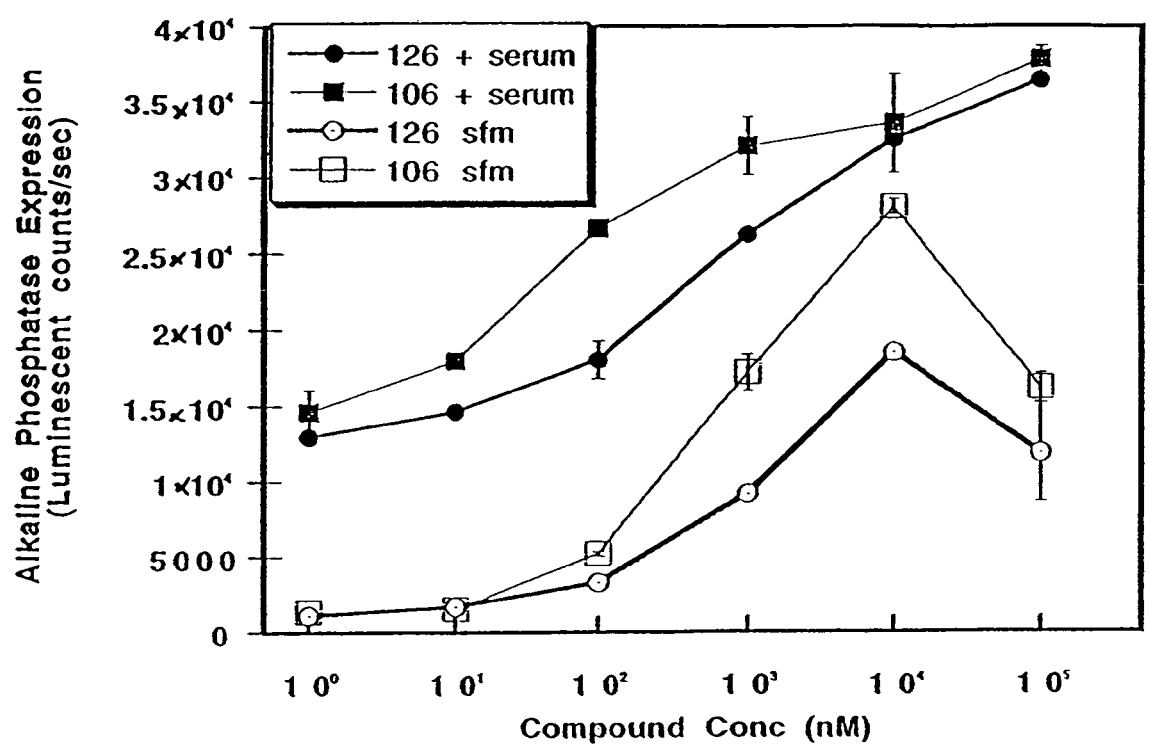
FIG. 3 is a graph that shows stimulation of alkaline phosphatase expression from an inducible reporter construct with the TNF promoter (TNF-PLAP) in THP-1 cells by compounds 106 and 126 in the absence and presence of 10% serum.
Figure 4:
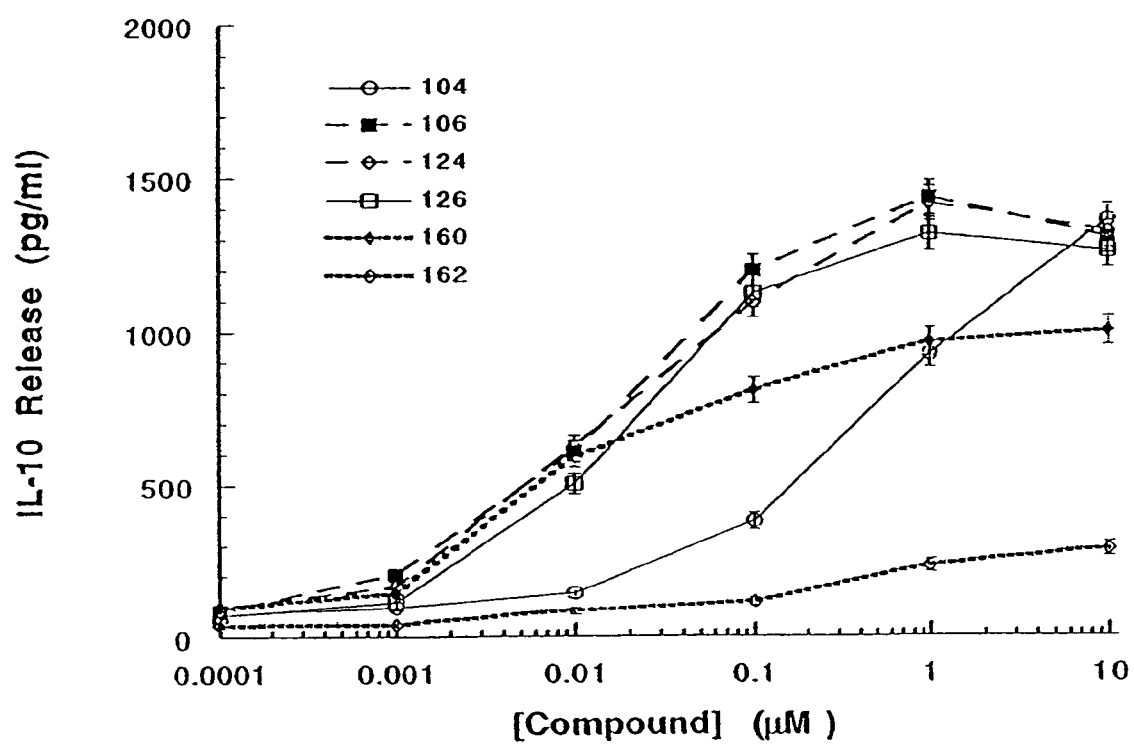
FIG. 4 is a graph showing stimulation of IL-10 release from normal mouse splenocytes by compounds 104, 106, 124, 126, 160, and 162 of the invention.
Figure 5:
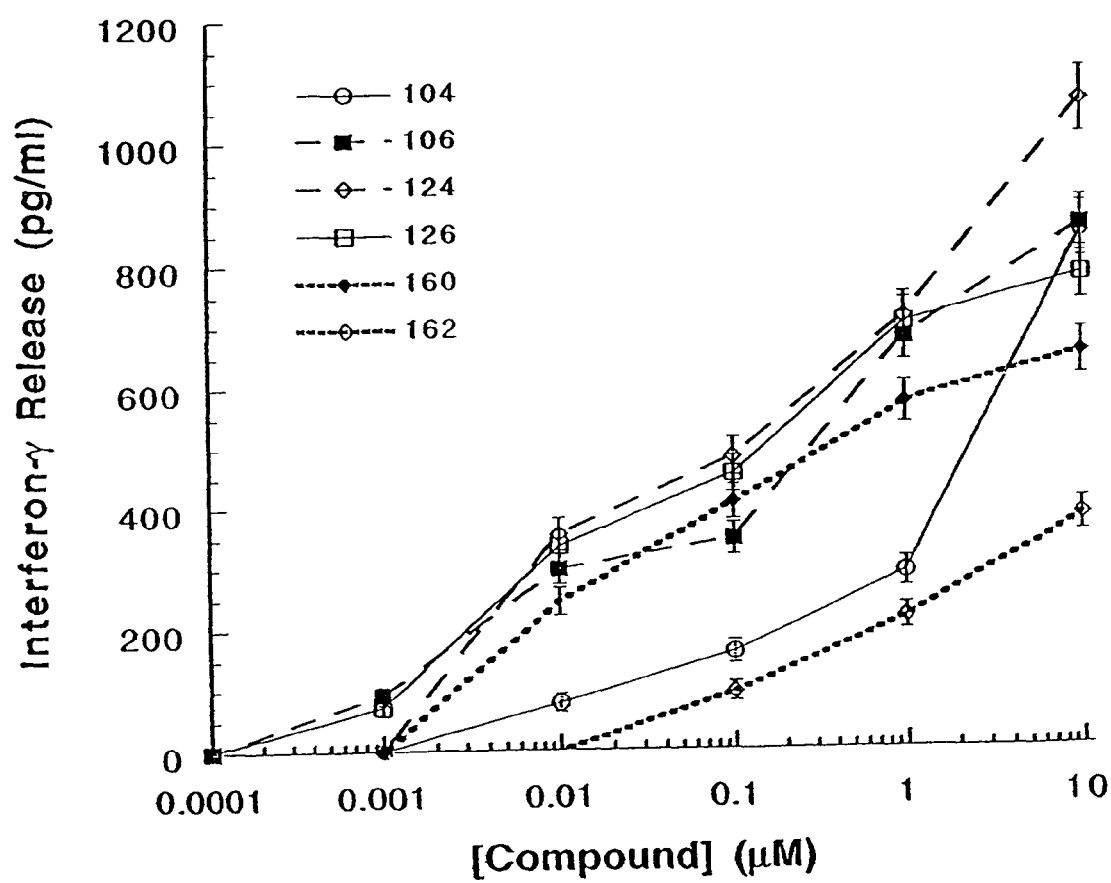
FIG. 5 is a graph showing stimulation of interferon-gamma release from normal mouse splenocytes by compounds 104, 106, 124, 126, 160, and 162 of the invention.

Spleen cells harvested from mice were cultured for 24 house with test compound and the supernatant was tested for release of cytokines. As shown in FIGS. 3 and 4, the release of cytokines such as IL-10 and interferon-gamma from splenocytes is stimulated by compounds such as 104, 106, 124, 160, and 162.

These assays utilized a heterogeneous population of cells derived from the spleen. This makes it possible that cytokine induction can be caused both by direct effects of test compounds on cells and through more indirect stimulation of cytokine "cascades" where the release of a cytokine by one type of cell can induce release of other cytokines in other cells present in the same media. It is possible that this cytokine "milieu" is responsible for part of this robust immune responses.

D. Tolerization to TLR Family Ligands

Figure 6:
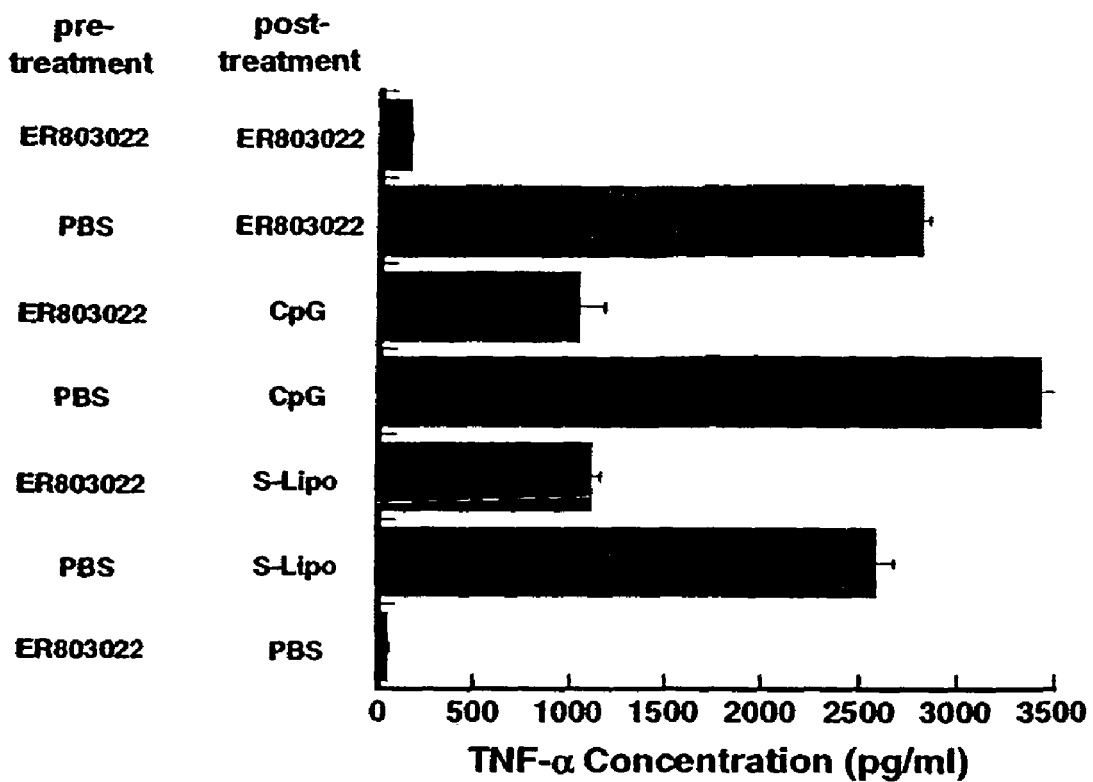
FIG. 6 is a graph showing stimulation of TNF-alpha release in response to TLR2, TLR4, and TLR9 ligands by untreated mouse macrophage cells and mouse macrophage cells pretreated with the immunomodulatory compound ER803022.

Preliminary experiments were carried out to determine dosage ranges for the different ligands so as to assay for comparable levels of secreted TNFα. Cells of the mouse macrophage line RAW 264.7 were plated in RPMI 1640 complete culture medium (10% fetal bovine serum, 1 mM sodium pyruvate, 2 mM L-glutamine, 100 U/mL penicillin/streptomycin and 50 µM β-mercaptoethanol). Cells were treated for 24 hours with the TLR4 ligand ER-803022 at 0.1 µg/mL by addition of a concentrated stock solution. Negative control cells were treated with an equivalent volume of PBS. After 24 hours, cells were washed twice in RPMI 1640 complete medium and incubated in medium alone for 3 hours. Cultures were then restimulated with the following synthetic TLR ligands: lipopeptide (S-lipo, a ligand for TLR2) at 0.1 µg/mL, ER-803022 at 0.1 µg/mL, a mouse CpG oligonucleotide of the sequence TCCATGACGTTCCTGATGCT (a ligand of murine TLR9) at 0.5 µg/mL, or PBS. Supernatants were taken at 3 and 4 hours nad cytokine levels were determined by ELISA. As shown in FIG. 6, mouse macrophage cells that were treated with an initial exposure to the immunomodulatory compound ER803022 released less TNF-alpha upon subsequent exposure to ER803022 compared to those that were not pretreated. In addition, cells that were pretreated with ER803022 displayed diminished release of TNF-alpha in response to exposure to the TLR2 ligand S-lipoprotein, and in response to the CpG oligonucleotide, a TLR9 ligand.

TABLE 3

WB ED$_{50}$ vs. % of LPS at 10 ng/ml

| ER# | Structure | WB ED$_{50}$ vs LPS @ 10 ng/ml |
|---|---|---|
| MPL Standard | 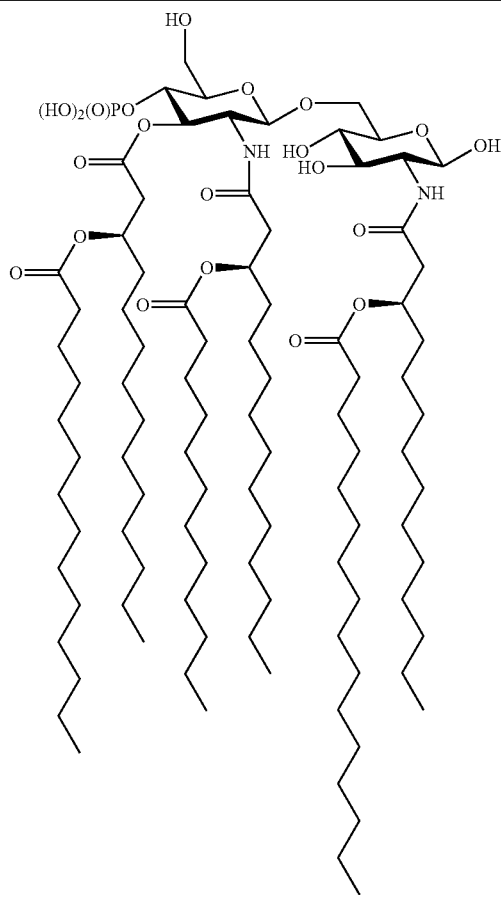 | >>10 μm |
| 112022 | 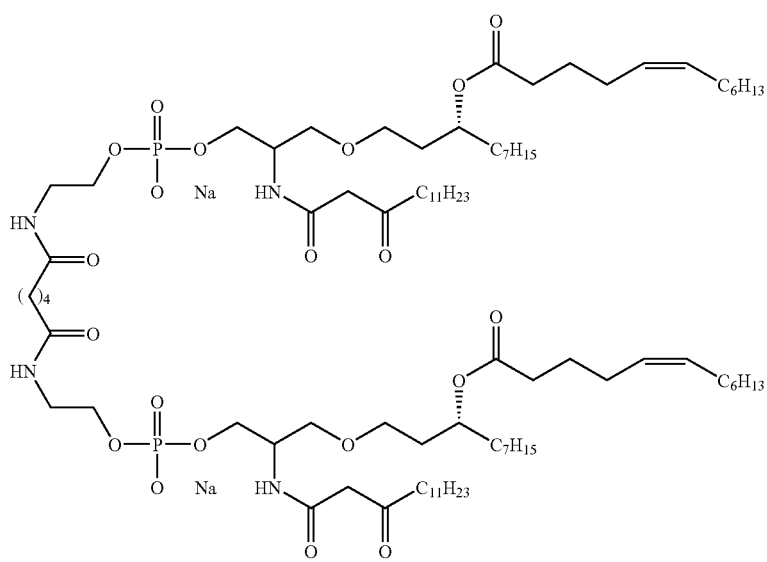 | 0.696 μm |

TABLE 3-continued

WB ED$_{50}$ vs. % of LPS at 10 ng/ml

| ER# | Structure | WB ED$_{50}$ vs LPS @ 10 ng/ml |
|---|---|---|
| 111230 | 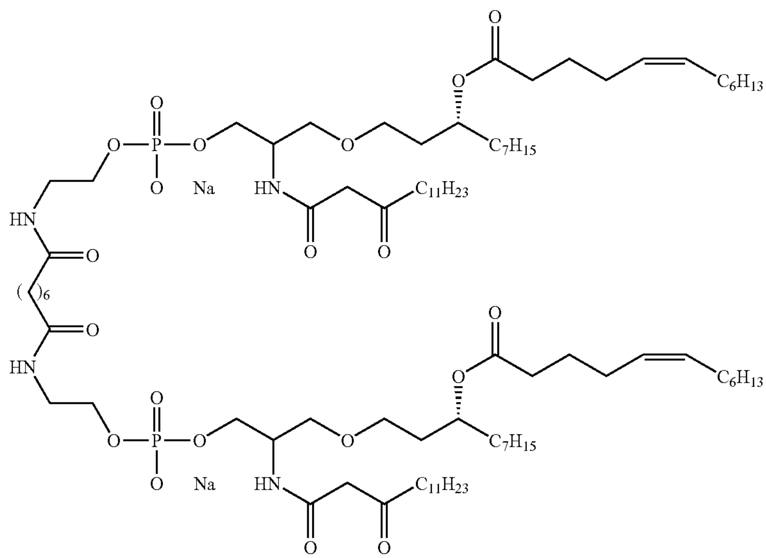 | |
| 111231 | 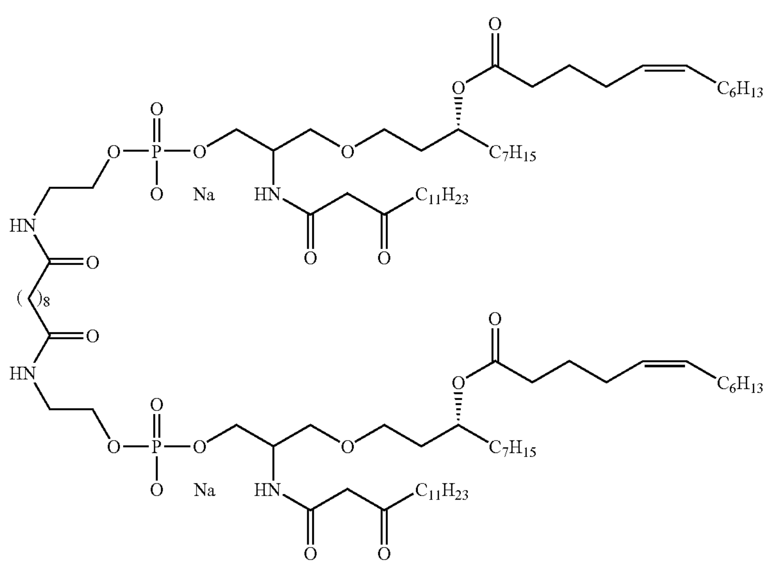 | 0.29 µm |

TABLE 3-continued
WB ED$_{50}$ vs. % of LPS at 10 ng/ml
| ER# | Structure | WB ED$_{50}$ vs LPS @ 10 ng/ml |
|---|---|---|
| 111232 | 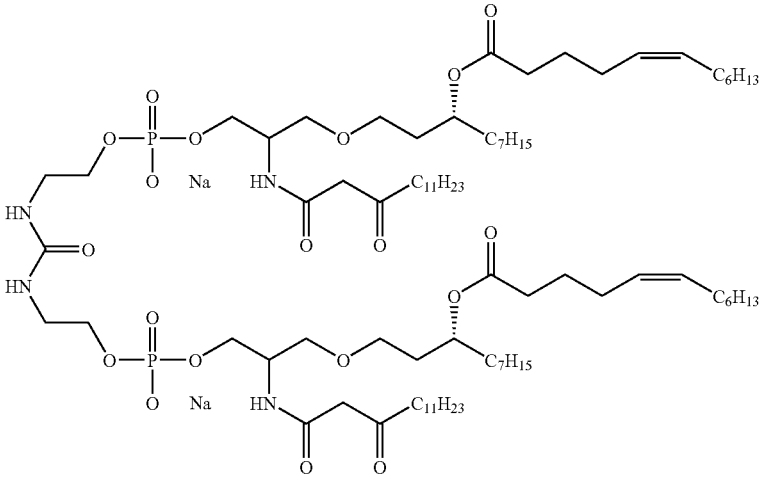 | |
| 111233 | 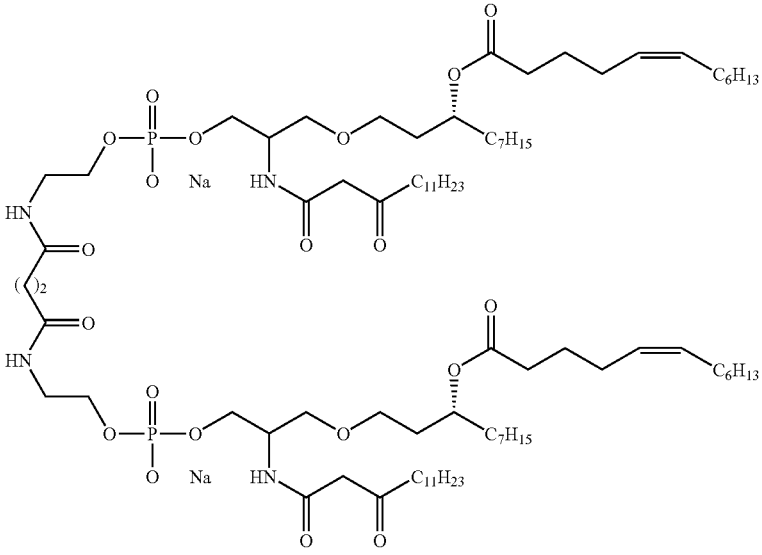 | |
| 112043 | 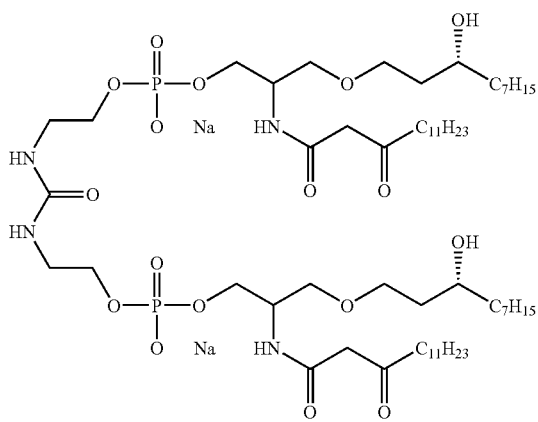 | |

TABLE 3-continued

WB ED$_{50}$ vs. % of LPS at 10 ng/ml

| ER# | Structure | WB ED$_{50}$ vs LPS @ 10 ng/ml |
|---|---|---|
| 112044 | 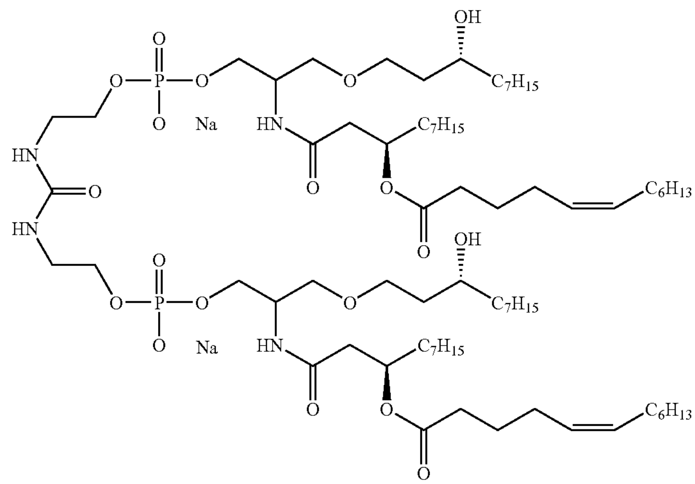 | |
| 112047 | 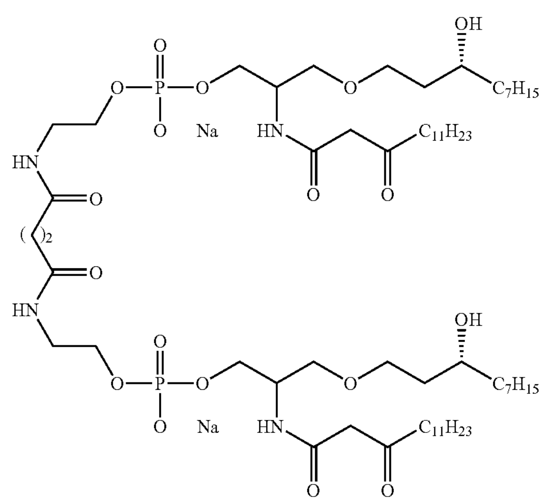 | |

TABLE 3-continued

WB ED$_{50}$ vs. % of LPS at 10 ng/ml

| ER# | Structure | WB ED$_{50}$ vs LPS @ 10 ng/ml |
|---|---|---|
| 112048 | 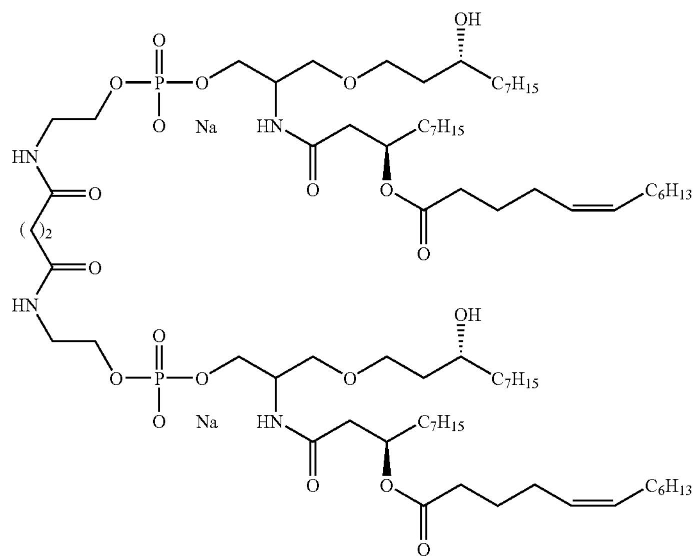 | >>10 μM |
| 112049 | 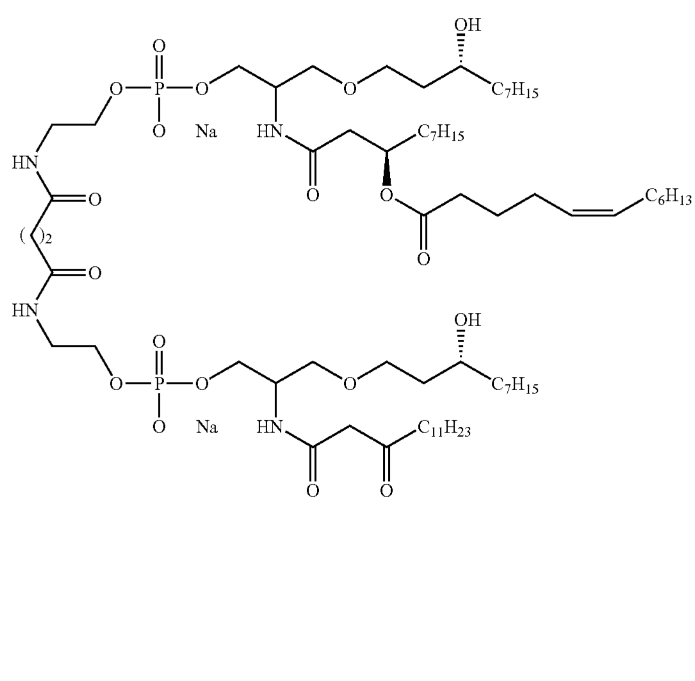 | |

TABLE 3-continued
WB ED$_{50}$ vs. % of LPS at 10 ng/ml
| ER# | Structure | WB ED$_{50}$ vs LPS @ 10 ng/ml |
|---|---|---|
112063
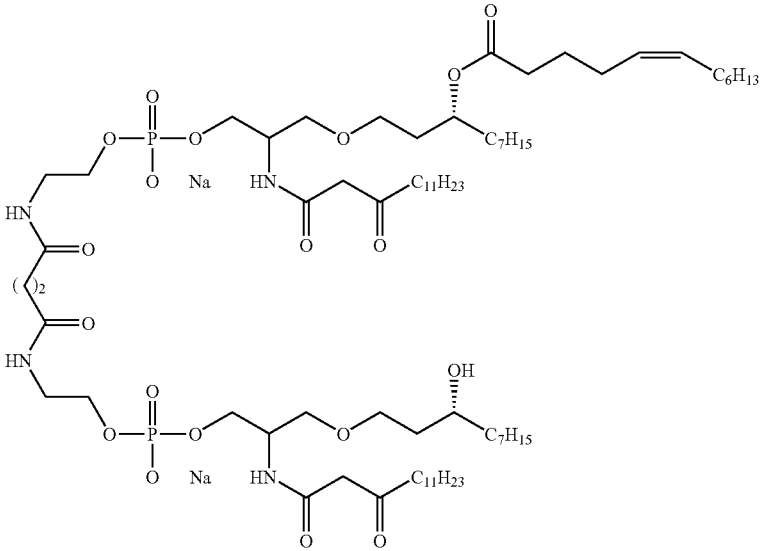
112064
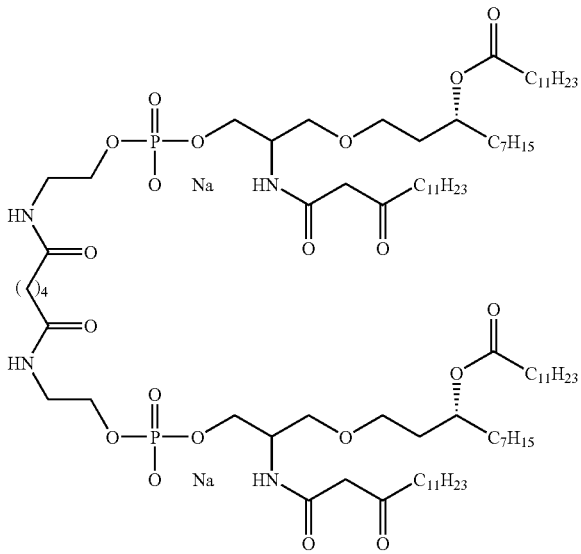

TABLE 3-continued

WB ED$_{50}$ vs. % of LPS at 10 ng/ml

| ER# | Structure | WB ED$_{50}$ vs LPS @ 10 ng/ml |
|---|---|---|
| 112065 | 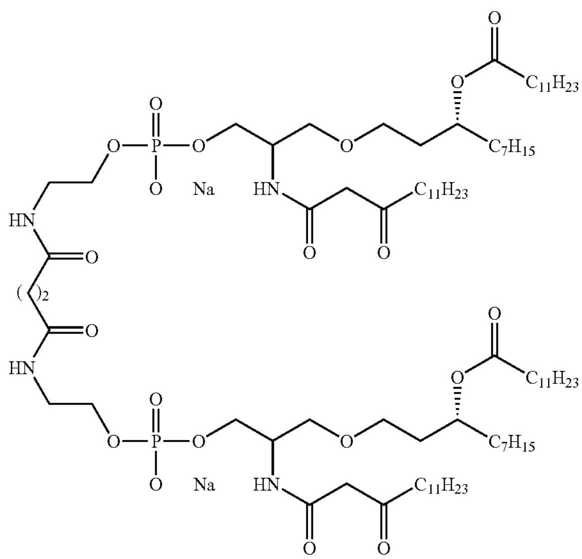 | 0.25 µM |
| 112066 | 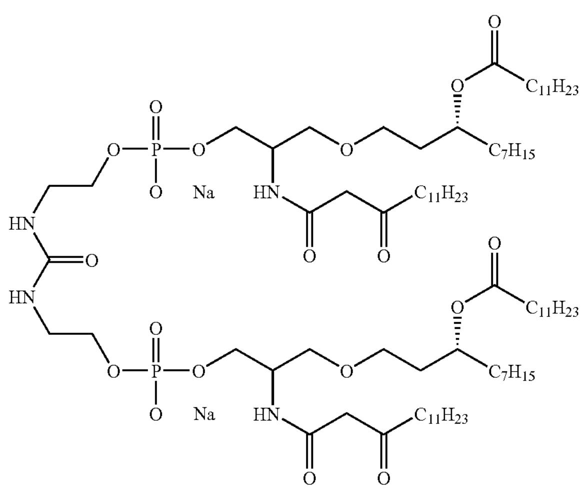 | 0.04 µM |
| 112071 | 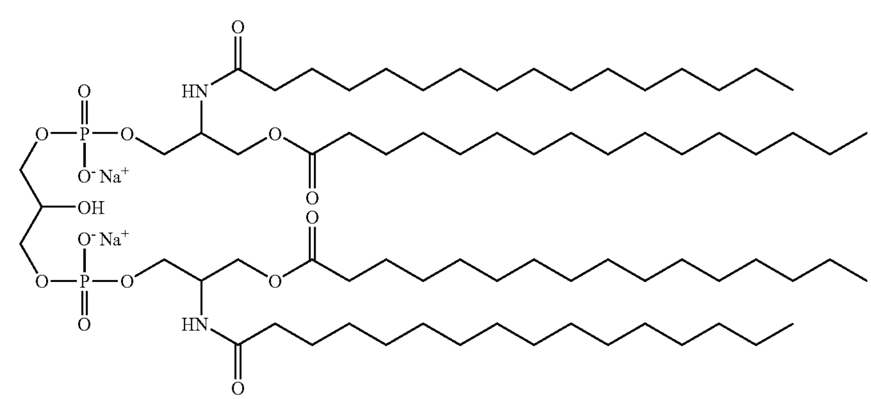 | |

TABLE 3-continued
WB ED$_{50}$ vs. % of LPS at 10 ng/ml
| ER# | Structure | WB ED$_{50}$ vs LPS @ 10 ng/ml |
|---|---|---|
112072
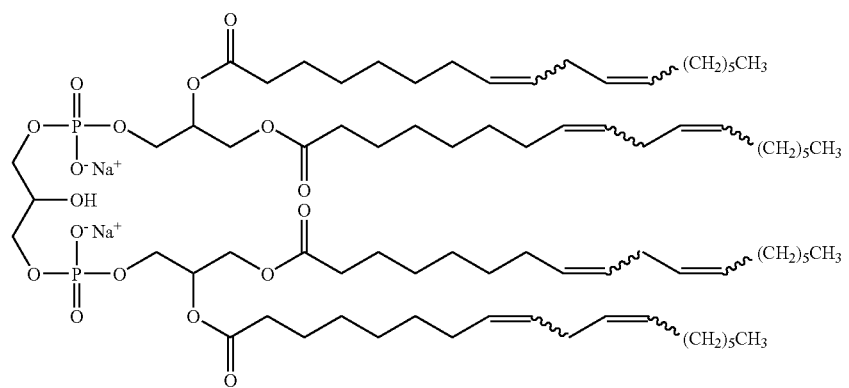
112091
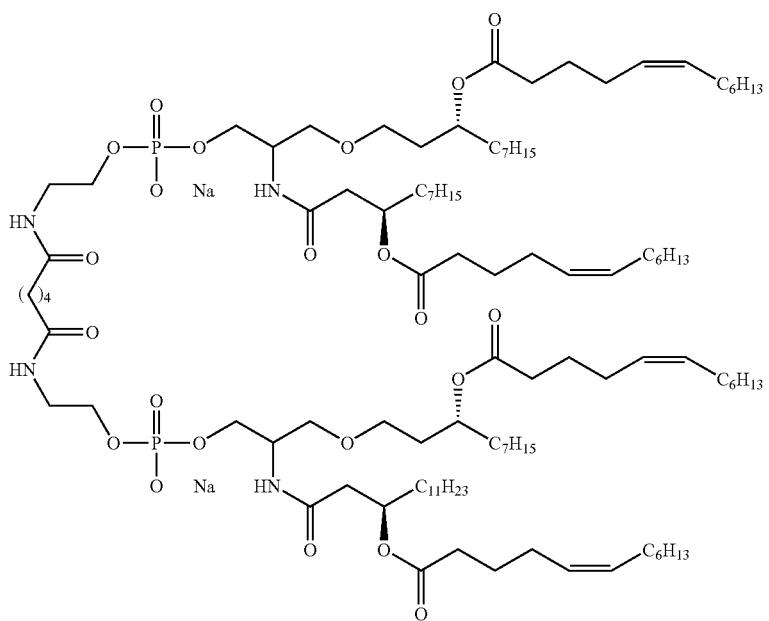

TABLE 3-continued

WB ED$_{50}$ vs. % of LPS at 10 ng/ml

| ER# | Structure | WB ED$_{50}$ vs LPS @ 10 ng/ml |
|---|---|---|
| 112092 | 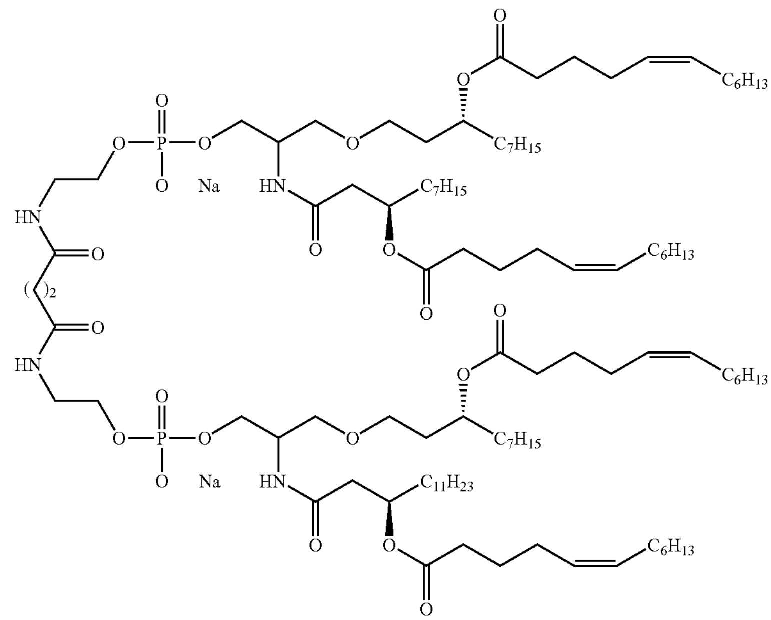 | |
| 112093 | 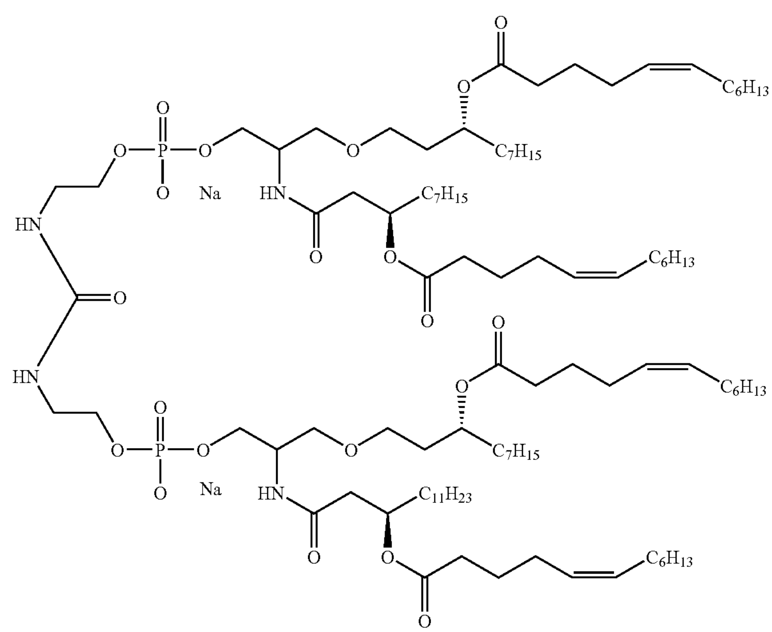 | |

TABLE 3-continued

WB ED$_{50}$ vs. % of LPS at 10 ng/ml

| ER# | Structure | WB ED$_{50}$ vs LPS @ 10 ng/ml |
|---|---|---|

112098

112099

TABLE 3-continued

WB ED$_{50}$ vs. % of LPS at 10 ng/ml

| ER# | Structure | WB ED$_{50}$ vs LPS @ 10 ng/ml |
|---|---|---|
| 112100 | 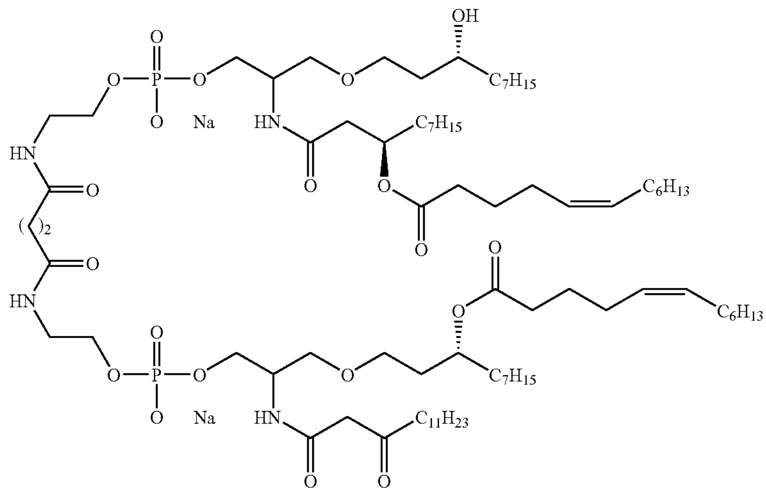 | |
| 112859 | 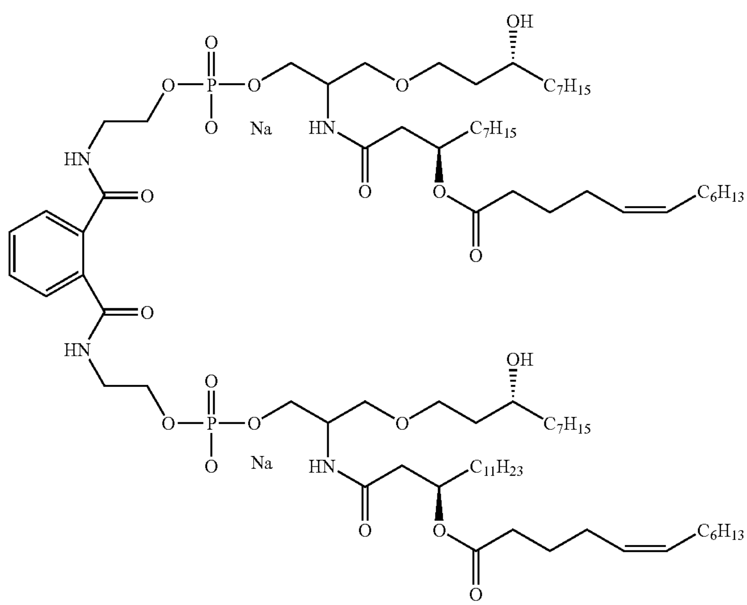 | |

TABLE 3-continued

WB ED$_{50}$ vs. % of LPS at 10 ng/ml

| ER# | Structure | WB ED$_{50}$ vs LPS @ 10 ng/ml |
|---|---|---|
| 112860 | 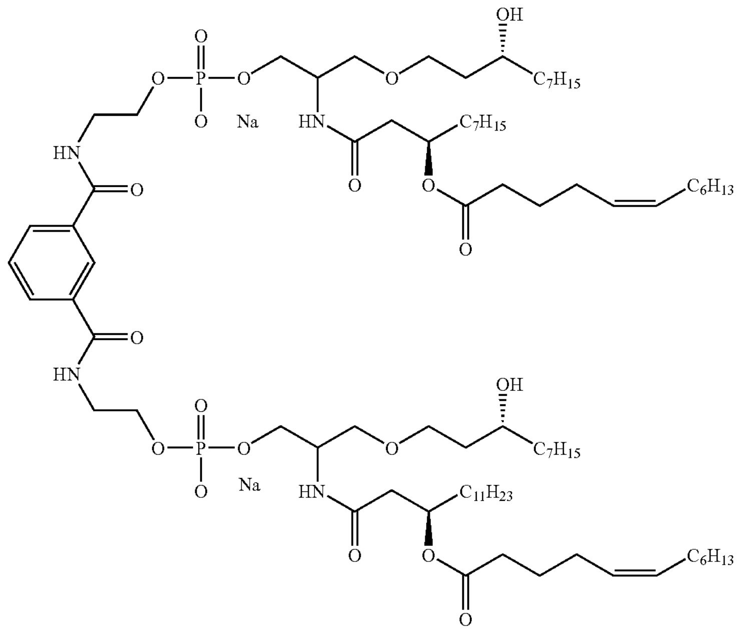 | |
| 112861 | 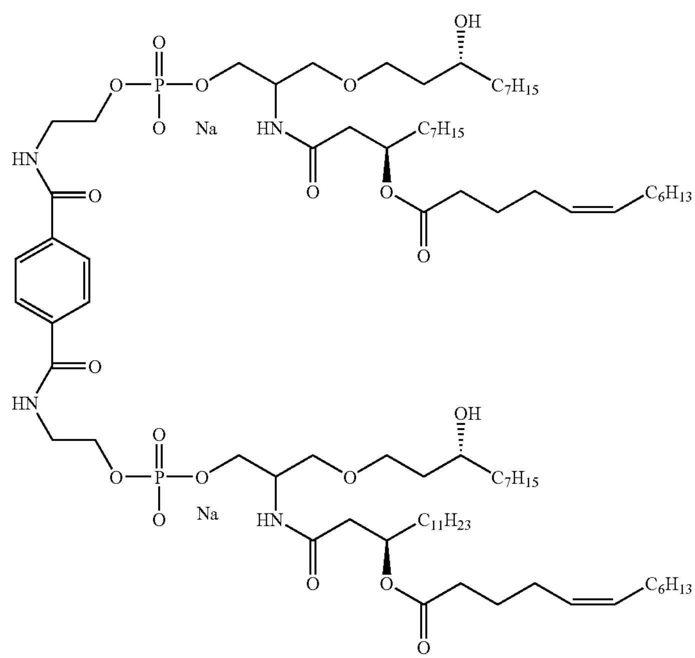 | |

TABLE 3-continued

WB ED$_{50}$ vs. % of LPS at 10 ng/ml

| ER# | Structure | WB ED$_{50}$ vs LPS @ 10 ng/ml |
|---|---|---|
| 113634 | 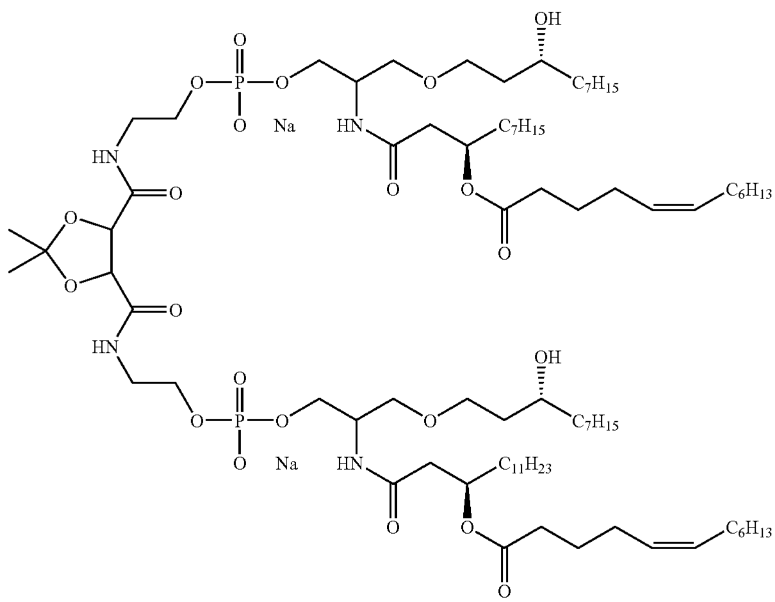 | |
| 113635 | 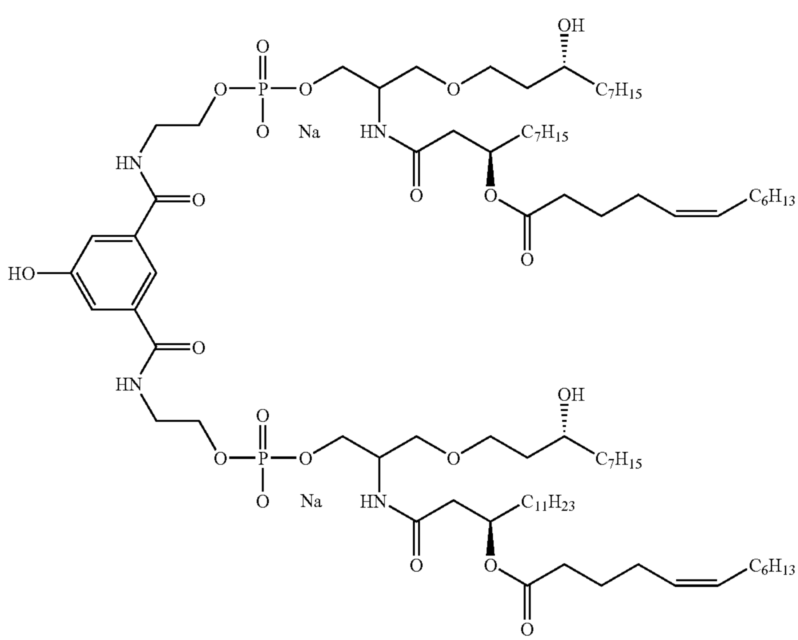 | |

TABLE 3-continued

WB ED$_{50}$ vs. % of LPS at 10 ng/ml

| ER# | Structure | WB ED$_{50}$ vs LPS @ 10 ng/ml |
|---|---|---|
| 113643 | 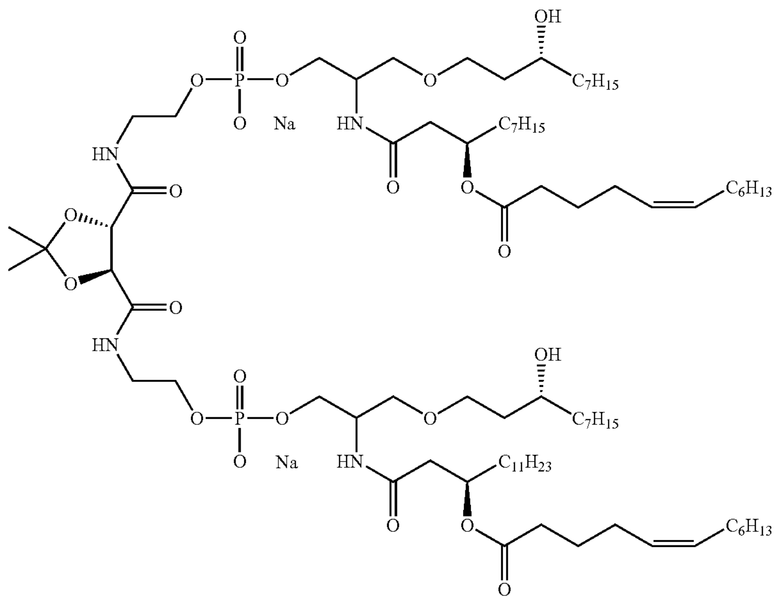 | |
| 113644 | 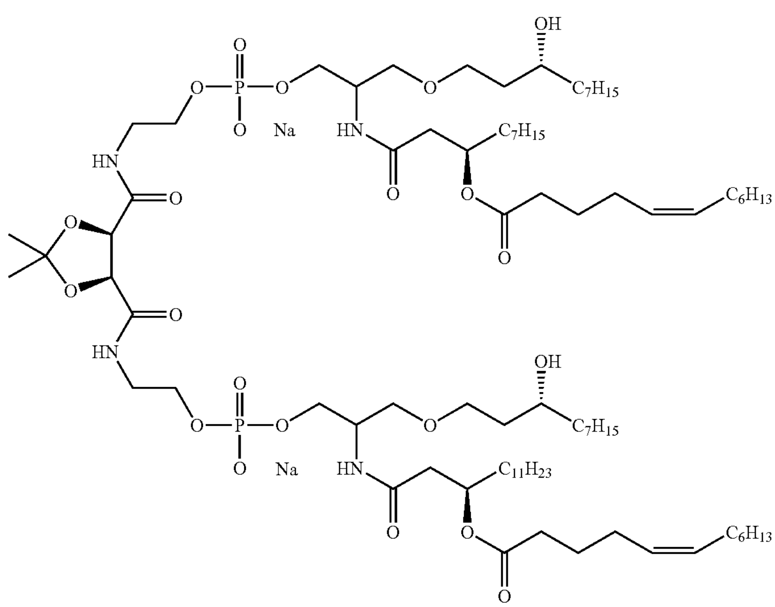 | |

TABLE 3-continued

WB ED$_{50}$ vs. % of LPS at 10 ng/ml

| ER# | Structure | WB ED$_{50}$ vs LPS @ 10 ng/ml |
|---|---|---|
| 113651 | 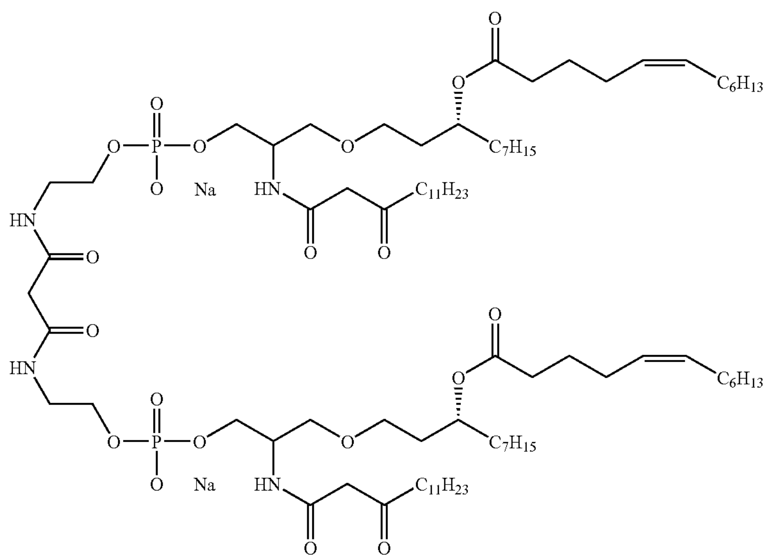 | 0.70 μM |
| 113665 | 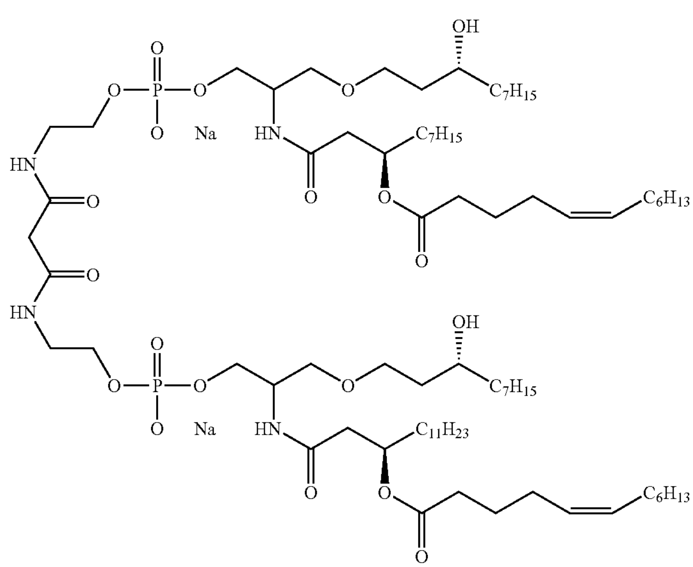 | |

TABLE 3-continued
WB ED$_{50}$ vs. % of LPS at 10 ng/ml
| ER# | Structure | WB ED$_{50}$ vs LPS @ 10 ng/ml |
|---|---|---|
| 113666 | 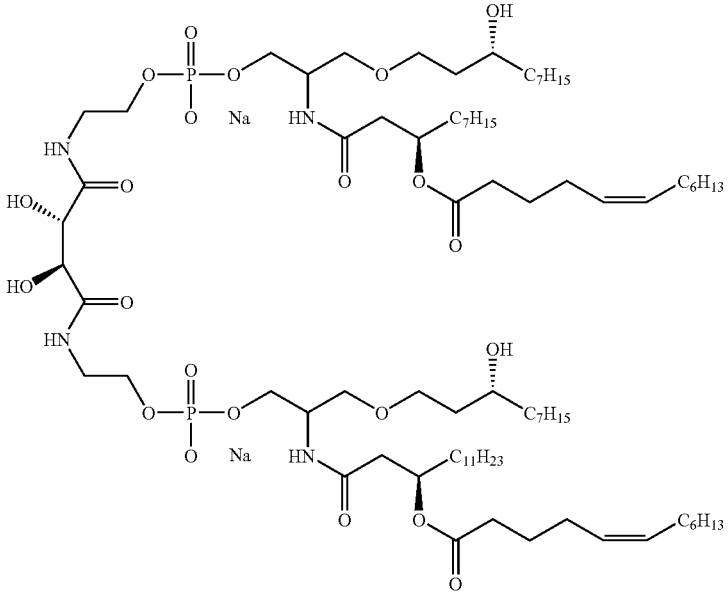 | |
| 118023 | 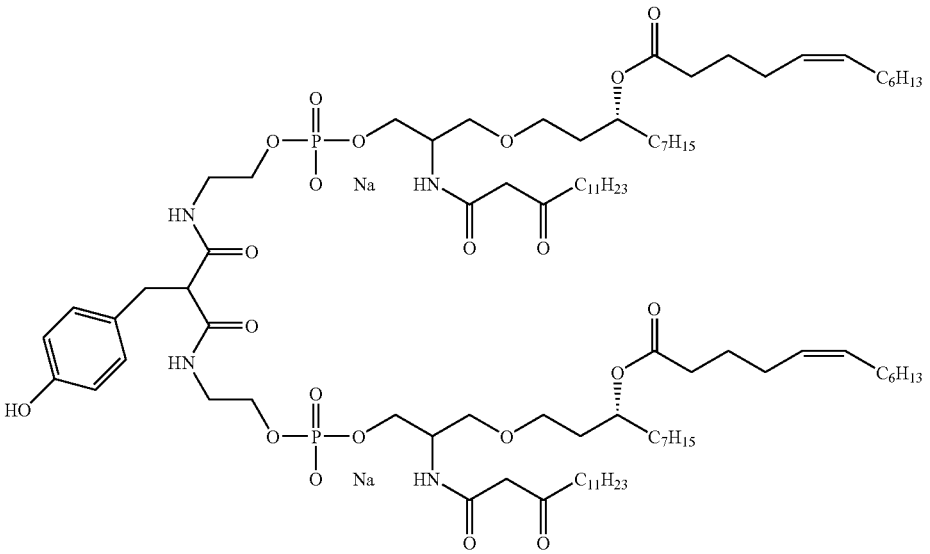 | |

TABLE 3-continued
| | | WB ED$_{50}$ vs. % of LPS at 10 ng/ml | |
|---|---|---|---|
| ER# | | Structure | WB ED$_{50}$ vs LPS @ 10 ng/ml |
| 019772 | 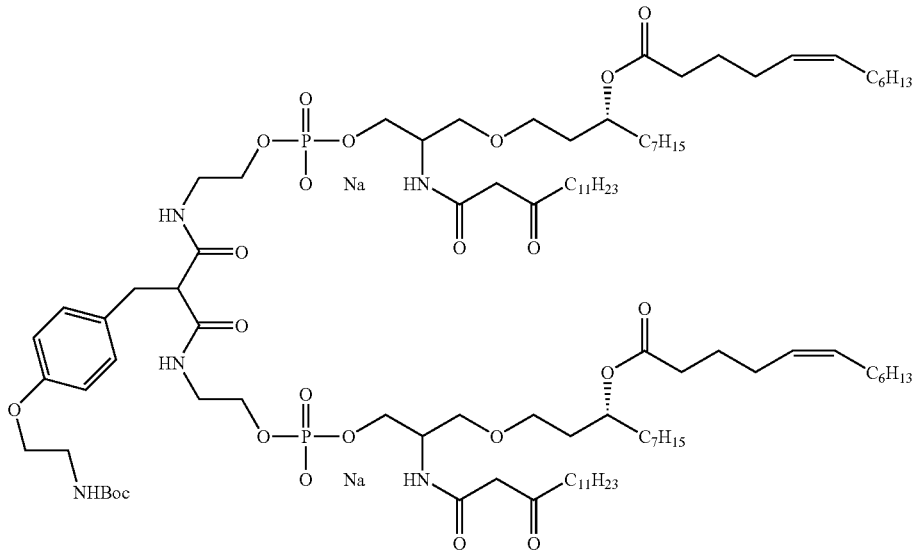 | | |
| 118989 | 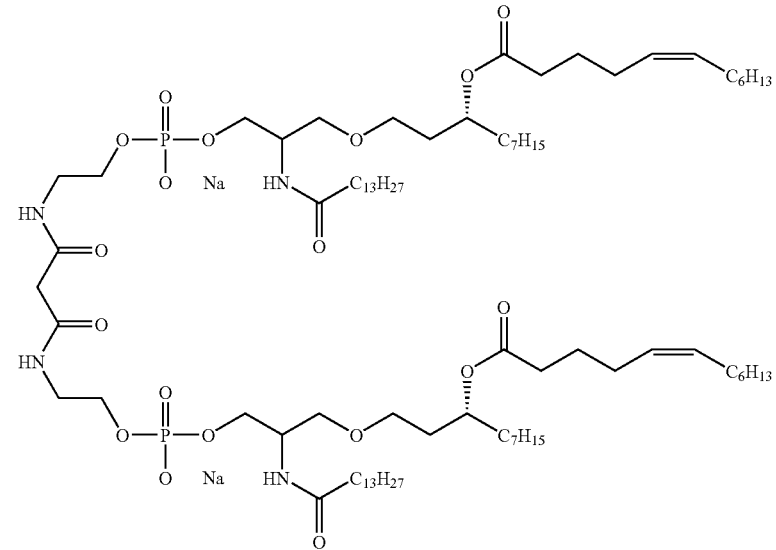 | | 0.1 µM |

TABLE 3-continued

WB ED$_{50}$ vs. % of LPS at 10 ng/ml

| ER# | Structure | WB ED$_{50}$ vs LPS @ 10 ng/ml |
|---|---|---|
| 118999 | 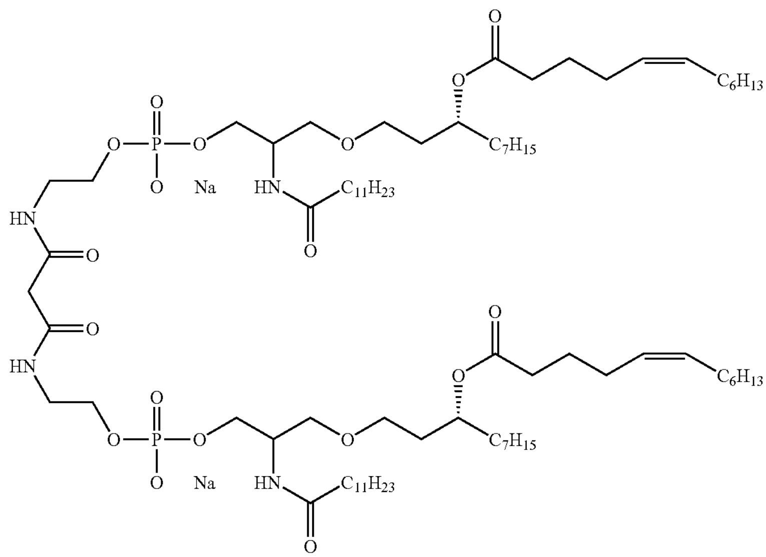 | |
| 119000 | 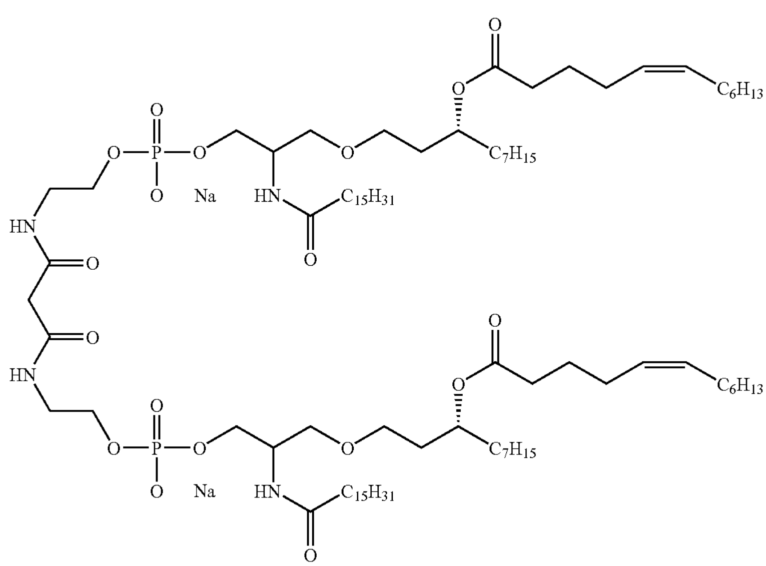 | |

TABLE 3-continued

WB ED$_{50}$ vs. % of LPS at 10 ng/ml

| ER# | Structure | WB ED$_{50}$ vs LPS @ 10 ng/ml |
|---|---|---|
| 119001 | 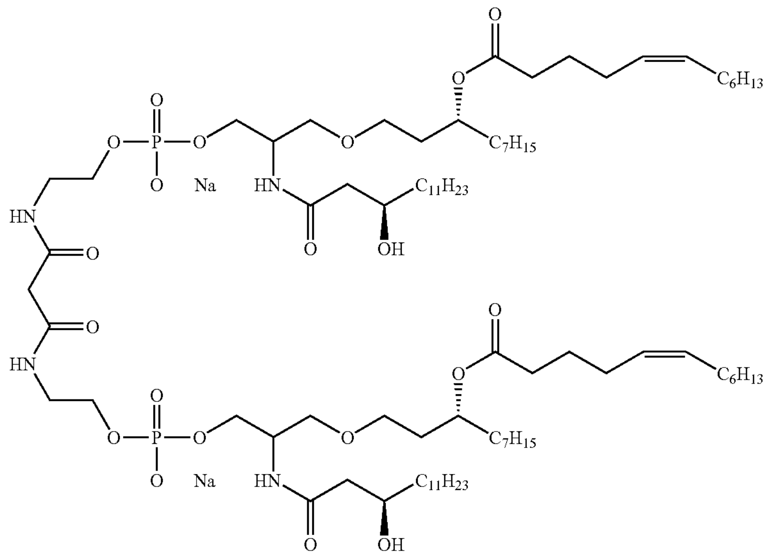 | 1.23 μM |
| 118949 | 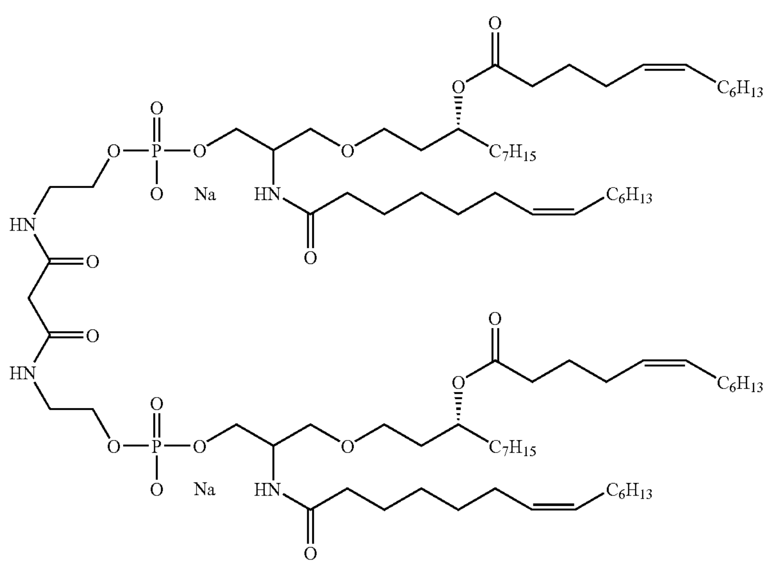 | |

TABLE 3-continued
WB ED$_{50}$ vs. % of LPS at 10 ng/ml
| ER# | Structure | WB ED$_{50}$ vs LPS @ 10 ng/ml |
|---|---|---|
| 119327 | 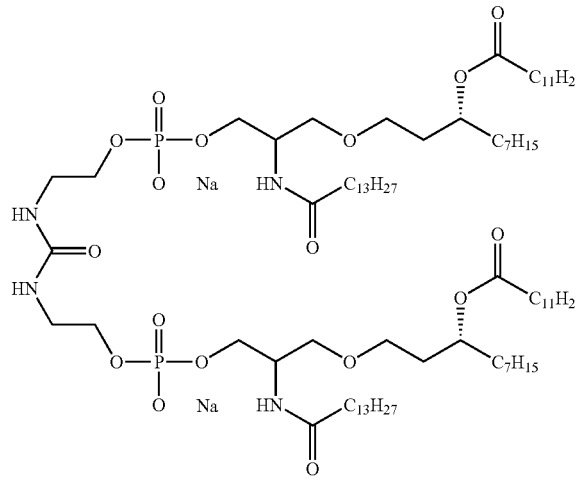 | 0.015 μM |
| 119328 | 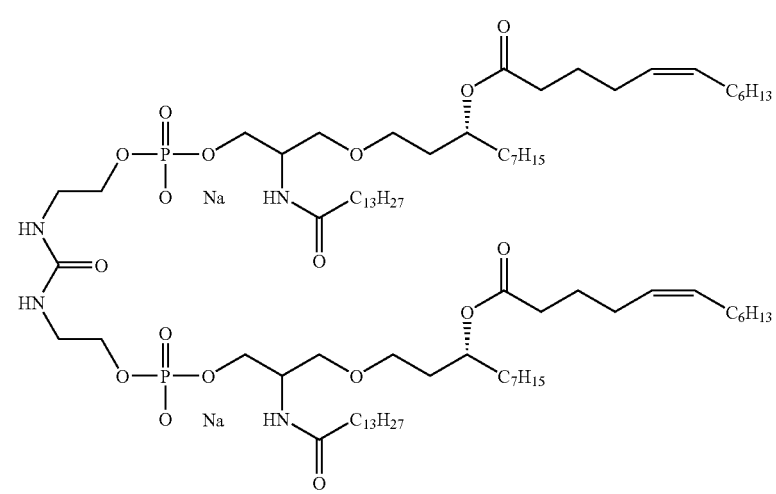 | >>10 μM |
| 119329 | 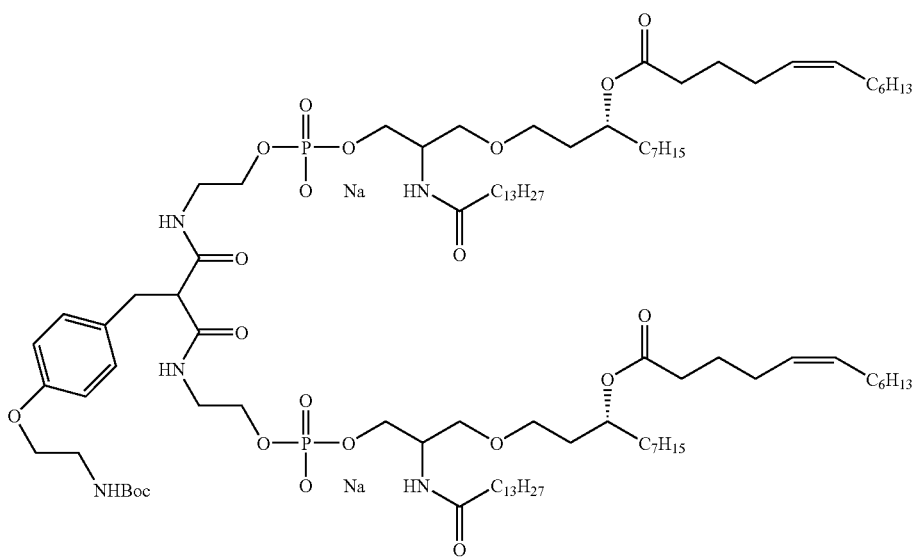 | |

TABLE 3-continued

WB ED$_{50}$ vs. % of LPS at 10 ng/ml

| ER# | Structure | WB ED$_{50}$ vs LPS @ 10 ng/ml |
|---|---|---|
| 119521 | 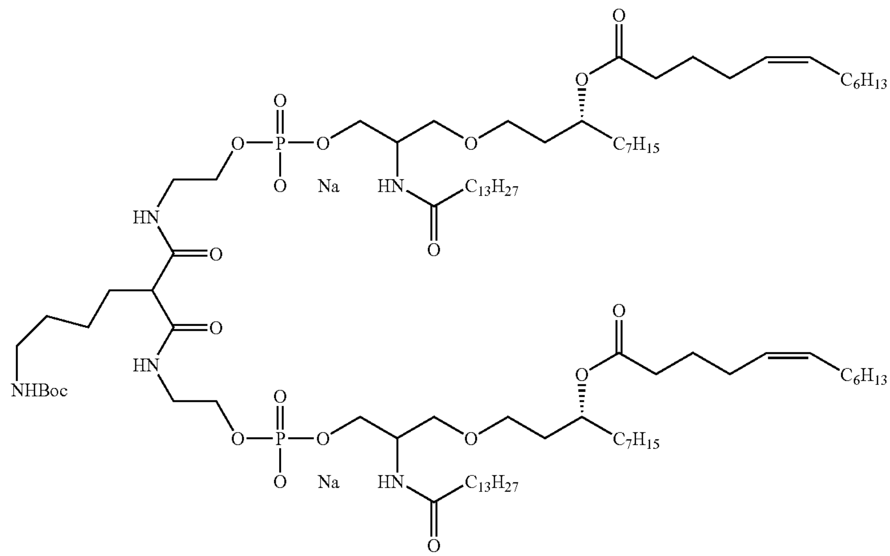 | |
| 119522 | 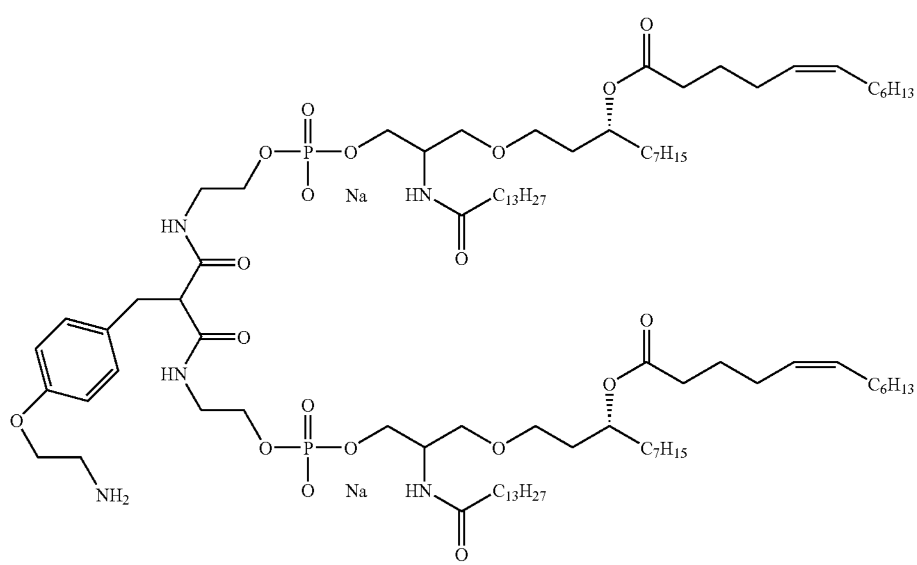 | |

TABLE 3-continued

| | | WB ED$_{50}$ vs. % of LPS at 10 ng/ml | |
|---|---|---|---|
| ER# | | Structure | WB ED$_{50}$ vs LPS @ 10 ng/ml |
| 119523 | | (structure) | |
| 803022 | | (structure) | 0.06 μM |

TABLE 3-continued

WB ED$_{50}$ vs. % of LPS at 10 ng/ml

| ER# | Structure | WB ED$_{50}$ vs LPS @ 10 ng/ml |
|---|---|---|
| 803028 | 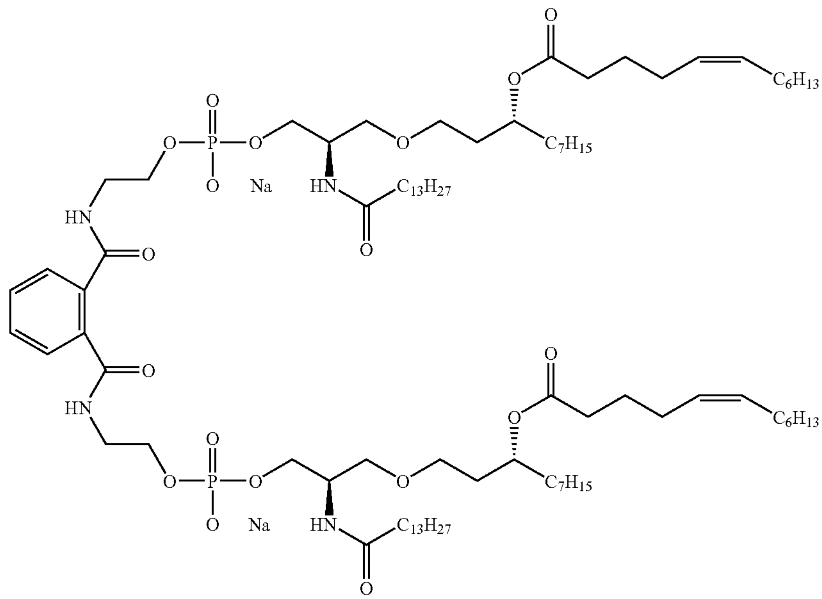 | |
| 803045 | 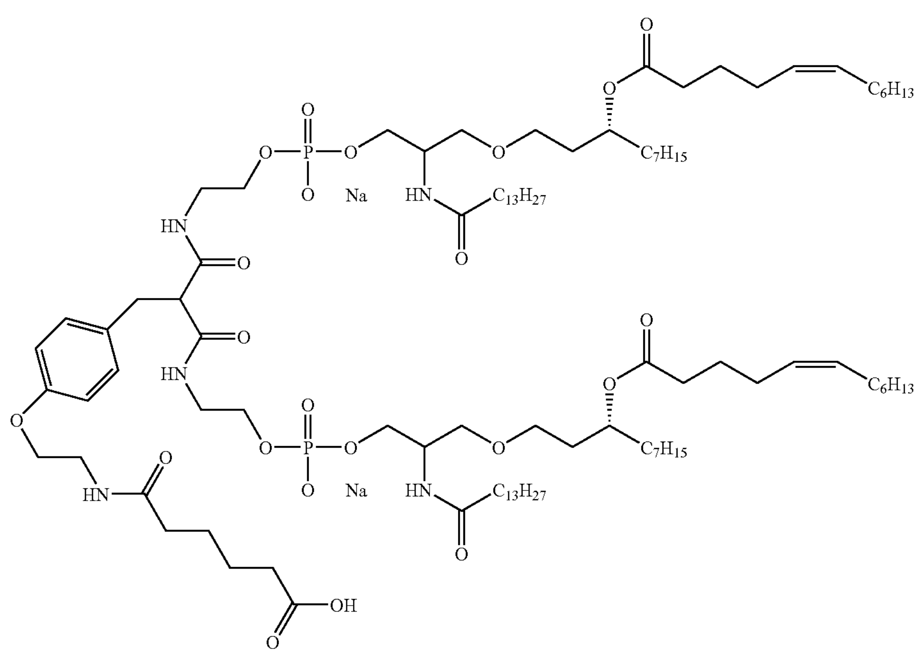 | |

TABLE 3-continued

WB ED$_{50}$ vs. % of LPS at 10 ng/ml

| ER# | Structure | WB ED$_{50}$ vs LPS @ 10 ng/ml |
|---|---|---|
| 803056 | 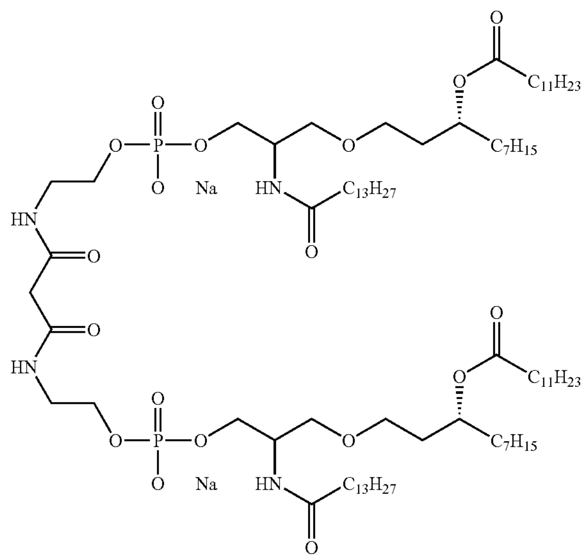 | |
| 803058 | 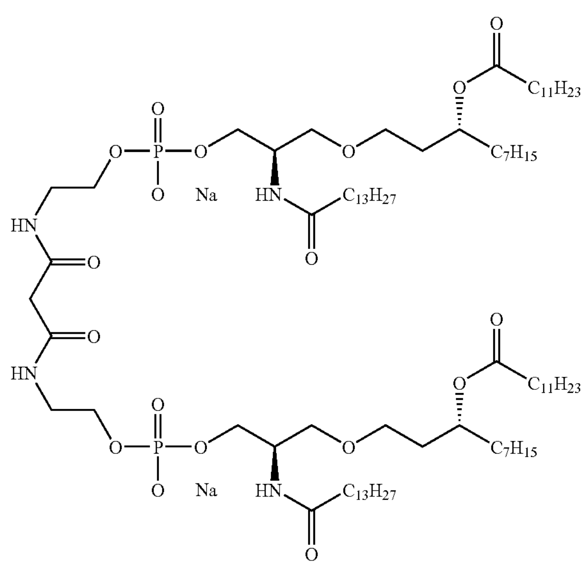 | 0.022 µM |

TABLE 3-continued

WB ED$_{50}$ vs. % of LPS at 10 ng/ml

| ER# | Structure | WB ED$_{50}$ vs LPS @ 10 ng/ml |
|---|---|---|
| 803059 | 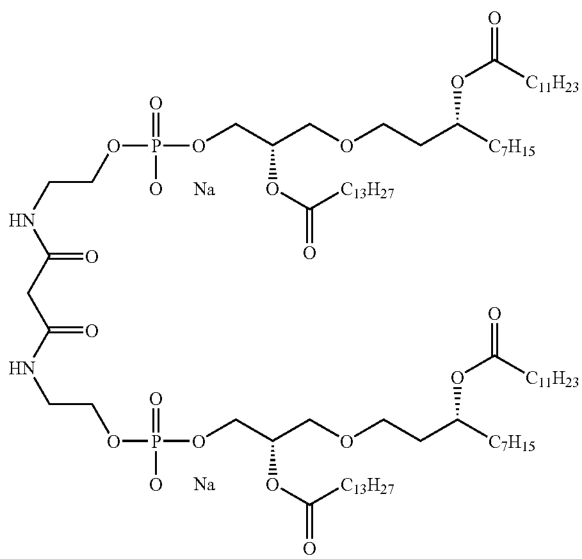 | 0.89 μM |
| 803592 | 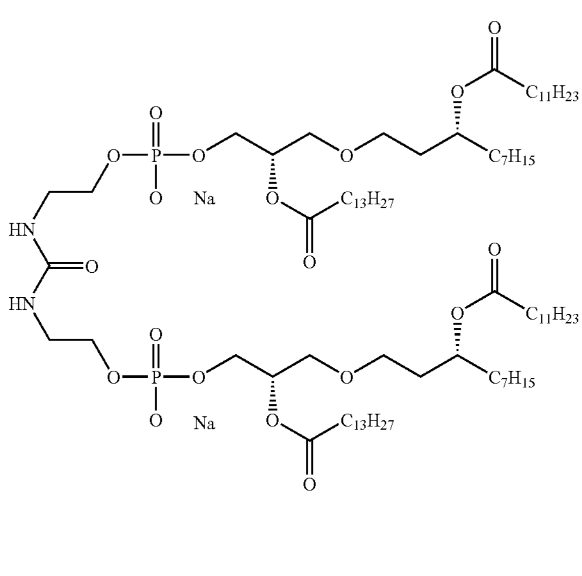 | |

TABLE 3-continued

WB ED$_{50}$ vs. % of LPS at 10 ng/ml

| ER# | Structure | WB ED$_{50}$ vs LPS @ 10 ng/ml |
|---|---|---|
| 803596 | 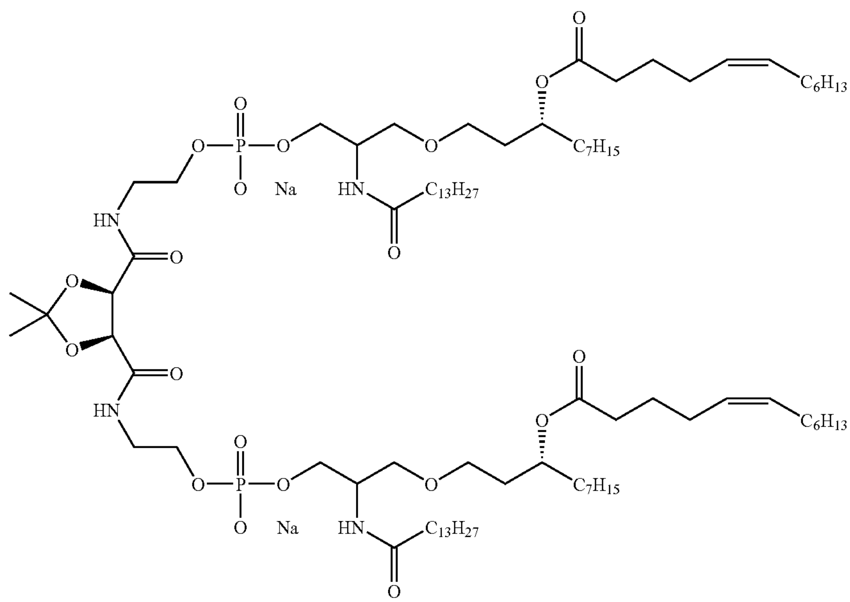 | |
| 803597 | 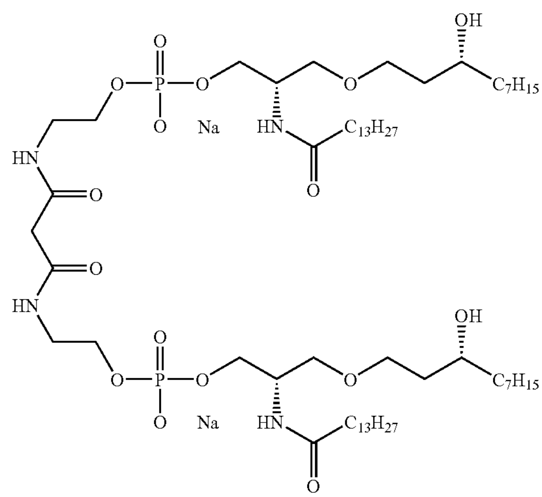 | |
| 803598 | 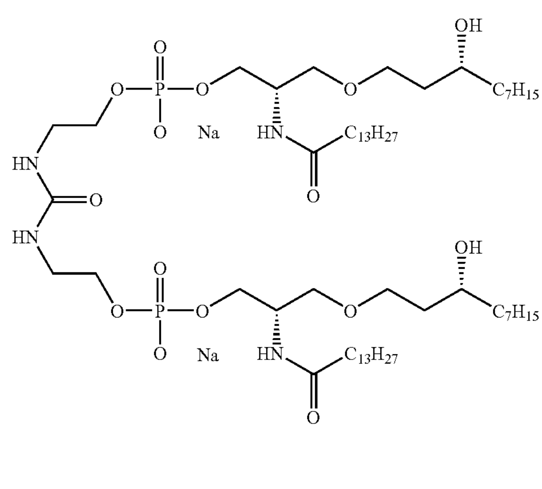 | |

TABLE 3-continued

WB ED$_{50}$ vs. % of LPS at 10 ng/ml

| ER# | Structure | WB ED$_{50}$ vs LPS @ 10 ng/ml |
|---|---|---|
| 803599 | 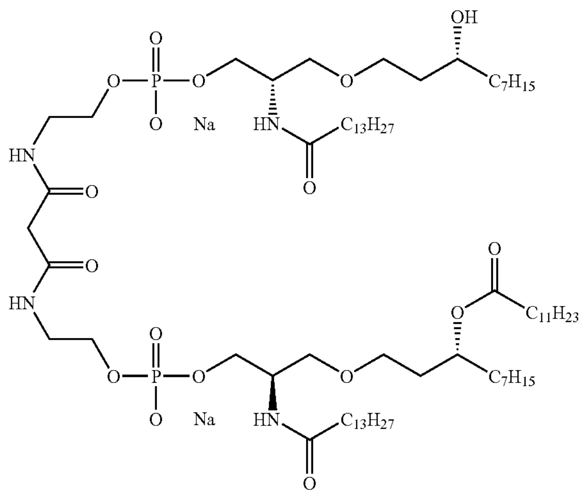 | |
| 803613 | 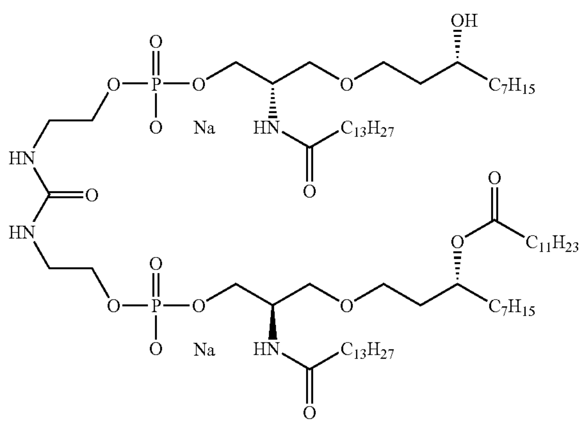 | |
| 803731 | 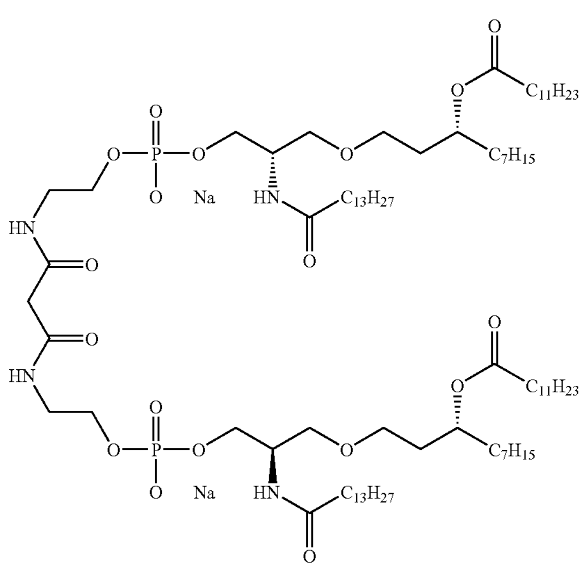 | >10 μM |

TABLE 3-continued

WB ED$_{50}$ vs. % of LPS at 10 ng/ml

| ER# | Structure | WB ED$_{50}$ vs LPS @ 10 ng/ml |
|---|---|---|
| 803732 | 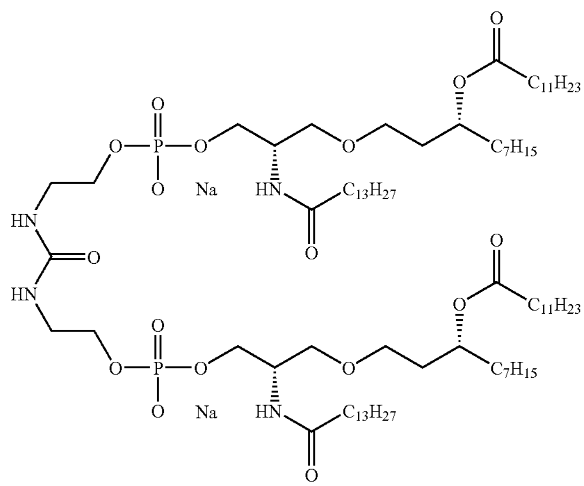 | 0.85 μM |
| 803733 | 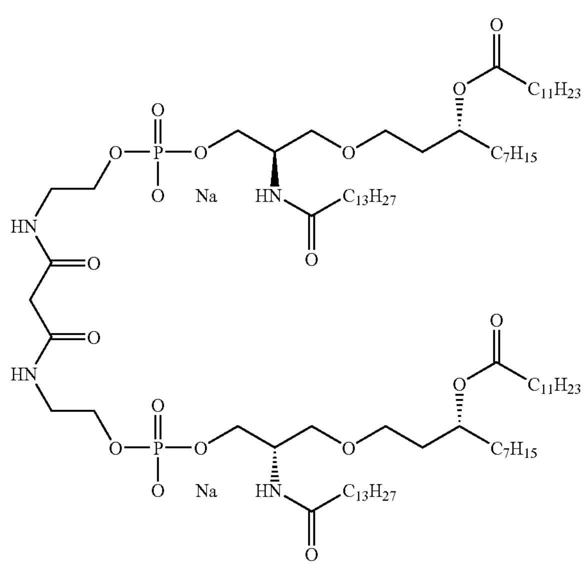 | 0.70 μM |

TABLE 3-continued

WB ED$_{50}$ vs. % of LPS at 10 ng/ml

| ER# | Structure | WB ED$_{50}$ vs LPS @ 10 ng/ml |
|---|---|---|
| 803751 | 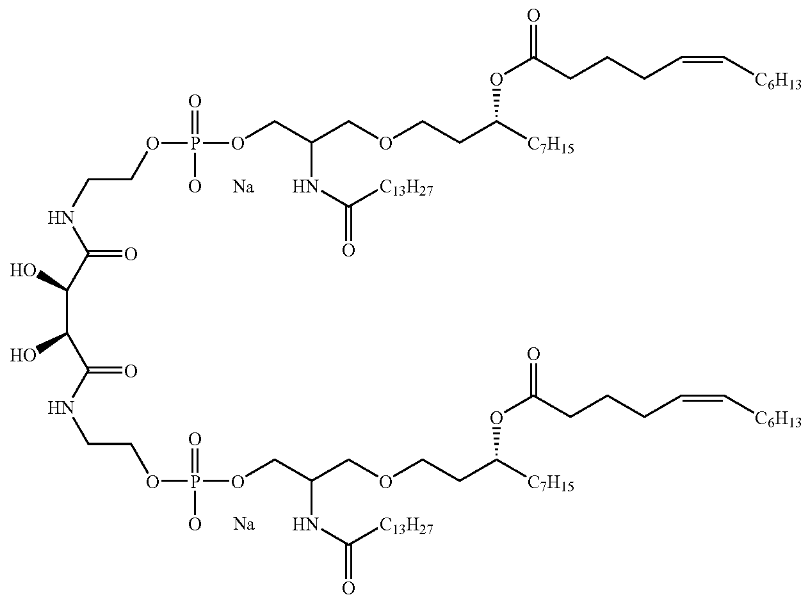 | |
| 803783 | 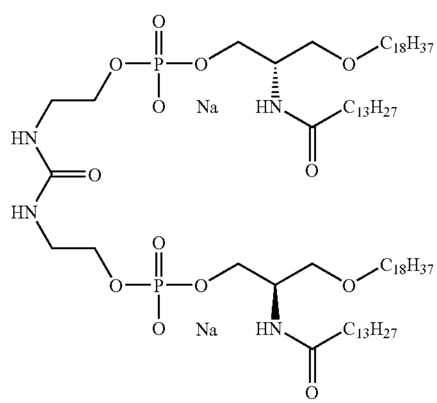 | |
| 803784 | 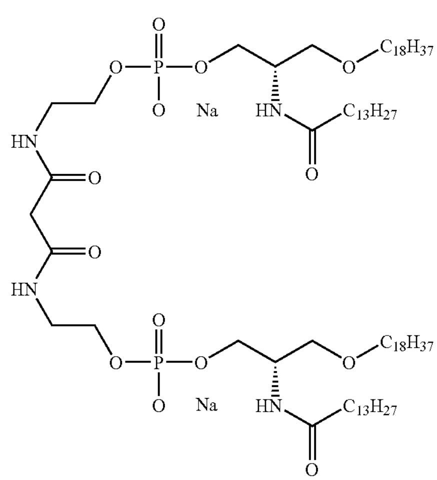 | |

TABLE 3-continued

WB ED$_{50}$ vs. % of LPS at 10 ng/ml

| ER# | Structure | WB ED$_{50}$ vs LPS @ 10 ng/ml |
|---|---|---|
| 803789 | 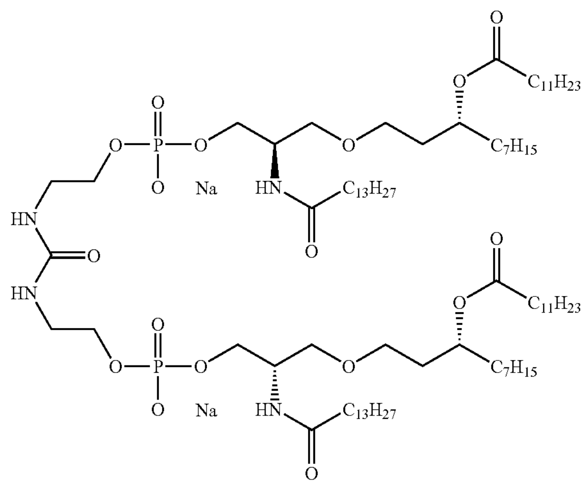 | 0.10 μM |
| 804053 | 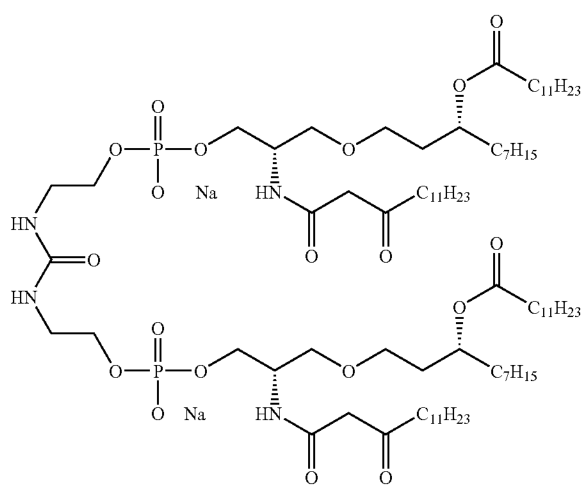 | 1.34 μM |
| 804057 | 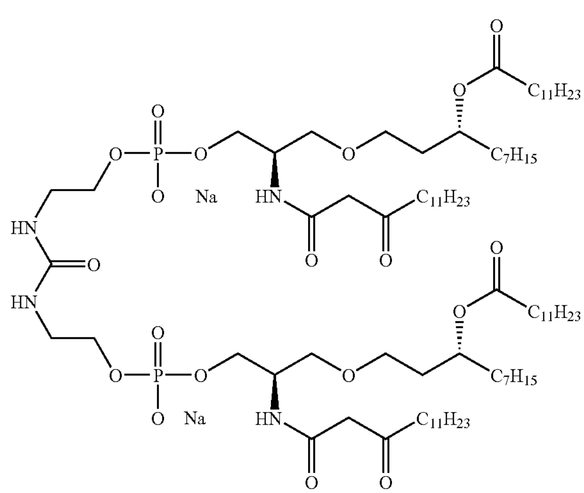 | 0.008 μM |

TABLE 3-continued
| | WB ED$_{50}$ vs. % of LPS at 10 ng/ml | |
|---|---|---|
| ER# | Structure | WB ED$_{50}$ vs LPS @ 10 ng/ml |
| 804058 | 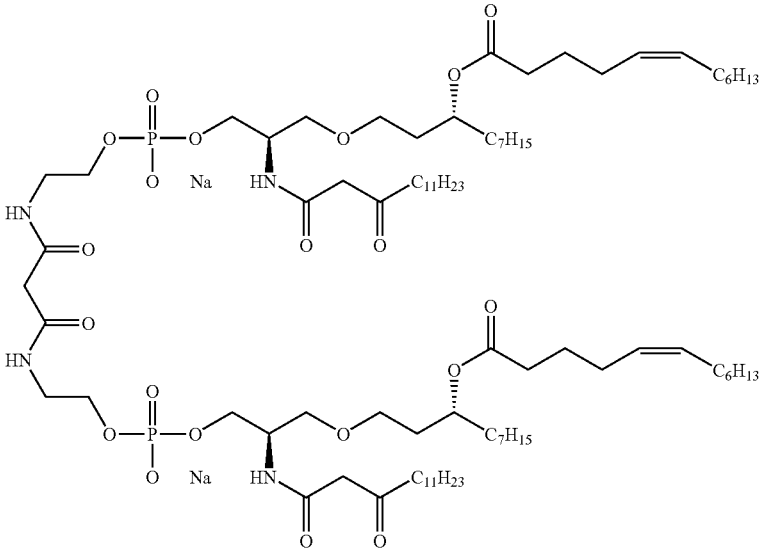 | 0.03 μM |
| 804059 | 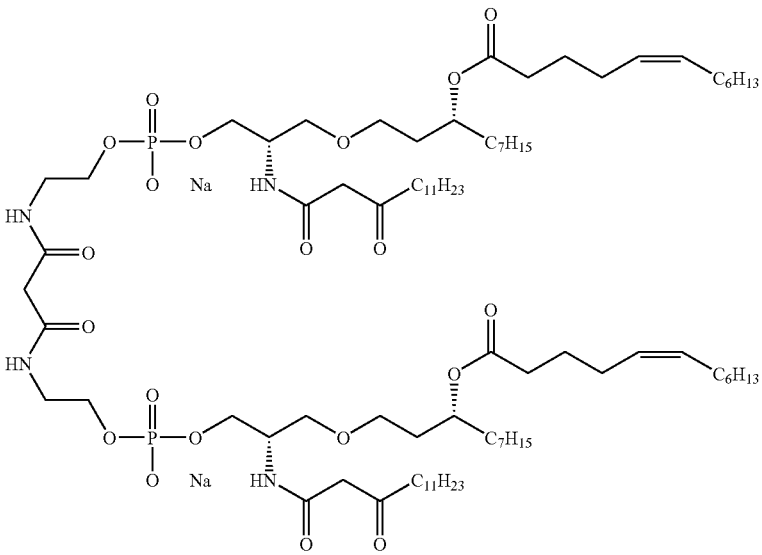 | >10 μM |

TABLE 3-continued
WB ED$_{50}$ vs. % of LPS at 10 ng/ml
| ER# | Structure | WB ED$_{50}$ vs LPS @ 10 ng/ml |
|---|---|---|
| 804061 | 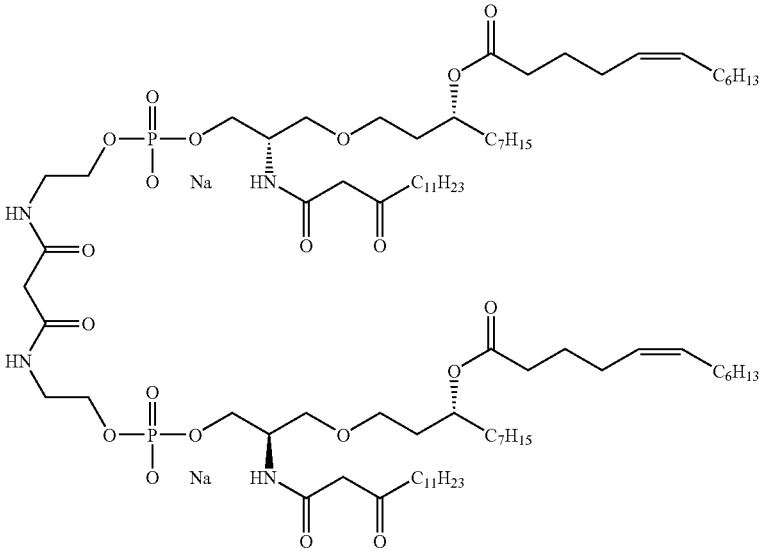 | 2.5 μM |
| 804097 | 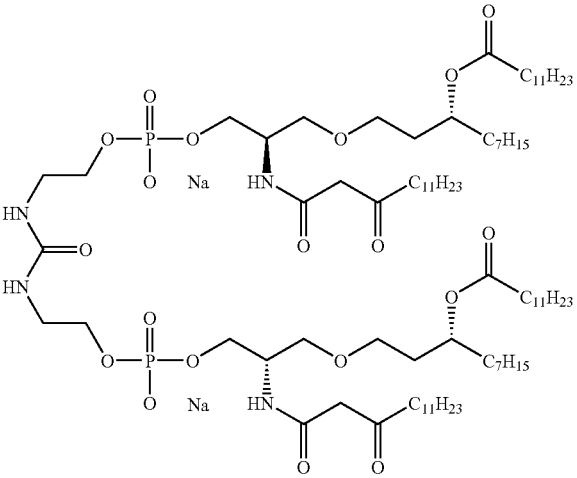 | 0.3 μM |
| 804121 | 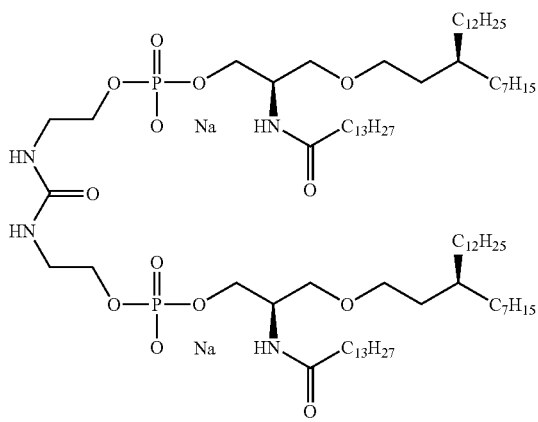 | 0.46 μM |

TABLE 3-continued

WB ED$_{50}$ vs. % of LPS at 10 ng/ml

| ER# | Structure | WB ED$_{50}$ vs LPS @ 10 ng/ml |
|---|---|---|
| 804130 | 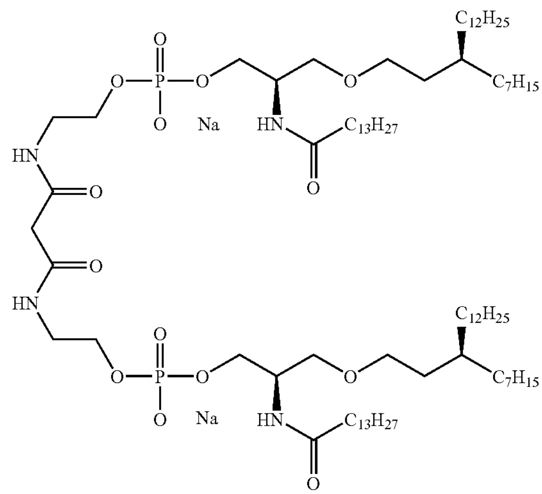 | 0.66 µM |
| 804221 | 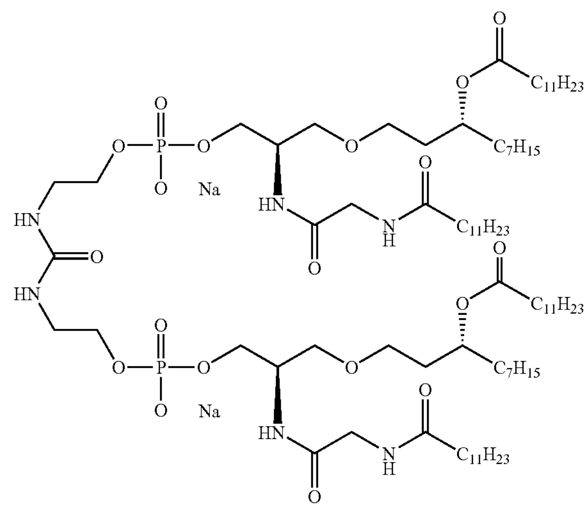 | 2.2 µM |
| 804222 | 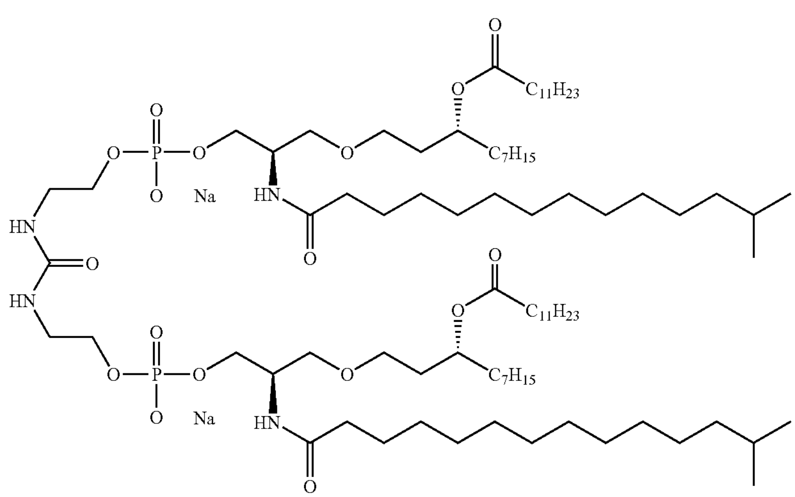 | 0.008 µM |

TABLE 3-continued

WB ED$_{50}$ vs. % of LPS at 10 ng/ml

| ER# | Structure | WB ED$_{50}$ vs LPS @ 10 ng/ml |
|---|---|---|
| 804252 | 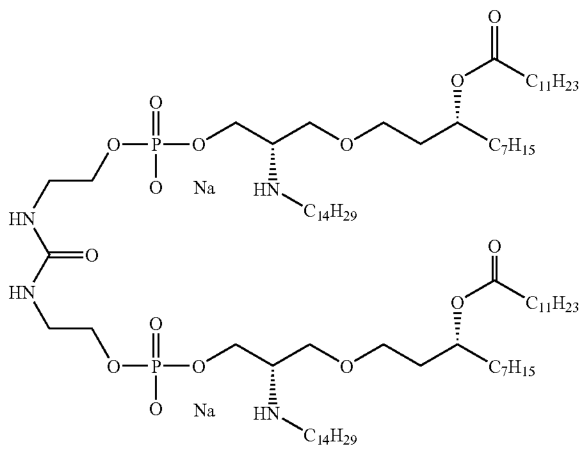 | 400 nM (576-021) + EtOH |
| 804253 | 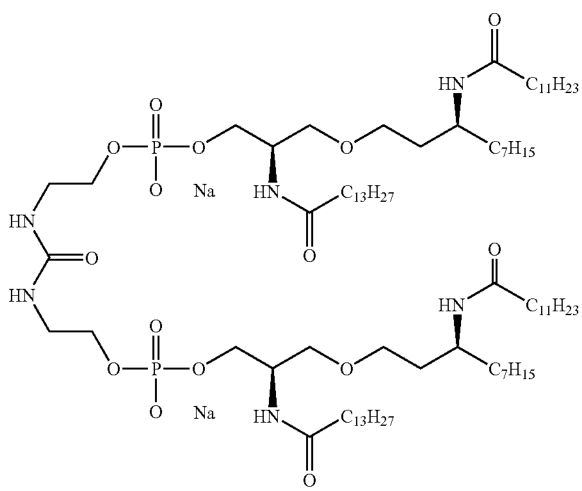 | >10 μM |
| 804281 | 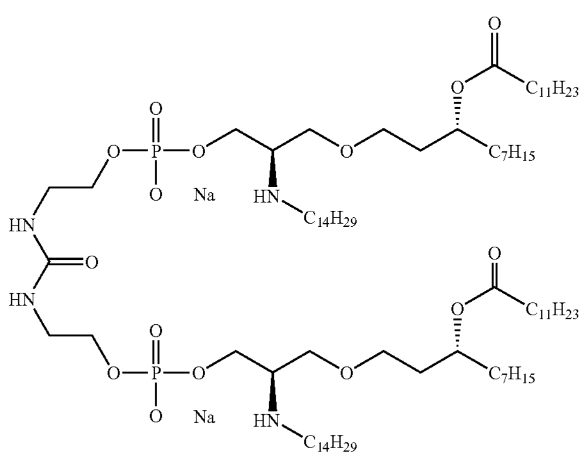 | 0.45 μM |

TABLE 3-continued

WB ED$_{50}$ vs. % of LPS at 10 ng/ml

| ER# | Structure | WB ED$_{50}$ vs LPS @ 10 ng/ml |
|---|---|---|
| 804313 | 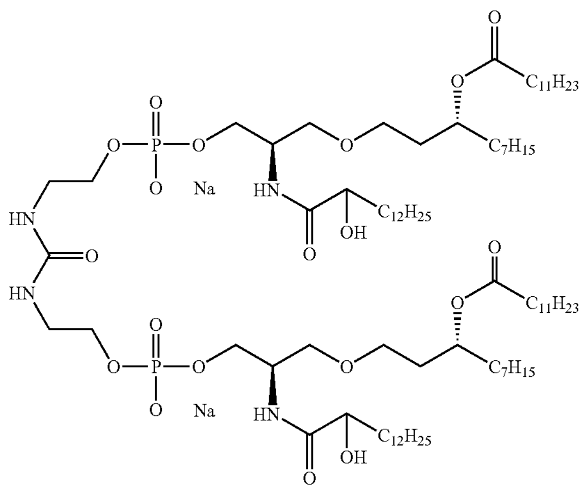 | 0.014 μM |
| 804339 | 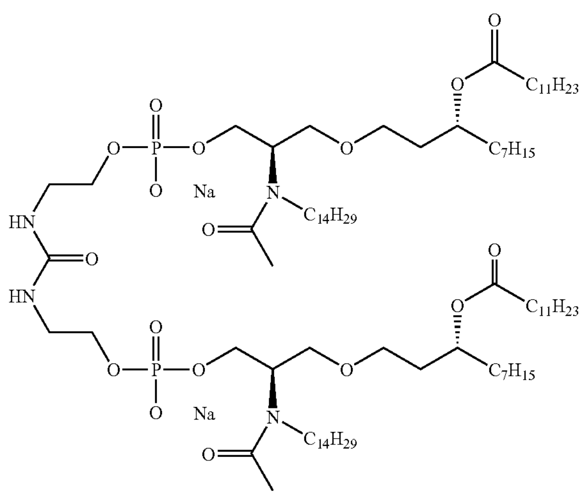 | 1.06 μM |
| 804372 | 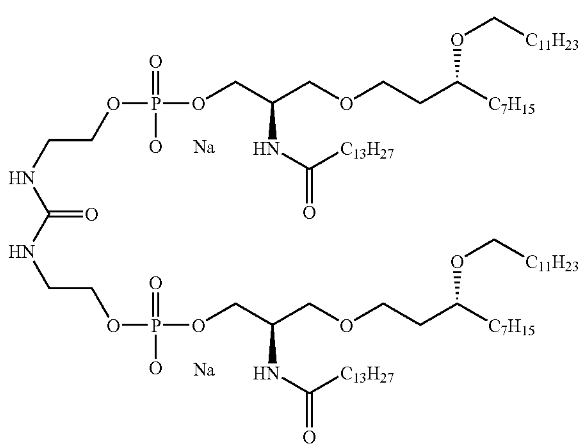 | 0.4 μM |

TABLE 3-continued

WB ED$_{50}$ vs. % of LPS at 10 ng/ml

| ER# | Structure | WB ED$_{50}$ vs LPS @ 10 ng/ml |
|---|---|---|
| 804442 | 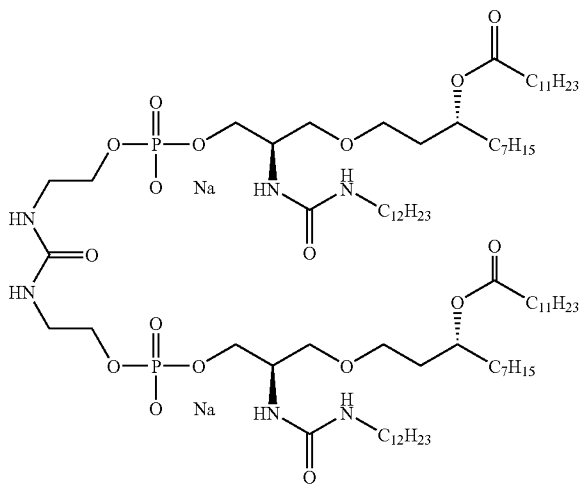 | 0.007 μM |
| 804503 | 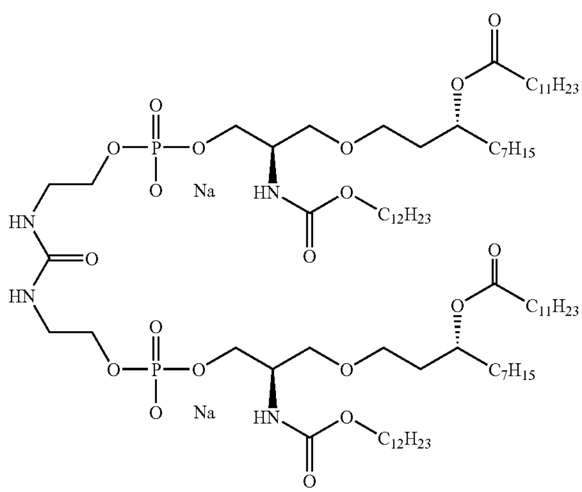 | 0.35 μM |
| 804558 | 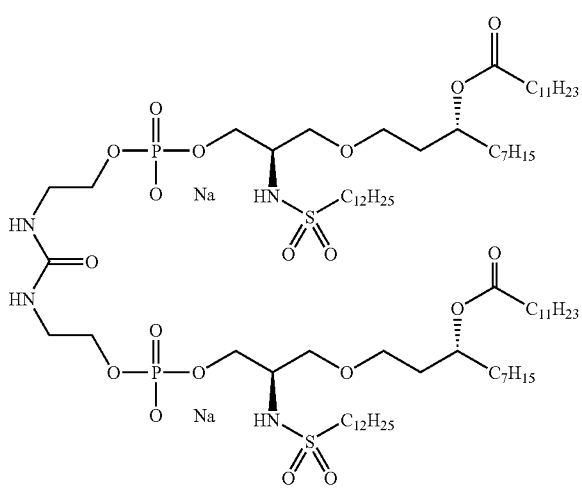 | 0.16 μM |

TABLE 3-continued
WB ED$_{50}$ vs. % of LPS at 10 ng/ml
| ER# | Structure | WB ED$_{50}$ vs LPS @ 10 ng/ml |
|---|---|---|
| 804596 | 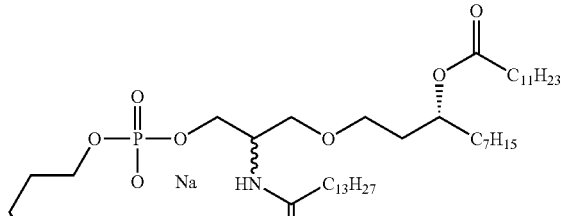 | >10 μM |
| 804674 | 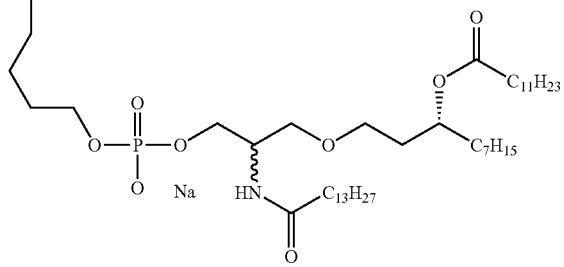 | 1.2 μM |
| 804678 | 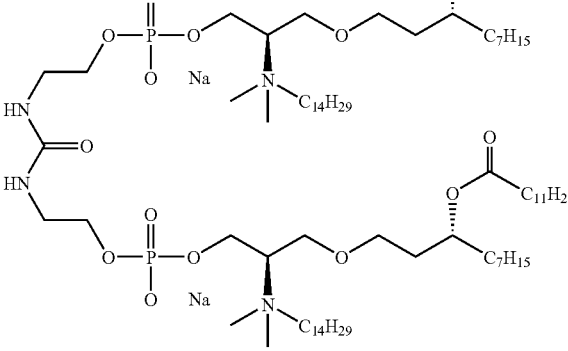 | 0.018 μM |

TABLE 3-continued

WB ED$_{50}$ vs. % of LPS at 10 ng/ml

| ER# | Structure | WB ED$_{50}$ vs LPS @ 10 ng/ml |
|---|---|---|
| 804679 | 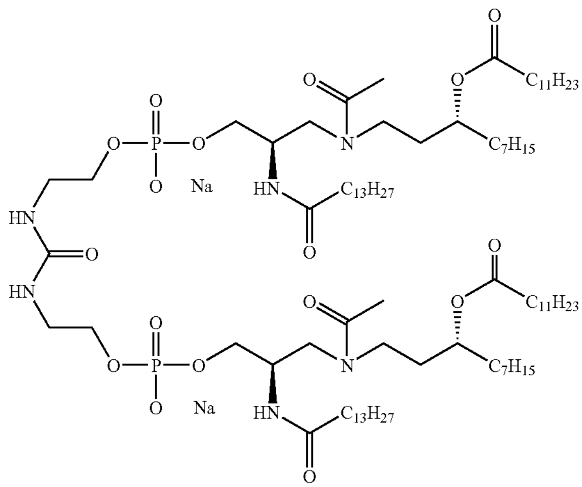 | 0.53 μM |
| 804680 | 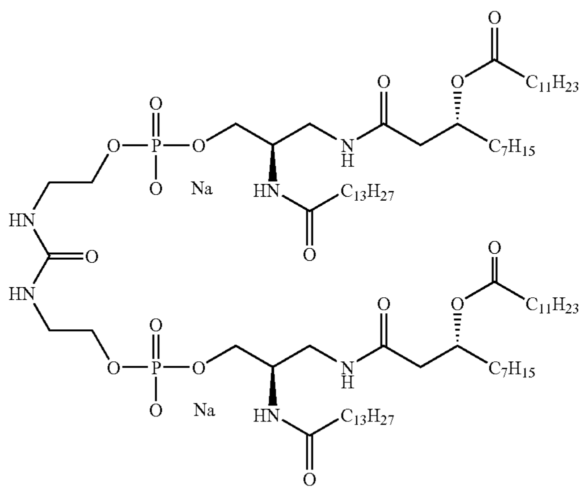 | 0.015 μM |
| 804732 | 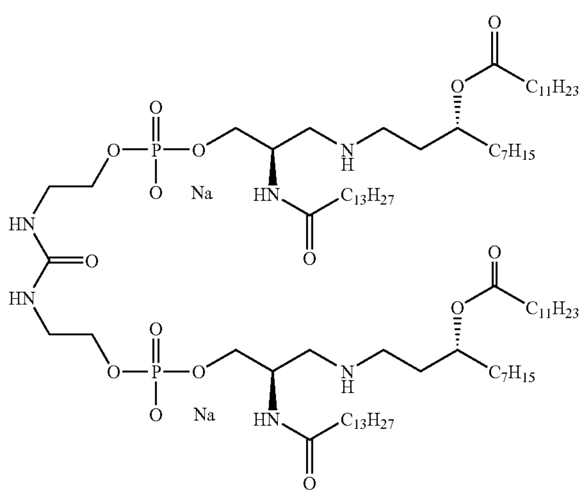 | <0.001 μM |

TABLE 3-continued

WB ED$_{50}$ vs. % of LPS at 10 ng/ml

| ER# | Structure | WB ED$_{50}$ vs LPS @ 10 ng/ml |
|---|---|---|
| 804764 | 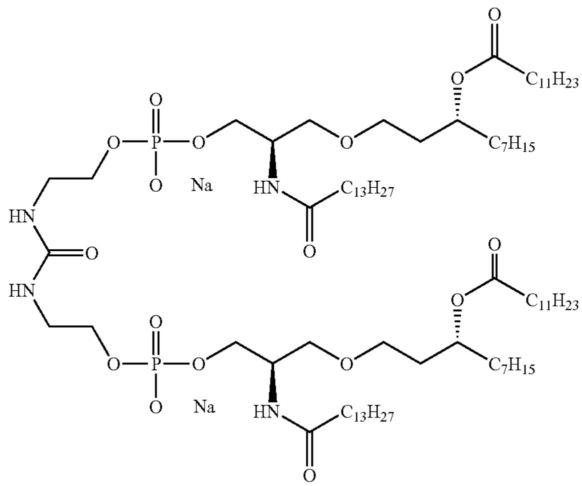 | 0.015 μM |
| 804772 | 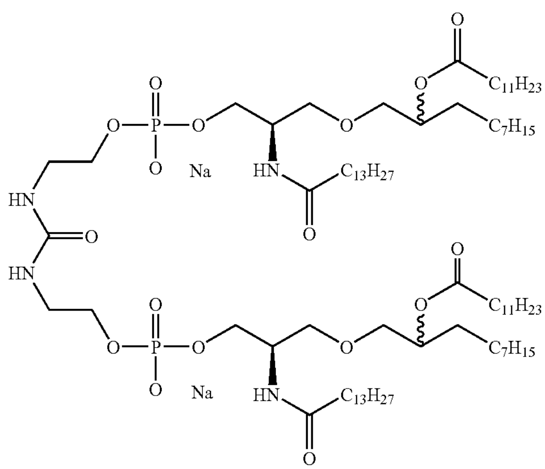 | 0.008 μM |
| 804947 | 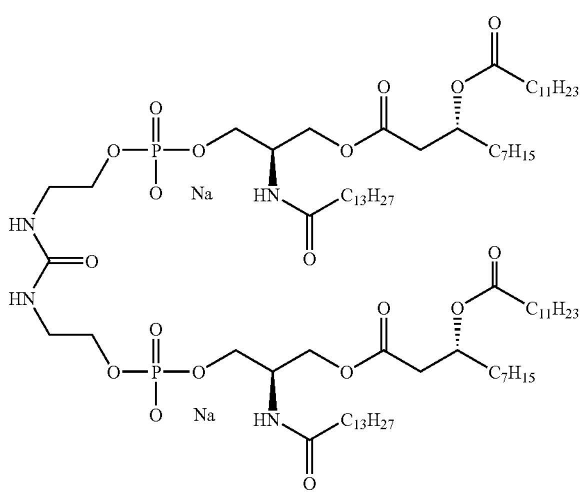 | >>10 μM |

Table 4 below contains the compound number as referenced herein to the corresponding ER number.

TABLE 4

Correspondence of Compound Nos. to ER Nos.

| Compound # | ER # |
|---|---|
| 16 | 112048 |
| 31 | 803058 |
| 48 | 803733 |
| 50 | 803022 |
| 62 | 803789 |
| 72 | 803592 |
| 100 | 112022 |
| 102 | 111230 |
| 104 | 111231 |
| 106 | 111232 |
| 108 | 111233 |
| 110 | 112043 |
| 112 | 112047 |
| 114 | 112047 |
| 116 | 112048 |
| 118 | 112049 |
| 120 | 112063 |
| 122 | 112064 |
| 124 | 112065 |
| 126 | 112066 |
| 128 | 112071 |
| 130 | 112072 |
| 132 | 112091 |
| 134 | 112092 |
| 136 | 112093 |
| 138 | 112098 |
| 140 | 112099 |
| 142 | 112100 |
| 146 | 112859 |
| 148 | 112860 |
| 150 | 112861 |
| 152 | 113634 |
| 154 | 113635 |
| 156 | 113643 |
| 158 | 113644 |
| 160 | 113651 |
| 164 | 113665 |
| 166 | 113666 |
| 168 | 118023 |
| 170 | 019772 |
| 172 | 118989 |
| 176 | 118999 |
| 178 | 119000 |
| 180 | 119001 |
| 182 | 118949 |
| 184 | 119327 |
| 186 | 119328 |
| 188 | 119329 |
| 190 | 119521 |
| 192 | 119522 |
| 194 | 119523 |
| 196 | 803022 |
| 198 | 803045 |
| 200 | 803056 |
| 202 | 803058 |
| 204 | 803059 |
| 206 | 803592 |

What is claimed is:

1. A method of inducing or stimulating an immune response in a subject in need thereof comprising administering an effective amount of a compound of the formula II, as the active ingredient:

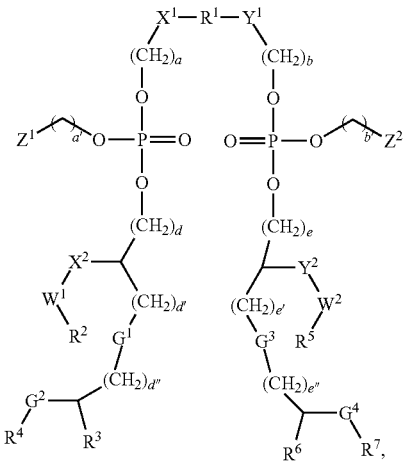

wherein:
R$^1$ is selected from the group consisting of
(a) C(O);
(b) C(O)—C$_{1-14}$ alkyl-C(O), wherein said C$_{1-14}$ alkyl is optionally substituted with hydroxy, C$_{1-5}$ alkoxy, C$_{1-5}$ alkylenedioxy, C$_{1-5}$ alkylamino, or C$_{1-5}$-alkyl-aryl, wherein said aryl moiety of said C$_{1-5}$-alkyl-aryl is optionally substituted with C$_{1-5}$ alkoxy, C$_{1-5}$ alkyl amino, C$_{1-5}$ alkoxy-amino, C$_{1-5}$ alkylamino-C$_{1-5}$ alkoxy, —O—C$_{1-5}$alkylamino-C$_{1-5}$ alkoxy, —O—C$_{1-5}$ alkylamino-C(O)—C$_{1-5}$ alkyl C(O)OH, —O—C$_{1-5}$ alkylamino-C(O)—C$_{1-5}$ alkyl-C(O)—C$_{1-5}$ alkyl;
(c) C$_2$ to C$_{15}$ straight or branched chain alkyl optionally substituted with hydroxy or alkoxy; and
(d) —C(O)—C$_{6-12}$ arylene-C(O)— wherein said arylene is optionally substituted with hydroxy, halogen, nitro or amino;
a and b are independently 0, 1, 2, 3 or 4;
d, d', d'', e, e' and e'' are independently an integer from 1 to 4;
X$^1$, X$^2$, Y$^1$ and Y$^2$ are independently selected from the group consisting of null, oxygen, NH and N(C(O)C$_{1-4}$ alkyl), and N(C$_{1-4}$ alkyl)$_2$;
W$^1$ and W$^2$ are independently selected from the group consisting of carbonyl, methylene, sulfone and sulfoxide;
R$^2$ and R$^5$ are independently selected from the group consisting of:
(a) C$_2$ to C$_{20}$ straight chain or branched chain alkyl which is optionally substituted with oxo, hydroxy or alkoxy,
(b) C$_2$ to C$_{20}$ straight chain or branched chain alkenyl or dialkenyl which is optionally substituted with oxo, hydroxy or alkoxy;
(c) C$_2$ to C$_{20}$ straight chain or branched chain alkoxy which is optionally substituted with oxo, hydroxy or alkoxy;
(d) —NH—C$_2$ to C$_{20}$ straight chain or branched chain alkyl, wherein said alkyl group is optionally substituted with oxo, hydroxy or alkoxy; and (e)

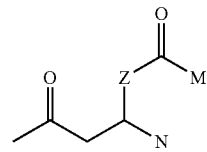

wherein Z is selected from the group consisting of O and NH, and M and N are independently selected from the group consisting of $C_2$ to $C_{20}$ straight chain or branched chain alkyl, alkenyl, alkoxy, acyloxy, alkylamino, and acylamino;

$R^3$ and $R^6$ are independently selected from the group consisting of $C_2$ to $C_{20}$ straight chain or branched chain alkyl or alkenyl optionally substituted with oxo or fluoro;

$R^4$ and $R^7$ are independently selected from the group consisting of $C(O)C_2$ to $C_{20}$ straight chain or branched chain alkyl or alkenyl; $C_2$ to $C_{20}$ straight chain or branched chain alkyl; $C_2$ to $C_{20}$ straight chain or branched chain alkoxy;

$C_2$ to $C_{20}$ straight chain or branched chain alkenyl; wherein said alkyl, alkenyl or alkoxy groups can be independently and optionally substituted with hydroxy, fluoro or $C_1$ to $C_5$ alkoxy;

$G^1$, $G^2$, $G^3$ and $G^4$ are independently selected from the group consisting of oxygen, methylene, amino, thiol, —NHC(O)—, and —N(C(O)$C_{1-4}$ alkyl)-;

or $G^2R^4$ or $G^4R^7$ may together be a hydrogen atom or hydroxyl;

a' and b' are independently 2, 3, 4, 5, 6, 7, or 8;

$Z^1$ is selected from the group consisting of —OP(O)(OH)$_2$, —P(O)(OH)$_2$, —OP(O)(OR$_8$)(OH) where $R^8$ is a $C_1$-$C_4$ alkyl chain, —OS(O)$_2$OH, —S(O)$_2$OH—, —CO$_2$H, —OB(OH)$_2$, —OH, —CH$_3$, —NH$_2$, NR$^9{}_3$ where $R^9$ is a $C_1$-$C_4$ alkyl chain;

$Z^2$ is —OP(O)(OH)$_2$, —P(O)(OH)$_2$', —OP(O)(OR$^{10}$)(OH) where $R^{10}$ is a $C_1$-$C_4$ alkyl chain, —OS(O)$_2$OH, —S(O)$_2$OH, CO$_2$H, —OB(OH)$_2$, —OH, CH$_3$, —NH$_2$, —NR$^{11}$, where $R^{11}$ is a $C_1$-$C_4$ alkyl chain;

or a pharmaceutically acceptable salt thereof.

2. The method of claim 1, wherein the subject is a human.

3. The method of claim 1, wherein the subject is a mammal, fish, or reptile.

4. A method for upregulation of the immune system in a subject in need thereof comprising administering a therapeutically effective amount of a compound of formula II,

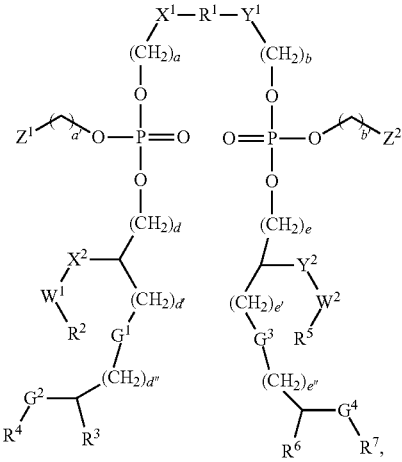

II.

wherein:
$R^1$ is selected from the group consisting of
(a) C(O);
(b) C(O)—$C_{1-14}$ alkyl-C(O), wherein said $C_{1-14}$ alkyl is optionally substituted with hydroxy, $C_{1-5}$ alkoxy, $C_{1-5}$ alkylenedioxy, $C_{1-5}$ alkylamino, or $C_{1-5}$-alkyl-aryl, wherein said aryl moiety of said $C_{1-5}$-alkyl-aryl is optionally substituted with $C_{1-5}$ alkoxy, $C_{1-5}$ alkyl amino, $C_{1-5}$ alkoxy-amino, $C_{1-5}$ alkylamino-$C_{1-5}$ alkoxy, —O—$C_{1-5}$ alkylamino-$C_{1-5}$ alkoxy, —O—$C_{1-5}$ alkylamino-C(O)—$C_{1-5}$ alkyl C(O)OH, —O—$C_{1-5}$ alkylamino-C(O)—$C_{1-5}$ alkyl-C(O)—$C_{1-5}$ alkyl;

(c) $C_2$ to $C_{15}$ straight or branched chain alkyl optionally substituted with hydroxy or alkoxy; and (d) —C(O)—$C_{6-12}$ arylene-C(O)—wherein said arylene is optionally substituted with hydroxy, halogen, nitro or amino;

a and b are independently 0, 1, 2, 3 or 4;

d, d', d", e, e' and e" are independently an integer from 1 to 4;

$X^1$, $X^2$, $Y^1$ and $Y^2$ are independently selected from the group consisting of null, oxygen, NH and N(C(O)$C_{1-4}$ alkyl), and N($C_{1-4}$ alkyl)$_2$;

$W^1$ and $W^2$ are independently selected from the group consisting of carbonyl, methylene, sulfone and sulfoxide;

$R^2$ and $R^5$ are independently selected from the group consisting of:

(a) $C_2$ to $C_{20}$ straight chain or branched chain alkyl which is optionally substituted with oxo, hydroxy or alkoxy, (b) $C_2$ to $C_{20}$ straight chain or branched chain alkenyl or dialkenyl which is optionally substituted with oxo, hydroxy or alkoxy;

(c) $C_2$ to $C_{20}$ straight chain or branched chain alkoxy which is optionally substituted with oxo, hydroxy or alkoxy;

(d) —NH—$C_2$ to $C_{20}$ straight chain or branched chain alkyl, wherein said alkyl group is optionally substituted with oxo, hydroxy or alkoxy; and (e)

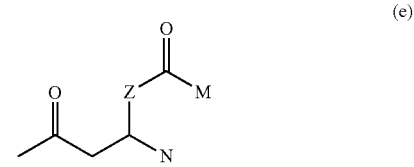

wherein Z is selected from the group consisting of O and NH, and M and N are independently selected from the group consisting of $C_2$ to $C_{20}$ straight chain or branched chain alkyl, alkenyl, alkoxy, acyloxy, alkylamino, and acylamino;

$R^3$ and $R^6$ are independently selected from the group consisting of $C_2$ to $C_{20}$ straight chain or branched chain alkyl or alkenyl optionally substituted with oxo or fluoro;

$R^4$ and $R^7$ are independently selected from the group consisting of C(0)$C_2$ to $C_{20}$ straight chain or branched chain alkyl or alkenyl; $C_2$ to $C_{20}$ straight chain or branched chain alkyl;

$C_2$ to $C_{20}$ straight chain or branched chain alkoxy; $C_2$ to $C_{20}$ straight chain or branched chain alkenyl; wherein said alkyl, alkenyl or alkoxy groups can be independently and optionally substituted with hydroxy, fluoro or $C_1$ to $C_5$ alkoxy;

$G^1$, $G^2$, $G^3$ and $G^4$ are independently selected from the group consisting of oxygen, methylene, amino, thiol, —NHC(O)—, and —N(C(O)$C_{1-4}$ alkyl)-; or $G^2R^4$ or $G^4R^7$ may together be a hydrogen atom or hydroxyl;

a' and b' are independently 2, 3, 4, 5, 6, 7, or 8;

$Z^1$ is selected from the group consisting of —OP(O)(OH)$_2$, —P(O)(OH)$_2$, —OP(O)(OR$^8$)(OH) where $R^8$ is a $C_1$-$C_4$ alkyl chain, —OS(O)₂OH, —S(O)₂OH—, —CO₂H, —OB(OH)₂, —OH, —CH₃, —NH₂, NR⁹₃ where R⁹ is a C₁-C₄ alkyl chain;

Z² is —OP(O)(OH)₂, —P(O)(OH)₂', —OP(O)(OR¹⁰)(OH) where R¹ᵒ is a C₁-C₄ alkyl chain, —OS(O)₂OH, —S(O)₂OH, CO₂H, —OB(OH)₂, —OH, CH₃, —NH₂, —NR¹¹, where R¹¹ is a C₁-C₄ alkyl chain;

or a pharmaceutically acceptable salt thereof, wherein said compound has immunostimulatory activity.

5. The method of claim 1, wherein a' and b' of Formula II are both 2.

6. The method of claim 4, wherein a' and b' of Formula II are both 2.

7. A method of inducing or stimulating an immune response in a subject in need thereof comprising administering an effective amount of a compound of formula I, as the active ingredient:

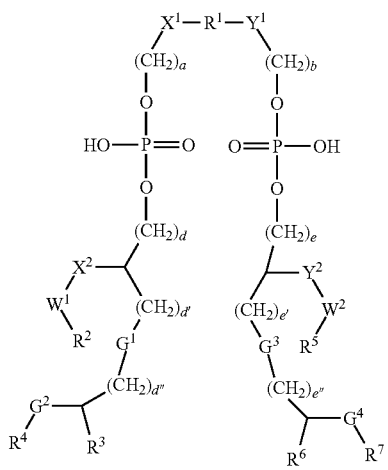

I.

wherein:

R¹ is selected from the group consisting of (a) C(O);

(b) C(O)—C₂₋₁₅ alkyl-C(O) optionally substituted with hydroxy or alkoxy;

(c) C₂ to C₁₅ straight or branched chain alkyl optionally substituted with hydroxy or alkoxy;

a and b are independently 2, 3, or 4;

d and e are independently an integer from 1 to 4;

d' and e' are 1;

d" and e" are 2;

X¹ and Y¹ are NH;

X² and Y² are independently selected from the group consisting of oxygen and NH;

W¹ and W² are carbonyl;

R² and R⁵ are independently selected from the group consisting of:

(a) C₂ to C₂₀ straight chain or branched chain alkyl which is optionally substituted with hydroxy or alkoxy, (b) C₂ to C₂₀ straight chain or branched chain alkenyl which is optionally substituted with hydroxy or alkoxy;

(c) CH₂-alkyl carbonyl;

(d) CH₂-alkenyl carbonyl; and

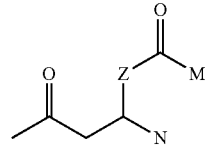

(e)

wherein Z is selected from the group consisting of O and NH, and M and N are independently selected from the group consisting of C₂ to C₂₀ straight chain or branched chain alkyl, alkenyl, alkoxy, acyloxy, alkylamino, and acylamino;

R³ and R⁶ are independently selected from the group consisting of C₂ to C₂₀ straight chain or branched chain alkyl or alkenyl;

R⁴ and R⁷ are independently selected from the group consisting of hydrogen, C₂ to C₂₀ straight chain or branched chain alkyl or alkenyl; C₂ to C₂₀ straight chain or branched chain alkyl carbonyl; and C₂ to C₂₀ straight chain or branched chain alkenyl carbonyl, optionally substituted with hydroxy or alkoxy; and G¹, G², G³, and G⁴ are oxygen;

or a pharmaceutically acceptable salt thereof.

8. The method of claim 7, wherein the subject is a human.

9. The method of claim 7, wherein the subject is a mammal, fish, or reptile.

10. A method for upregulation of the immune system in a subject in need thereof comprising administering a therapeutically effective amount of a compound of formula I,

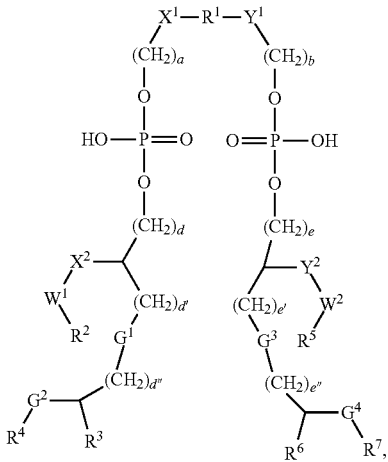

I.

wherein:

R¹ is selected from the group consisting of (a) C(O);

(b) C(O)—C₂₋₁₅ alkyl-C(O) optionally substituted with hydroxy or alkoxy;

(c) C₂ to C₁₅ straight or branched chain alkyl optionally substituted with hydroxy or alkoxy;

a and b are independently 2, 3, or 4;

d and e are independently an integer from 1 to 4;

d' and e' are 1;

d" and e" are 2;

X¹ and Y¹ are NH;

$X^2$ and $Y^2$ are independently selected from the group consisting of oxygen and NH;

$W^1$ and $W^2$ are carbonyl;

$R^2$ and $R^5$ are independently selected from the group consisting of:
(a) $C_2$ to $C_{20}$ straight chain or branched chain alkyl which is optionally substituted with hydroxy or alkoxy,
(b) $C_2$ to $C_{20}$ straight chain or branched chain alkenyl which is optionally substituted with hydroxy or alkoxy;
(c) $CH_2$-alkyl carbonyl;
(d) $CH_2$-alkenyl carbonyl; and

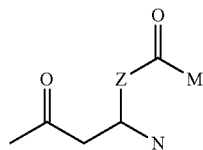

wherein Z is selected from the group consisting of O and NH, and M and N are independently selected from the group consisting of $C_2$ to $C_{20}$ straight chain or branched chain alkyl, alkenyl, alkoxy, acyloxy, alkylamino, and acylamino;

$R^3$ and $R^6$ are independently selected from the group consisting of $C_2$ to $C_{20}$ straight chain or branched chain alkyl or alkenyl;

$R^4$ and $R^7$ are independently selected from the group consisting of hydrogen, $C_2$ to $C_{20}$ straight chain or branched chain alkyl or alkenyl; $C_2$ to $C_{20}$ straight chain or branched chain alkyl carbonyl; and $C_2$ to $C_{20}$ straight chain or branched chain alkenyl carbonyl, optionally substituted with hydroxy or alkoxy; and $G^1$, $G^2$, $G^3$, and $G^4$ are oxygen;

or a pharmaceutically acceptable salt thereof;

wherein said compound has immunostimulatory activity.

11. The method of claim 10, wherein the subject is a human.

12. The method of claim 10, wherein the subject is a mammal, fish, or reptile.

* * * * *

UNITED STATES PATENT AND TRADEMARK OFFICE
CERTIFICATE OF CORRECTION

PATENT NO. : 7,833,993 B2
APPLICATION NO. : 11/077344
DATED : November 16, 2010
INVENTOR(S) : Hawkins et al.

It is certified that error appears in the above-identified patent and that said Letters Patent is hereby corrected as shown below:

Column 226, Claim 4, Line 52: Please correct "C(0)C$_2$" to read -- C(O)C$_2$ --

Column 227, Claim 4, Line 5: Please correct "where R$^{1o}$" to read -- where R$^{10}$ --

Signed and Sealed this
Thirty-first Day of May, 2011

David J. Kappos
*Director of the United States Patent and Trademark Office*